United States Patent
Zeng et al.

(10) Patent No.: US 7,105,505 B2
(45) Date of Patent: Sep. 12, 2006

(54) BENZIMIDAZOLE DERIVATIVES USEFUL AS HISTAMINE H3 ANTAGONISTS

(75) Inventors: Qingbei Zeng, Edison, NJ (US); Robert G. Aslanian, Rockaway, NJ (US); Michael Y. Berlin, Flemington, NJ (US); Christopher W. Boyce, Flemington, NJ (US); Jianhua Cao, Scotch Plains, NJ (US); Joseph A. Kozlowski, Princeton, NJ (US); Pietro Mangiaracina, Monsey, NY (US); Kevin D. McCormick, Edison, NJ (US); Mwangi W. Mutahi, Orange, NJ (US); Stuart B. Rosenblum, West Orange, NJ (US); Neng-Yang Shih, North Caldwell, NJ (US); Daniel M. Solomon, Edison, NJ (US); Wing C. Tom, Cedar Grove, NJ (US)

(73) Assignee: Schering Corporation, Kenilworth, NJ (US)

( * ) Notice: Subject to any disclaimer, the term of this patent is extended or adjusted under 35 U.S.C. 154(b) by 313 days.

(21) Appl. No.: 10/417,391

(22) Filed: Apr. 16, 2003

(65) Prior Publication Data

US 2004/0097483 A1    May 20, 2004

Related U.S. Application Data

(60) Provisional application No. 60/373,731, filed on Apr. 18, 2002.

(51) Int. Cl.
*A61K 31/495* (2006.01)

(52) U.S. Cl. ................. 514/210.21; 544/224; 544/336; 546/184; 546/192; 546/193; 546/194

(58) Field of Classification Search ........... 514/210.21; 544/224, 336; 546/184, 192, 193, 194
See application file for complete search history.

(56) References Cited

U.S. PATENT DOCUMENTS

| 5,869,479 A | 2/1999 | Kreutner et al. ............ 514/212 |
| 6,211,199 B1 | 4/2001 | Kane et al. |

FOREIGN PATENT DOCUMENTS

| CA | 2 387 613 | 5/2001 |
| EP | 0 580 541 | 1/1994 |
| EP | 0 626 373 | 11/1994 |
| WO | WO 98/06394 | 2/1998 |
| WO | 02/24659 | 3/2002 |
| WO | WO 02/32893 | 4/2002 |
| WO | WO 02/072570 | 9/2002 |

OTHER PUBLICATIONS

"Abbot's H3 histamine receptor antagonist, ABT-239, a candidate treatment of cognitive disorders, ADHD, Alzheimer's and schizophrenia," TherapeuticAdvances, LeadDiscovery's bulletin, www.leaddiscovery.co.uk, Jan. 2005, pp. 1-5.*
Basic and Clinical Pharmacology, 7th edition, Bertram G. Katzung, pp. 268-269.*
Janssens et al, *Journal of Medicinal Chemistry*, 28(12) (1985)1943-1947.
McLeod et al, *Am. J. Rhinology*, 13, 5 (1999), p. 391-399..
Taylor-Clark et al, *Brit. J. Pharmacology*, 144 (2005), p. 867-874.
Leurs et al, *TIPS*, 19 (1998), p. 177-183.
Henning et al, *Journal of Medicinal Chemistry*, vol. 30, 1987, pp. 814-819.
Hey et al, *European Journal of Pharmacology*, vol. 294 (1995) pp. 329-335.
Heinlsch et al, *Monatshefte für Chemie*, vol. 104 (1973), pp. 1372-1382.
U.S. Appl. No. 10/414,943.
U.S. Application, filed Jun. 20, 2003, "Indole Derivatives Useful as Histamine H$_3$ Anatagonists"(Claims Benefit of U.S. Appl. 60/390,987).

* cited by examiner

*Primary Examiner*—James O. Wilson
*Assistant Examiner*—Jason H. Johnsen
(74) *Attorney, Agent, or Firm*—Mark W. Russell

(57) ABSTRACT

Disclosed are novel compounds of the formula $$R^1-X-\underset{(R^{12})_a}{\overset{}{\underset{n}{\bigcirc}}}-M^1-Y-\underset{(R^{13})_b}{\overset{}{\underset{p}{\bigcirc}}}-M^2-N-Z-R^2 \qquad I$$

wherein $R^1$ is optionally substituted benzimidazolyl or a derivative thereof; $R^2$ is optionally substituted aryl or heteroaryl; $M^1$ and $M^2$ are $C(R^3)$ or N; and the remaining variables are as defined in the specification; also disclosed are pharmaceutical compositions comprising the compounds of formula I and methods of treating various diseases or conditions, such as allergy, allergy-induced airway responses, and congestion (e.g., nasal congestion) using the compounds of formula I, as well as methods of treating said diseases or conditions using the compounds of formula I in combination with an $H_1$ receptor antagonist.

22 Claims, No Drawings

BENZIMIDAZOLE DERIVATIVES USEFUL AS HISTAMINE H3 ANTAGONISTS

CROSS REFERENCE TO RELATED APPLICATION

This application claims the benefit of U.S. Provisional Application 60/373,731, filed Apr. 18, 2002.

FIELD OF THE INVENTION

The present invention relates to novel substituted benzimidazoles and aza- and diaza-derivatives thereof useful as histamine $H_3$ antagonists. The invention also relates to pharmaceutical compositions comprising said compounds and their use in treating inflammatory diseases, allergic conditions and central nervous system disorders. The invention also relates to the use of a combination of novel histamine $H_3$ antagonists of this invention with histamine $H_1$ compounds for the treatment of inflammatory diseases and allergic conditions, as well as pharmaceutical compositions comprising a combination of one or more novel histamine $H_3$ antagonist compounds of the invention with one or more histamine $H_1$ compounds.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation.

Imidazole $H_3$ receptor antagonists are well known in the art. More recently, non-imidazole $H_3$ receptor antagonists have been disclosed in PCT US01/32151, filed Oct. 15, 2001, and U.S. Provisional Application 60/275,417, filed Mar. 13, 2001.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides novel compounds of formula I:

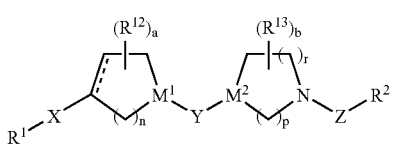

I or a pharmaceutically acceptable salt or solvate thereof, wherein:

the dotted line represents an optional double bond;

a is 0 to 2;

b is 0 to 2;

n is 1, 2 or 3;

p is 1, 2 or 3;

r is 0, 1, 2, or 3;

with the provisos that when $M^2$ is N, p is not 1; and that when r is 0, $M^2$ is $C(R^3)$; and that the sum of p and r is 1 to 4;

$M^1$ is $C(R^3)$ or N;

$M^2$ is $C(R^3)$ or N;

X is a bond or $C_1$–$C_6$ alkylene;

Y is —C(O)—, —C(S)—, —(CH$_2$)$_q$—, —NR$^4$C(O)—, —C(O)NR$^4$—, —C(O)CH$_2$—, —SO$_2$—, —N(R$^4$)—, —NH—C(=N—CN)— or —C(=N—CN)—NH—; with the provisos that when $M^1$ is N, Y is not —NR$^4$C(O)— or —NH—C(=N—CN)—; when $M^2$ is N, Y is not —C(O)NR$^4$— or —C(=N—CN)—NH—; and when Y is —N(R$^4$)—, $M^1$ is CH and $M^2$ is $C(R^3)$;

q is 1 to 5, provided that when both $M^1$ and $M^2$ are N, q is 2 to 5;

Z is a bond, $C_1$–$C_6$ alkylene, $C_1$–$C_6$ alkenylene, —C(O)—, —CH(CN)—, —SO$_2$— or —CH$_2$C(O)NR$^4$—;

$R^1$ is

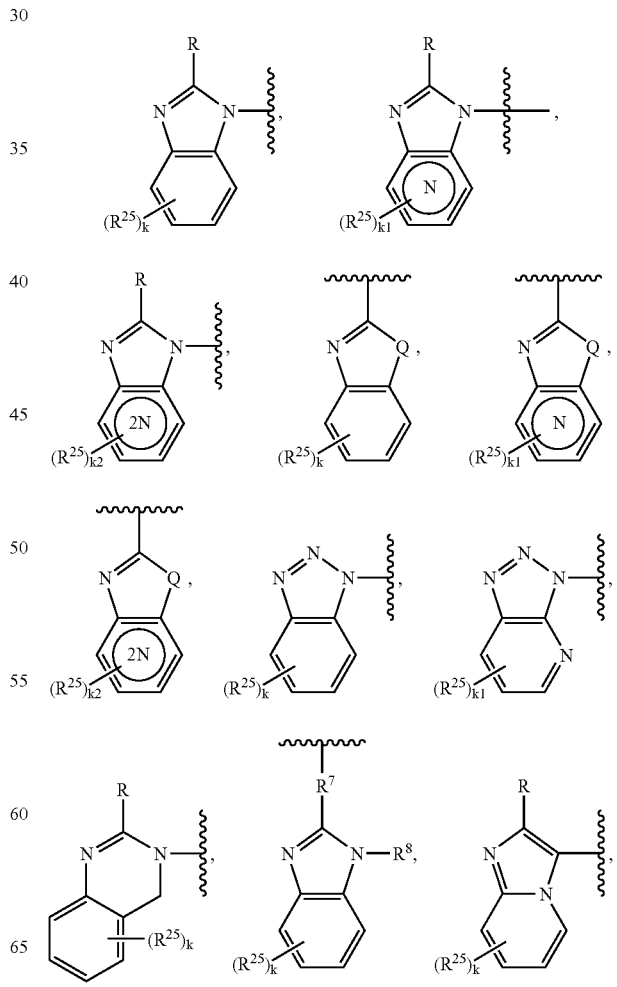

-continued

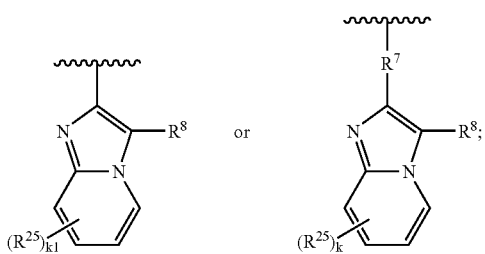

Q is —N(R$^8$)—, —S— or —O—;

k is 0, 1, 2, 3 or 4;

k1 is 0, 1, 2 or 3;

k2 is 0, 1 or 2;

R is H, C$_1$–C$_6$ alkyl, halo(C$_1$–C$_6$)alkyl-, C$_1$–C$_6$ alkoxy, (C$_1$–C$_6$)alkoxy-(C$_1$–C$_6$)alkyl-, (C$_1$–C$_6$)-alkoxy-(C$_1$–C$_6$) alkoxy, (C$_1$–C$_6$)alkoxy-(C$_1$–C$_6$)alkyl-SO$_{0-2}$, R$^{32}$-aryl (C$_1$–C$_6$)alkoxy-, R$^{32}$-aryl(C$_1$–C$_6$)alkyl-, R$^{32}$-aryl, R$^{32}$-aryloxy, R$^{32}$-heteroaryl, (C$_3$–C$_6$)cycloalkyl, (C$_3$–C$_6$) cycloalkyl-(C$_1$–C$_6$)alkyl, (C$_3$–C$_6$)cycloalkyl-(C$_1$–C$_6$) alkoxy, (C$_3$–C$_6$)cycloalkyl-oxy-, R$^{37}$-heterocycloalkyl, R$^{37}$-heterocycloalkyl-oxy-, R$^{37}$-heterocycloalkyl-(C$_1$–C$_6$) alkoxy, N(R$^{30}$)(R$^{31}$)—(C$_1$–C$_6$)alkyl-, —N(R$^{30}$)(R$^{31}$), —NH—(C$_1$–C$_6$)alkyl-O—(C$_1$–C$_6$)alkyl, —NHC(O)NH (R$^{29}$); R$^{29}$—S(O)$_{0-2}$—, halo(C$_1$–C$_6$)alkyl-S(O)$_{0-2}$—, N(R$^{30}$)(R$^{31}$)—(C$_1$–C$_6$)alkyl-S(O)$_{0-2}$— or benzoyl;

R$^8$ is H, C$_1$–C$_6$ alkyl, halo(C$_1$–C$_6$)alkyl-, (C$_1$–C$_6$)alkoxy-(C$_1$–C$_6$)alkyl-, R$^{32}$-aryl(C$_{1-C6}$)alkyl-, R$^{32}$-aryl, R$^{32}$-heteroaryl, (C$_3$–C$_6$)cycloalkyl, (C$_3$–C$_6$)cycloalkyl-(C$_1$–C$_6$) alkyl, R$^{37}$-heterocycloalkyl, N(R$^{30}$)(R$^{31}$)—(C$_1$–C$_6$)alkyl-, R$^{29}$—S(O)$_2$—, halo(C$_1$–C$_6$)alkyl-S(O)$_2$—, R$^{29}$—S(O)$_{0-1}$—(C$_2$–C$_6$)alkyl-, halo(C$_1$–C$_6$)alkyl-S(O)$_{0-1}$—(C$_2$–C$_6$)alkyl-;

R$^2$ is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; R$^{32}$-quinolyl; R$^{32}$-aryl; heterocycloalkyl; (C$_3$–C$_6$)cycloalkyl; C$_1$–C$_6$ alkyl; hydrogen; thianaphthenyl;

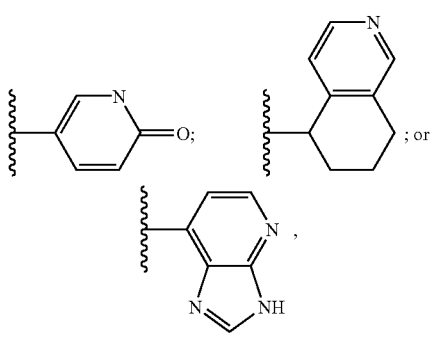

wherein said six-membered heteroaryl ring or said five-membered heteroaryl ring is optionally substituted by R$^6$;

R$^3$ is H, halogen, C$_1$–C$_6$ alkyl, —OH, (C$_1$–C$_6$)alkoxy or —NHSO$_2$—(C$_1$–C$_6$)alkyl;

R$^4$ is independently selected from the group consisting of hydrogen, C$_1$–C$_6$ alkyl, C$_3$–C$_6$ cycloalkyl, (C$_3$–C$_6$)cycloalkyl(C$_1$–C$_6$)alkyl, R$^{33}$-aryl, R$^{33}$-aryl(C$_1$–C$_6$)alkyl, and R$^{32}$-heteroaryl;

R$^5$ is hydrogen, C$_1$–C$_6$ alkyl, —C(O)R$^{20}$, —C(O)$_2$R$^{20}$, —C(O)N(R$^{20}$)$_2$, (C$_1$–C$_6$)alkyl-SO$_2$—, or (C$_1$–C$_6$)alkyl-SO$_2$—NH—;

or R$^4$ and R$^5$, together with the nitrogen to which they are attached, form an azetidinyl, pyrrolidinyl, piperidinyl, piperazinyl or morpholinyl ring;

R$^6$ is 1 to 3 substituents independently selected from the group consisting of —OH, halogen, C$_1$–C$_6$ alkyl-, C$_1$–C$_6$ alkoxy, C$_1$–C$_6$ alkylthio, —CF$_3$, —NR$^4$R$^5$, —CH$_2$—NR$^4$R$^5$, —NHSO$_2$R$^{22}$, —N(SO$_2$R$^{22}$)$_2$, phenyl, R$^{33}$-phenyl, NO$_2$, —CO$_2$R$^4$, —CON(R$^4$)$_2$,

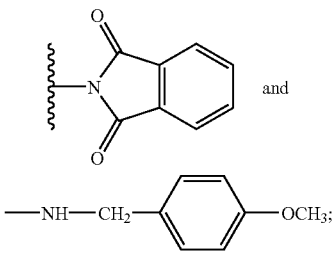

R$^7$ is —N(R$^{29}$)—, —O— or —S(O)$_{0-2}$—;

R$^{12}$ is independently selected from the group consisting of C$_1$–C$_6$ alkyl, hydroxyl, C$_1$–C$_6$ alkoxy, or fluoro, provided that when R$^{12}$ is hydroxy or fluoro, then R$^{12}$ is not bound to a carbon adjacent to a nitrogen; or two R$^{12}$ substituents form a C$_1$ to C$_2$ alkyl bridge from one ring carbon to another non-adjacent ring carbon; or R$^{12}$ is =O;

R$^{13}$ is independently selected from the group consisting of C$_1$–C$_6$ alkyl, hydroxyl, C$_1$–C$_6$ alkoxy, or fluoro, provided that when R$^{13}$ is hydroxy or fluoro then R$^{13}$ is not bound to a carbon adjacent to a nitrogen; or two R$^{13}$ substituents form a C$_1$ to C$_2$ alkyl bridge from one ring carbon to another non-adjacent ring carbon; or R$^{13}$ is =O;

R$^{20}$ is independently selected from the group consisting of hydrogen, C$_1$–C$_6$ alkyl, or aryl, wherein said aryl group is optionally substituted with from 1 to 3 groups independently selected from halogen, —CF$_3$, —OCF$_3$, hydroxyl, or methoxy; or when two R$^{20}$ groups are present, said two R$^{20}$ groups taken together with the nitrogen to which they are bound can form a five or six membered heterocyclic ring;

R$^{22}$ is C$_1$–C$_6$ alkyl, R$^{34}$-aryl or heterocycloalkyl;

R$^{24}$ is H, C$_1$–C$_6$ alkyl, —SO$_2$R$^{22}$ or R$^{34}$-aryl;

R$^{25}$ is independently selected from the group consisting of C$_1$–C$_6$ alkyl, halogen, —CN, —NO$_2$, —CF$_3$, —OH, C$_1$–C$_6$ alkoxy, (C$_1$–C$_6$)alkyl-C(O)—, aryl-C(O)—, —C(O)OR$^{29}$, —N(R$^4$)(R$^5$), N(R$^4$)(R$^5$)—C(O)—, N(R$^4$)(R$^5$)—S(O)$_{1-2}$—, R$^{22}$—S(O)$_{0-2}$—, halo-(C$_1$–C$_6$)alkyl- or halo-(C$_1$–C$_6$) alkoxy-(C$_1$–C$_6$)alkyl-;

R$^{29}$ is H, C$_1$–C$_6$ alkyl, C$_3$–C$_6$ cycloalkyl, R$^{35}$-aryl or R$^{35}$-aryl(C$_1$–C$_6$)alkyl-;

R$^{30}$ is H, C$_1$–C$_6$ alkyl-, R$^{35}$-aryl or R$^{35}$-aryl(C$_1$–C$_6$)alkyl-;

R$^{31}$ is H, C$_1$–C$_6$ alkyl-, R$^{35}$-aryl, R$^{35}$-aryl(C$_1$–C$_6$)alkyl-, R$^{35}$-heteroaryl, (C$_1$–C$_6$)alkyl-C(O)—, R$^{35}$-aryl-C(O)—, N(R$^4$)(R$^5$)—C(O)—, (C$_1$–C$_6$)alkyl-S(O)$_2$— or R$^{35}$-aryl-S (O)$_2$—;

or R$^{30}$ and R$^{31}$ together are —(CH$_2$)$_{4-5}$—, —(CH$_2$)$_2$—O—(CH$_2$)$_2$— or —(CH$_2$)$_2$—N(R$^{38}$)—(CH$_2$)$_2$— and form a ring with the nitrogen to which they are attached;

$R^{32}$ is 1 to 3 substituents independently selected from the group consisting of H, —OH, halogen, $C_1$–$C_6$ alkyl, $C_1$–$C_6$ alkoxy, $R^{35}$-aryl-O—, —$SR^{22}$, —$CF_3$, —$OCF_3$, —$OCHF_2$, —$NR^{39}R^{40}$, phenyl, $R^{33}$-phenyl, $NO_2$, —$CO_2R^{39}$, —CON$(R^{39})_2$, —$S(O)_2R^{22}$, —$S(O)_2N(R^{20})_2$, —$N(R^{24})S(O)_2R^{22}$, —CN, hydroxy-($C_1$–$C_6$)alkyl-, —$OCH_2CH_2OR^{22}$, and $R^{35}$-aryl($C_1$–$C_6$)alkyl-O—, or two $R^{32}$ groups on adjacent carbon atoms together form a —$OCH_2O$— or —$O(CH_2)_2O$— group;

$R^{33}$ is 1 to 3 substituents independently selected from the group consisting of $C_1$–$C_6$ alkyl, halogen, —CN, —$NO_2$, —$CF_3$, —$OCF_3$, —$OCHF_2$ and —O—($C_1$–$C_6$)alkyl;

$R^{34}$ is 1 to 3 substituents independently selected from the group consisting of H, halogen, —$CF_3$, —$OCF_3$, —OH and —$OCH_3$;

$R^{35}$ is 1 to 3 substituents independently selected from hydrogen, halo, $C_1$–$C_6$ alkyl, hydroxy, $C_1$–$C_6$ alkoxy, phenoxy, —$CF_3$, —$N(R^{36})_2$, —$COOR^{20}$ and —$NO_2$;

$R^{36}$ is independently selected form the group consisting of H and $C_1$–$C_6$ alkyl;

$R^{37}$ is 1 to 3 substituents independently selected from hydrogen, halo, $C_1$–$C_6$ alkyl, hydroxy, $C_1$–$C_6$ alkoxy, phenoxy, —$CF_3$, —$N(R^{36})_2$, —$COOR^{20}$, —$C(O)N(R^{29})_2$ and —$NO_2$, or $R^{37}$ is one or two =O groups;

$R^{38}$ is H, $C_1$–$C_6$ alkyl, $R^{35}$-aryl, $R^{35}$-aryl($C_1$–$C_6$)alkyl-, ($C_1$–$C_6$)alkyl-$SO_2$ or halo($C_1$–$C_6$)alkyl-$SO_2$—;

$R^{39}$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$–$C_6$)alkyl, and $R^{32}$-heteroaryl; and $R^{40}$ is hydrogen, $C_1$–$C_6$ alkyl, —$C(O)R^{20}$, —$C(O)_2R^{20}$, —$C(O)N(R^{20})_2$, ($C_1$–$C_6$)alkyl-$SO_2$—, or ($C_1$–$C_6$)alkyl-$SO_2$—NH—;

or $R^{39}$ and $R^{40}$, together with the nitrogen to which they are attached, form an azetidinyl, pyrrolidinyl, piperidinyl, piperazinyl or morpholinyl ring;

This invention also provides a pharmaceutical composition comprising an effective amount of compound of at least one compound of formula I and a pharmaceutically acceptable carrier.

This invention further provides a method of treating: allergy, allergy-induced airway (e.g., upper airway) responses, congestion (e.g., nasal congestion), hypotension, cardiovascular disease, diseases of the GI tract, hyper and hypo motility and acidic secretion of the gastro-intestinal tract, obesity, sleeping disorders (e.g., hypersomnia, somnolence, and narcolepsy), disturbances of the central nervous system, attention deficit hyperactivity disorder (ADHD), hypo and hyperactivity of the central nervous system (for example, agitation and depression), and/or other CNS disorders (such as Alzheimer's, schizophrenia, and migraine) comprising administering to a patient in need of such treatment (e.g., a mammal, such as a human being) an effective amount of at least one compound of formula I.

Compounds of this invention are particularly useful for treating allergy, allergy-induced airway responses and/or congestion.

This invention further provides a pharmaceutical composition comprising an effective amount of a combination of at least one compound of formula I and at least one $H_1$ receptor antagonist in combination with a pharmaceutically acceptable carrier.

This invention further provides a method of treating allergy, allergy-induced airway (e.g., upper airway) responses, and/or congestion (e.g., nasal congestion) comprising administering to a patient in need of such treatment (e.g., a mammal, such as a human being) an effective amount of a combination of at least one compound of formula I and at least one $H_1$ receptor antagonist.

Kits comprising a compound of formula I in a pharmaceutical composition, and a separate $H_1$ receptor antagonist in a pharmaceutical compositions in a single package are also contemplated.

DETAILED DESCRIPTION OF THE INVENTION

Preferred definitions of the variables in the structure of formula I are as follows:

$R^1$ is preferably optionally substituted benzimidazolyl or 7-azabenzimidazolyl, wherein R is preferably alkyl, alkoxy, alkoxyalkoxy, alkylthio, heteroaryl or $R^{32}$-aryl. More preferably, R is —$CH_3$, —$CH_2CH_3$, —$OCH_3$, —$OCH_2CH_3$, —$OCH_2CH_2CH_3$, —$OCH((CH_3)_2$, —$SCH_3$, —$SCH_2CH_3$, pyridyl (especially 2-pyridyl), pyrimidyl, pyrazinyl, furanyl, oxazolyl or $R^{32}$-phenyl.

$R^{25}$ is preferably halogen or —$CF_3$ and k is 0 or 1.

$R^2$ is preferably a six-membered heteroaryl ring, optionally substituted with one substituent. More preferably, $R^2$ is pyrimidyl, $R^6$-pyrimidyl, pyridyl, $R^6$-pyridyl or pyridazinyl, wherein $R^6$ is —$NR^4R^5$, wherein $R^4$ and $R^5$ are independently selected from the group consisting of H and ($C_1$–$C_6$) alkyl, or $R^4$ and $R^5$ together with the nitrogen to which they are attached form a pyrrolidinyl, piperidinyl or morpholinyl ring. More preferably, $R^6$ is —$NH_2$.

X is preferably a bond.

Y is preferably —C(O)—.

Z is preferably straight or branched $C_1$–$C_3$ alkyl.

$M^1$ is preferably N; a is preferably 0; and n is preferably 2; the optional double bond is preferably not present (i.e., a single bond is present).

$M^2$ is preferably $C(R^3)$ wherein $R^3$ is hydrogen or fluorine; b is preferably 0; r is preferably 1; and p is preferably 2.

As used herein, the following terms have the following meanings, unless indicated otherwise:

alkyl (including, for example, the alkyl portions of arylalkyl and alkoxy) represents straight and branched carbon chains and contains from one to six carbon atoms;

alkylene represents a divalent straight or branched alkyl chain, e.g., ethylene (—$CH_2CH_2$—) or propylene (—$CH_2CH_2CH_2$—);

Haloalkyl and haloalkoxy represent alkyl or alkoxy chains wherein one or more hydrogen atoms are replaced by halogen atoms, e.g., —$CF_3$, $CF_3CH_2CH_2$—, $CF_3CF_2$— or $CF_3S$;

aryl (including the aryl portion of arylalkyl) represents a carbocyclic group containing from 6 to 14 carbon atoms and having at least one aromatic ring (e.g., aryl is a phenyl or naphthyl ring), with all available substitutable carbon atoms of the carbocyclic group being intended as possible points of attachment;

arylalkyl represents an aryl group, as defined above, bound to an alkyl group, as defined above, wherein said alkyl group is bound to the compound;

cycloalkyl represents saturated carbocyclic rings of from 3 to 6 carbon atoms;

halogen (halo) represents fluoro, chloro, bromo and iodo;

heteroaryl represents cyclic groups, having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms; examples include but are not limited to isothiazolyl, isoxazolyl, oxazolyl, furazanyl, triazolyl, tetrazolyl, thiazolyl, thiadiazolyl, isothiadiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoqinolinyl, quinolinyl, naphthyridinyl; the 5- and 6-membered heteroaryl groups included in the definition of $R^2$ are exemplified by the heteroaryl groups listed above; all available substitutable carbon and nitrogen atoms can be substituted as defined;

heterocycloalkyl represents a saturated, carbocyclic ring containing from 3 to 15 carbon atoms, preferably from 4 to 6 carbon atoms; examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperazinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

In the definition of $R^{32}$, when two $R^{32}$ groups on adjacent carbon atoms of an aryl or heteroaryl ring are said to be taken together form a —OCH$_2$O— or —O(CH$_2$)$_2$O— group, this means that the two $R^{32}$ groups form a methylenedioxy or ethylenedioxy ring fused to the aryl or heteroaryl ring. When $R^{12}$, $R^{13}$ or $R^{37}$ is said to be one or two =O groups, this means that two hydrogen atoms on the same carbon atom of the ring can be replaced by =O; two such groups can be present on a ring.

Ⓝ for example in the structure

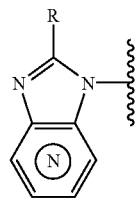

represents a nitrogen atom that is located at one of the 4 non-fused positions of the ring, i.e., positions 4, 5, 6 or 7 indicated below:

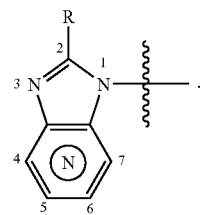

Similarly, means that two nitrogens are located at any two of the 4 non-fused positions of the ring, e.g., the 4 and 6 positions, the 4 and 7 positions, or the 5 and 6 positions.

Also, as used herein, "upper airway" usually means the upper respiratory system—i.e., the nose, throat, and associated structures.

Also, as used herein, "effective amount" generally means a therapeutically effective amount.

"Patient" means a mammal, typically a human, although veterinary use is also contemplated.

Lines drawn into the rings indicate that the indicated bond may be attached to any of the substitutable ring carbon atoms.

Certain compounds of the invention may exist in different isomeric (e.g., enantiomeric, diastereoisomeric and geometric) forms. The invention contemplates all such isomers both in pure form and in admixture, including racemic mixtures. Enol forms and tautomers are also included.

The compounds of this invention are ligands for the histamine $H_3$ receptor. The compounds of this invention can also be described as antagonists of the $H_3$ receptor, or as $H_3$ antagonists.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases. Thus, for example, if there are carboxylic acid substituents in the molecule, salts may be formed with inorganic as well as organic bases such as, for example, NaOH, KOH, NH$_4$OH, tetraalkylammonium hydroxide, and the like.

The compounds of formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

The compounds of this invention can be combined with an $H_1$ receptor antagonist (i.e., the compounds of this invention can be combined with an $H_1$ receptor antagonist in a pharmaceutical composition, or the compounds of this invention can be administered with $H_1$ receptor antagonist).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of an $H_3$ antagonist of this invention (compound of formula I) is administered with a $H_1$ antagonist, the antagonists can be administered simultaneously or sequentially (first one and then the other over a period of time). In general, when the antagonists are administered sequentially, the $H_3$ antagonist of this invention (compound of formula I) is administered first.

Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities.

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

One skilled in the art will recognize that the synthesis of compounds of formula I may require the construction of carbon-nitrogen bond. Methods include but are not limited to the use of a substituted aromatic compound or heteroaromatic compound and amine at 0° C. to 200° C. The reaction may be carried out neat or in a solvent. Suitable solvents for the reaction are halogenated hydrocarbons, ethereal solvents, toluene, dimethylformamide and the like.

One skilled in the art will recognize that the synthesis of compounds of formula I may require the construction of heterocycle. Methods include but are not limited to the use of a diamino compound and a carbonyl equivalent at 0° C. to 200° C. The reaction may be carried out in acidic, basic or neutral conditions. Suitable solvents for the reaction are water, halogenated hydrocarbons, ethereal solvents, alcoholic solvents, toluene, ketones, dimethylformamide and the like.

One skilled in the art will recognize that the synthesis of compounds of formula I may require the need for the protection of certain functional groups (i.e. derivatization for the purpose of chemical compatibility with a particular reaction condition). See, for example, Green et al, *Protective Groups in Organic Synthesis*. A suitable protecting group for an amine is methyl, benzyl, ethoxyethyl, t-butoxycarbonyl, phthaloyl and the like which can appended to and removed by literature methods known to those skilled in the art.

One skilled in the art will recognize that the synthesis of compounds of formula I may require the construction of an amide bond. Methods include but are not limited to the use of a reactive carboxy derivative (e.g. acid halide) or the use of an acid with a coupling reagent (e.g. EDCI, DCC, HATU) with an amine at 0° C. to 100° C. Suitable solvents for the reaction are halogenated hydrocarbons, ethereal solvents, dimethylformamide and alike.

One skilled in the art will recognize that the synthesis of compounds of formula I may require the reduction of a functional group. Suitable reducing reagents for the reaction include $NaBH_4$, lithium aluminum hydride, diborane and the like at −20° C. to 100° C. Suitable solvents for the reaction are halogenated hydrocarbons, ethereal solvents, and the like.

The starting materials and the intermediates of the reaction may be isolated and purified if desired using conventional techniques, including but not limited to filtration, distillation, crystallization, chromatography and alike. Such materials can be characterized using conventional means, including physical constants and spectral data.

One method shown in Scheme 1, below, is for the preparation of compounds of formula IA wherein $R^1$ is 1-benzimidazolyl or 2-benzamidazolyl and X is a bond or alkyl. Similar procedures can be used to prepare compounds wherein the benzene ring of the benzimidazolyl group is substituted, as well as the aza-benzimidazoles compounds (i.e., compounds wherein $R^1$ is other than benzimidazolyl as defined above) and the benzoxazolyl and benzothiazolyl derivatives.

SCHEME 1.

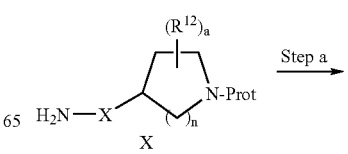

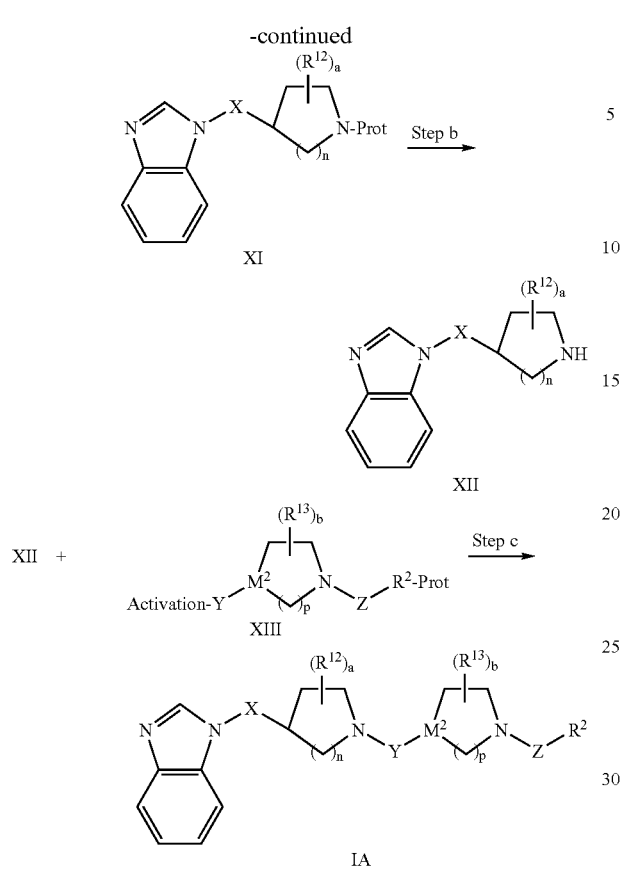

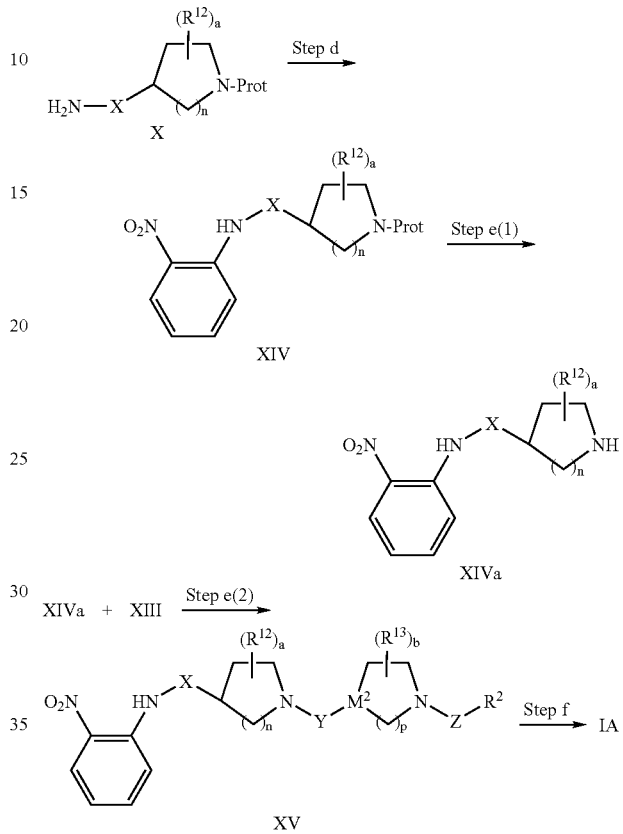

Step a: A suitably monoprotected diamine of formula X, wherein X is a bond or alkyl, Prot is a protecting group, and the remaining variables are as defined above is alkylated or arylated with a halide. The intermediate diamine is then cyclized with an appropriate carbonyl or formyl equivalent to form a compound of formula XI. Suitable protecting groups are methyl, benzyl, butoxycarbonyl, or ethoxycarbonyl. A suitable halide for alkylation is a substituted aromatic compound or a substituted hetero-aromatic compound as described by Henning et al, *J. Med. Chem.* 30, (1987), 814–819.

Step b: The protected amine of formula XI is deprotected using methods known to those skilled in the art. A suitable method for methyl deprotection is reaction with a haloformate or the like. A suitable method for benzyl deprotection is cleavage with hydrogen at or above atmospheric pressure and a catalyst such as palladium. Suitable methods for carbamate deprotection are treatment with an acid, base or trimethylsilyl iodide.

Step c: An amine of formula XII is reacted with an activated functional group Y of formula XIII to form the bond between the nitrogen and functional group Y in formula IA. When Y is a carbonyl group and $M^2$ is carbon, activation can be via a halide (i.e. acid chloride intermediate) or other coupling reagents (EDCI, DCC, HATU, or like). Suitable reaction conditions may require a base such as triethylamine or N,N-diisopropylethylamine.

Another method for the preparation of compounds of formula IA wherein $R^1$ is 1-benzimidazolyl or 2-benzimidazolyl and X is a bond or alkyl is shown in Scheme 2, below. Similar procedures can be used to prepare compounds wherein the benzene ring of the benzimidazolyl group is substituted, as well as the aza-benzimidazoles compounds (i.e., compounds wherein $R^1$ is other than benzimidazolyl as defined above).

Step d: A suitably monoprotected diamine of formula X, wherein X is a bond or alkyl, Prot is a protecting group, and the remaining variables are as defined above, is alkylated or arylated with a halide to form a compound of formula XIV. Suitable protecting groups are methyl, benzyl, butoxycarbonyl, and ethoxycarbonyl. A suitable halide for alkylation is a substituted aromatic compound or a substituted heteroaromatic compound as described by Henning et al.

Step e:
(1) The protected amine of formula XIV is deprotected using methods known to those skilled in the art. A suitable method for methyl deprotection is reaction with a haloformate or the like. A suitable method for benzyl deprotection is cleavage with hydrogen at or above atmospheric pressure and a catalyst such as palladium. Suitable methods for carbamate deprotection are treatment with an acid, base or trimethylsilyl iodide.
(2) The resulting amine from Step e(1) is reacted with an activated functional group Y of formula XIII to form the bond between the nitrogen and functional group Y to obtain the compound of formula XV. When Y is a carbonyl group and $M^2$ is carbon, activation can be via a halide (i.e. acid chloride intermediate) or other coupling reagents (EDCI, DCC, HATU, or the like). Suitable reaction conditions may require a base such as triethylamine, N,N-diisopropylethylamine, pyridine, or the like.

Step f: After reduction of formula XV, the resulting compound is reacted with a carbonyl equivalent to give the cyclized compound of formula IA. The reduction conditions can be hydrogen in the presence of catalyst, metal in the presence of an acid or a base, or other reduction reagent. The cyclization can be performed in acidic or basic conditions.

More detailed methods for synthesis of compounds are shown in Scheme 3 below. The preparation of compounds of formula IB wherein $R^1$ is 1-benzimidazolyl (Methods A, B, C and F), Y is —C(O)— and $R^2$ is substituted pyridyl, and compounds of formulas IC and IC' wherein $R^1$ is 2-benzimidazolyl (Methods D and E), Y is —C(O)— and $R^2$ is substituted pyridyl are shown, but those skilled in the art will recognize that similar procedures can be used to prepare compounds wherein the benzene ring of the benzimidazolyl group is substituted, $R^2$ is other than pyridyl, and azabenzimidazoles compounds (i.e., compounds wherein $R^1$ is other than benzimidazolyl as defined above).

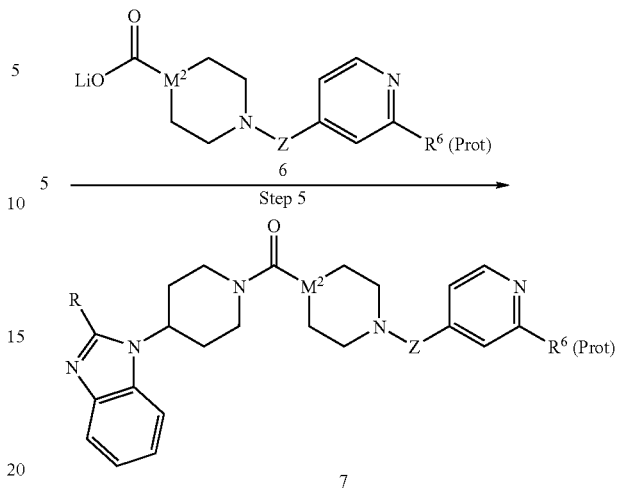

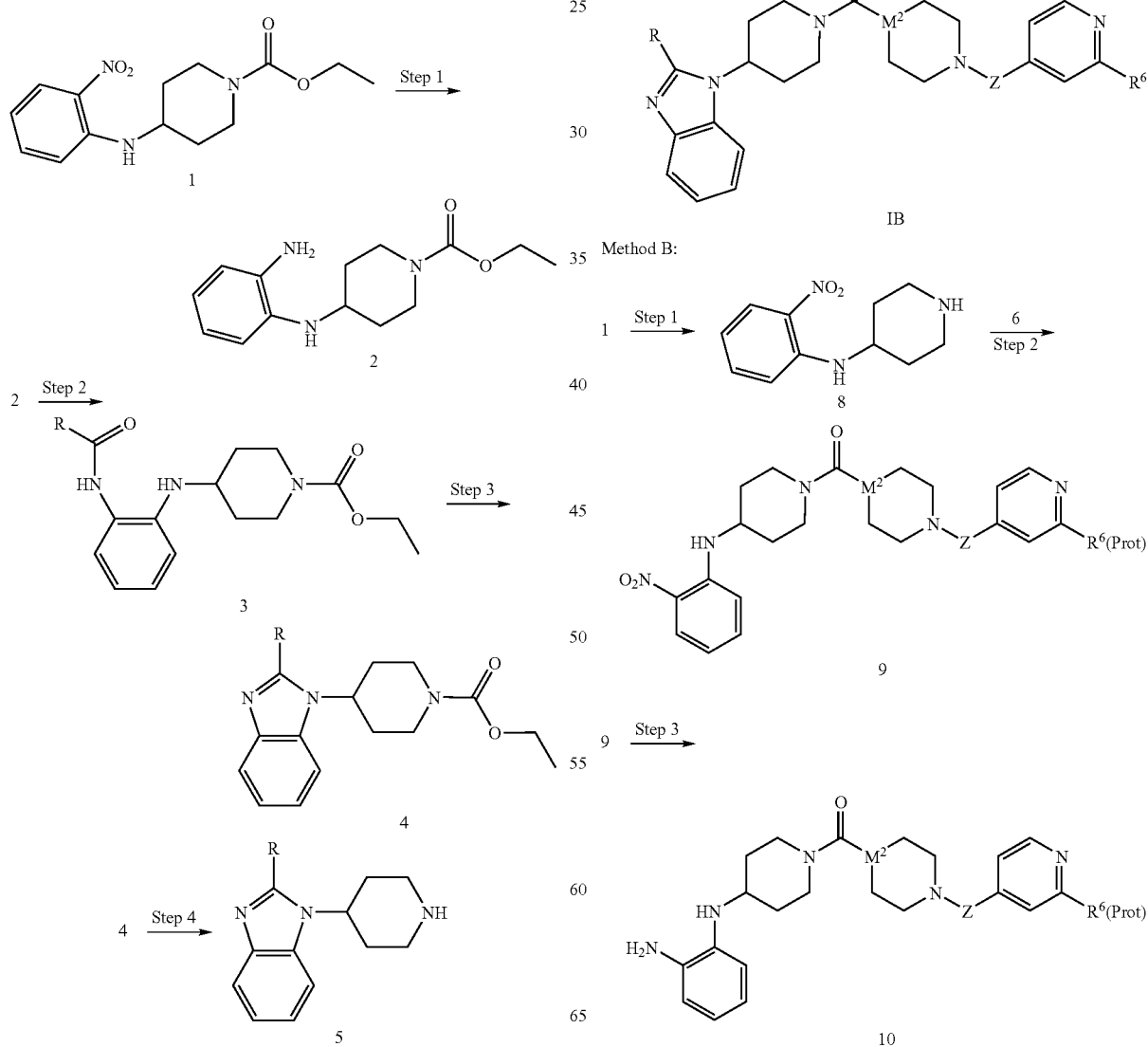

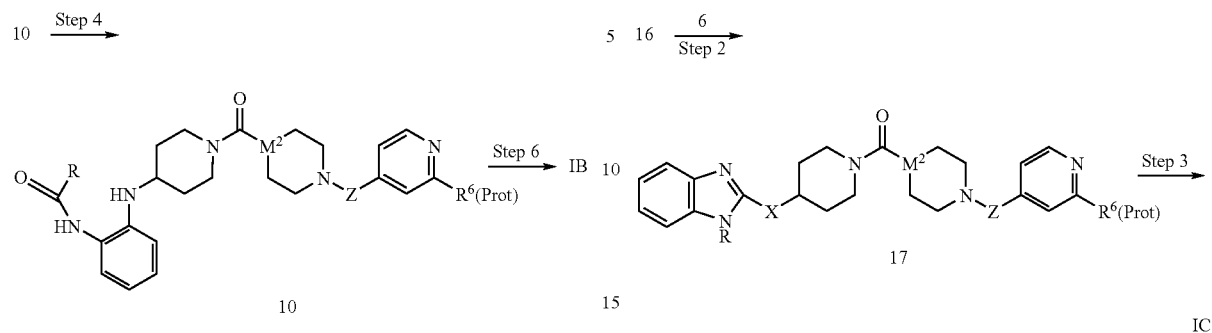
Method C:
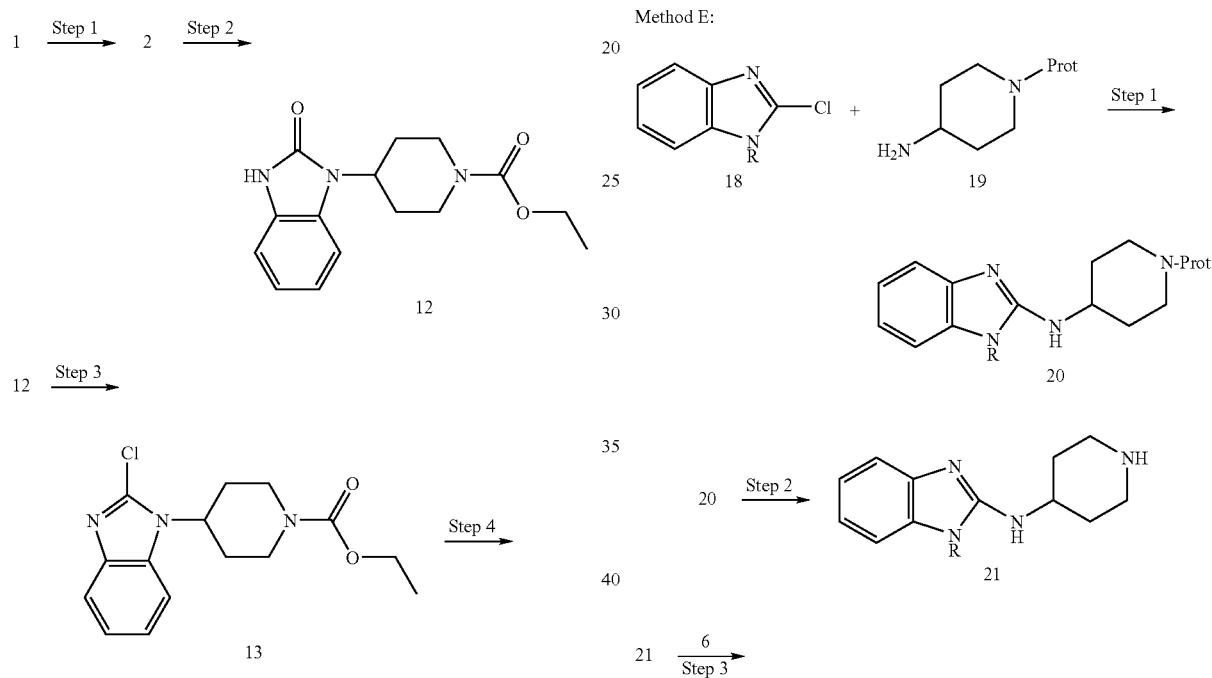
Method D:
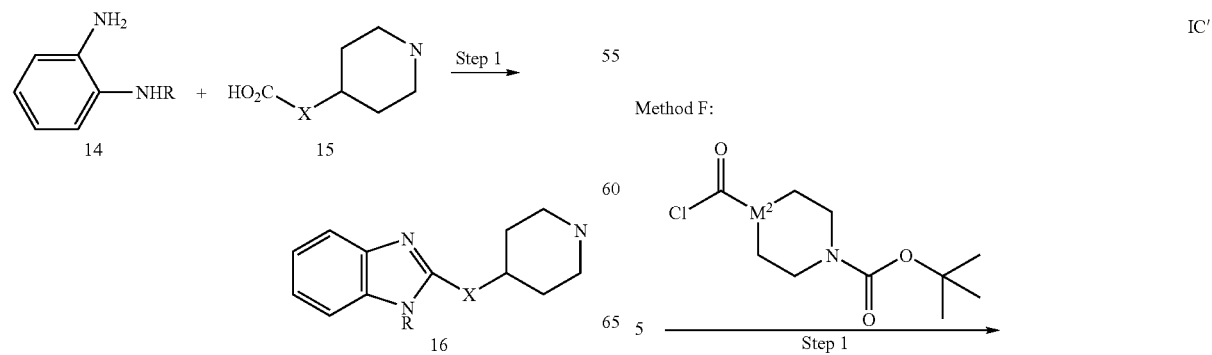
Method E:
Method F:

-continued

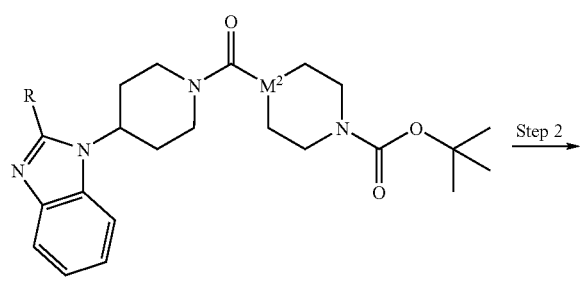

23

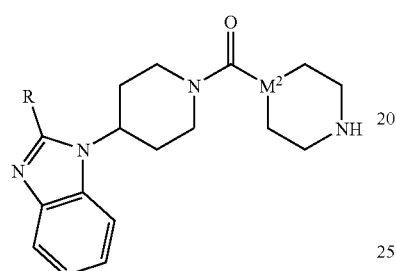

24

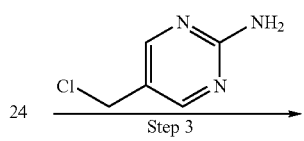

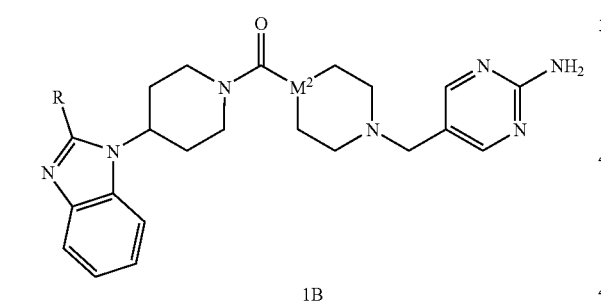

1B

Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

Unless otherwise stated, the following abbreviations have the stated meanings in the Examples below:

Me=methyl; Et=ethyl; Bu=butyl; Pr=propyl; Ph=phenyl; t-BOC=tert-butyloxycarbonyl;
CBZ=carbobenzyloxy; and Ac=acetyl
DCC=dicyclohexylcarbodiimide
DMAP=4-dimethylaminopyridine
DMF=dimethylformamide
EDCI=1-(3-dimethylaminopropyl)-3-ethylcarbodiimide
ESMS=Electron spray mass spectroscopy
FAB=Fast atom bombardment mass spectroscopy
HATU=O-(7-Azabenzotriazol-1-yl)-N,N,N',N'-tetramethyl uronium hexafluorophosphate
HOBT=1-hydroxybenzotriazole
LAH=lithium aluminum hydride
LDA=lithium diisopropylamide
NaBH(OAc)$_3$=sodium triacetoxyborohydride
NBS=N-bromosuccinimide
PPA=polyphosphoric acid
RT=room temperature
TBAF=tetrabutylammonium fluoride
TBDMS=t-butyldimethylsilyl
TMEDA=N,N,N',N'-tetramethylethylenediamine
TEMPO=2,2,6,6-tetramethyl-1-piperidinyloxy, free radical
TLC=thin layer chromatography
HRMS=High Resolution Mass Spectrometry
LRMS=Low Resolution Mass Spectrometry
nM=nanomolar
Ki=Dissociation Constant for substrate/receptor complex
pA2=-log EC$_{50}$, as defined by J. Hey, *Eur. J. Pharmacol.*, (1995), Vol. 294, 329–335.
Ci/mmol=Curie/mmol (a measure of specific activity)

Preparation 1

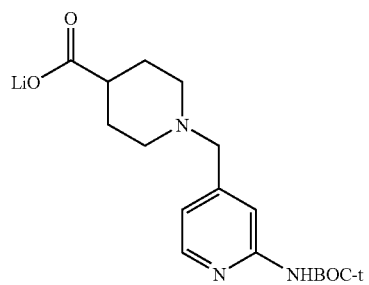

Step 1:

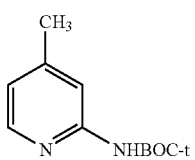

To a solution of 2-amino-4-methylpyridine (10.81 g, 100 mmol) in tert-butanol (250 ml) was added t-BOC anhydride (26.19 g, 120 mmol). The reaction mixture was stirred at 23° C. overnight, and then concentrated to an oil. The crude product was dry loaded onto a silica gel column and flash chromatographed (eluant: 30% hexanes-CH$_2$Cl$_2$ to 0–2% acetone-CH$_2$Cl$_2$) to produce 15.25 g (73.32 mmol; 73%) of the desired product as a white solid.

Step 2:

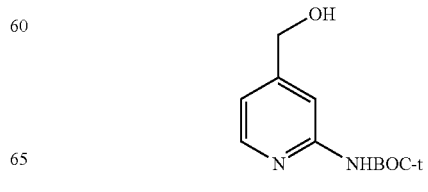

To a solution of the product of Step 1 (35.96 g, 173 mmol) in THF (1.4 l) at −78° C. was added a n-BuLi solution (1.4 M, 272 ml, 381 mmol) in hexanes portionwise over 30 min. The reaction mixture was then allowed to warm slowly and was stirred for 2 h at 23° C., which resulted in the formation of an orange precipitate. The mixture was then cooled back to −78° C., and pre-dried oxygen (passed through a Drierite column) was bubbled through the suspension for 6 h while the temperature was maintained at −78° C. The color of the reaction mixture changed from orange to yellow during this time. The reaction was quenched at −78° C. with $(CH_3)_2S$ (51.4 ml, 700 mmol) followed by AcOH (22 ml, 384 mmol) and allowed to warm with stirring to 23° C. After 48 h, water was added and the product extracted into EtOAc. Purification by silica gel flash chromatography (eluant: 0–15% acetone/$CH_2Cl_2$) provided 20.15 g (90 mmol; 52%) of the alcohol as a pale yellow solid.

Step 3:

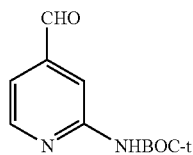

To a solution of the product of Step 2 (19.15 g, 85.5 mmol) in $CH_2Cl_2$ (640 ml) was added a saturated aqueous solution of $NaHCO_3$ (8.62 g, 103 mmol) and NaBr (444 mg, 4.3 mmol). The reaction mixture was cooled to 0° C., and TEMPO (140 mg, 0.90 mmol) was introduced. Upon vigorous stirring, commercial bleach solution (122 ml, 0.7 M, 85.4 mmol) (5.25% in NaOCl) was added portionwise over 40 min. After an additional 20 min at 0° C., the reaction mixture was quenched with saturated aqueous $Na_2S_2O_3$ and allowed to warm to 23° C. Dilution with water and extraction with $CH_2Cl_2$, followed by concentration and flash chromatography (eluant: 30% hexanes-$CH_2Cl_2$ to 0–2% acetone-$CH_2Cl_2$) afforded 15.97 g (71.9 mmol; 84% yield) of the aldehyde as an off-white solid.

Step 4:

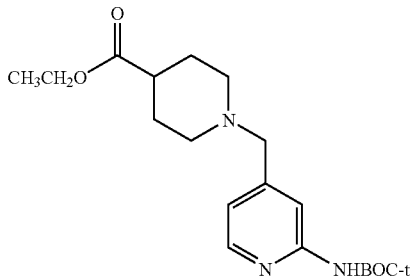

To a solution of the product of Step 3 (11.87 g, 53.5 mmol) in $CH_2Cl_2$ (370 ml) was added ethyl isonipecotate (9.07 ml, 58.8 mmol) followed by four drops of AcOH. The reaction mixture was then stirred for 40 min at 23° C., after which $NaB(OAc)_3H$ (22.68 g, 107 mmol) was added. The reaction mixture was stirred overnight at 23° C., neutralized with saturated aqueous $NaHCO_3$, diluted with water and extracted with $CH_2Cl_2$. Concentration of the organic extracts, followed by silica gel flash chromatography (eluant: 0–4% sat. $NH_3$ in $CH_3OH$—$CH_2Cl_2$) provided 19.09 g (52.6 mmol; 98%) of the ester as an off-white solid.

Step 5:

To a solution of the product of Step 4 (1.57 g, 4.33 mmol) in THF-water-$CH_3OH$ (10 ml of a 3:1:1 mixture) was added LiOH monohydrate (0.125 g, 5.21 mmol). The reaction mixture was stirred overnight at 23° C., concentrated and exposed to high vacuum to obtain 1.59 g of crude title compound as a yellowish solid which was used without purification.

Preparation 2

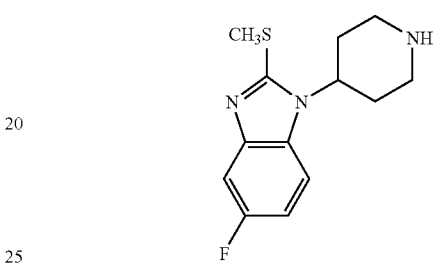

Step 1:

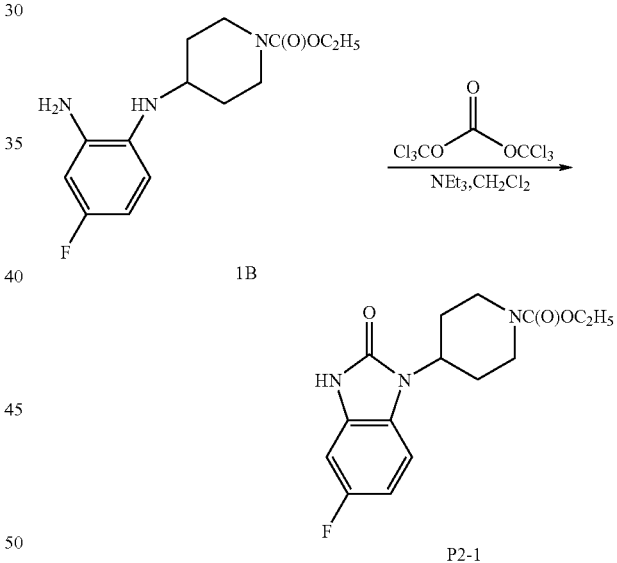

A solution of diamine 1B (see Method A, Step 1) (20 g, 71.1 mmol) and $Et_3N$ (30 ml, 213 mmol) in $CH_2Cl_2$ (400 ml) was cooled to 0° C. in an ice-water bath. To the well-stirred solution was added triphosgene (14.2 g, 47.3 mmol) cautiously (exotherm!) and portionwise over a period of 30 min. When addition was complete, stirring was continued at 0° C. for 1 h, then at RT for 16 h. The mixture was washed with 0.5N NaOH (200 ml), the organic layer was dried over anhydrous $MgSO_4$ and concentrated under vacuum. Hot EtOAc (200 ml) was added to the semi-solid residue, and the resultant mixture was cooled to RT. Filtration yielded compound P2-1 as a white solid (16.5 g); and silica gel flash chromatography [$CH_2Cl_2$/$CH_3OH$ (2N $NH_3$)=40:1] of the filtrate provided additional product as a white solid (2.7 g) [combined yield: 88%]. FABMS: 308 ($MH^+$; 100%).

Step 2:

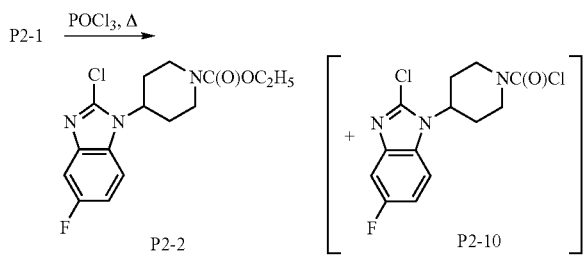

POCl₃ (100 ml) was added to P2-1 (17.2 g; 56 mmol) in a round-bottomed flask flushed with dry N₂. The mixture was placed in an oil bath heated to 108° C. and was maintained at reflux for 6 h. POCl₃ was then removed in vacuo. The residue was adjusted to pH~9–10 with 7N methanolic ammonia and was concentrated to dryness under vacuum. CH₂Cl₂ was added to the residue, insoluble material was filtered off, and the filtrate was again concentrated in vacuo. The residue was crystallized from EtOH to obtain compound P2-2 as a white solid (12.6 g; 67%). ES-MS: 326.1 (MH⁺; 100%).

Varying amounts of compound P2-10 may be formed in this process and can be converted to desired product P2-2 by careful in situ treatment in CH₂Cl₂ solution at 0° C. with one equivalent each of EtOH and NaH, followed by workup with ice-water and CH₂Cl₂. Low temperature is maintained in order to minimize reaction at the 2-position of the benzimidazole nucleus.

Step 3:

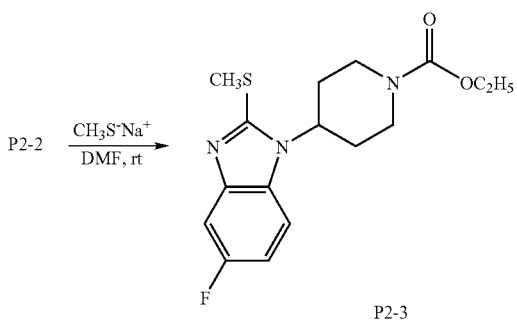

Sodium thiomethoxide (1.05 g; 15.0 mmol) was added to DMF (15 ml) in a round-bottomed flask flushed with N₂. After stirring at RT for 30 min, solid chloride P2-2 (3.25 g, 10 mmol) was added, and the resultant mixture was kept stirring at RT for 16 h. EtOAc (100 ml) and water (50 ml) were added to the reaction mixture. The aqueous layer was separated and further extracted with EtOAc (50 ml). The combined extracts were dried over anhydrous MgSO₄ and concentrated under vacuum. The residue was purified via flash chromatography on silica gel, eluting with EtOAc-hexanes (3:4), to obtain compound P2-3 as a white solid (2.12 g; 63%). FABMS: 338.3 (MH⁺; 100%).

Step 4:
To a stirred solution of P2-3 (300 mg, 12.5 mmol) in EtOH (40 ml)-isopropyl alcohol (40 ml) was added 25% (w/w) aqueous NaOH solution (20 ml). The resultant mixture was stirred at 85° C. for 24 h, then at 100° C. for an additional 4 h. Alcohols were removed under vacuum, and the aqueous residue was extracted sequentially with CH₂Cl₂ (2×40 ml), then EtOAc (30 ml). Combined extracts were dried over anhydrous MgSO₄. Drying agent was removed by filtration, and the filtrate was concentrated under vacuum. The residue was purified by silica gel flash chromatography (CH₂Cl₂/2N methanolic ammonia=12:1) to obtain Preparation 2 as an off-white solid (2.85 g, 70%). ES-MS: 266 (MH⁺; 100%).

Preparation 3

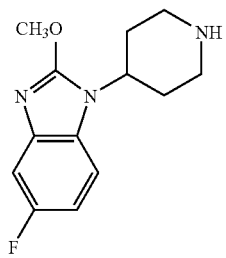

Step 1:

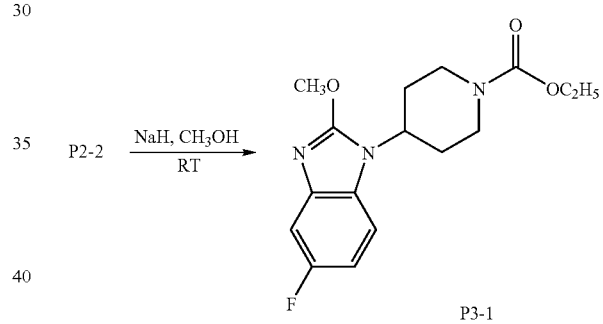

NaH (60 mg of a 60% dispersion; 1.48 mmol) was added to CH₃OH (4 ml) in a flask charged with N₂. After stirring at RT for 30 min, chloride P2-2 (400 mg, 1.23 mmol) was added, and the resultant mixture was stirred at RT for 16 h. CH₃OH was removed in vacuo, and to the residue were added CH₂Cl₂ (30 ml) and water (10 ml). The organic layer was dried over anhydrous MgSO₄, filtered, and the filtrate concentrated under vacuum. The residue was purified via flash chromatography on silica gel, eluting with EtOAc-hexanes (3:2) to obtain P3-1 as a white foam (0.232 g; 59%). ES-MS: 322.1 (MH⁺; 100%).

Step 2:
1N aqueous KOH (4.82 mL; 4.82 mmol) was added to a solution of P3-1 in EtOH (15 ml), and the resultant mixture was stirred at 80° C. for 48 h. The mixture was concentrated under vacuum. Water (3 ml) and CH₂Cl₂ (15 ml) were added to the residue, and the organic layer was separated and dried over anhydrous MgSO₄. Drying agent was filtered, and the filtrate was concentrated in vacuo to obtain Preparation 3 as a colorless glass (160 mg; 95%). FABMS: 250.2 (MH⁺; 100%).

Preparation 4

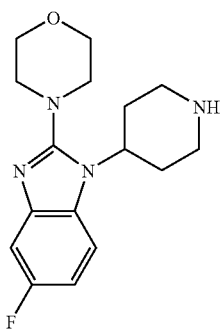

Step 1:

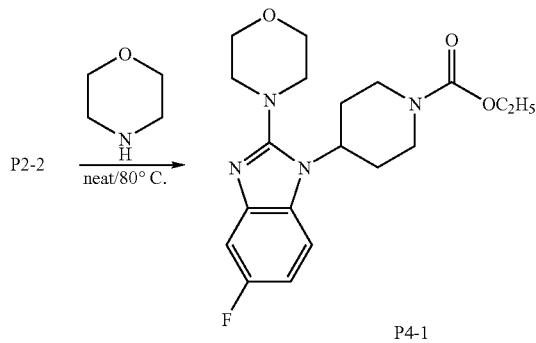

P2-2 (300 mg; 0.923 mmol) and morpholine (3 ml) were mixed in a round-bottomed flask under $N_2$, and the resultant mixture was heated to 80° C. for 16 h. Morpholine was removed under vacuum, and the residue was dissolved in $CH_2Cl_2$ (20 ml). An insoluble white precipitate was filtered off, and the filtrate was concentrated and purified by means of flash chromatography on silica gel, eluting with $CH_2Cl_2$/ 2N methanolic ammonia (45:1), to obtain P4-1 as a colorless glass (0.325 g; 94%). ES-MS: 377.1 (MH+; 100%).

Step 2:

Trimethylsilyl iodide (240 microliters; 1.64 mmol) was added to a solution of P4-1 (316 mg; 0.843 mmol) in $CHCl_3$ (2 ml) under $N_2$, and the resultant solution was stirred at 55° C. for 7 h. The reaction was quenched with EtOH (2 ml), and the mixture was concentrated to dryness under vacuum. The residue was basified with a 1:1 (v/v) mixture of concentrated $NH_4OH$ and water to pH ~10 and extracted with $CH_2Cl_2$ (2×5 ml). The combined extracts were dried over anhydrous $MgSO_4$. Drying agent was filtered, and the filtrate was concentrated under vacuum. The residue was purified via flash chromatography on silica gel, eluting with $CH_2Cl_2$-2N methanolic ammonia (13:1), to obtain compound Preparation 4 as a colorless glass. (181 mg; 70%). ES-MS: 305.1 (MH+; 100%).

Preparation 5

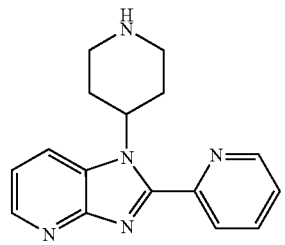

Step 1:

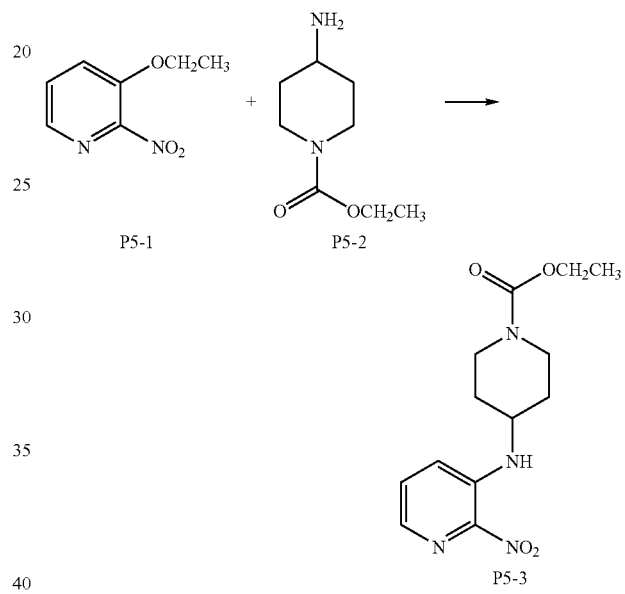

A solution of P5-1 (3.5 g, 21 mmol) and P5-2 (6.5 g, 38 mmol) in $CH_2Cl_2$ (3 ml) was heated to 110° C. for 24 h and RT for 24 h. The reaction was diluted with $CH_2Cl_2$, washed with water and brine, and dried ($Na_2SO_4$). Purification on a flash column ($SiO_2$, 40% to 60% EtOAc in hexanes) gave P5-3 (1.3 g, 21%; M+H=295).

Step 2:

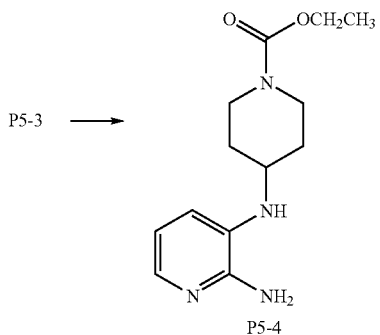

To a solution of P5-3 (1.3 g, 4.4 mmol) in $CH_3OH$ (30 ml) was added Ra—Ni (0.5 g) and the mixture was hydrogenated under a $H_2$ atmosphere (50 psi) for 18 h. Filtration through a pad of celite gave P5-4 as a grey solid that was used without further purification (1.05 g, 90%; M+H=265).

Step 3:

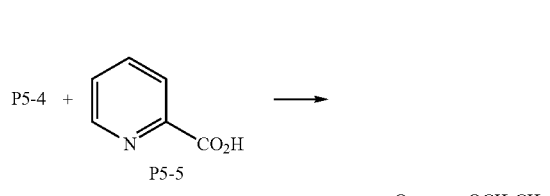

P5-5

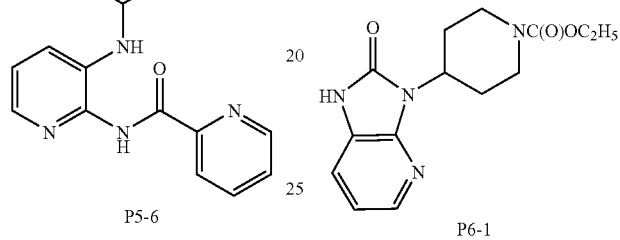

P5-6

A solution of P5-4 (1.05 g, 3.97 mmol), P5-5 (0.49 g, 3.97 mmol), DEC (1.14 g, 5.96 mmol) and HOBT (0.8 g, 5.96 mmol) in $CH_2Cl_2$ (10 ml) were stirred for 18 h at RT. The crude reaction mixture was diluted with additional $CH_2Cl_2$ and washed with 5% aqueous NaOH and brine and dried ($Na_2SO_4$). Purification using flash chromatography (SiO, 8% EtOAc in hexane to 10% $CH_3OH$ in EtOAc) gave P5-6 (0.35 g, 24%; M+H=370).

Step 4:

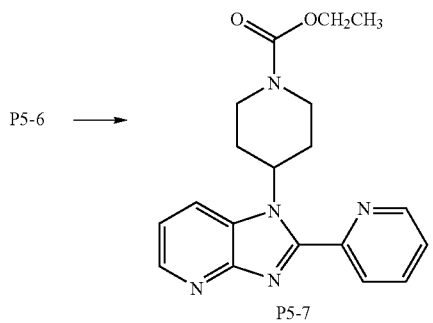

P5-7

Compound P5-6 (0.7 g, 1.89 mmol) was dissolved in HOAc (10 ml) and heated to 120° C. for 3.5 h. The reaction was cooled to RT, concentrated in vacuo, neutralized by the addition of 10% aqueous NaOH and extracted with $CH_2Cl_2$. The combined organic layers were dried ($Na_2SO_4$) and concentrated to give P5-7 (0.58 g, 87%; M+H=352) which was used in the next step without further purification.

Step 5:

A solution of P5-7 (0.58 g, 1.65 mmol) and NaOH (0.43 g, 13.2 mmol) in $EtOH/H_2O$ (9/1, 10 ml) was heated to 100° C. for 18 h. The reaction was cooled and concentrated and the residue purified on a flash column ($SiO_2$, 10% $CH_3OH$ saturated with ammonia in $CH_2Cl_2$) to give Preparation 5 (0.42 g, 91%; M+H=280).

Preparation 6

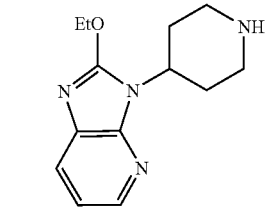

Step 1:

P6-1

P6-2

A solution of compound P6-1 (prepared by procedures analogous to P2-1) (10.5 g, 36.2 mmol) and 2,6-di-tert-butylpyridine (12.2 ml, 54.4 mmol) in $CH_2Cl_2$ (400 ml) was treated with 1M sol. of $Et_3O^+BF_4^{-31}$ (in $CH_2Cl_2$, 55 ml, 55 mmol). The reaction mixture was stirred at RT for 2 h, quenched with 1N NaOH (100 ml), extracted with $CH_2Cl_2$ (3×), dried with $Na_2SO_4$ and concentrated. Purification by silica gel chromatography (eluant: 5–10% acetone/$CH_2Cl_2$) to give 6.37 g of P6-2 (20.0 mmol, 55%).

Step 2:

In a manner similar to that described in Preparation 3, Step 2, P6-2 was converted to Preparation 6.

Preparation 7

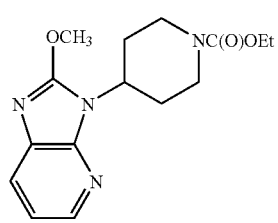

Step 1:

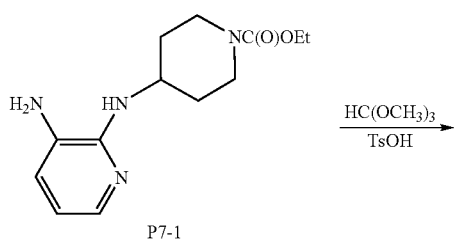

P7-1

A mixture of P7-1 (40 g, 150 mmol), trimethyl orthoformate (66 ml, 64.0 g, 600 mmol) and a catalytic amount of p-toluenesulfonic acid monohydrate (300 mg, 1.58 mmol) was stirred under $N_2$ at 120° C. for 3 h. Excess orthoformate was removed under vacuum. The residue was partitioned between EtOAc (200 ml) and 1N NaOH (100 ml). The organic layer was washed with brine (100 ml) and dried over anhydrous $MgSO_4$. Drying agent was removed by filtration, and the filtrate was concentrated under vacuum. The residue was purified by silica gel flash chromatography ($CH_2Cl_2$/$CH_3OH$ (2N $NH_3$)=45:1) to obtain P7-2 as a dark purple syrup (27.2 g, 66%), which solidified upon standing. ES-MS: 275 ($MH^+$; 100%).

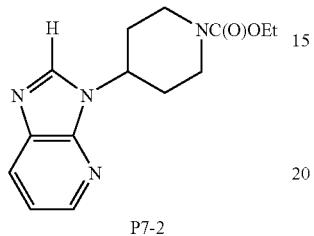

P7-2

Step 2:

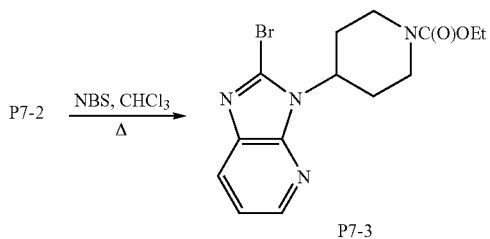

NBS was added portionwise (exotherm) to a solution of P7-2 (27 g, 100 mmol) in $CHCl_3$ (300 ml), and the resultant solution was stirred at 60° C. for 16 h. Solvent was then removed under vacuum, and the residue was partitioned between EtOAc (200 ml) and 0.7N $Na_2S_2O_4$ (250 ml). The organic layer was washed with brine (150 ml) and dried over anhydrous $MgSO_4$. Drying agent was removed by filtration, and the filtrate was concentrated under vacuum. The residue was purified by silica gel flash chromatography [$CH_2Cl_2$/acetone=45:1] to obtain P7-3 as a yellow solid (24.2 g, 69%). ES-MS: 353 ($MH^+$; 100%).

Step 3:
NaH (544 mg of a 60% dispersion, 13.6 mmol) was added to a solution of $CH_3OH$ (0.551 ml, 436 mg, 13.6 mmol) in DMF (5 ml). The resultant mixture was stirred at RT for 30 min before adding solid bromide P7-3 (3.99 g, 11.3 mmol). The reaction suspension was stirred at RT for 16 h. The mixture was then partitioned between EtOAc (800 ml) and water (40 ml). The aqueous layer was extracted with EtOAc (40 ml). Combined extracts were washed with brine (30 ml) and dried over anhydrous $MgSO_4$. Drying agent was removed by filtration, and the filtrate was concentrated under vacuum to obtain Preparation 7 as a white syrup (2.81 g, 81%), which was used without further purification. ES-MS: 305 ($MH^+$; 100%).

Preparation 8

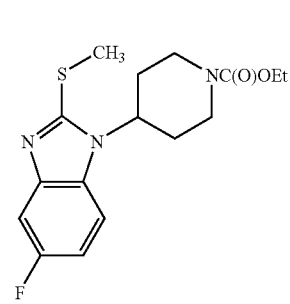

Step 1:

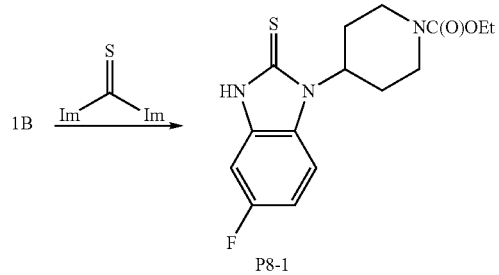

A solution of 1B (15 g, 52.8 mmol) and 1,1'-thiocarbonyldiimidazole (25 g, 140 mmol) in THF (300 ml) was stirred at 72° C. under $N_2$ for 16 h, during which time a precipitate formed. THF was removed under vacuum, and the residue was purified by silica gel flash chromatography ($CH_2Cl_2$/acetone=20:1) to obtain P8-1 as a light yellow solid (16.7 g, >95%). ES-MS: 324 ($MH^+$; 100%).

Step 2:
To a stirred mixture of P8-1 (4.00 g, 12.5 mmol) and $K_2CO_3$ (2.05 g, 13.6 mmol) in DMF (40 ml) under a $N_2$ atmosphere was added $CH_3I$ (0.85 ml, 1.94 g, 13.6 mmol). The resultant mixture was stirred at RT for 16 h before partitioning between EtOAc (100 ml) and water (40 ml). The aqueous layer was extracted with EtOAc (40 ml). Combined extracts were washed with brine (30 ml) and dried over anhydrous $MgSO_4$. Drying agent was removed by filtration, and the filtrate was concentrated under vacuum to obtain Preparation 8 as a foamy white solid (4.20 g, >95%; contained a small amount of DMF), which was used without further purification. ES-MS: 338 ($MH^+$; 100%).

Preparation 9

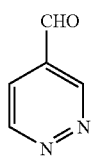

Step 1:

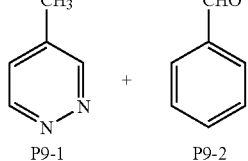

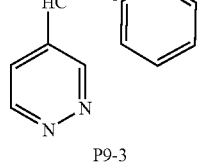

(Modified published procedure: G. Heinisch, E. Luszczak, and M. Pailer: *Monatshefte für Chemie,* 1973 (104), 1372.

P9-1 (4.5 g, 47.8 mmoles), P9-2 (8.12 g, 76.5 mmoles), and anhydrous $ZnCl_2$ were heated, under $N_2$, in a dry apparatus, at a bath temperature of 160° C. for 5 h. The resulting oil was purified by flash chromatography on silica gel using 30% Hexanes/EtOAc, yielding 5.92 grams (67%) of the product.

Step 2:

$OsO_4$ (5.0 ml in t-butanol, 2.5% w/w) was added to P9-3 (5.9 g, 32.38 mmoles) dissolved in p-dioxane (87 ml) and water (29 ml). $NaIO_4$ (14.1 g, 65.92 mmoles) was added, with good stirring, in small portions, over a period of 6 h. The mixture was then diluted with p-dioxane and filtered. After removing most of the solvent under reduced pressure, the residue was taken in $CH_2Cl_2$ (600 ml) and dried over anhydrous $Na_2SO_4$. After removal of the solvent, the mixture was purified by flash chromatography on silica gel using 5% $CH_3OH/CH_2Cl_2$ as eluent to obtain Preparation 9. Yield: 2.89 g (82%).

Preparation 10

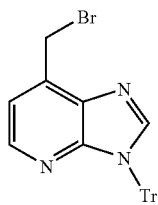

Step 1:

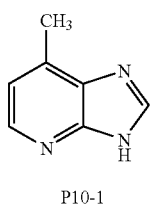
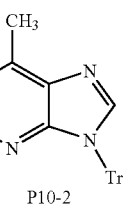

A solution of P10-1 (2 g, 15 mmol) in $CH_2Cl_2$ (50 ml) was treated with $Et_3N$ (3 g, 30 mmol) and triphenylmethyl chloride (TrCl, 4.25 g, 15.3 mmol) and stirred at RT overnight. The solvent was removed in vacuo and the residue purified via flash column chromatography ($SiO_2$, 20% EtOAc in hexane) to give P10-2 (5.2 g, 46%).

Step 2:

A solution of P10-2 (5.2 g, 14.6 mmol) in $CCl_4$ (80 ml) was treated with NBS (7.8 g, 43 mmol) and the reaction heated to 80° C. overnight. The reaction was cooled, filtered and concentrated, and the residue was purified via flash column chromatography ($SiO_2$, 20% to 30% EtOAc in hexane) to give Preparation 10 (2.8 g, 42%, M+H=453, 455)

Preparation 11

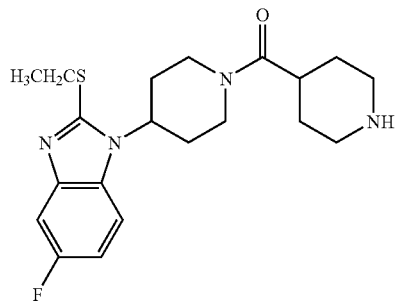

Step 1:

To a stirred solution of P8-1 (6.5 g, 20.1 mmol) in EtOH (80 ml) was added 25% (w/w) aqueous NaOH solution (20 ml). The resultant mixture was stirred at 90° C. for 16 h. EtOH was removed under vacuum, and the residue was adsorbed directly onto silica gel and subjected to flash chromatography ($CH_2Cl_2$/2N methanolic ammonia=9:1) to obtain P11-1 as a white solid (4.46 g, 70%). ES-MS: 252 ($MH^+$; 100%).

Step 2:

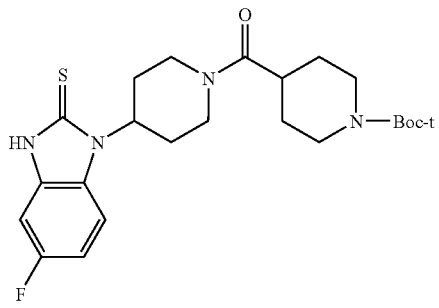

P11-2

A mixture of P11-1 (3.95 g; 15.7 mmol), BOC-isonipecotic acid (3.60 g; 15.7 mmol), HOBT (3.19 g; 23.6 mmol), DIPEA (3 ml; 2.23 g; 17.2 mmol) and EDCI (4.50 g; 23.6 mmol) in DMF (30 ml) was stirred under $N_2$ at RT for 16 h. The reaction mixture was partitioned between EtOAc (60 ml) and water (40 ml). The aqueous phase was extracted with EtOAc (40 ml), and the combined extracts were washed with brine (40 ml) and dried over anhydrous $MgSO_4$. Drying agent was removed by filtration, and the filtrate was concentrated under vacuum. The residue was purified by silica gel flash chromatography ($CH_2Cl_2/CH_3OH$ (2N $NH_3$)=40:1) to obtain P11-2 as a white solid (~7.3 g, ~100%), containing a small amount of DMF, used without further purification in Step 3 below. ES-MS: 463 (MH$^+$; 70%); 407 (100%).

Step 3.

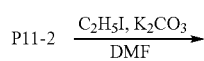

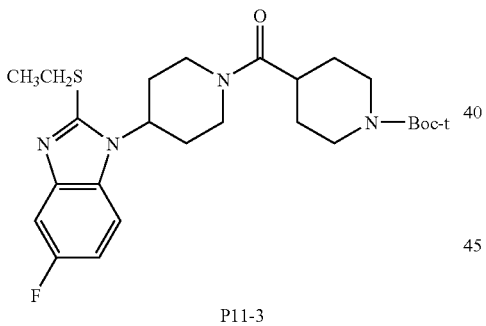

P11-3

To a stirred mixture of P11-2 (460 mg; 1 mmol) and $K_2CO_3$ (165 mg; 1.20 mmol) in DMF (4 ml) under a $N_2$ atmosphere was added EtI (92 microliters; 179 mg; 1.15 mmol). The resultant mixture was stirred at RT for 16 h and was then partitioned between EtOAc (20 ml) and water (10 ml). The aqueous phase was extracted with EtOAc (10 ml), and the combined extracts were washed with brine (20 ml) and dried over anhydrous $MgSO_4$. Drying agent was removed by filtration, and the filtrate was concentrated under vacuum to obtain P11-3 as a pale yellow foam (471 mg, 96%), containing a small amount of DMF, used without further purification in Step 4 below. ES-MS: 463 (MH$^+$; 85%); 435 (100%).

Step 4:

To a solution of P11-3 (465 mg; 0.949 mmol) in $CH_2Cl_2$ (4 ml) was added TFA (1 ml; 1.54 g; 13.5 mmol). The resultant solution was stirred for 2 h at RT and was then partitioned between $CH_2Cl_2$ (20 ml) and 1:1 (v/v) concentrated $NH_4OH$:water (5 ml). The aqueous phase was extracted successively with 95:5 $CH_2CL_2$:EtOH (5 ml) and EtOAc (5 ml). The combined extracts were dried over anhydrous $MgSO_4$. Drying agent was removed by filtration, and the filtrate was concentrated under vacuum to obtain Preparation 11 as a pale white foam (353 mg, 95%), used without further purification. ES-MS: 391 (MH$^+$; 100%).

EXAMPLE 1

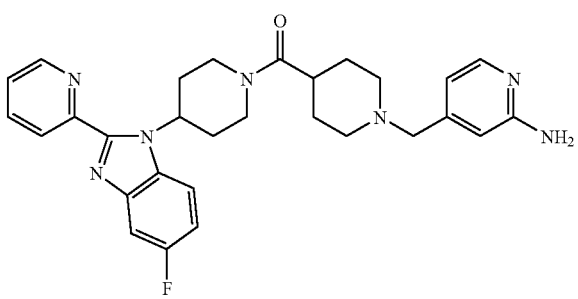

Method A

Step 1:

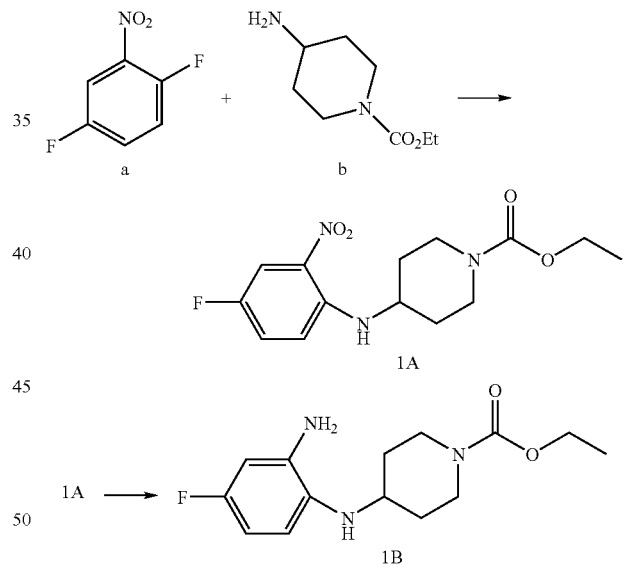

A mixture of a (25 g, 0.16 mol), b (27 g, 0.16 mol), $K_2CO_3$ (26 g, 0.19 mol), and NaI (2.4 g, 0.016 mol) in dimethylacetamide (50 ml) was heated at 140° C. for 3.5 h. The reaction mixture was concentrated to one-third volume, poured onto saturated aqueous $NaHCO_3$, and extracted with EtOAc (4×). The combined organic layers were washed with water (2×) and brine, dried over $Na_2SO_4$, and concentrated. Recrystallization with EtOH provided 1A (48 g, 98%).

A suspension of 1A (20.00 g, 64.2 mmol,) and Raney® 2800 Nickel (5.0 g) in ethanol (70 ml) and THF (140 ml) was shaken under $H_2$ (40 psi) for 2 h. The mixture was filtered through a short pad of celite. The filtrate was concentrated and dried on vacuum to deliver a tan solid (18.20 g, ~100%).

Step 2:

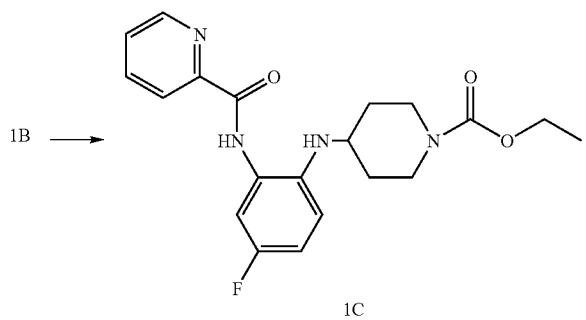

1B →  1C

A solution of 1B (5.00 g, 17.77 mmol) and picolinoyl chloride hydrochloride (3.16 g, 17.75 mmol) in $CH_2Cl_2$ (400 ml) and $Et_3N$ (15 ml) was stirred at RT. After 15 h, the reaction was diluted with $CH_2Cl_2$, washed with water, dried over $Na_2SO_4$, concentrated, and dried on vacuum to provide a brown foam (6.47 g, 94%).

Step 3:

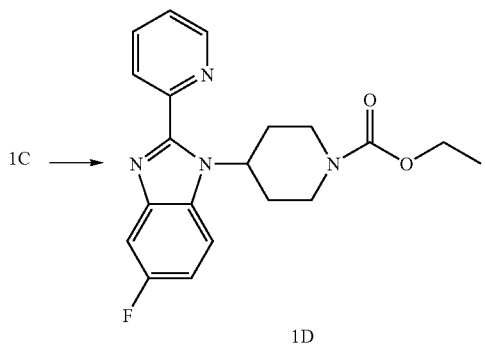

1C →  1D

A solution of 1C (1.77 g, 4.58 mmol) in ethanol (50 ml) and concentrated $H_2SO_4$ (5.0 ml) was refluxed for 3 h, cooled to RT, and neutralized with 1.0 M NaOH until pH=10. The resulting mixture was extracted with $CH_2Cl_2$. The combined organic solutions were dried over $Na_2SO_4$ and concentrated on reduced pressure. The residue was purified by flash chromatography (silica gel, 5% $CH_3OH$ in $CH_2Cl_2$ as eluent) to provide a tan foam (1.58 g, 94%).

Step 4:

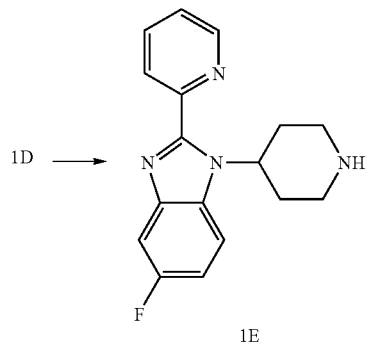

1D →  1E

Iodotrimethylsilane (6.30 g, 31.48 mmol) was added to a solution of 1D (3.88 g, 10.53 mmol) in anhydrous 1,2-dichloroethane (40 ml). The resulting solution was stirred at 75° C. for 4 hours, cooled to RT, and treated with 1.0 M NaOH solution. The mixture was then extracted with $CH_2Cl_2$. The combined extracts were washed with water, dried over $Na_2SO_4$, and the solvent evaporated. Purification of the residue by flash chromatography (silica gel, 10% $CH_3OH$ in $CH_2Cl_2$ as eluent) delivered an off-white foam (2.10 g, 67%).

Step 5:

1E + Prep. 1 →

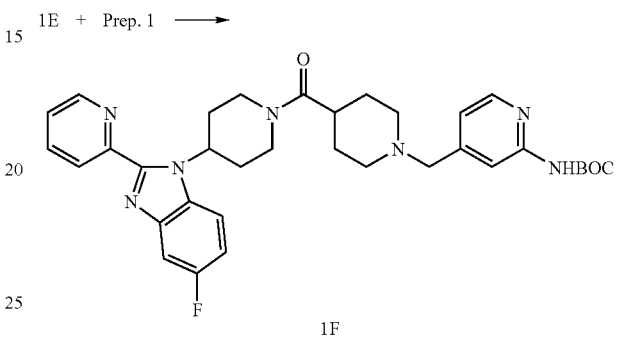

1F

Amine 1E (5.80 g, 19.6 mmol) and Preparation 1 (5.32 g, 23.4 mmol) were dissolved in DMF (60 ml) and $CH_2Cl_2$ (60 ml). To the resulting solution, EDCI hydrochloride (5.70 g, 24.50 mmol), HOBT (1.30 g, 24.50 mmol), and diisopropylethylamine (5.08 g, 39.6 mmol) were added successively. The resulting reaction mixture was stirred at 70° C. for 4 hours, cooled to RT, diluted with $CH_2Cl_2$, washed with water, dried over $Na_2SO_4$, and concentrated. Flash chromatography ($SiO_2$, 5% $CH_3OH$ in $CH_2Cl_2$→90:10:0.5 $CH_2Cl_2$:$CH_3OH$:$NH_4OH$) of the residue provided a tan foam (7.89 g, 65%).

Step 6:

A solution of 1F (7.89 g, 12.88 mmol) and TFA (29 g, 257 mmol) in $CH_2Cl_2$ (65 ml) was stirred at RT for 12 h, neutralized with 1.0 M NaOH, and extracted with $CH_2Cl_2$. The combined organic layers were washed with water, dried over $Na_2SO_4$ and concentrated. Purification of the crude product by flash chromatography ($SiO_2$, 5% $CH_3OH$ in $CH_2Cl_2$ to 90:10:0.5 $CH_2Cl_2$:$CH_3OH$:$NH_4OH$) provided the title compound as a white solid (5.80 g, 88%). MS: 514 ($MH^+$).

EXAMPLE 2

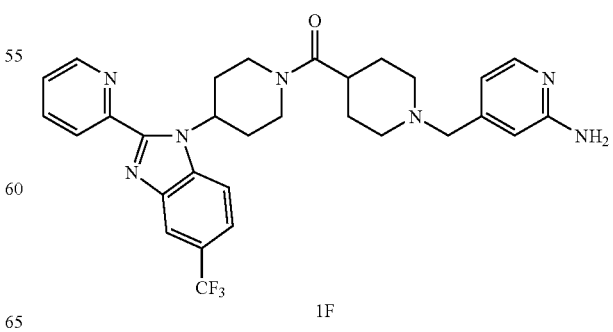

1F

Method B

Step 1:

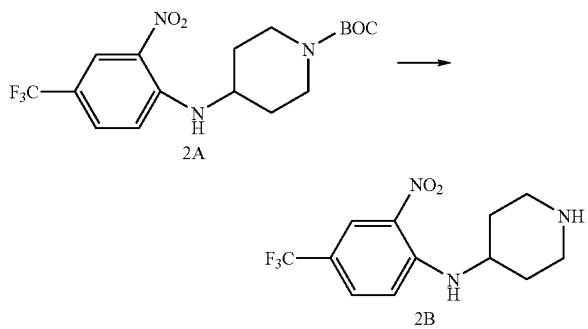

TFA (200 ml, 2.596 mol) was added to a solution of 2A (20 g, 51.36 mmol) in CH$_2$Cl$_2$ (100 ml). The resulting reaction mixture was stirred at RT for 6 h, neutralized with 1.0 M NaOH, and extracted. The combined extracts were washed with water, dried over Na$_2$SO$_4$, and concentrated. Flash chromatography gave an orange solid (13.50 g, 91%).

Step 2:

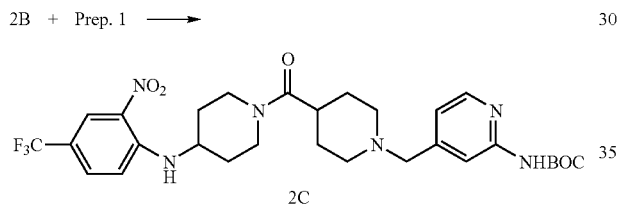

Amine 2B (1.50 g, 5.19 mmol) and Preparation 1 (1.75 g, 5.13 mmol) were dissolved in DMF (10 ml) and CH$_2$Cl$_2$ (10 ml). To the resulting solution, EDCI hydrochloride (1.50 g, 7.83 mmol), HOBT (1.05 g, 7.82 mmol), and diisopropylethylamine (3.71 g, 28.70 mmol) were added successively. The resulting reaction mixture was stirred at 70° C. for 18 h, cooled to RT, diluted with CH$_2$Cl$_2$, washed with water, dried over Na$_2$SO$_4$, and concentrated. Flash chromatography of the residue provided an orange gel (2.31 g, 74%).

Step 3:

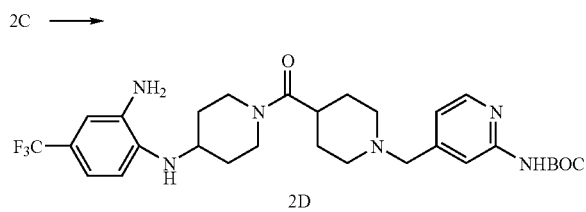

A suspension of 2C (2.10 g, 3.46 mmol,) and Raney® 2800 Nickel (1.0 g) in CH$_3$OH (100 ml) was shaken under H$_2$ (30 psi) for 6 h. The mixture was filtered through a short pad packed with celite. The filtrate was concentrated and dried on vacuum to deliver an orange solid (1.80 g, 90%).

Step 4:

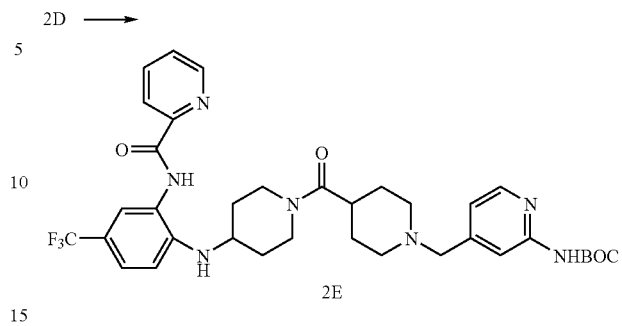

Amine 2D (200 mg, 0.347 mmol) and picolinoyl chloride hydrochloride (62 mg, 0.348 mmol) were dissolved in CH$_2$Cl$_2$. Et$_3$N was then introduced via a syringe. The resulting solution was stirred at RT for 6 h, treated with 1.0 M NaOH solution, and extracted. The extracts were washed with water, dried over Na$_2$SO$_4$, and concentrated. Purification of the residue by flash chromatography gave a white foam (167 mg, 71% yield).

Step 5:

A solution of 2E (160 mg, 0.235 mmol) and H$_2$SO$_4$ (concentrated, 0.50 ml) in ethanol (10 ml) was refluxed for 2.5 h, cooled to RT, and neutralized with 1.0 M NaOH. After extraction of the mixture, the combined organic layers were washed with water, dried over Na$_2$SO$_4$, and concentrated. Purification of the crude product using prep TLC (10% CH$_3$OH in CH$_2$Cl$_2$) provided the title compound as a white solid (88 mg, 66%). MS: 564 (MH$^+$)

EXAMPLE 3

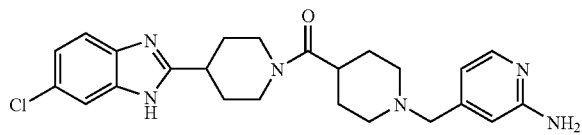

Method D

Step 1:

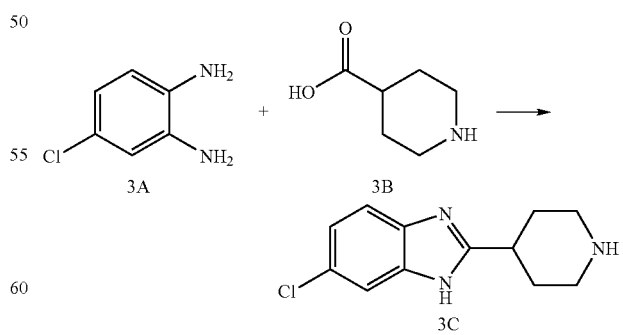

Diamine 3A (1.43 g, 10 mmol) and isonipecotic acid 3B (1.29 g, 10 mmol) were mixed, and PPA (20 g) was added. The resulting mixture was heated at 180° C. for 3.5 h, cooled to RT and diluted with water to 100 ml. The solution was then basified with solid NaOH to pH 14. The resultant copious precipitate was filtered off. The precipitate was washed repeatedly with CH₃OH, and combined CH₃OH extracts were concentrated-dry loaded on silica gel and flash chromatographed (25–40% 5N NH₃ in CH₃OH/CH₂Cl₂) to provide 3C as a dark solid (1.90 g, 81%).

Step 2:

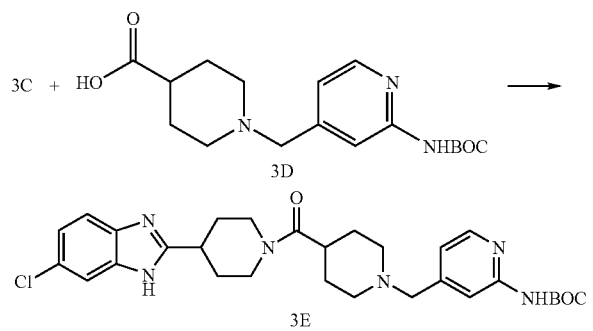

To the mixture of acid 3D (181 mg, 0.54 mmol), HATU (247 mg, 0.65 mmol) and Et₃N (84 µl, 0.6 mmol) in DMF (12 ml) was added amine 3C (126 mg, 0.54 mmol). The resulting mixture was stirred at RT for 24 h, concentrated, redissolved in CH₃OH, concentrated-dry loaded on silica gel and flash chromatographed (5–10% 5N NH₃ in CH₃OH/CH₂Cl₂) to provide 3E as a yellow oil (210 mg, 70%).

Step 3:

A solution of 3E (96 mg, 0.174 mmol) in 15 ml of 1M HCl in 25% CH₃OH/dioxane was stirred at RT for 48 h. The mixture was concentrated, exposed to high vacuum, redissolved in CH₃OH, concentrated-dry loaded on silica gel and flash chromatographed (10–15% 5N NH₃ in CH₃OH/CH₂Cl₂) to provide the title compound as a colorless oil (48 mg, 61%). MS: 453 (MH⁺)

EXAMPLE 4

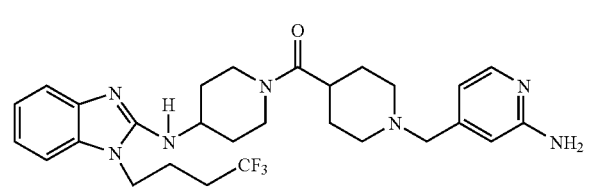

Method E

Step 1:

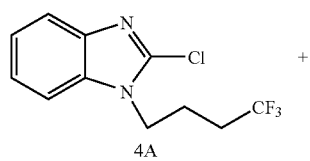

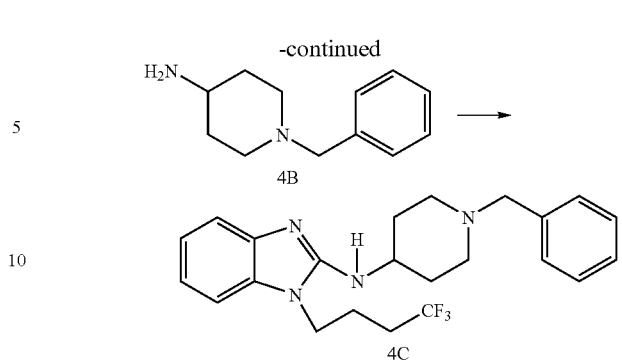

A mixture of neat 4A (1.75 g, 6.66 mmol) and 4B (2.93 g, 15.07 mmol) was stirred at 120° C. for 2 days, cooled to RT, treated with 1.0 M NaOH solution (30 ml), and extracted with EtOAc. The combined organic layers were washed with water and dried over Na₂SO₄. After evaporation to dryness, the crude residue was flash chromatographed (silica gel, 50% EtOAc in hexanes as eluent) to give 510 mg of 4C (18%).

Step 2:

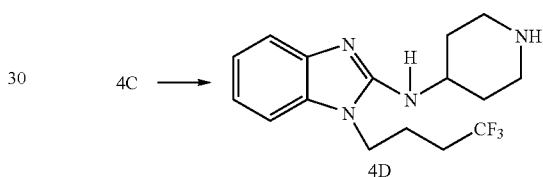

To a 500 ml pressure bottle was added 4C (490 mg, 1.18 mmol) in CH₃OH (20 ml). Under N₂ stream, palladium hydroxide (300 mg, 20 wt. % on carbon) solid was added. The reaction mixture was shaken under 55 psi of hydrogen for 40 h and filtered. The filtrate was concentrated and dried on vacuum to deliver a yellow solid (340 mg, 88%).

Step 3:

4D + Prep. 1 ⟶

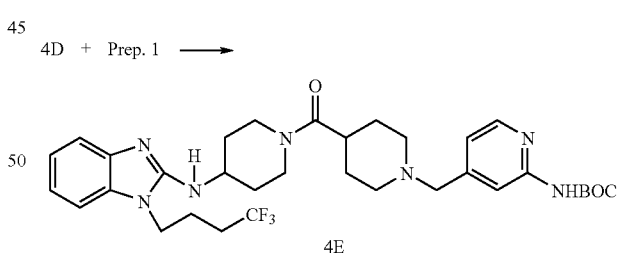

To a 50 ml round-bottomed flask were successively added 4D (287 mg, 0.88 mmol), Preparation 1 (300 mg, 0.88 mmol), EDCI hydrochloride (210 mg, 1.10 mmol), HOBT (149 mg, 1.10 mmol), and diisopropylethylamine (228 mg, 1.76 mmol). DMF (3 ml) and CH₂Cl₂ (3 ml) were introduced via a syringe. The resulting reaction mixture was stirred at 70° C. for 15 h and cooled to RT. After addition of 1 N NaHCO₃ solution, the resulting mixture was extracted with CH₂Cl₂. The combined organic solutions were dried over Na₂SO₄ and concentrated. Purification of the crude product by flash chromatography on silica gel with 10% CH₃OH in CH₂Cl₂ as the eluent provided 4E as a solid (231 mg, 41%).

Step 4:

To a 25 ml round-bottomed flask was added 4E (200 mg, 0.31 mmol) in CH$_2$Cl$_2$ (2.5 ml). TFA was then introduced via a syringe. The resulting solution was stirred at RT for 15 h, diluted with CH$_2$Cl$_2$, neutralized with 1.0 M NaOH solution, and separated. The organic solution was washed with water and dried over Na$_2$SO$_4$. After evaporation of the solvent, the crude product was purified on a preparative TLC plate with 10% CH$_3$OH in CH$_2$Cl$_2$ as the eluent to provide the title compound as a white solid (85 mg, 50%). MS: 544 (MH$^+$).

EXAMPLE 5

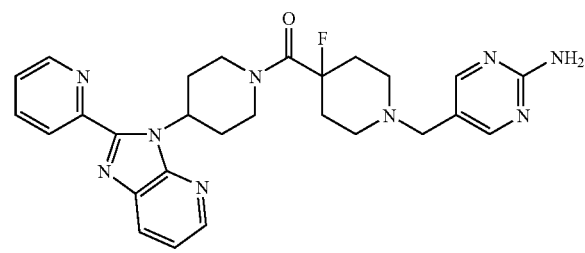

Step 1:

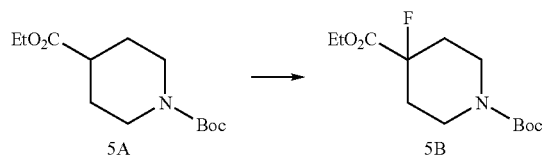

A solution of compound 5A (100 g, 0.389 mol) in THF (400 ml) was added dropwise over 1.0 h to a solution of LDA (233 mL, 2.0 M in THF/heptane/ethyl-benzene, 0.466 mol) in THF (300 ml) at 0° C. The red-orange solution was stirred at 0° C. for 30 min, and then transferred by cannula to a pre-cooled (0° C.) solution of N-fluorobenzenesulfonimide (153 g, 0.485 mol) in dry THF (600 ml). The reaction mixture was stirred at 0° C. for 30 min, and then at 20° C. for 18 h. The total solvent volume was reduced to approximately one third, and EtOAc (1l) was added. The solution was washed successively with water, 0.1 N aq. HCl, saturated aq. NaHCO$_3$, and brine. The organic layer was dried over MgSO$_4$, filtered, and concentrated under reduced pressure to yield a crude liquid. Separation by flash chromatography (6:1 hexanes-EtOAc) gave compound 5B (93.5 g, 87%).

Step 2:

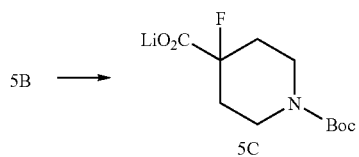

A solution of 5B (50 g, 0.181 mol) in THF (300 ml) and CH$_3$OH (200 ml) was treated with a solution of LiOH—H$_2$O (9.2 g, 0.218 mol) in water (100 ml) and then heated to 45° C. for 6 h. The mixture was then concentrated and dried in vacuo to provide 5C (45 g, 100%).

Step 3:

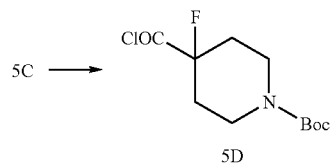

Compound 5C (20.4 g, 0.081 mol) was added slowly to a stirred flask of CH$_2$Cl$_2$ (250 ml) at 20° C. The resulting white slurry was cooled to 0° C. and treated slowly with oxalyl chloride (6.7 ml, 0.075 mol) and a drop of DMF. After stirring at 20° C. for 0.5 h, the mixture was concentrated and dried in vacuo to provide 5D.

Step 4A:

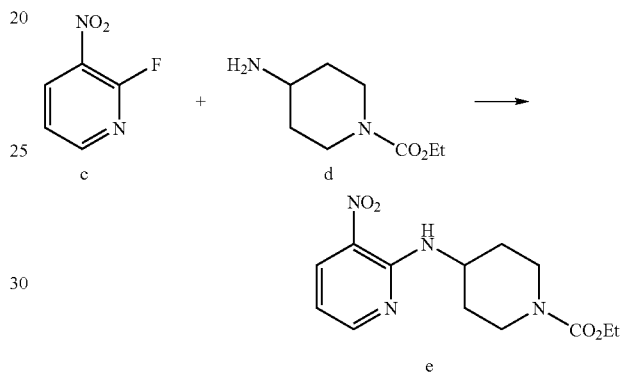

A mixture of c (64 g, 0.40 mol), d (84 ml, 0.52 mol), and K$_2$CO$_3$ (66 g, 0.48 mol) in anhydrous toluene (350 ml) was heated at reflux overnight. The reaction mixture was diluted with CH$_2$Cl$_2$, washed three times with 5% aqueous NaOH, dried over Na$_2$SO$_4$, and concentrated. Recrystallization with MeOH provided e (121 g, ~100%) as a yellow solid.

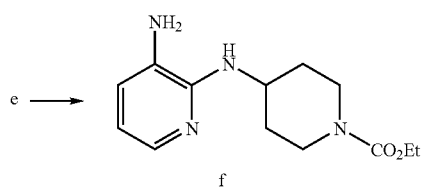

A suspension of e (121 g, 0.41 mol) and Raney Nickel (10 g) in EtOH (400 ml) was shaken under H$_2$ (40 psi) for 4 h. The mixture was filtered through a short pad of Celite (washing with CH$_3$OH). The filtrate was concentrated and dried in vacuo to provide f (109 g, ~100%) as a dark brown solid.

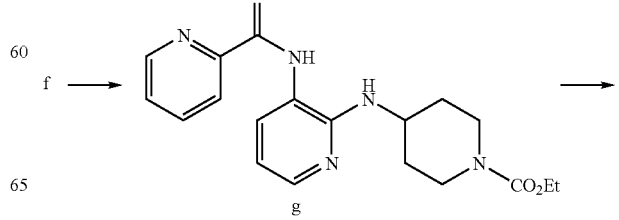

-continued

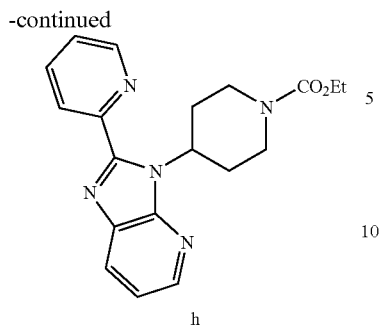

h

A solution of f (109 g, 0.41 mol) in CH$_2$Cl$_2$-DMF (1:1, 500 ml) was treated with picolinic acid (61 g, 0.50 mol), EDCI (119 g, 0.62 mol), HOBt (84 g, 0.62 mol) and iPr$_2$NEt (141 ml, 1.03 mol). The mixture was stirred at 70° C. for 6 h and then overnight at 20° C. The reaction mixture was diluted with EtOAc, washed 3 times with 5% aqueous NaOH, dried over Na$_2$SO$_4$, and concentrated. Flash chromatography (0–100% EtOAc/hexane) provided g (131 g, 86%).

A solution of g (131 g, 0.36 mol) in AcOH (200 ml) was heated at 120° C. overnight. The reaction mixture was cooled, carefully basified with 5% aqueous NaOH and extracted with CH$_2$Cl$_2$. The combined organic extracts were dried over Na$_2$SO$_4$ and concentrated. Flash chromatography (0–80% EtOAc/hexane) provided h (95 g, 76%) as a yellow solid.

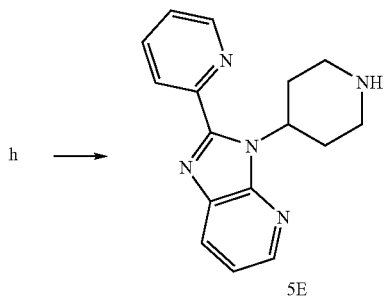

5E

A solution of h (95 g, 0.27 mol) in anhydrous CHCl$_3$ (300 ml) was treated with iodotrimethylsilane (272 g, 1.36 mol) and heated at 70° C. for 5 h. The reaction mixture was cooled, quenched with cold 10% aqueous NaOH, and extracted with CH$_2$Cl$_2$. The combined organic extracts were dried over Na$_2$SO$_4$ and concentrated. Flash chromatography (2N NH$_3$—CH$_3$OH/EtOAc) provided 5E (43 g, 57%) as a pale yellow solid.

Step 4B:

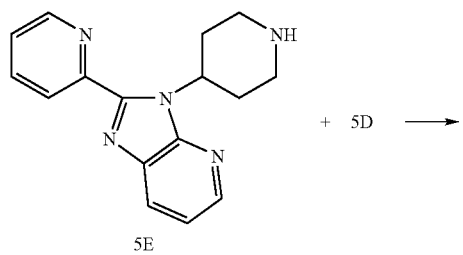

5E + 5D ⟶

-continued

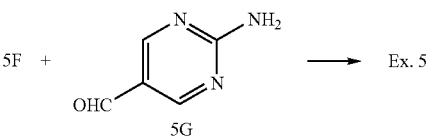

5F

A mixture of 5D (0.075 mol) in CH$_2$Cl$_2$ (250 ml) was treated with 5E (15 g, 0.054 mol) and iPr$_2$NEt (25 ml, 0.135 mol) while maintaining a temperature of 20° C. After 1 h, the mixture was concentrated and then stirred in CH$_3$OH (200 ml)/CH$_2$Cl$_2$ (200 ml)/H$_2$O (1 ml) for 1 h at 20° C. The solvent was then evaporated. Treatment with TFA (200 ml) in CH$_2$Cl$_2$ (250 ml) at 20° C. followed by flash chromatography (0–7% 7N NH$_3$—CH$_3$OH/CH$_2$Cl$_2$) provided 5F (80–90% from 5C).

Step 5:

Method A:

5F + (structure 5G: 2-amino-5-formylpyrimidine) ⟶ Ex. 5

A solution of 5F (0.41 g, 1.0 mmol) in CH$_2$Cl$_2$ (20 ml) was treated with 5G (0.31 g, 2.5 mmol, JP Patent 63227573, 1988), NaBH(OAc)$_3$ (0.53 g, 2.5 mmol) and few drops of AcOH and then stirred overnight at 20° C. The mixture was partitioned between 10% NaOH and CH$_2$Cl$_2$. The organic layer was dried with Na$_2$SO$_4$ and concentrated. Flash chromatography (0–5% 7N NH$_3$—CH$_3$OH/CH$_2$Cl$_2$) provided the title compound (0.45 g, 87%). MS: 516 (M+H).

Method B:

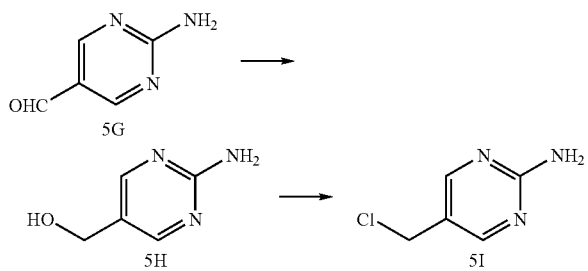

A solution of 5G (50 g, 0.41 mol) in CH$_3$OH (300 ml) was cooled to 0° C. and carefully treated with NaBH$_4$ (20 g, 0.53 mol in 6 batches) over 20 min. The reaction was then allowed to warm to 20° C. and was stirred for 4 h. The mixture was again cooled to 0° C., carefully quenched with saturated aqueous NH$_4$Cl, and concentrated. Flash chromatography (5–10% 7N NH$_3$—CH$_3$OH/CH$_2$Cl$_2$) provided 5H (31 g, 62%) as a light yellow solid.

A slurry of 5H (31 g, 0.25 mol) in CH$_2$Cl$_2$ (500 ml) was cooled to 0° C. and slowly treated with SOCl$_2$ (55 ml, 0.74 mol over 30 min). The reaction was then stirred overnight at 20° C. The material was concentrated, slurried in acetone, and then filtered. The resulting beige solid 5I was dried overnight in vacuo (38.4 g, 52%, HCl salt).

A homogeneous solution of 5F (16.4 g, 40 mmol) in anhydrous DMF (200 ml) was cooled to 0° C., carefully treated with NaH (8 g, 200 mmol), and stirred at 20° C. for 20 min. The reaction mixture was then cooled to 0° C., treated with NaI (6 g, 40 mmol) and 5I (14.5 g, 80 mmol), and then stirred overnight at 20° C. The reaction was diluted with CH₂Cl₂ (500 ml), washed with 1N aqueous NaOH, washed with brine, filtered through Celite, and concentrated. Flash chromatography (0–4% 7N NH₃—CH₃OH/CH₂Cl₂) provided Ex. 5 (16.9 g, 82%) as a beige solid.

EXAMPLE 6

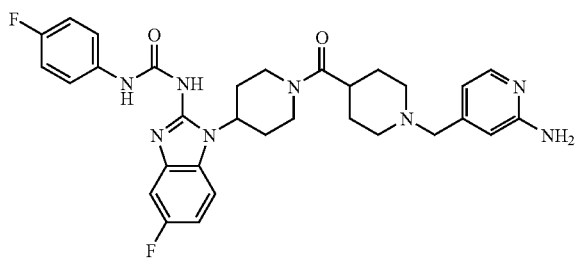

Step 1:

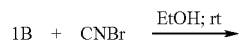

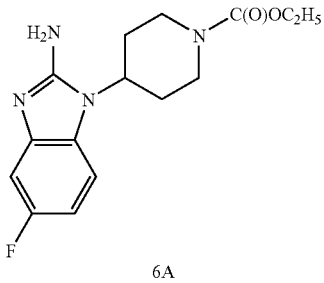

6A

To a stirred solution of diamine 1B (1.0 g, 3.55 mmol) in C₂H₅OH (25 ml), at RT was added portionwise solid CNBr (564 mg; 5.33 mmol). The resultant solution was allowed to stir at RT for 5 days before removing solvent under vacuum. The residual oil was partitioned between EtOAc (30 ml) and 2M Na₂CO₃ (10 ml). The aqueous layer was adjusted to pH~10 by addition of a few drops of 6N NaOH and was then re-extracted with EtOAc (2×10 ml). Combined extracts were washed with brine (5 ml) and filtered through anhydrous MgSO₄. The filtrate was stripped in vacuo to obtain compound 6A as brown powder (1.03 g; 94%) sufficiently pure for use without purification. FABMS: 307 (MH⁺; 100%).

Step 2.

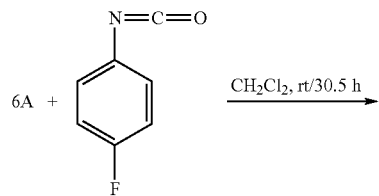

-continued

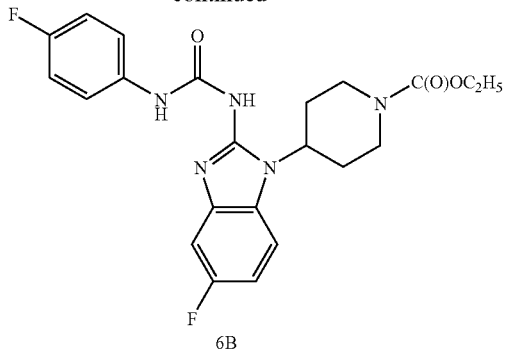

6B

In a dry flask, under an inert atmosphere, a mixture of compound 6A (369 mg; 1.20 mmol) and CH₂Cl₂ (11 ml) was stirred and sonicated until the formation of a clear, amber solution to which was added via syringe 4-fluorophenyl isocyanate (158 microliters; 190 mg; 1.38 mmol). After 30.5 h at RT, a few drops of CH₃OH were added to the reaction solution, and solvent was removed under vacuum. The residual solid was dissolved in boiling Et₂O (~30 ml). Insoluble matter was filtered, and the filtrate was diluted to a volume of ~60 ml with hot hexanes. The solution was concentrated on a steam bath to a volume of ~30 ml, by which point precipitation had begun. The mixture was allowed to stand at RT for ~3 h. Filtration and washing with Et₂O-hexanes (1:1 v/v) yielded compound 6B as a reddish-brown powder (394 mg; 74%). FABMS: 444 (MH⁺; 100%). Although TLC and NMR indicated the presence of minor impurities, the product was sufficiently pure for use in Step 3 below.

Step 3:

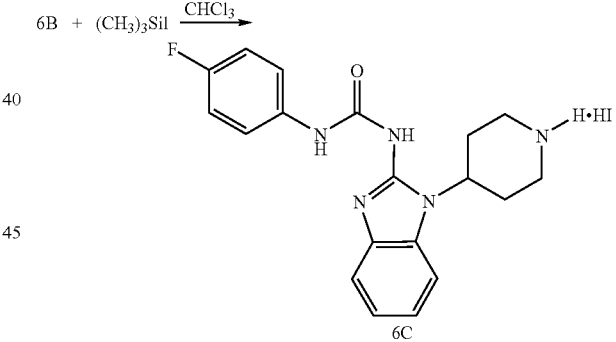

6C

To a stirred suspension of compound 6B (333 mg; 0.751 mmol) in CHCl₃ (2 ml), contained in a flask equipped for reflux under an inert atmosphere, was added via syringe (CH₃)₃SiI (214 microliters; 301 mg; 1.51 mmol). Solids dissolved rapidly to produce a dark reddish-brown solution. Stirring was continued at RT for 20 min before placing the reaction mixture in an oil bath preheated to 50° C. After 5 h at 50° C., a second portion of (CH₃)₃SiI (54 microliters; 75 mg; 0.378 mmol) was added and heating continued at 50° C. for another 2.5 h. The reaction mixture (consisting of solid and solution phases) was removed from the heating bath and was treated with CH₃OH (2.5 ml) added in two portions. The reaction mixture was stirred and warmed to 50° C. for a few minutes, allowed to cool and was then filtered. Collected solids were washed with 1:1 (v/v) CH₃OH-EtOAc to obtain the hydriodide salt form of 6C as a pale reddish-brown powder (356 mg) wich was used in the next step without further purification. FABMS: 372 (MH⁺; 100%).

Step 4:

6C + Prep. 1 ⟶

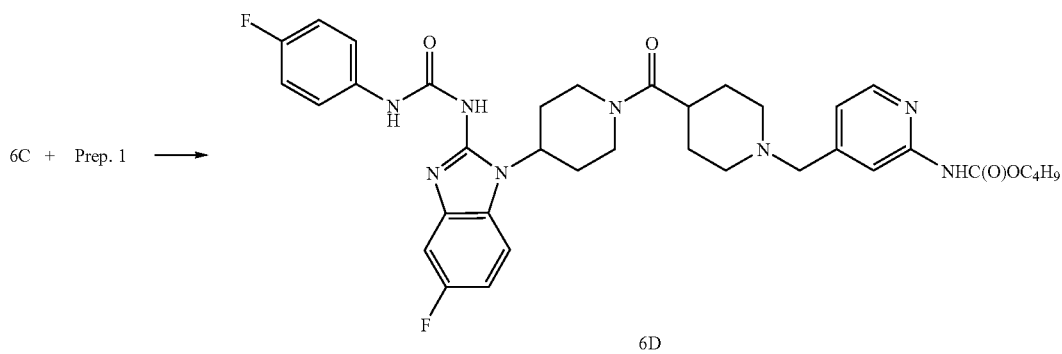

6D

To a stirred suspension of 6C (340 mg; 0.681 mmol), Prep. 1 (228 mg; 0.681 mmol), HOBT (9.2 mg; 0.0681 mmol) and NEt$_3$ (379 microliters; 275 mg; 2.72 mmol) in DMF (13 ml) was added solid EDCI (163 mg; 0.851 mmol). The cloudy reaction mixture was placed in a preheated oil bath and was stirred at 50° C. for 30 min, after which the resultant clear, amber solution was stirred for 23.5 h at RT. A few drops of water were added, and the reaction mixture was concentrated at 60° C. under vacuum. The concentrate was partitioned between EtOAc (20 ml) and water (5 ml)-brine (2.5 ml). The aqueous phase was extracted with EtOAc (2×5 ml). Combined extracts were washed with brine (2.5 ml) and filtered through anhydrous MgSO$_4$. The filtrate was evaporated under vacuum, and the residue was purified by flash chromatography on silica gel, eluting with a gradient of CH$_2$Cl$_2$—CH$_3$OH—NH$_4$OH (97:3:0.5->96:4:0.5). Product 6D (222 mg; 47%) was obtained as pale yellow powder. FABMS: 689 (MH$^+$; ~93%); 578 (~58%); 478 (100%).

Step 5:

To a solution of 6D (208 mg; 0.302 mmol) in CH$_2$Cl$_2$ (3 ml) was added TFA (928 microliters; 1.37 g; 12.1 mmol) with swirling of the flask, which was then flushed with dry N$_2$, sealed and allowed to stand at RT for 6 h. The reaction solution was evaporated under vacuum, and the residue was partitioned between EtOAc (20 ml) and 2M Na$_2$CO$_3$ (3 ml) plus sufficient water to produce two clear phases. The aqueous phase was extracted with EtOAc (3×5 ml). Combined extracts were washed with brine (3 ml) and filtered through anhydrous MgSO$_4$. The filtrate was stripped of solvent in vacuo, and the residue was subjected to flash chromatography on silica gel, eluting with CH$_2$Cl$_2$—CH$_3$OH—NH$_4$OH (97:3:0.5). The title compound (130 mg; 72%) was obtained as pale yellow powder. FABMS: 589 (MH$^+$; ~64%); 478 (100%).

Using procedures similar to those described above, employing the appropriate starting materials, compounds in the following tables are prepared:

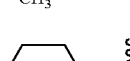

| No. | R | R$^{25}$ | R$^3$ | R$^{13}$ | Z | R$^6$ | Physical Data MS (MH$^+$) |
|---|---|---|---|---|---|---|---|
| 7 | —CH$_3$ | 5-OCH$_3$ | H | H | —CH$_2$— | 2-NH$_2$ | 463 |
| 8 | —CH$_3$ | 6-Cl | H | H | —CH$_2$— | 2-NH$_2$ | 467 |
| 9 | —CH$_3$ | 5-Cl | H | H | —CH$_2$— | 2-NH$_2$ | 467 |
| 10 | —CH$_3$ | 5-Br | H | H | —CH$_2$— | 2-NH$_2$ | 512 |
| 11 | cyclohexylmethyl | 5-Cl | H | H | —CH$_2$— | 2-NH$_2$ | 535 |
| 12 | benzyl | 5-F | H | H | —CH$_2$— | 2-NH$_2$ | 527 |
| 13 | —CH(CH$_3$)$_2$ | 5-Br | H | H | —CH$_2$— | 2-NH$_2$ | 540 |
| 14 | —CH$_2$NH$_2$ | H | H | H | —CH$_2$— | 2-NH$_2$ | 488 |

-continued
| | | | | | | | |
|---|---|---|---|---|---|---|---|
| 15 | —CH₂NHSO₂CH₃ | H | H | H | —CH₂— | 2-NH₂ | 526 |
| 16 | —CH₂NHC(O)CH₃ | 5-Cl | H | H | —CH₂— | 2-NH₂ | 524 |
| 17 | —CH₂OCH₃ | 5-F | H | H | —CH₂— | 2-NH₂ | 481 |
| 18 | —CH₂NH₂ | 5-Cl | H | H | —CH₂— | 2-NH₂ | 482 |
| 19 | —CH₂OCH₃ | 6,7-di-F | H | H | —CH₂— | 2-NH₂ | 499 |
| 20 | 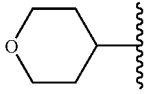 | 6-F | H | H | —CH₂— | 2-NH₂ | 521 |
| 21 | 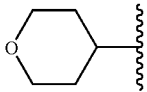 | 5-F | H | H | —CH₂— | 2-NH₂ | 521 |
| 22 | 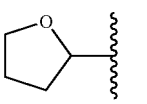 | 6-F | H | H | —CH₂— | 2-NH₂ | 507 |
| 23 | 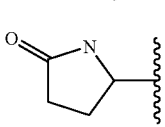 | 5-F | H | H | —CH₂— | 2-NH₂ | 520 |
| 24 | 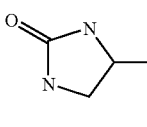 | 5-F | H | H | —CH₂— | 2-NH₂ | 521 |
| 25 | 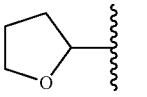 | 5-Br | H | H | —CH₂— | 2-NH₂ | 568 |
| 26 | 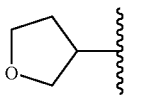 | 5-F | H | H | —CH₂— | 2-NH₂ | 507 |
| 27 | 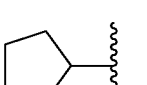 | 5-F | H | H | —CH₂— | 2-NH₂ | 507 |
| 28 | 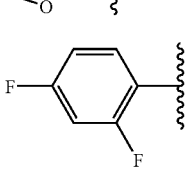 | H | H | H | —CH₂— | 2-NH₂ | 531 |
| 29 | 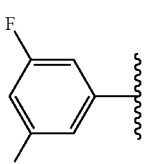 | 5-F | H | H | —CH₂— | 2-NH₂ | 549 |
| 30 | 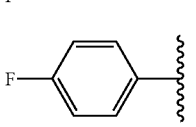 | 6-F | H | H | —CH₂— | 2-NH₂ | 531 |
| 31 | 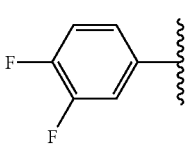 | 6,7-di-F | H | H | —CH₂— | 2-NH₂ | 567 |

-continued

| # | Ar | R1 | R2 | R3 | L | R | MS |
|---|---|---|---|---|---|---|---|
| 32 | 4-F-C6H4- | 6-Cl | H | H | —CH2— | 2-NH2 | 547 |
| 33 | 4-F-C6H4- | 5-F | H | H | —CH2— | 2-NH2 | 531 |
| 34 | 3,5-diF-C6H3- | 5-Cl | H | H | —CH2— | 2-NH2 | 565 |
| 35 | 3,4-diF-C6H3- | H | H | H | —CH2— | 2-NH2 | 531 |
| 36 | 4-F-C6H4- | 5-Cl | H | H | —CH2— | 2-NH2 | 547 |
| 37 | C6H5- | 5-Cl | H | H | —CH2— | 2-NH2 | 529 |
| 38 | 3,4-methylenedioxy-C6H3- | 6-F | H | H | —CH2— | 2-NH2 | 557 |
| 39 | 2-F-C6H4- | 5-Br | H | H | —CH2— | 2-NH2 | 592 |
| 40 | 3,4-diF-C6H3- | 5-Br | H | H | —CH2— | 2-NH2 | 610 |
| 41 | 4-Cl-C6H4- | 5-F | H | H | —CH2— | 2-NH2 | 547 |
| 42 | 2-OH-C6H4- | 5-F | H | H | —CH2— | 2-NH2 | 529 |
| 43 | benzofuran-2-yl | 6-F | H | H | —CH2— | 2-NH2 | 553 |

| | | | | | | |
|---|---|---|---|---|---|---|
| 44 | 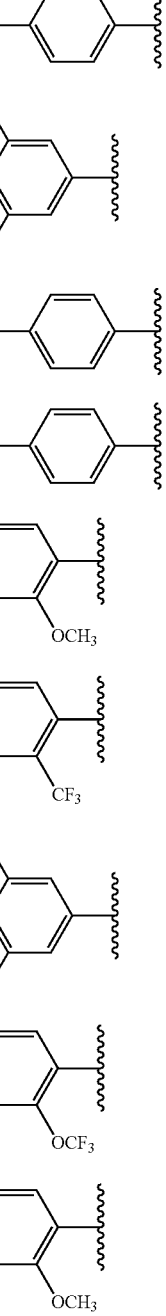 | 6-F | H | H | —CH$_2$— | 2-NH$_2$ | 564 |
| 45 | 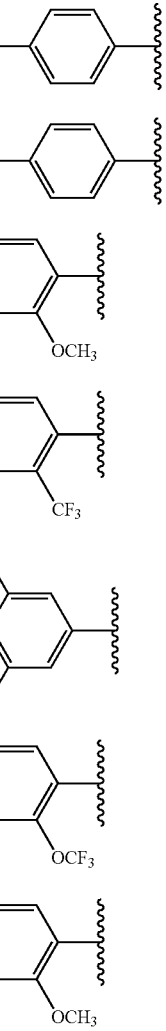 | H | H | H | —CH$_2$— | 2-NH$_2$ | 529 |
| 46 | 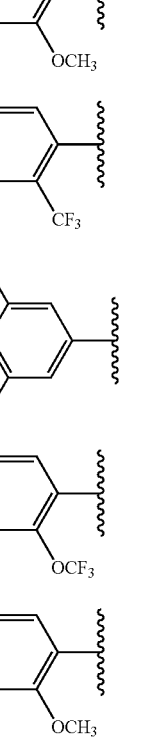 | 5-F | H | H | —CH$_2$— | 2-NH$_2$ | 581 |
| 47 | 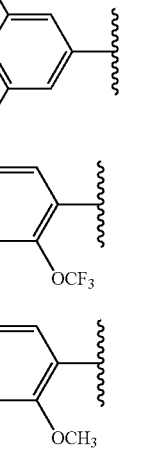 | 5-Cl | H | H | —CH$_2$— | 2-NH$_2$ | 563 |
| 48 | 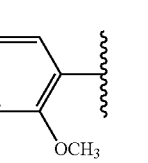 | 6-Cl | H | H | —CH$_2$— | 2-NH$_2$ | 563 |
| 49 | 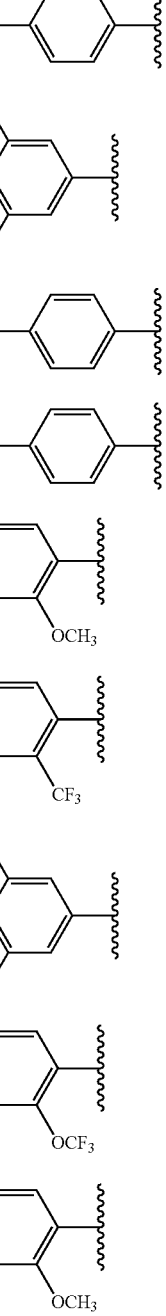 | 5-F | H | H | —CH$_2$— | 2-NH$_2$ | 543 |
| 50 | 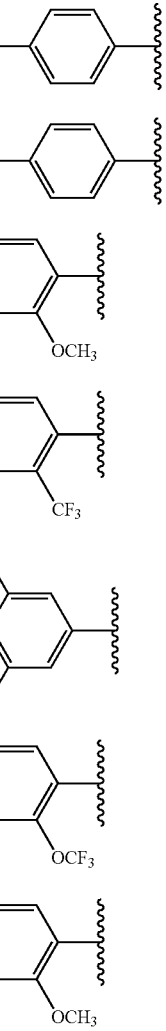 | 5-F | H | H | —CH$_2$— | 2-NH$_2$ | 581 |
| 51 | 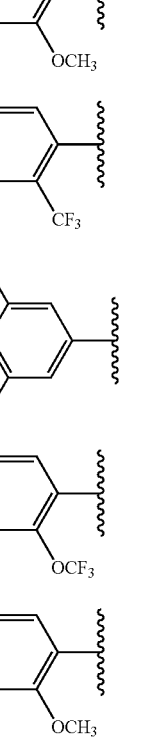 | 5-Cl | H | H | —CH$_2$— | 2-NH$_2$ | 597 |
| 52 | 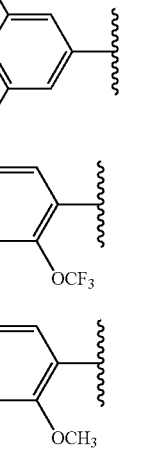 | 5-F | H | H | —CH$_2$— | 2-NH$_2$ | 597 |
| 53 | 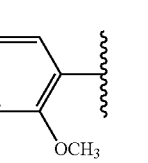 | 5-Br | H | H | —CH$_2$— | 2-NH$_2$ | 604 |
| 54 |  | 6-Cl | H | H | —CH$_2$— | 2-NH$_2$ | 597 |

-continued
| | | | | | | | |
|---|---|---|---|---|---|---|---|
| 55 | 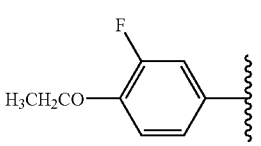 | 5-CH$_3$ | H | H | —CH$_2$— | 2-NH$_2$ | 571 |
| 56 | 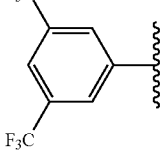 | 5-Cl | H | H | —CH$_2$— | 2-NH$_2$ | 665 |
| 57 |  | 5-Br | H | H | —CH$_2$— | 2-NH$_2$ | 710 |
| 58 | 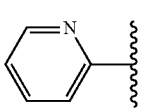 | 6-ethoxy | H | H | —CH$_2$— | 2-NH$_2$ | 540 |
| 59 | 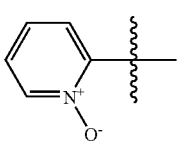 | 5-Cl | H | H | —CH$_2$— | 2-NH$_2$ | 546 |
| 60 | 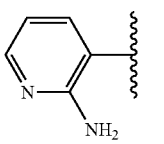 | H | H | H | —CH$_2$— | 2-NH$_2$ | 511 |
| 61 | 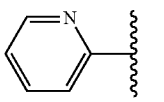 | 5-F | H | H | —CH$_2$— | H | 499 |
| 62 | 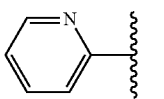 | 6-Cl | H | H | —CH$_2$— | 2-NH$_2$ | 530 |
| 63 | 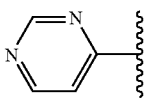 | 5-F | H | H | —CH$_2$— | 2-NH$_2$ | 515 |
| 64 | 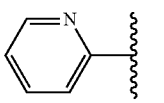 | 6-F | H | H | —CH$_2$— | 2-NH$_2$ | 514 |
| 65 | 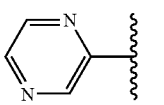 | 6-F | H | H | —CH$_2$— | 2-NH$_2$ | 515 |
| 66 | 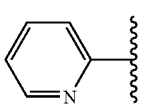 | 7-Cl | H | H | —CH$_2$— | 2-NH$_2$ | 531 |

-continued
| | | | | | | | |
|---|---|---|---|---|---|---|---|
| 67 | 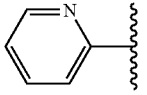 | H | H | H | —CH$_2$— | 2-NH$_2$ | 496 |
| 68 | 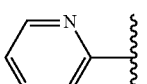 | 5-F | H | H | —CH$_2$— | 2-NH$_2$ | 515 |
| 69 | 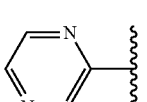 | 5-Cl | H | H | —CH$_2$— | 2-NH$_2$ | 531 |
| 70 | 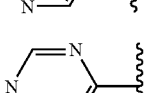 | 5-Cl | H | H | —CH$_2$— | 2-NH$_2$ | 531 |
| 71 | 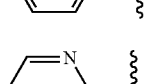 | 5,6-di-F | H | H | —CH$_2$— | 2-NH$_2$ | 532 |
| 72 | 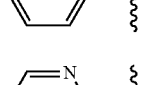 | 5-Br | H | H | —CH$_2$— | 2-NH$_2$ | 575 |
| 73 | 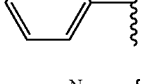 | 6-ethoxy | H | H | —CH$_2$— | 2-NH$_2$ | 541 |
| 74 | 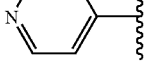 | 5-F | H | H | —CH$_2$— | 2-NH$_2$ | 528 |
| 75 | 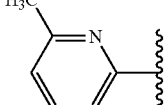 | 6-F | H | H | —CH$_2$— | 2-NH$_2$ | 515 |
| 76 | 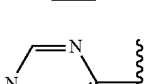 | 5-Br | H | H | —CH$_2$— | 2-NH$_2$ | 591 |
| 77 | 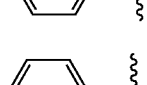 | 5-Cl | H | H | —CH$_2$— | 2-NH$_2$ | 530 |
| 78 | 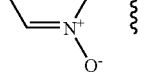 | 5-Cl | H | H | —CH$_2$— | 2-NH$_2$ | 530 |
| 79 | 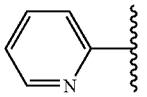 | 5-F | H | H | —CH$_2$— | 2-NH$_2$ | 548 |

-continued

| # | Structure | | | | | |
|---|---|---|---|---|---|---|
| 80 | pyrimidin-4-yl | 5-CF₃ | H | H | —CH₂— | 2-NH₂ 565 |
| 81 | pyrimidin-4-yl | H | H | H | —CH₂— | 2-NH₂ 497 |
| 82 | 4-chloropyridin-2-yl | 6,7-di-F | H | H | —CH₂— | 2-NH₂ 567 |
| 83 | pyridin-2-yl | 6,7-di-F | H | H | —CH₂— | 2-NH₂ 532 |
| 84 | 2-hydroxypyridin-3-yl | 5-F | H | H | —CH₂— | 2-NH₂ 530 |
| 85 | 4-chloropyridin-2-yl | 5-CF₃, 7-F | H | H | —CH₂— | 2-NH₂ 617 |
| 86 | 2-aminopyridin-4-yl | 5-F | H | H | —CH₂— | 2-NH₂ 529 |
| 87 | 5-methylisoxazol-3-yl | H | H | H | —CH₂— | 2-NH₂ 500 |
| 88 | furan-2-yl | H | H | H | —CH₂— | 2-NH₂ 485 |
| 89 | pyrrol-2-yl | H | H | H | —CH₂— | 2-NH₂ 489 |
| 90 | thiophen-3-yl | 6-F | H | H | —CH₂— | 2-NH₂ 514 |

-continued
| | | | | | | |
|---|---|---|---|---|---|---|
| 91 | 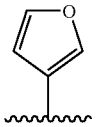 | 6-F | H | H | —CH$_2$— | 2-NH$_2$ 503 |
| 92 | 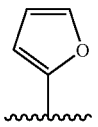 | 5-F | H | H | —CH$_2$— | 2-NH$_2$ 503 |
| 93 | 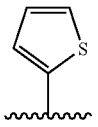 | H | H | H | —CH$_2$— | 2-NH$_2$ 501 |
| 94 | 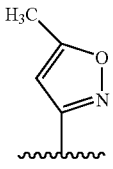 | 5-F | H | H | —CH$_2$— | 2-NH$_2$ 518 |
| 95 | 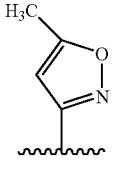 | 5-Cl | H | H | —CH$_2$— | 2-NH$_2$ 534 |
| 96 | 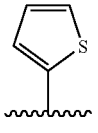 | 5-F | H | H | —CH$_2$— | 2-NH$_2$ 519 |
| 97 | 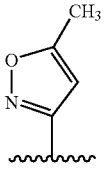 | 6,7-di-F | H | H | —CH$_2$— | 2-NH$_2$ 536 |
| 98 | 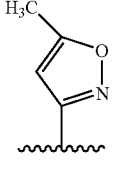 | 5-Br | H | H | —CH$_2$— | 2-NH$_2$ 579 |
| 99 | 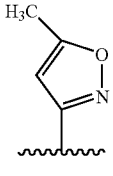 | 6-ethoxy | H | H | —CH$_2$— | 2-NH$_2$ 544 |
| 100 | 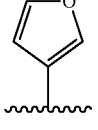 | 5-F | H | H | —CH$_2$— | 2-NH$_2$ 503 |

-continued

| | | | | | | | |
|---|---|---|---|---|---|---|---|
| 101 | pyrrol-2-yl | 5-Br | H | H | —CH₂— | 2-NH₂ | 563 |
| 102 | pyrrol-2-yl | 5-F | H | H | —CH₂— | 2-NH₂ | 502 |
| 103 | 5-methylisoxazol-3-yl | 5-CF₃ | H | H | —CH₂— | 2-NH₂ | 568 |
| 104 | 5-methylisoxazol-3-yl | 5-CF₃, 7-F | H | H | —CH₂— | 2-NH₂ | 586 |
| 105 | 5-(4-fluorophenyl)isoxazol-3-yl | 5-F | H | H | —CH₂— | 2-NH₂ | 598 |
| 106 | 2-methylfuran-3-yl | 5-F | H | H | —CH₂— | 2-NH₂ | 517 |
| 107 | 5-tert-butyl-2-methylfuran-3-yl | 5-F | H | H | —CH₂— | 2-NH₂ | 573 |
| 108 | 3-methylfuran-2-yl | 5-F | H | H | —CH₂— | 2-NH₂ | 517 |
| 109 | CH₃—S— | 5-F | H | H | —CH₂— | 2-NH₂ | 483 |
| 110 | CH₃—CH₂—S— | 5-F | H | H | —CH₂— | 2-NH₂ | 497 |
| 111 | CH₃—SO₂— | 5-F | H | H | —CH₂— | 2-NH₂ | 515 |
| 112 | phenyl-S— | 5-F | H | H | —CH₂— | 2-NH₂ | 545 |
| 113 | (CH₃)₂CH—S— | 5-F | H | H | —CH₂— | 2-NH₂ | 511 |

-continued
| | | | | | | | |
|---|---|---|---|---|---|---|---|
| 114 | 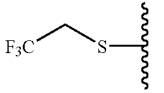 | 5-F | H | H | —CH$_2$— | 2-NH$_2$ | 551 |
| 115 | 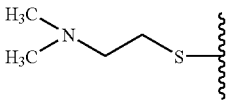 | 5-F | H | H | —CH$_2$— | 2-NH$_2$ | 540 |
| 116 | HS— | 5-F | H | H | —CH$_2$— | 2-NH$_2$ | 469 |
| 117 | CH$_3$—S— | 5-F | H | 2-CH$_3$ | —CH$_2$— | 2-NH$_2$ | 497 |
| 118 | CH$_3$—S— | 5-F | F | H | —CH$_2$— | 2-NH$_2$ | 501 |
| 119 | 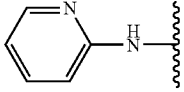 | 5-F | H | H | —CH$_2$— | 2-NH$_2$ | 529 |
| 120 | 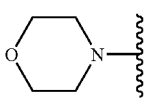 | 5-F | H | H | —CH$_2$— | 2-NH$_2$ | 522 |
| 121 | 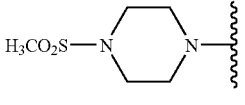 | 5-F | H | H | —CH$_2$— | 2-NH$_2$ | 599 |
| 123 | 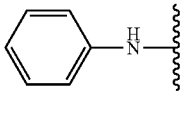 | 5-F | H | H | —CH$_2$— | 2-NH$_2$ | 528 |
| 124 | 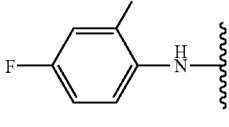 | 5-F | H | H | —CH$_2$— | 2-NH$_2$ | 564 |
| 125 | 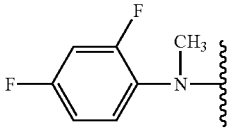 | 5-F | H | H | —CH$_2$— | 2-NH$_2$ | 578 |
| 126 | 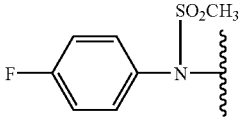 | 5-F | H | H | —CH$_2$— | 2-NH$_2$ | 624 |
| 127 | 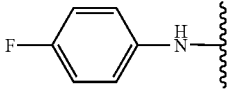 | 5-F | H | H | —CH$_2$— | 2-NH$_2$ | 546 |
| 128 | 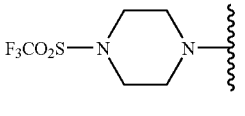 | 5-F | H | H | —CH$_2$— | 2-NH$_2$ | 653 |
| 129 | CH$_3$—O—(CH$_2$)$_2$—NH— | 5-F | H | H | —CH$_2$— | 2-NH$_2$ | 510 |
| 130 | 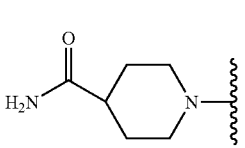 | 5-F | H | H | —CH$_2$— | 2-NH$_2$ | 563 |

-continued
| | | | | | | |
|---|---|---|---|---|---|---|
| 131 |  | 5-F | H | H | —CH$_2$— | 2-NH$_2$ 480 |
| 132 | CH$_3$—O— | 5-F | H | H | —CH$_2$— | 2-NH$_2$ 467 |
| 133 | CH$_3$—CH$_2$—O— | 5-F | H | H | —CH$_2$— | 2-NH$_2$ 481 |
| 134 | CH$_3$—O—(CH$_2$)$_2$—O— | 5-F | H | H | —CH$_2$— | 2-NH$_2$ 511 |
| 135 | (CH$_3$)$_2$—CH—O— | 5-F | H | H | —CH$_2$— | 2-NH$_2$ 495 |
| 136 | 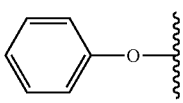 | 5-F | H | H | —CH$_2$— | 2-NH$_2$ 529 |
| 137 | 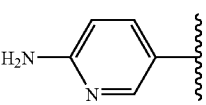 | H | H | H | —CH$_2$— | 2-NH$_2$ 511 |
| 138 | 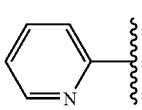 | 5-CF$_3$, 7-F | H | H | —CH$_2$— | 2-NH$_2$ 582 |
| 139 | 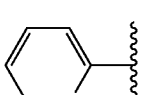 | 5-F | H | H |  | 2-NH$_2$ 528 |
| 140 | 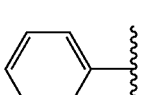 | 5-F | F | H | —CH$_2$— | 2-NH$_2$ 532 |
| 141 | 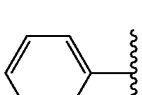 | 5-F | OH | H | —CH$_2$— | 2-NH$_2$ 530 |
| 142 | 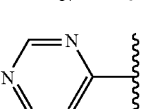 | 5-F | H | H |  | 2-NH$_2$ 529 |
| 143 | 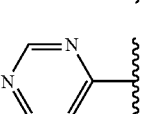 | 5-F | H | H |  | 2-NH$_2$ 529 |
| 144 | 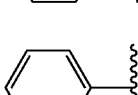 | 5-F | —CH$_3$ | H | —CH$_2$— | 2-NH$_2$ 528 |
| 145 | 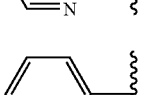 | 6-F | H | H |  | 2-NH$_2$ 528 |
| 146 | H | 5-F | H | H | —CH$_2$— | 2-NH$_2$ 437 |
| 147 | 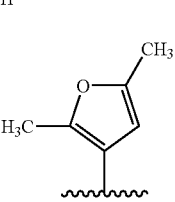 | 5-F | H | H | —CH$_2$— | 2-NH$_2$ 531 |

-continued

| # | R | | | | | MW |
|---|---|---|---|---|---|---|
| 148 | 2,3-dimethyl-furan-5-yl (H₃C, CH₃ on furan) | 5-F | H | H | —CH₂— | 2-NH₂ | 531 |
| 149 | 5-methyl-2-(trifluoromethyl)furan-3-yl | 5-F | H | H | —CH₂— | 2-NH₂ | 585 |
| 150 | 2,2-dimethyl-tetrahydropyran-4-yl | 5-F | H | H | —CH₂— | 2-NH₂ | 549 |
| 151 | 5-(trifluoromethyl)furan-2-yl | 5-F | H | H | —CH₂— | 2-NH₂ | 571 |
| 152 | pyridin-2-yl | H | F | H | —CH₂— | 2-NH₂ | 514 |
| 153 | (CH₃)₂N—(CH₂)₂—NH— | 5-F | H | H | —CH₂— | 2-NH₂ | 523 |
| 154 | CH₃—S— | 5-F | H | H | —CH(CH₃)— | 2-NH₂ | 497 |
| 155 | pyridin-2-yl | 5-F | H | 2-CH₃ | —CH₂— | 2-NH₂ | 528 |
| 156 | pyridin-3-yl | 5-F | H | H | —CH₂— | 2-NH₂ | 514 |
| 157 | pyridin-2-yl | 5-F | H | H | —CH₂— | 3-NH₂ | 514 |
| 158 | thiomorpholin-4-yl | 5-F | H | H | —CH₂— | 2-NH₂ | 589 |
| 159 | piperidin-1-yl | 5-F | H | H | —CH₂— | 2-NH₂ | 520 |
| 160 | CH₃CH₂O— | 5-F | F | H | —CH₂— | 2-NH₂ | 499 |

-continued
| No. | (structure) | | | | | |
|---|---|---|---|---|---|---|
| 161 | H3C-N(CH3)-(CH2)2-N(CH3)- | 5-F | H | H | —CH2— | 2-NH2 | 537 |
| 162 | H3C-N(piperazinyl)- | 5-F | H | H | —CH2— | 2-NH2 | 535 |
| 163 | 2-pyridyl | 5-F | H | 5-OH | —CH2— | 2-NH2 | 530 |
| 164 | 2-pyridyl | 5-F | F | H | —CH2— | 3-NH2 | 532 |
| 165 | morpholinyl | 5-F | F | H | —CH2— | 2-NH2 | 540 |
| 166 | 4-pyrimidinyl | 5-F | H | H | —CH2— | 3-NH2 | 515 |
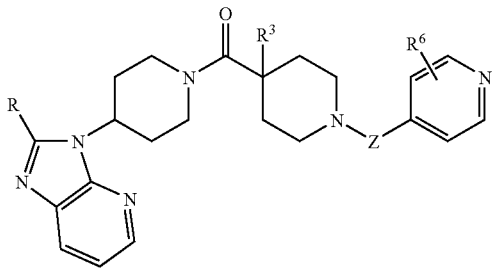
| No. | R | R³ | Z | R⁶ | Physical Data MS (MH⁺) |
|---|---|---|---|---|---|
| 167 | cyclohexyl | H | —CH2— | 2-NH2 | 502 |
| 168 | —CH2OCH3 | H | —CH2— | 2-NH2 | 464 |
| 169 | tetrahydropyran-4-yl | H | —CH2— | 2-NH2 | 504 |
| 170 | cyclopropyl | H | —CH2— | 2-NH2 | 460 |
| 171 | (CH3)2—CH— | H | —CH2— | 2-NH2 | 462 |
| 172 | (CH3)2N—CH2— | H | —CH2— | 2-NH2 | 477 |

-continued

| # | Structure | | | | |
|---|---|---|---|---|---|
| 173 | 4-F-phenyl | H | —CH₂— | 2-NH₂ | 514 |
| 174 | 3,4-diF-phenyl | H | —CH₂— | 2-NH₂ | 532 |
| 175 | 4-Cl-phenyl | H | —CH₂— | 2-NH₂ | 530 |
| 176 | 3,6-diF-pyridyl | H | —CH₂— | 2-NH₂ | 532 |
| 177 | benzo[1,3]dioxol-5-yl | H | —CH₂— | 2-NH₂ | 540 |
| 178 | 3,5-diCl-phenyl | H | —CH₂— | 2-NH₂ | 564 |
| 179 | 2-OCH₃-phenyl | H | —CH₂— | 2-NH₂ | 526 |
| 180 | 3-OEt-5-F-phenyl | H | —CH₂— | 2-NH₂ | 558 |
| 181 | pyridin-3-yl | H | —CH₂— | 2-NH₂ | 497 |
| 182 | 2-NH₂-pyridin-3-yl | H | —CH₂— | 2-NH₂ | 512 |
| 183 | 4-Cl-pyridin-2-yl | H | —CH₂— | 2-NH₂ | 531 |

-continued
| | | | | | |
|---|---|---|---|---|---|
| 184 | 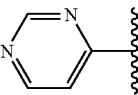 | H | —CH$_2$— | 2-NH$_2$ | 498 |
| 185 | 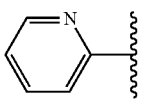 | H | —CH$_2$— | 2-NH$_2$ | 497 |
| 186 | 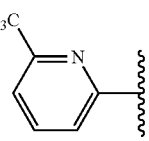 | H | —CH$_2$— | 2-NH$_2$ | 511 |
| 187 | 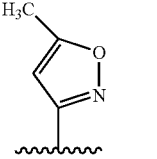 | H | —CH$_2$— | 3-NH$_2$ | 501 |
| 188 | 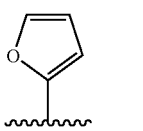 | H | —CH$_2$— | 2-NH$_2$ | 486 |
| 189 | 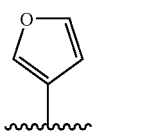 | H | —CH$_2$— | 2-NH$_2$ | 486 |
| 190 | 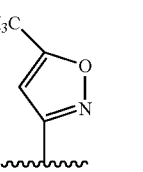 | H | —CH$_2$— | 2-NH$_2$ | 501 |
| 191 | 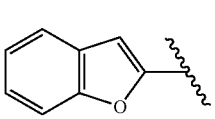 | H | —CH$_2$— | 2-NH$_2$ | 536 |
| 192 | 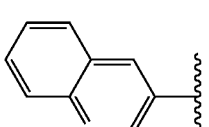 | H | —CH$_2$— | 2-NH$_2$ | 547 |
| 193 | 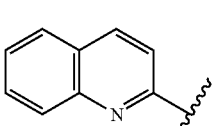 | H | —CH$_2$— | 2-NH$_2$ | 547 |
| 194 | 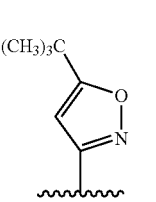 | H | —CH$_2$— | 2-NH$_2$ | 543 |

-continued

| | | | | | |
|---|---|---|---|---|---|
| 195 | 5-(4-fluorophenyl)isoxazol-3-yl | H | —CH$_2$— | 2-NH$_2$ | 581 |
| 196 | 5-methylisoxazol-3-yl | F | —CH$_2$— | 2-NH$_2$ | 519 |
| 197 | 5-methylisoxazol-3-yl | H | —CH(CH$_3$)— | 2-NH$_2$ | 515 |
| 198 | 5-methylisoxazol-3-yl | OH | —CH$_2$— | 2-NH$_2$ | 517 |
| 199 | 5-methylisoxazol-3-yl | phenyl | —CH$_2$— | 2-NH$_2$ | 577 |
| 200 | pyridin-2-yl | F | —CH$_2$— | 2-NH$_2$ | 515 |
| 201 | furan-3-yl | F | —CH$_2$— | 2-NH$_2$ | 504 |
| 202 | pyridin-2-yl | H | —CH$_2$— | 3-NH$_2$ | 497 |
| 203 | 2,4-difluorophenyl | H | —CH$_2$— | 3-NH$_2$ | 532 |
| 204 | pyridin-2-yl | F | —CH$_2$— | 3-NH$_2$ | 515 |
| 205 | 2,4-difluorophenyl | F | —CH$_2$— | 3-NH$_2$ | 550 |

-continued
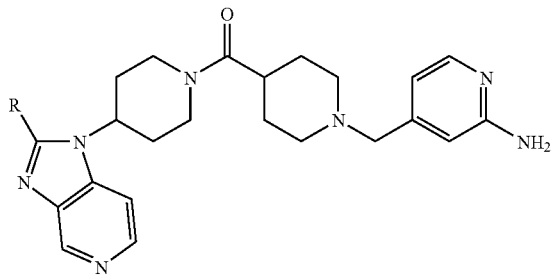
| No. | R | Physical Data MS (MH+) |
|---|---|---|
| 206 | —CH$_3$ | 434 |
| 207 | 2-pyridyl | 497 |
| 208 | 4-F-phenyl | 514 |
| 209 | 4-Cl-phenyl | 530 |
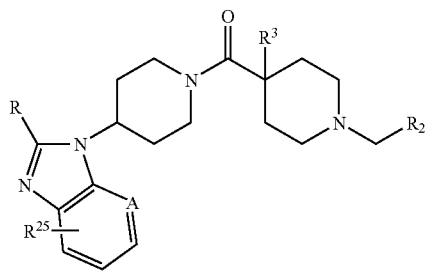
| No. | R | R$^{25}$ | A | R$^3$ | R$^2$ | Physical Data MS (MH+) |
|---|---|---|---|---|---|---|
| 210 | 4-pyrimidinyl | 5-Cl | C | H | 2-amino-5-pyrimidinyl | 532 |
| 211 | 2-pyridyl | 5-F | C | H | 2-amino-5-pyrimidinyl | 515 |
| 212 | 2-pyrazinyl | 5-Cl | C | H | 2-amino-5-pyrimidinyl | 532 |
| 213 | 4-pyrimidinyl | 5-F | C | H | 2-amino-5-pyrimidinyl | 516 |
| 214 | cyclohexyl | H | N | H | 2-amino-5-pyrimidinyl | 503 |

-continued
| | | | | | | |
|---|---|---|---|---|---|---|
| 215 | 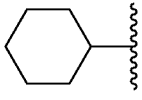 | H | N | H | 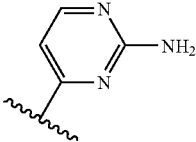 | 503 |
| 216 | (CH₃)₂CH— | H | N | H | 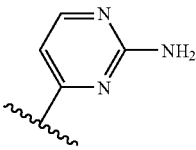 | 463 |
| 217 | 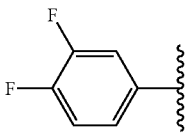 | 5-F | C | H | 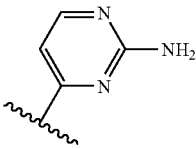 | 550 |
| 218 | 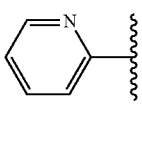 | 5-F | C | H | 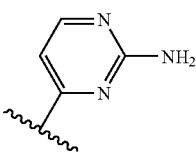 | 515 |
| 219 | 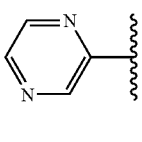 | 5-Cl | C | H | 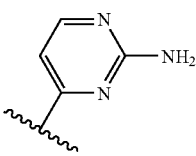 | 532 |
| 220 | 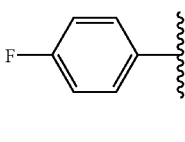 | 6-Cl | C | H | 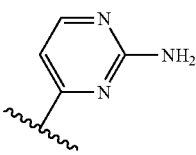 | 548 |
| 221 | 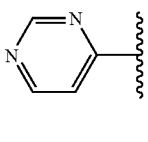 | 5-F | C | H | 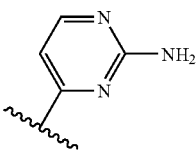 | 516 |
| 222 | 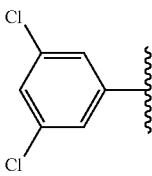 | 6-Cl | C | H | 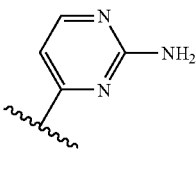 | 600 |
| 223 | 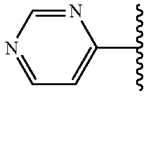 | 5-Cl | C | H | 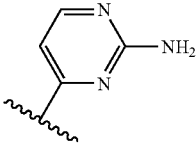 | 532 |
| 224 | 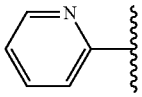 | 6-F | C | H | 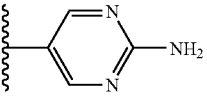 | 515 |

-continued
| | | | | | | |
|---|---|---|---|---|---|---|
| 225 | 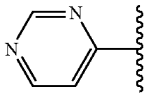 | H | N | H | 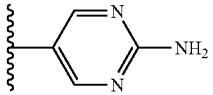 | 499 |
| 226 | 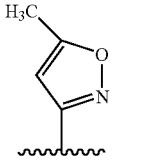 | H | N | H | 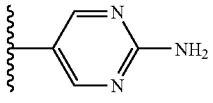 | 502 |
| 227 | 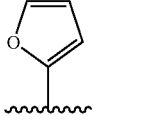 | H | N | H | 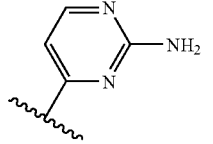 | 487 |
| 228 | 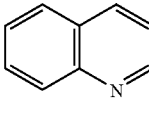 | H | N | H | 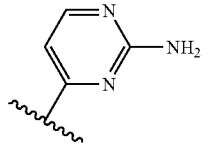 | 548 |
| 229 | 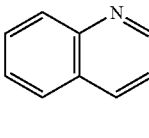 | H | N | H | 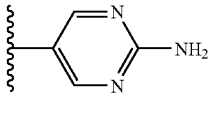 | 548 |
| 230 | 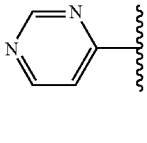 | H | N | H | 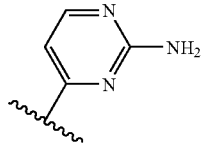 | 499 |
| 231 | 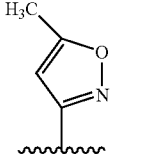 | H | N | H | 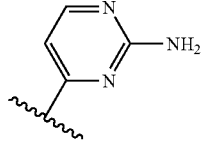 | 502 |
| 232 | 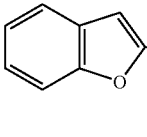 | H | N | H | 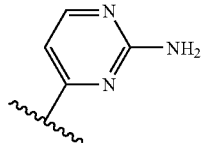 | 537 |
| 233 | 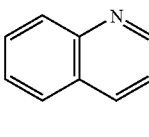 | H | N | H | 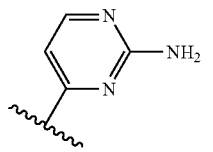 | 548 |
| 234 | 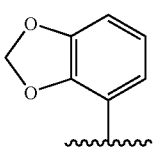 | H | N | H | 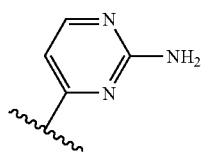 | 541 |

-continued

| | | | | | | |
|---|---|---|---|---|---|---|
| 235 | CH₃CH₂O— (3-position), F (5-position) phenyl | H | N | H | 5-(2-aminopyrimidinyl) | 559 |
| 236 | 2-pyridyl | H | N | H | 5-(2-aminopyrimidinyl) | 498 |
| 237 | 2-pyridyl | 5-F | C | F | 5-(2-aminopyrimidinyl) | 533 |
| 238 | 2,4-difluorophenyl | 5-F | C | H | 5-(2-aminopyrimidinyl) | 550 |
| 239 | 3,4-difluorophenyl | 5-F | C | H | 5-(2-aminopyrimidinyl) | 550 |
| 240 | 3-pyridyl | 5-F | C | H | 5-(2-aminopyrimidinyl) | 515 |
| 241 | 5-pyrimidinyl | 5-F | C | H | 5-(2-aminopyrimidinyl) | 516 |
| 242 | 2-pyridyl | H | C | H | 5-(2-aminopyrimidinyl) | 497 |
| 243 | (CH₃)₂N—CH₂— | H | N | H | 5-(2-aminopyrimidinyl) | 478 |
| 244 | 5-methylisoxazol-3-yl | 5-F | C | H | 5-(2-aminopyrimidinyl) | 519 |
| 245 | 5-methylisoxazol-3-yl | H | C | H | 5-(2-aminopyrimidinyl) | 501 |

-continued

| # | R1 | R2 | X | R3 | R4 | MW |
|---|----|----|---|----|----|----|
| 246 | 5-methyl-isoxazol-3-yl | 5,6-di-F | C | H | 2-amino-pyrimidin-5-yl | 537 |
| 247 | pyridin-2-yl | 5-F | C | H | pyrimidin-4-yl | 500 |
| 248 | pyrazin-2-yl | 5,6-di-F | C | H | 2-amino-pyrimidin-5-yl | 534 |
| 249 | 5-methyl-isoxazol-3-yl | 5-F | C | F | 2-amino-pyrimidin-5-yl | 537 |
| 250 | pyrazin-2-yl | 5-F | C | F | 2-amino-pyrimidin-5-yl | 534 |
| 251 | pyrimidin-4-yl | 5-F | C | F | 2-amino-pyrimidin-5-yl | 534 |
| 252 | pyridin-3-yl | 5-F | C | F | 2-amino-pyrimidin-5-yl | 533 |
| 253 | 3,4-difluorophenyl | 5-F | C | F | 2-amino-pyrimidin-5-yl | 568 |
| 254 | 2,4-difluorophenyl | 5-F | C | F | 2-amino-pyrimidin-5-yl | 568 |
| 255 | furan-3-yl | H | N | H | 2-amino-pyrimidin-5-yl | 487 |
| 256 | pyridin-2-yl | H | C | F | 2-amino-pyrimidin-5-yl | 515 |
| 257 | 5-methyl-isoxazol-3-yl | H | C | F | 2-amino-pyrimidin-5-yl | 519 |

-continued

| # | R1 | R2 | X | R3 | Y | MW |
|---|---|---|---|---|---|---|
| 258 | pyridin-3-yl | H | N | F | 5-(2-aminopyrimidinyl) | 516 |
| 259 | tetrahydropyran-4-yl | H | N | H | 5-(2-aminopyrimidinyl) | 505 |
| 260 | pyridin-2-yl | H | N | F | 5-(2-aminopyrimidinyl) | 516 |
| 261 | 5-methylisoxazol-3-yl | H | N | F | 5-(2-aminopyrimidinyl) | 520 |
| 262 | furan-3-yl | 5-F | C | H | 5-(2-aminopyrimidinyl) | 504 |
| 263 | tetrahydropyran-4-yl | 5-F | C | H | 5-(2-aminopyrimidinyl) | 522 |
| 264 | furan-2-yl | 5-F | C | H | 5-(2-aminopyrimidinyl) | 504 |
| 265 | benzofuran-2-yl | H | N | H | 5-(2-aminopyrimidinyl) | 537 |
| 266 | $(CH_3)_2N-CH_2-$ | H | N | F | 5-(2-aminopyrimidinyl) | 496 |
| 267 | furan-2-yl | H | N | F | 5-(2-aminopyrimidinyl) | 505 |
| 268 | $CH_3CH_2-O-$ | 5-F | C | H | 5-(2-aminopyrimidinyl) | 482 |
| 269 | $CH_3-S-$ | 5-F | C | H | 5-(2-aminopyrimidinyl) | 484 |
| 270 | $CH_3CH_2-O-$ | 5-F | C | F | 5-(2-aminopyrimidinyl) | 500 |

| | | | | | | |
|---|---|---|---|---|---|---|
| 271 | benzofuran-2-yl | H | N | F | 5-(2-aminopyrimidinyl) | 555 |
| 272 | quinolin-3-yl | H | N | F | 5-(2-aminopyrimidinyl) | 566 |
| 273 | pyridin-3-yl | H | N | H | 5-(2-aminopyrimidinyl) | 498 |
| 274 | pyridin-2-yl | 5,6-di-F | C | F | 5-(2-aminopyrimidinyl) | 551 |
| 275 | morpholin-4-yl | 5-F | C | F | 5-(2-aminopyrimidinyl) | 541 |
| 276 | morpholin-4-yl | 5-F | C | H | 5-(2-aminopyrimidinyl) | 523 |
| 277 | pyridin-2-yl | 5-F | C | H | 2-aminopyridin-5-yl | 514 |
| 278 | pyridin-2-yl | 5-F | C | H | imidazo[4,5-b]pyridin-7-yl | 539 |
| 279 | 2,5-dimethylfuran-3-yl | H | N | H | 5-(2-aminopyrimidinyl) | 515 |
| 280 | 3-methylfuran-2-yl | H | N | H | 5-(2-aminopyrimidinyl) | 501 |
| 281 | furan-3-yl | H | N | F | 5-(2-aminopyrimidinyl) | 505 |
| 282 | indol-2-yl | H | N | H | 5-(2-aminopyrimidinyl) | 536 |

-continued

| | | | | | | |
|---|---|---|---|---|---|---|
| 283 | tetrahydropyran-4-yl | H | N | F | 5-(2-aminopyrimidin-5-yl) | 523 |
| 284 | pyridin-2-yl | 5-F | C | F | 6-amino-pyridin-3-yl | 532 |
| 285 | 5-methylfuran-3-yl | H | N | H | 5-(2-aminopyrimidin-5-yl) | 501 |
| 286 | 2,4-difluorophenyl | H | N | H | 5-(2-aminopyrimidin-5-yl) | 533 |
| 287 | pyrimidin-4-yl | H | N | F | 5-(2-aminopyrimidin-5-yl) | 517 |
| 288 | quinolin-2-yl | H | N | H | 5-(2-aminopyrimidin-5-yl) | 548 |
| 289 | 3,4-difluorophenyl | H | N | H | 5-(2-aminopyrimidin-5-yl) | 533 |
| 290 | CH₃S— | 5-F | C | F | 5-(2-aminopyrimidin-5-yl) | 502 |
| 291 | pyridin-2-yl | H | N | F | 5-(2-aminopyridin-5-yl) | 515 |
| 292 | pyridin-2-yl | 5-F | C | F | 5-(2-aminopyridin-5-yl) | 532 |
| 293 | pyridin-2-yl | 5-F | C | H | 5-(2-aminopyrimidin-5-yl) | 514 |
| 294 | pyridin-2-yl | H | N | H | 5-(2-aminopyridin-5-yl) | 497 |

-continued
| | | | | | | |
|---|---|---|---|---|---|---|
| 295 | (CH₃)₂N— | 5-F | C | F | 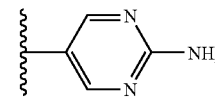 | 499 |
| 296 | CH₃CH₂—S— | 5-F | C | F | 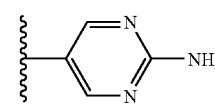 | 516 |
| 297 | CH₃—O— | 5-F | C | F | 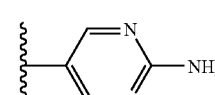 | 486 |
| 298 | 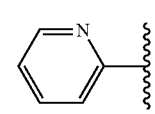 | H | N | H | 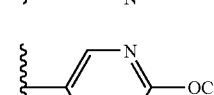 | 512 |
| 299 | 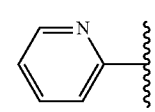 | H | N | F | 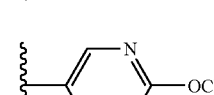 | 530 |
| 300 | 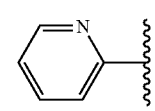 | 5-F | C | F | 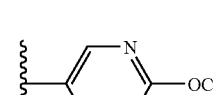 | 547 |
| 301 | 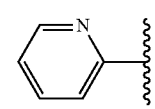 | 5-F | C | H | 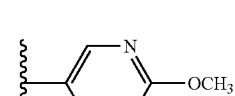 | 529 |
| 302 | 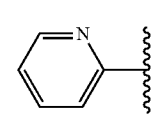 | 5-F | C | H | 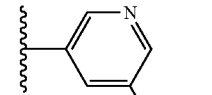 | 517 |
| 303 | 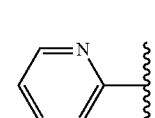 | 5-F | C | F | 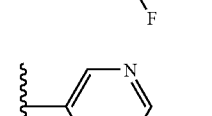 | 535 |
| 304 | 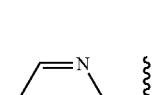 | H | N | H | 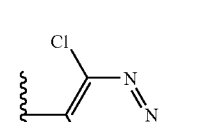 | 551 |
| 305 | 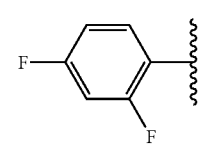 | H | N | F | 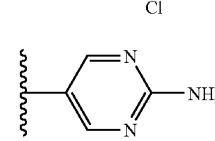 | 551 |
| 306 | 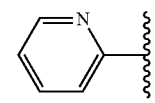 | 5-F | C | H | 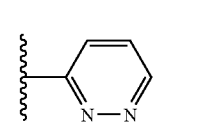 | 500 |

-continued
| | | | | | | |
|---|---|---|---|---|---|---|
| 307 | 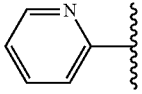 | 5-F | C | H | 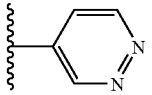 | 500 |
| 308 | 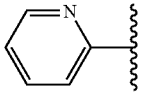 | 5-F | C | F | 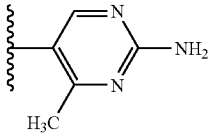 | 547 |
| 309 | (CH₃CH₂)₂N— | 5-F | C | F | 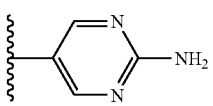 | 527 |
| 310 | 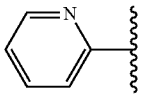 | H | N | H | 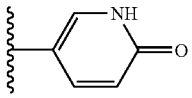 | 498 |
| 311 | 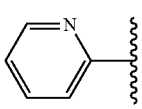 | H | N | F | 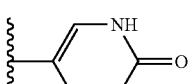 | 516 |
| 312 | 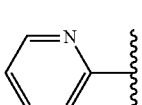 | 5-F | C | H | 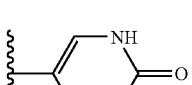 | 515 |
| 313 | 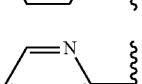 | 5-F | C | F | 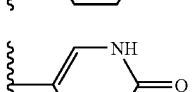 | 533 |
| 314 | 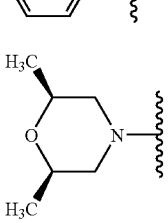 | 5-F | C | F | 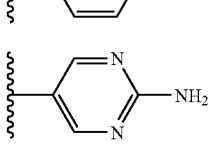 | 569 |
| 315 | CH₃—S— | H | N | F | 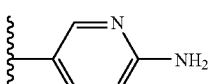 | 485 |
| 316 | CH₃CH₂—O— | H | N | F | 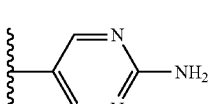 | 483 |
| 317 | 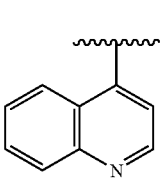 | H | N | F | 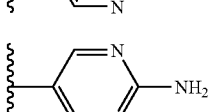 | 566 |
| 318 | 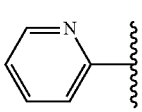 | H | N | F | 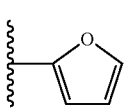 | 489 |
| 319 | 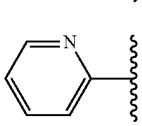 | H | N | F | 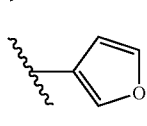 | 489 |

-continued

| | | | | | | |
|---|---|---|---|---|---|---|
| 320 | 2-pyridyl | H | N | F | 2-thienyl | 505 |
| 321 | 2-pyridyl | H | N | F | 3-thienyl | 505 |
| 322 | 2-pyridyl | 5-F | C | F | 4-amino-pyrimidin-6-yl | 533 |
| 323 | 2-pyridyl | H | N | F | 4-amino-pyrimidin-6-yl | 516 |
| 325 | 2,4-difluorophenyl | H | N | F | 3-thienyl | 540 |
| 325 | morpholin-4-yl | H | N | F | 2-amino-pyrimidin-5-yl | 524 |
| 326 | (CH$_3$)$_2$CH—O— | 5-F | C | F | 2-amino-pyrimidin-5-yl | 514 |
| 327 | 2-pyridyl | H | N | F | thiazol-2-yl | 506 |
| 328 | 2-pyridyl | H | N | F | 2-pyrrolyl | 488 |
| 329 | 2-pyridyl | H | N | F | pyrazol-3-yl | 489 |
| 330 | 2-pyridyl | H | N | F | thiadiazol-4-yl | 507 |
| 331 | 2-pyridyl | H | N | F | 5-(methylthio)thien-2-yl | 551 |
| 332 | 2-pyridyl | H | N | F | thiazol-4-yl | 506 |

-continued
| | | | | | | |
|---|---|---|---|---|---|---|
| 333 | 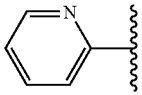 | H | N | F | 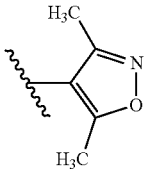 | 518 |
| 334 | 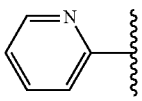 | H | N | F | 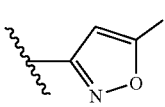 | 504 |
| 335 | CH₃—O— | H | N | F | 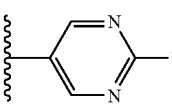 | 464 |
| 336 | 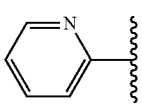 | H | N | F | 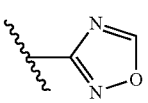 | 491 |
| 337 | 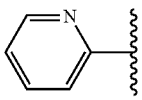 | H | N | F | 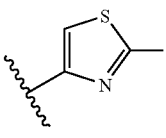 | 563 |
| 338 | 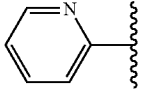 | 5-F | C | H | 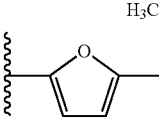 | 545 |
| 339 | 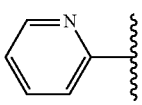 | 5-F | C | F | 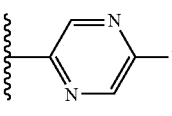 | 533 |
| 340 | 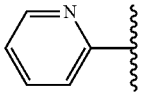 | H | N | F | 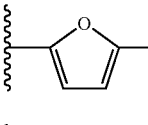 | 518 |
| 341 | 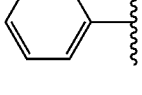 | 5-F | C | H | 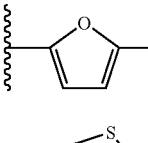 | 535 |
| 342 | 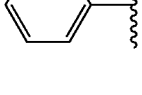 | H | N | F | 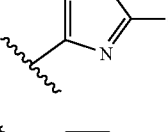 | 520 |
| 343 | 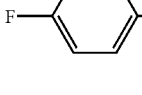 | 6-Cl | C | H | 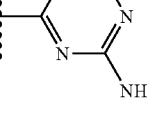 | 548 |
| 345 | 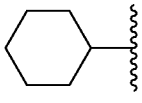 | H | N | H | 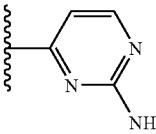 | 503 |

-continued
| 346 | (CH₃)₂—CH— | H | N H | 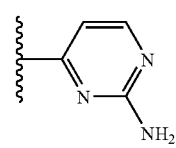 | 463 |
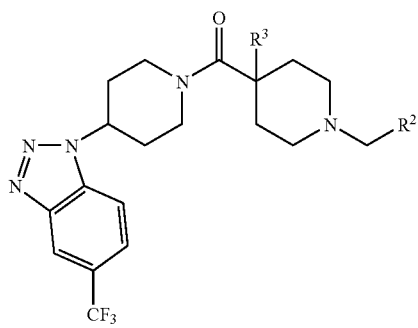
| No. | R³ | R² | Physical Data MS (MH⁺) |
|-----|----|----|------------------------|
| 347 | H | 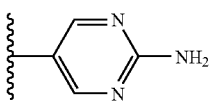 | 489 |
| 348 | F | 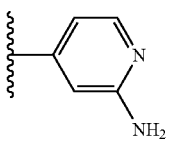 | 506 |
| 349 | F | 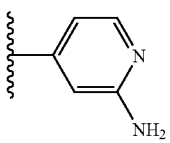 | 488 |
| 350 | F | 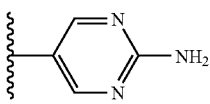 | 507 |
| 351 | F | 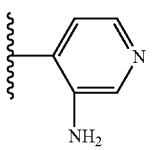 | 506 |

-continued

| No. | R¹—X— | Z | R³ | R² | Physical Data MS (MH⁺) |
|---|---|---|---|---|---|
| 352 | 2-phenyl-benzimidazol-1-yl-CH₂– | —CH₂— | H | 2-aminopyridin-4-yl | 509 |
| 353 | 2-(pyridin-2-yl)-benzimidazol-1-yl-CH₂– | —CH₂— | H | 2-aminopyridin-4-yl | 510 |
| 354 | 2-benzyl-benzimidazol-1-yl-CH₂– | —CH₂— | H | 2-aminopyridin-4-yl | 523 |
| 355 | 4,6-difluoro-1-(pyridin-2-yl)-benzimidazol-2-yl– | —CH₂— | H | 2-aminopyridin-4-yl | 532 |
| 356 | 1-(pyridin-2-yl)-benzimidazol-2-yl– | —CH₂— | H | 2-aminopyridin-4-yl | 496 |
| 357 | [1-(2-propoxyethyl)-benzimidazol-2-yl]-NH– | —CH₂— | H | 2-aminopyridin-4-yl | 506 |

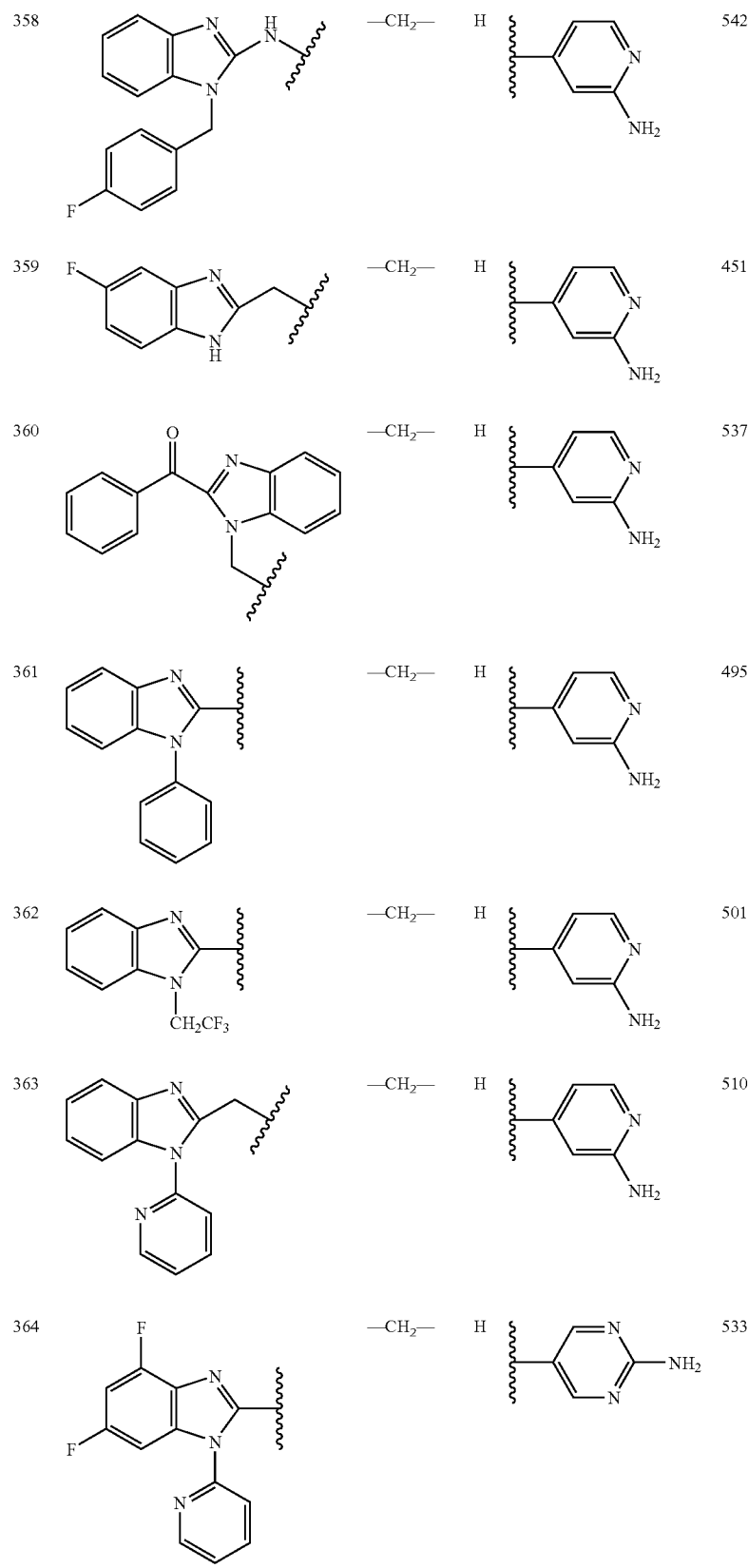

-continued

| | | | | | |
|---|---|---|---|---|---|
| 365 | imidazo[4,5-b]pyridin-2-yl | —CH₂— | H | 4-(2-aminopyridyl) | 420 |
| 366 | 5-methoxy-1H-benzimidazol-2-yl | —CH₂— | H | 4-(2-aminopyridyl) | 449 |
| 367 | 1-(2-pyridyl)-1H-benzimidazol-2-ylmethyl | —CH₂— | H | 5-(2-aminopyrimidyl) | 497 |
| 368 | 5-fluoro-1-(2,2,2-trifluoroethyl)-1H-benzimidazol-2-ylmethyl | —CH₂— | H | 4-(2-aminopyridyl) | 533 |
| 369 | 5,6-dichloro-1H-benzimidazol-2-yl | —CH₂— | H | 4-(2-aminopyridyl) | 487 |
| 370 | 1-phenyl-1H-benzimidazol-2-ylmethyl | —CH₂— | H | 4-(2-aminopyridyl) | 509 |
| 371 | 1H-benzimidazol-1-ylmethyl | —CH₂— | H | 4-(2-aminopyridyl) | 433 |
| 372 | 5-trifluoromethylbenzothiazol-2-yl | —CH₂— | H | 4-(2-aminopyridyl) | 504 |
| 373 | benzothiazol-2-yl | —CH₂— | H | 5-(2-aminopyridyl) | 436 |

-continued
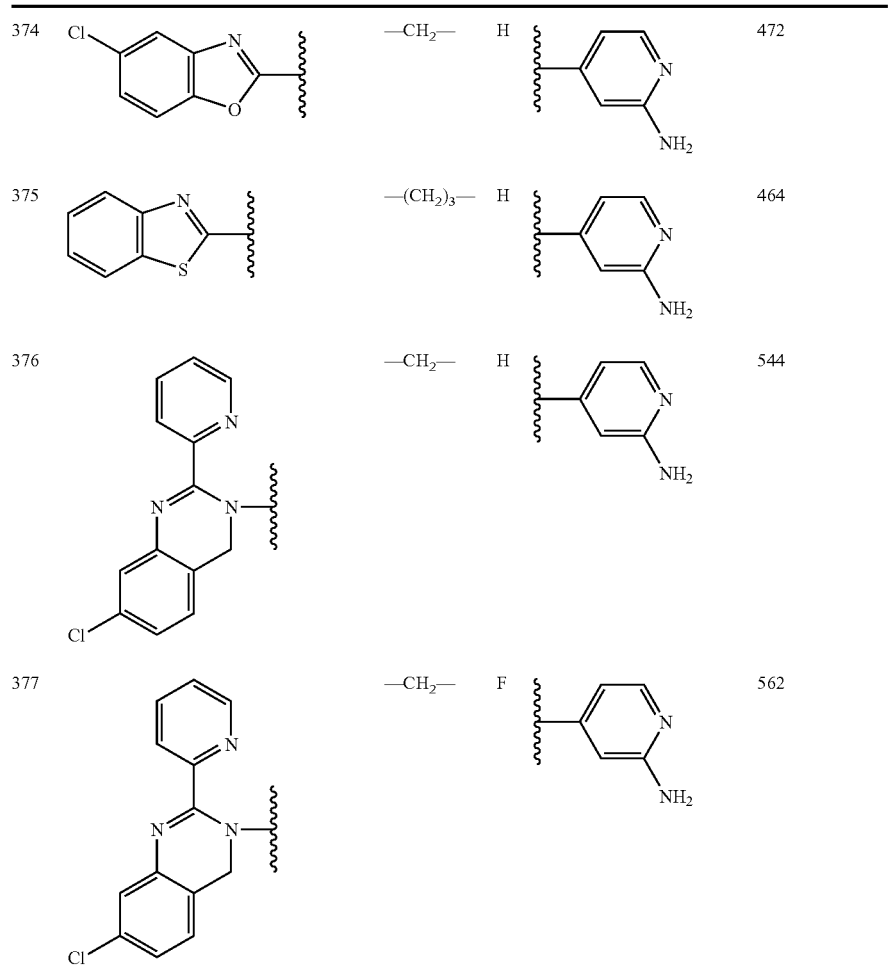
| No. | R | M¹ | Y | R² | Physical Data MS (MH⁺) |
|---|---|---|---|---|---|
| 378 | 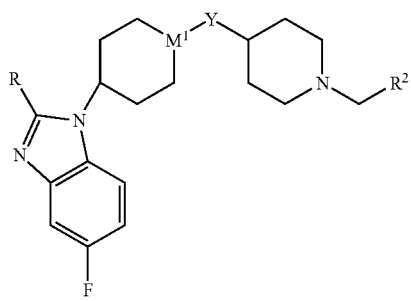 | CH | —CH₂— | (4-aminopyridin-4-yl) | 500 |
| 379 | (pyrimidin-5-yl) | N | —NH— | (2-aminopyrimidin-5-yl) | 502 |

| | | | | | |
|---|---|---|---|---|---|
| 380 | 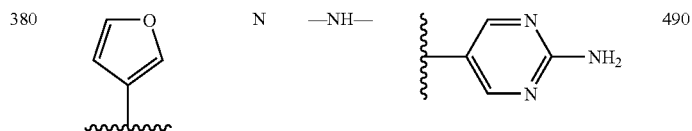 | N | —NH— | 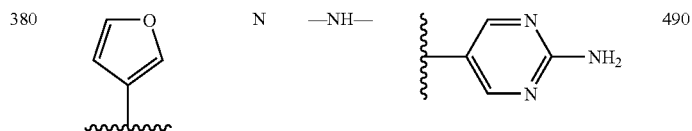 | 490 |
| 381 |  | N | —NH— |  | 494 |
| 382 | 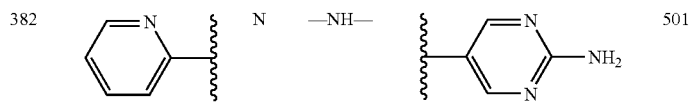 | N | —NH— | 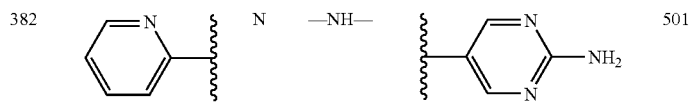 | 501 |
| 383 | 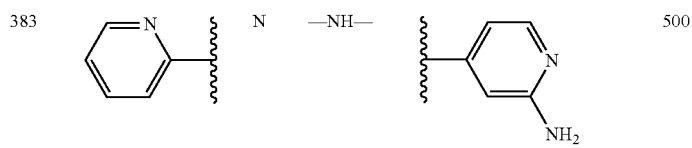 | N | —NH— | 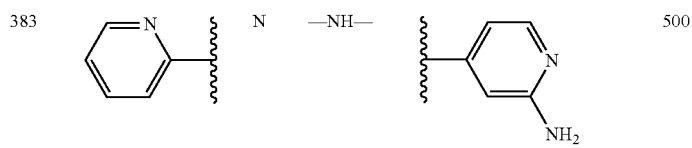 | 500 |
384: 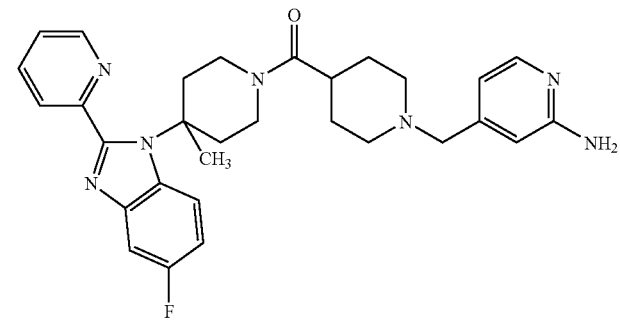 MS: 528 (MH+)
385: 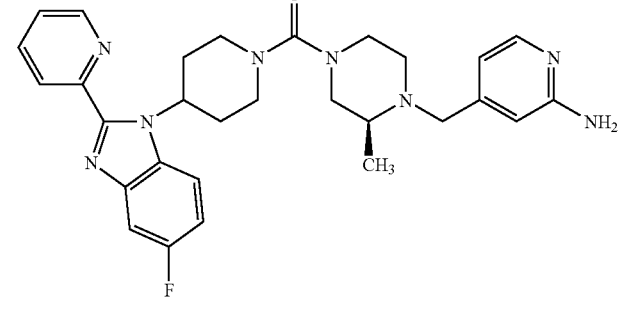 MS: 385 (MH+)
386: 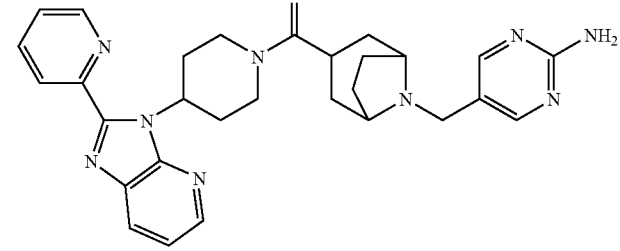 MS: 529 (MH+)

387:

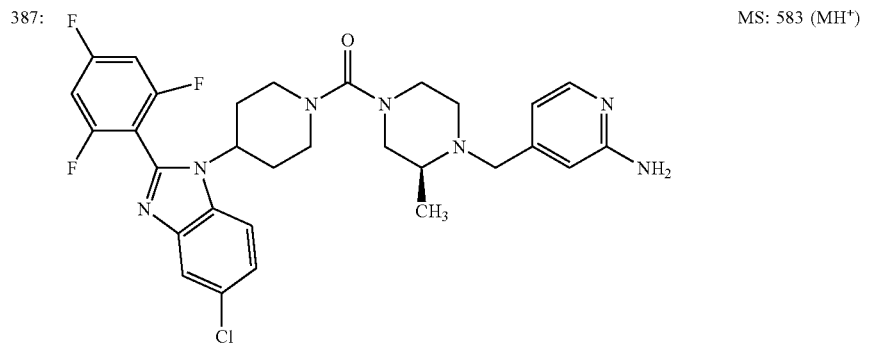

MS: 583 (MH+)

EXAMPLE 388

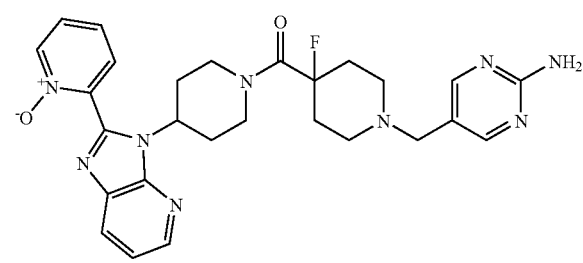

Step 1:

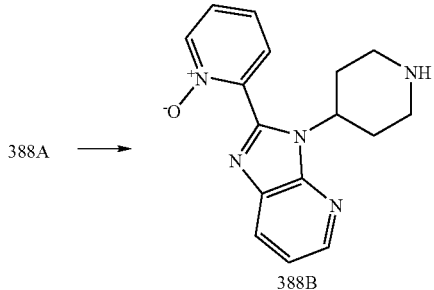

A solution of P7-1 (2.3 g, 8.9 mmol) in CH₂Cl₂-DMF (1:1, 50 ml) was treated with picolinic acid N-oxide (1.5 g, 10.6 mmol), EDCI (2.6 g, 13.3 mmol) and HOBT (1.8 g, 13.3 mmol). The mixture was stirred at 70° C. overnight. The reaction mixture was concentrated, diluted with EtOAc, washed three times with 5% aqueous NaOH, dried over Na₂SO₄, and concentrated. Flash chromatography (50% EtOAc/hexane) provided 388A (2.5 g, 74%).

Step 2:

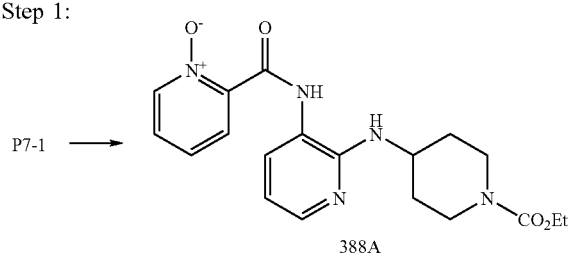

In a manner similar to that described in Preparation 5, Step 4, compound 388A was converted to compound 388B.

Step 3:

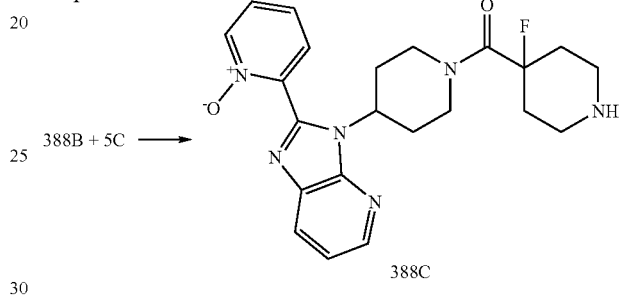

A solution of 388B (0.66 g, 2.2 mmol) in DMF (15 ml) was treated with 5C (0.62 g, 2.5 mmol), 1-propanephosphonic acid cyclic anhydride (3.3 ml, 11.2 mmol, 50 wt. % in EtOAc) and N-ethylmorpholine (1.4 ml, 10.7 mmol). The mixture was stirred at 50° C. for 3 h. The reaction mixture was concentrated and diluted with EtOAc. The solution was washed three times with 5% aqueous NaOH, dried over Na₂SO₄, concentrated and subjected to flash chromatography (10% 2N NH₃—CH₃OH/EtOAc). The material was then taken up in CH₂Cl₂ (20 ml) and treated with 4 M HCl-dioxane (4 ml). After stirring overnight at 20° C., the reaction was carefully basified with 10% aqueous NaOH and extracted with CH₂Cl₂. The combined organic layers were dried over Na₂SO₄, concentrated and subjected to flash chromatography (30% 2N NH₃—CH₃OH/EtOAc) to provide 388C as a white solid (0.08 g, 10%).

Step 4:

In a manner similar to that described in Example 5, Step 5, compound 388C was converted to Example 388.

EXAMPLE 389

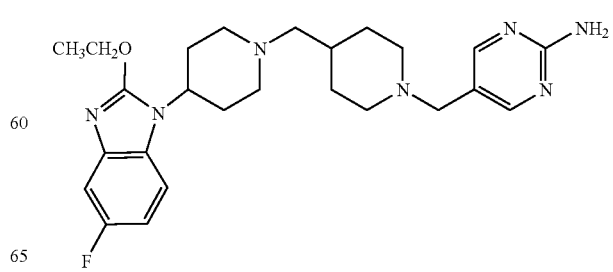

Step 1:

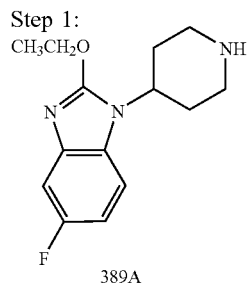

389A

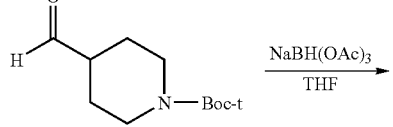

389B

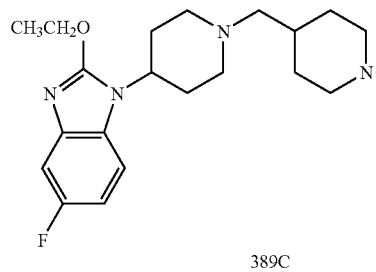

389C

To a stirred, cloudy solution of 389A (300 mg, 1.14 mmol) in THF (15 ml) were added a solution of 389B (292 mg, 1.37 mmol) in THF (1 ml), followed by NaBH(OAc)₃ (483 mg, 2.28 mmol). After stirring at RT for 39 h, TLC revealed the presence of unchanged starting materials in the cloudy white reaction suspension. Therefore, another quantity of NaBH(OAc)₃ (242 mg, 1.14 mmol) was added and stirring at RT continued for a total of 113 h. The reaction mixture was then filtered and collected solids washed thoroughly with CH₂Cl₂. The combined filtrate and washings were stripped of solvent under vacuum, and the residue was partitioned between EtOAc (60 ml) and a solution consisting of water (2.5 ml), 2M Na₂CO₃ (6.5 ml) and 6N NaOH (5 ml). The aqueous layer was further extracted with EtOAc (3×15 ml). The combined extracts were washed with brine (5 ml) and dried over anhydrous MgSO₄. Drying agent was removed by filtration, and the filtrate was concentrated under vacuum. The residue was purified by silica gel flash chromatography (EtOAc/hexanes=1:1) to obtain 389C as a mixture of colorless gum and white foam (368 mg, 70%), homogeneous to TLC, which solidified upon standing. ES-MS: 461 (MH$^+$; 100%).

Step 2:

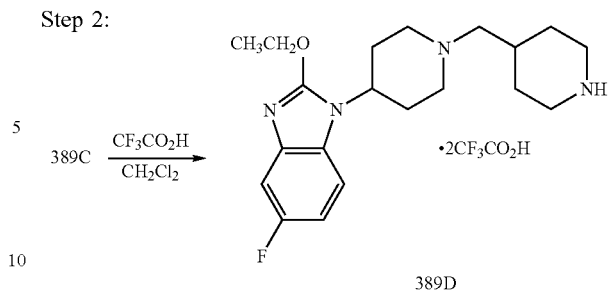

389D

To a stirred, ice-cold solution of 389C (358 mg, 0.777 ml) in CH₂Cl₂ (7 ml) was added via syringe cold, neat TFA (576 microliters, 886 mg, 7.77 mmol). The resultant solution was stirred in an ice-water bath for 30 min, then at RT for 29.5 h. Volatiles were removed under vacuum, and the gummy residue was triturated (magnetic stirrer) with Et₂O (35 ml) for 16 h. Filtration and washing with Et₂O yielded the bis-trifluoroacetate salt of 389D as a white powder (449 mg, 98%).

Step 3:

To a stirred suspension of 389D (100 mg, 0.170 mmol) in CH₂Cl₂ (5 ml) was added Et₃N (47.4 microliters, 34.4 mg, 0.340 mmol), whereupon all solids dissolved. To the stirred solution were then added 5G (25.1 mg, 0.204 mmol), followed by NaBH(OAc)₃ (72.1 mg, 0.340 mmol). After stirring at RT for 66 h, TLC revealed the presence of unchanged starting materials in the light yellow reaction suspension. Therefore, another quantity of NaBH(OAc)₃ (72.1 mg, 0.340 mmol) was added and stirring at RT continued for a total of 90 h. The reaction mixture was then filtered and collected solids washed thoroughly with CH₂Cl₂. The combined filtrate and washings were stripped of solvent under vacuum, and the residue was partitioned between EtOAc (20 ml) and a solution consisting of water (0.6 ml), 2M Na₂CO₃ (1.5 ml) and 6N NaOH (1.2 ml). The aqueous layer was further extracted with EtOAc (3×5 ml). The combined extracts were washed with brine (2 ml) and dried over anhydrous MgSO₄. Drying agent was removed by filtration, and the filtrate was concentrated under vacuum. The residue was purified by preparative TLC (silica gel; CH₂Cl₂/CH₃OH/conc. NH₄OH=90:9:1) to obtain the title compound as a light beige foam (36 mg, 45%). FABMS: 468 (MH$^+$; 100%).

Using procedures similar to those described above in Examples 1–6 and 388–389, following compounds were prepared:

| Ex. | Structure | Mass Spec (M + H) |
|---|---|---|
| 390 | 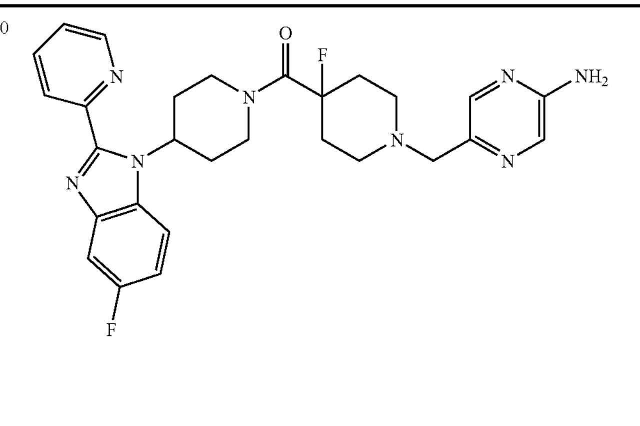 | 533 (ESMS) |

-continued

| Ex. | Structure | Mass Spec (M + H) |
|---|---|---|
| 391 | 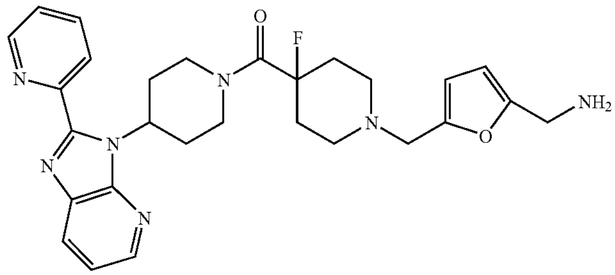 | 518 (ESMS) |
| 392 | 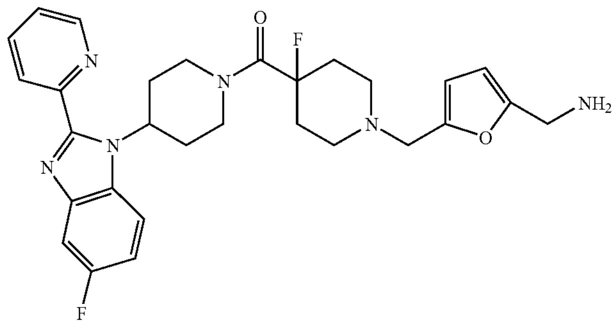 | 535 (ESMS) |
| 393 | 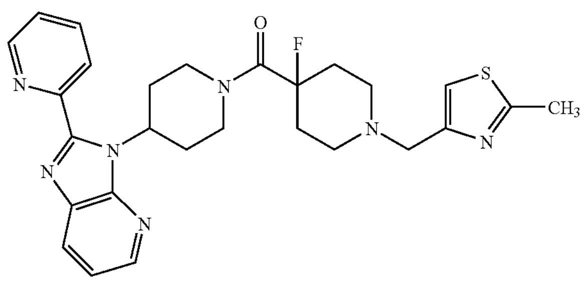 | 520 (ESMS) |
| 394 | 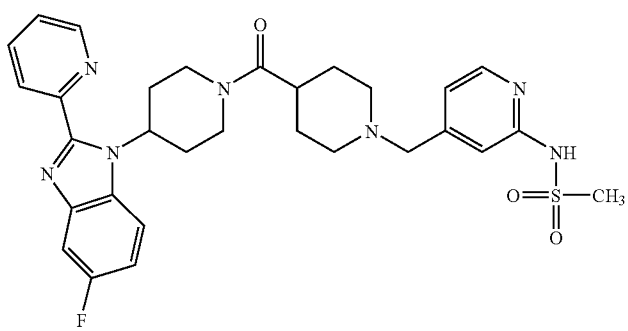 | 592 (FAB) |
| 395 | 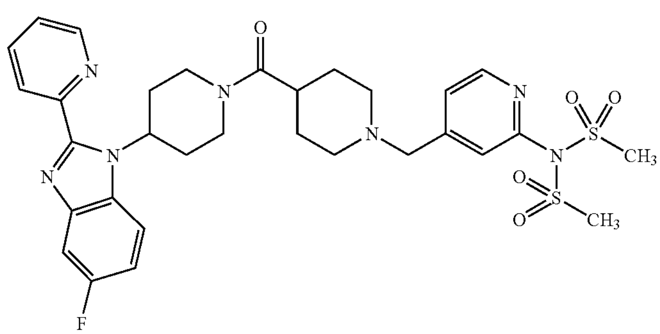 | 670 (FAB) |

| Ex. | Structure | Mass Spec (M + H) |
|---|---|---|
| 396 | 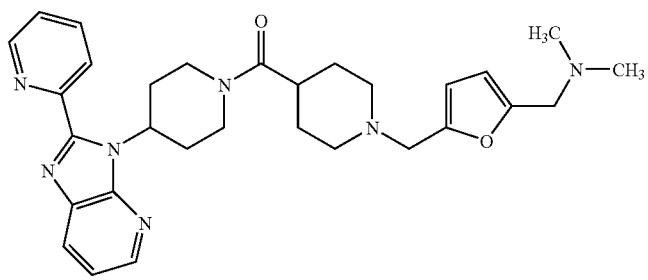 | 528 (ESMS) |
| 397 | 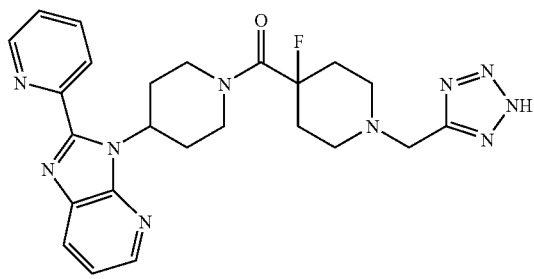 | 491 (ESMS) |
| 398 | 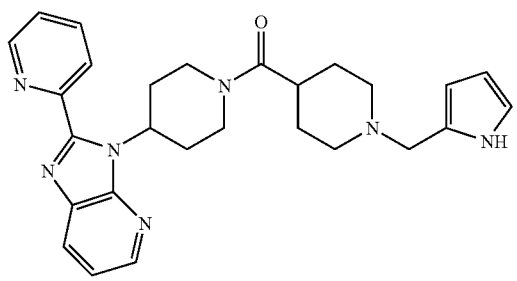 | 470 (ESMS) |
| 399 | 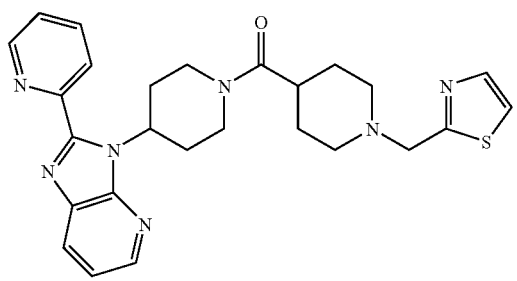 | 488 (ESMS) |
| 400 | 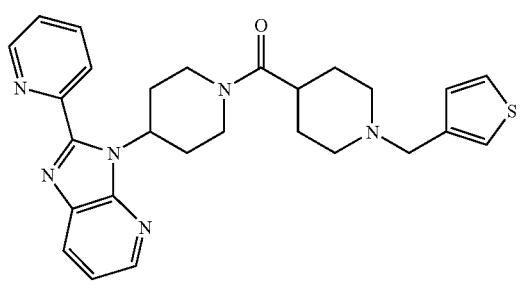 | 487 (ESMS) |

-continued
| Ex. | Structure | Mass Spec (M + H) |
|---|---|---|
| 401 | 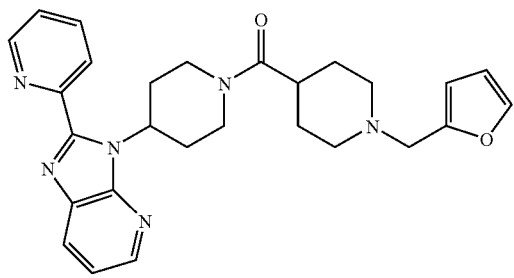 | 471 (ESMS) |
| 402 | 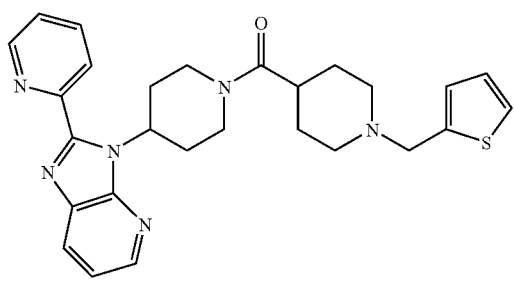 | 487 (ESMS) |
| 403 | 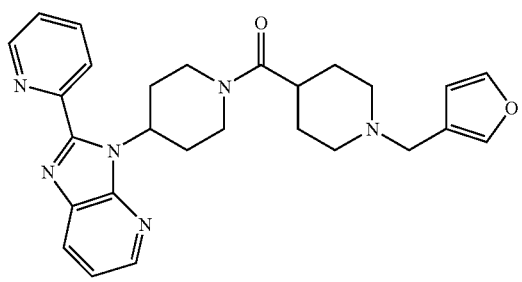 | 471 (ESMS) |
| 404 | 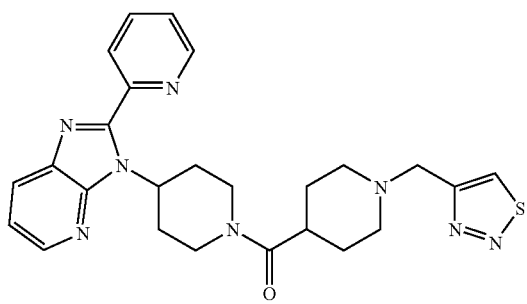 | 489 (ESMS) |
| 405 | 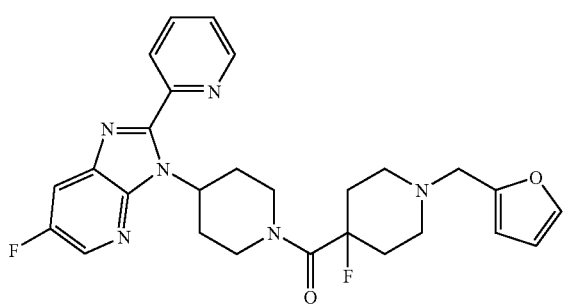 | 506 (ESMS) |

| Ex. | Structure | Mass Spec (M + H) |
|---|---|---|
| 406 | 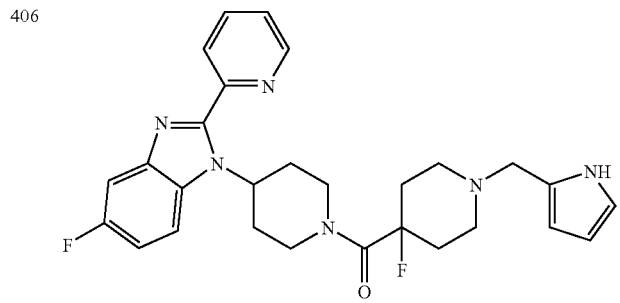 | 505 (ESMS) |
| 407 | 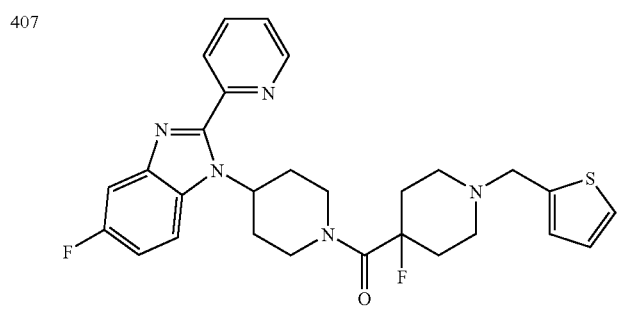 | 522 (ESMS) |
| 408 | 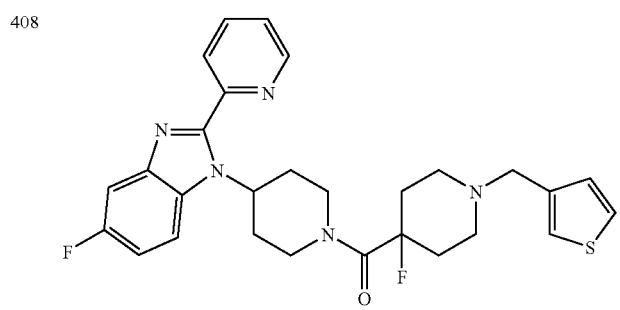 | 522 (ESMS) |
| 409 | 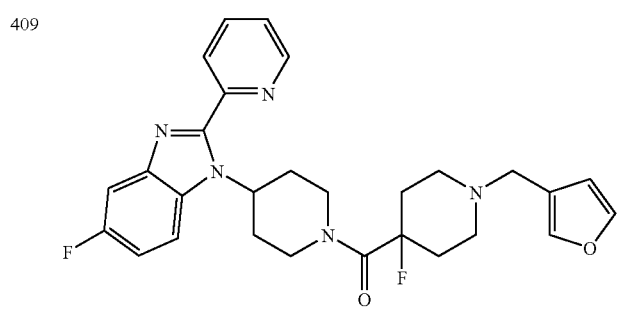 | 506 (ESMS) |
| 410 | 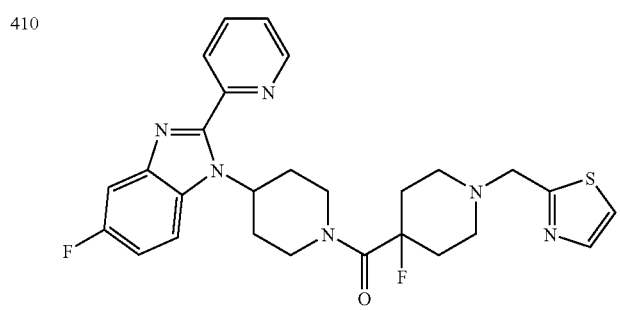 | 523 (ESMS) |

| Ex. | Structure | Mass Spec (M + H) |
|---|---|---|
| 411 | 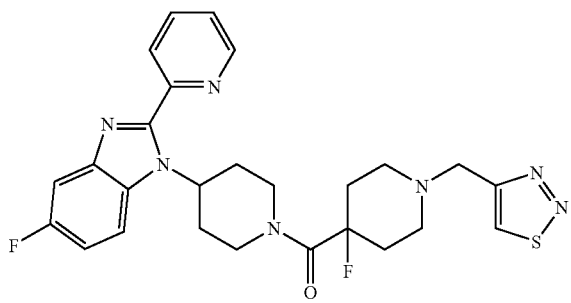 | 524 (ESMS) |
| 412 | 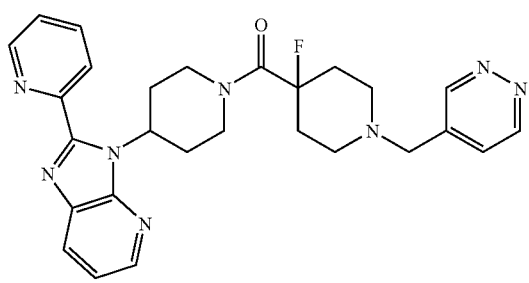 | 501 (ESMS) |
| 413 | 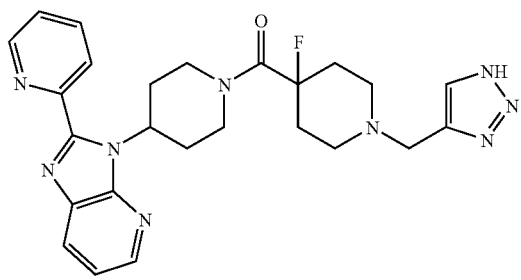 | 490 (ESMS) |
| 414 | 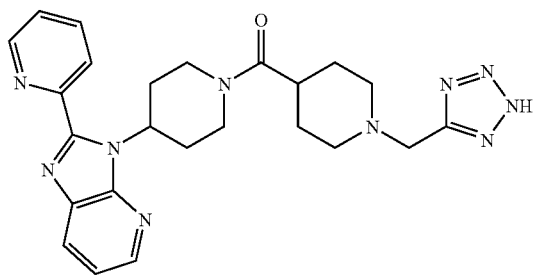 | 473 (ESMS) |
| 415 | 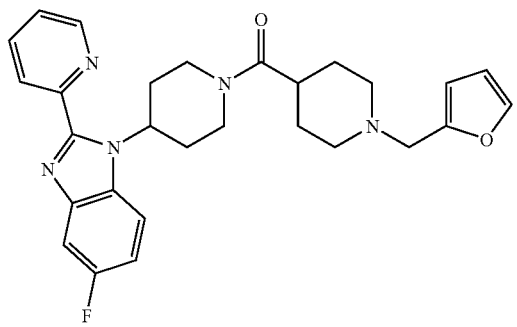 | 488 (ESMS) |

| Ex. | Structure | Mass Spec (M + H) |
|---|---|---|
| 416 | 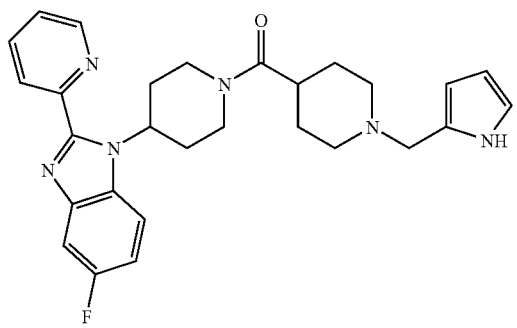 | 487 (ESMS) |
| 417 | 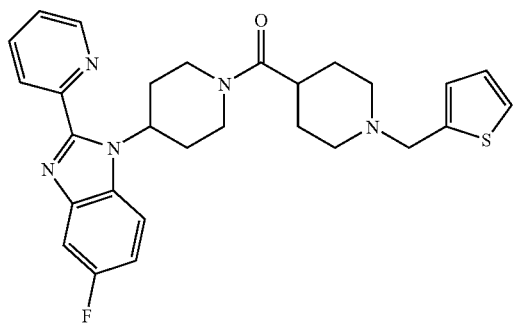 | 504 (ESMS) |
| 418 | 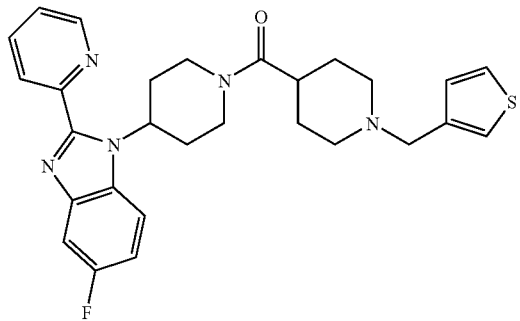 | 504 (ESMS) |
| 419 | 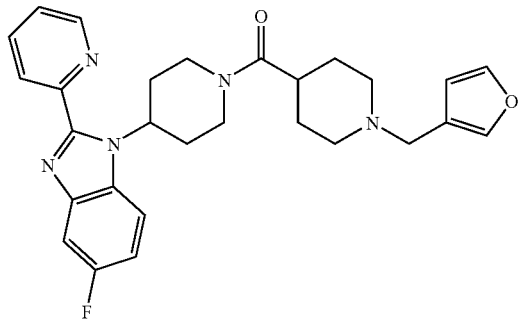 | 488 (ESMS) |

-continued
| Ex. | Structure | Mass Spec (M + H) |
|---|---|---|
| 420 | 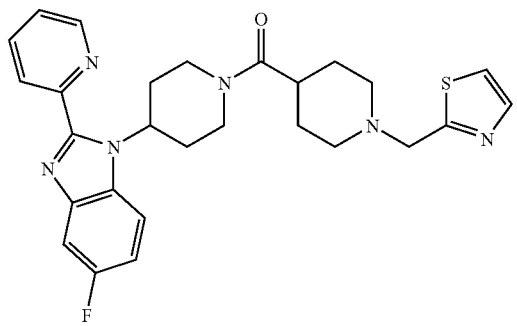 | 505 (ESMS) |
| 421 | 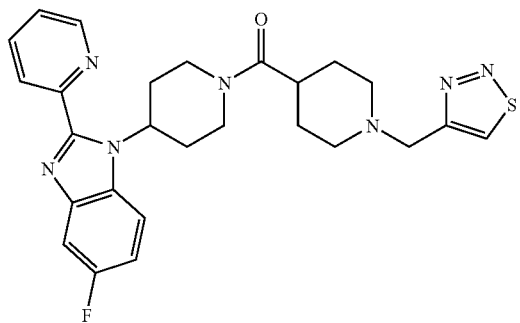 | 506 (ESMS) |
| 422 | 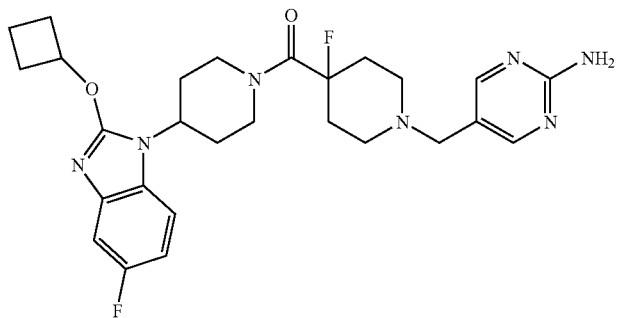 | 526 (FAB) |
| 423 | 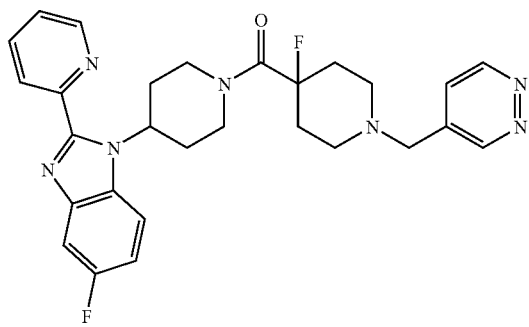 | 518 (ESMS) |

| Ex. | Structure | Mass Spec (M + H) |
|---|---|---|
| 424 | 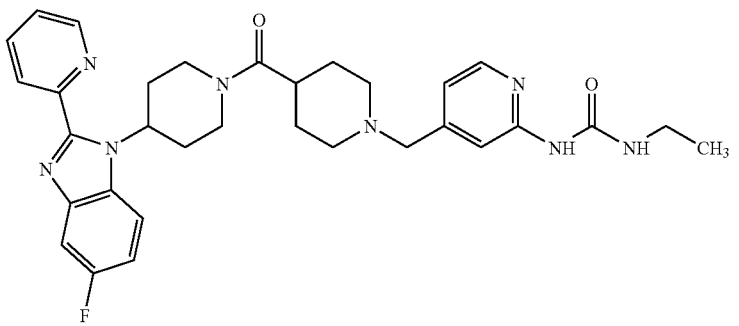 | 585 (FAB) |
| 425 | 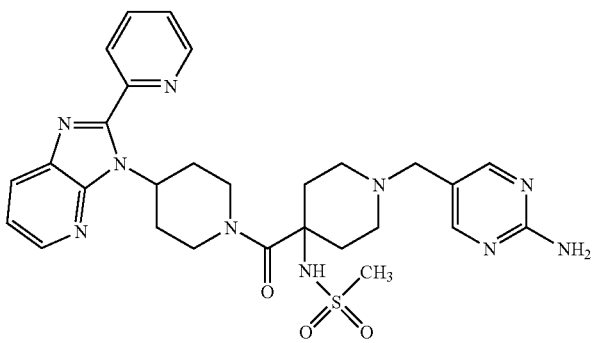 | 591 (ESMS) |
| 426 | 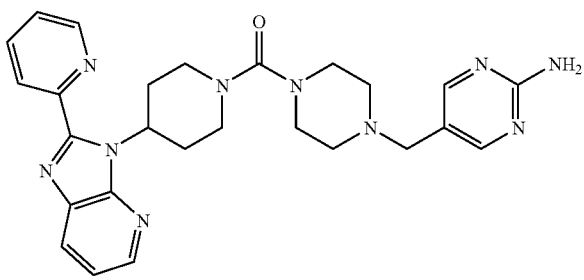 | 499 (ESMS) |
| 427 | 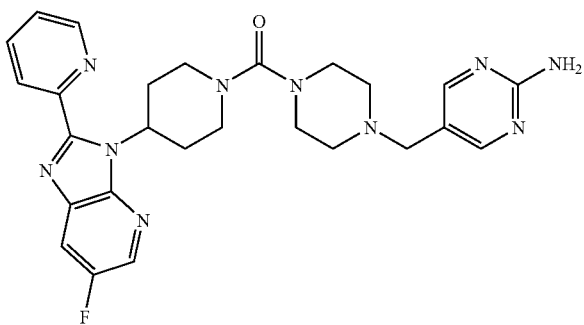 | 516 (ESMS) |

| Ex. | Structure | Mass Spec (M + H) |
|---|---|---|
| 428 | 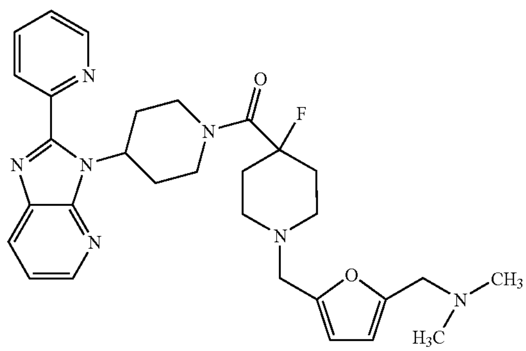 | 546 (ESMS) |
| 429 | 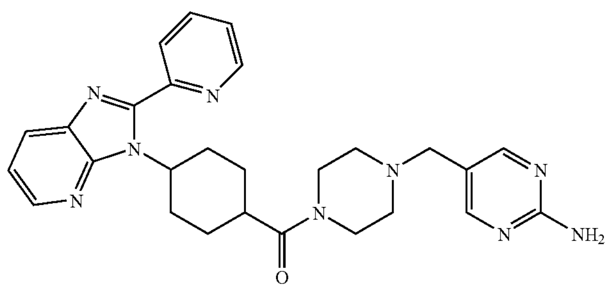 | 498 (ESMS) |
| 430 | 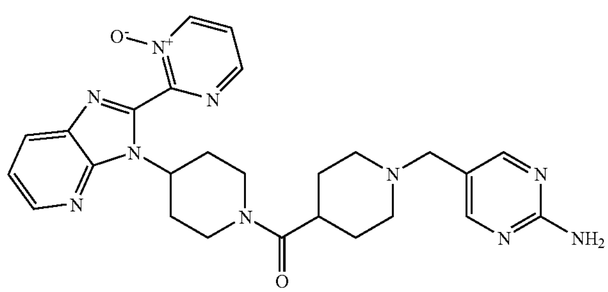 | 514 (ESMS) |
| 431 | 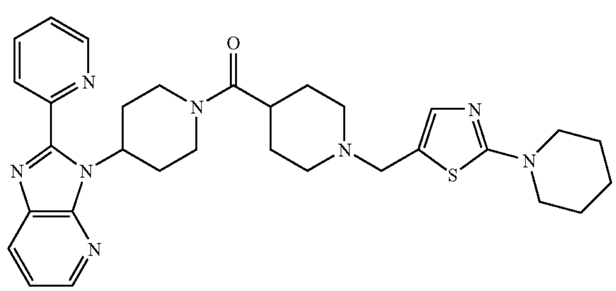 | 571 (ESMS) |
| 432 | 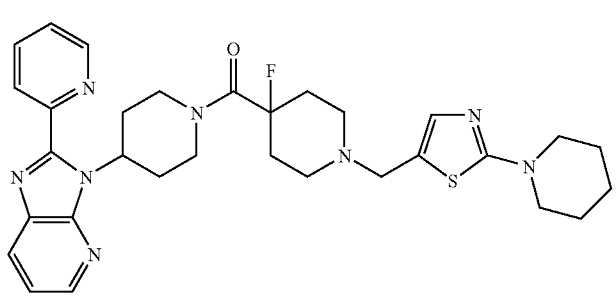 | 589 (ESMS) |

| Ex. | Structure | Mass Spec (M + H) |
|---|---|---|
| 433 | 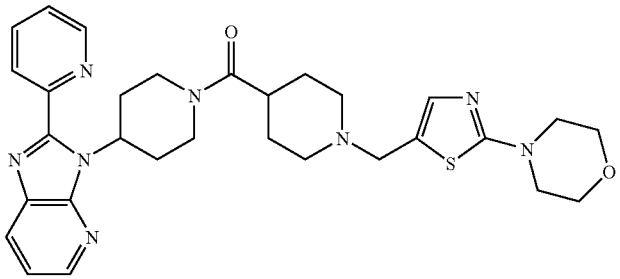 | 573 (ESMS) |
| 434 | 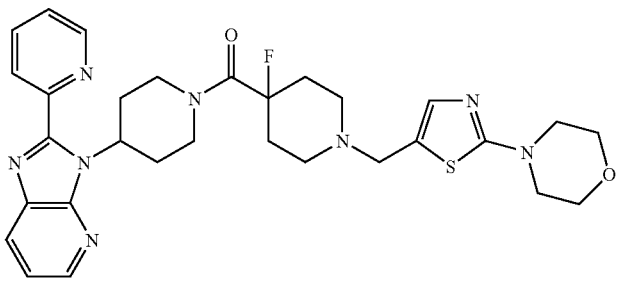 | 591 (ESMS) |
| 435 | 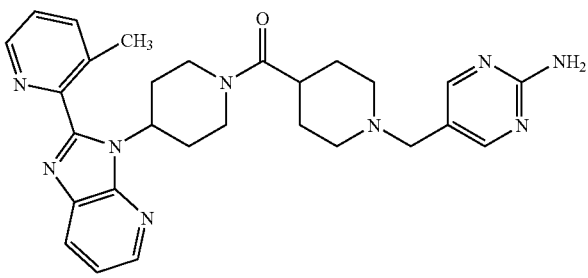 | 512 (ESMS) |
| 436 | 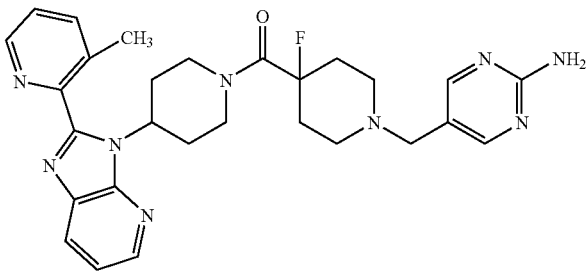 | 530 (ESMS) |
| 437 | 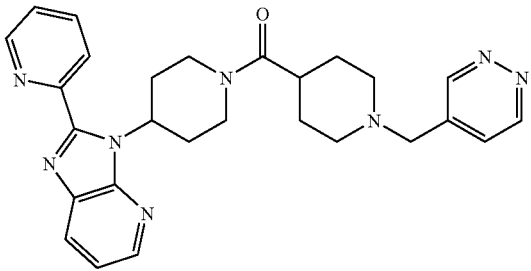 | 483 (ESMS) |

| Ex. | Structure | Mass Spec (M + H) |
|---|---|---|
| 438 | 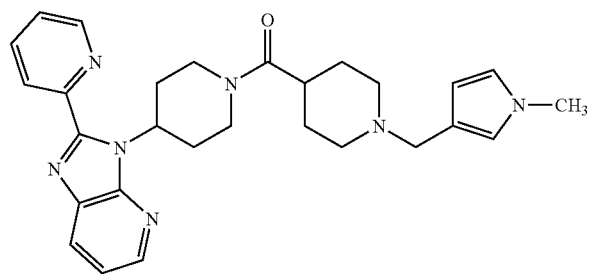 | 484 (ESMS) |
| 439 | 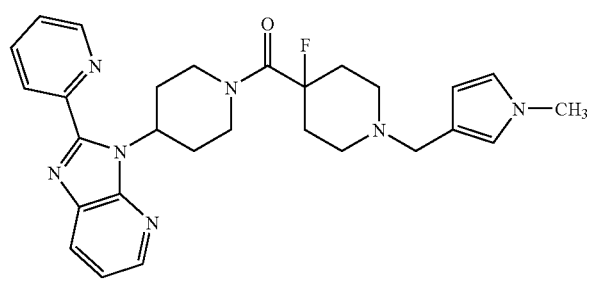 | 502 (ESMS) |
| 440 | 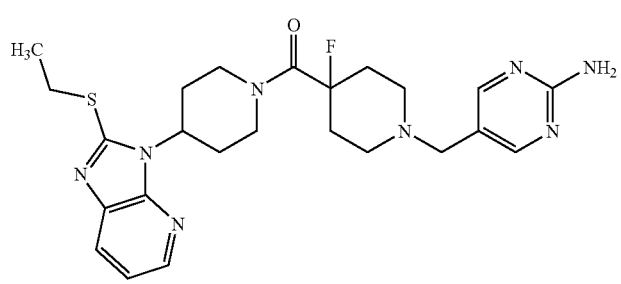 | 499 (FAB) |
| 441 | 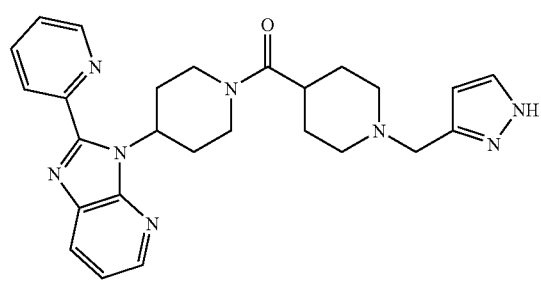 | 471 (ESMS) |
| 442 | 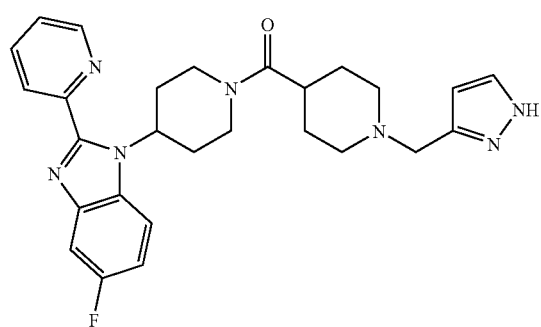 | 488 (ESMS) |

| Ex. | Structure | Mass Spec (M + H) |
|---|---|---|
| 443 | 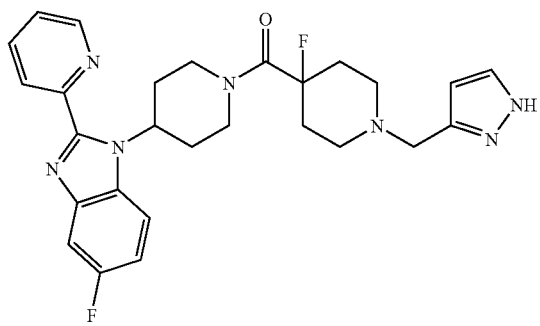 | 506 (ESMS) |
| 444 | 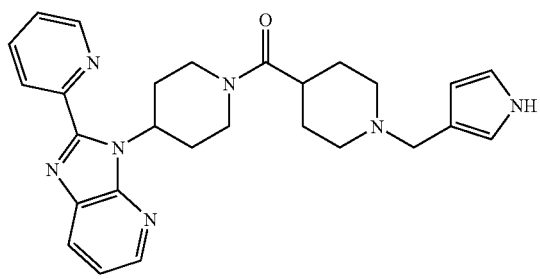 | 470 (ESMS) |
| 445 | 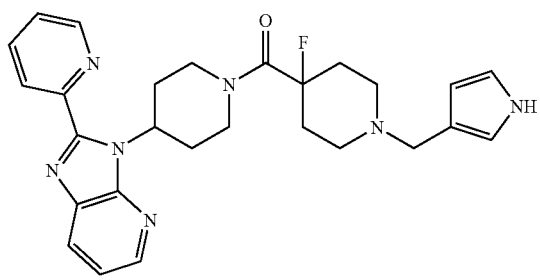 | 488 (ESMS) |
| 446 | 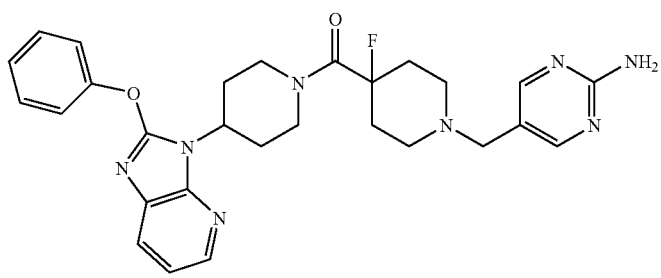 | 531 (FAB) |
| 447 | 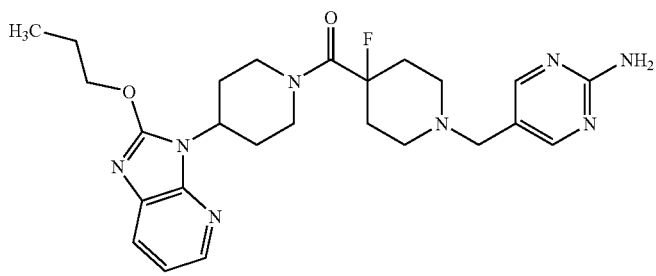 | 497 (FAB) |

-continued
| Ex. | Structure | Mass Spec (M + H) |
|---|---|---|
| 448 | 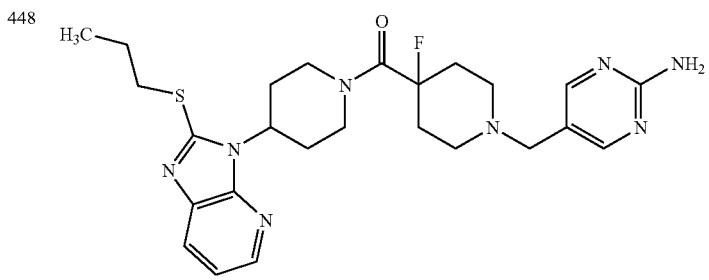 | 513 (FAB) |
| 449 | 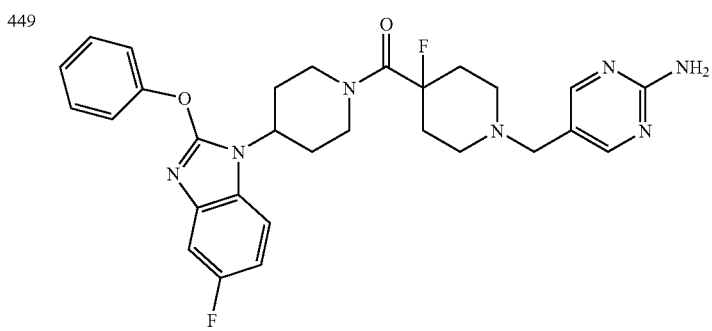 | 548 (FAB) |
| 450 | 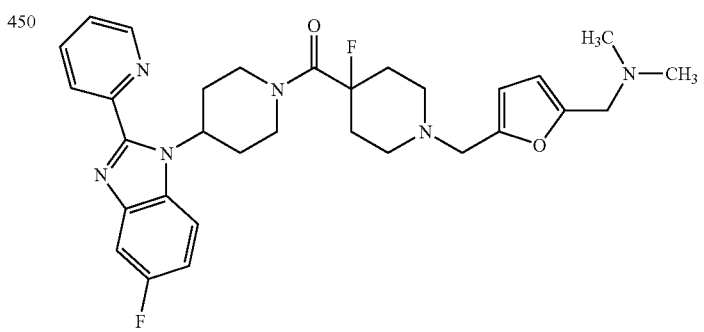 | 563 (ESMS) |
| 451 | 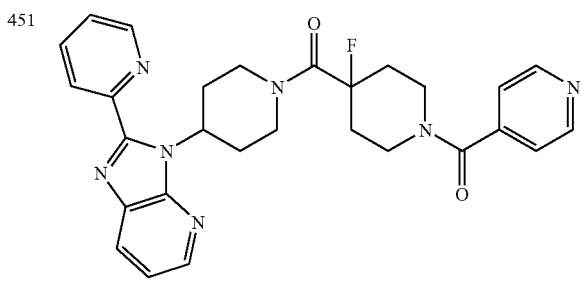 | 514 (ESMS) |
| 452 | 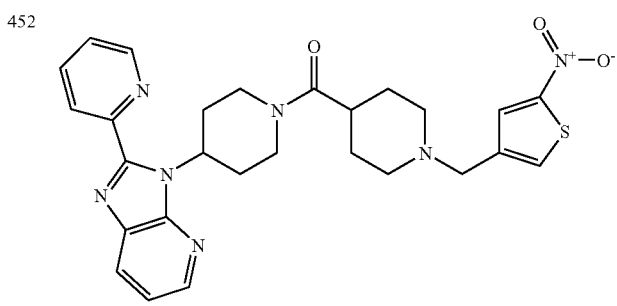 | 532 (ESMS) |

| Ex. | Structure | Mass Spec (M + H) |
|---|---|---|
| 453 | 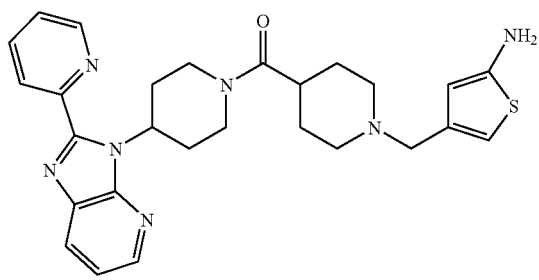 | 502 (ESMS) |
| 454 | 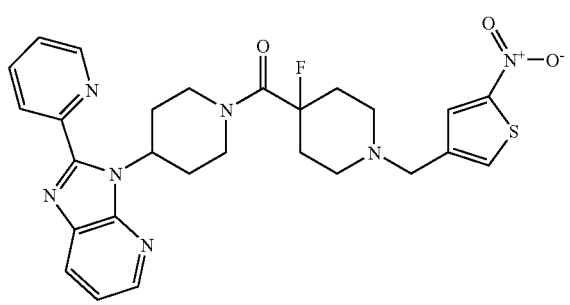 | 550 (ESMS) |
| 455 | 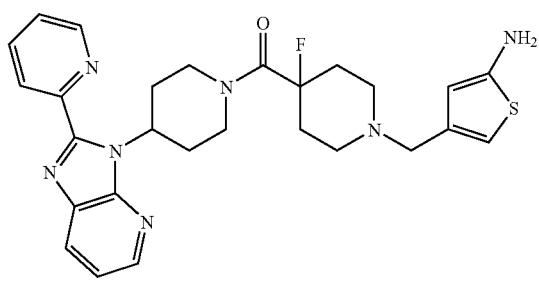 | 520 (ESMS) |
| 456 | 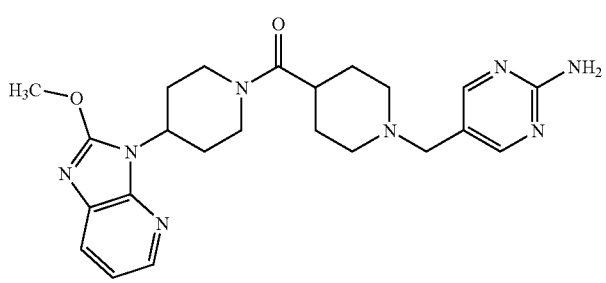 | 451 (ESMA) |
| 457 | 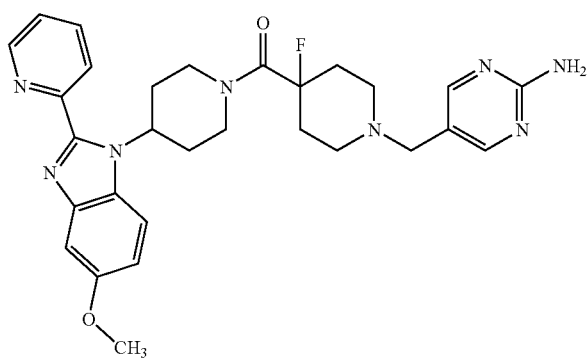 | 545 (ESMS) |

145                                                                                              146
-continued
| Ex. | Structure | Mass Spec (M + H) |
|---|---|---|
| 458 | 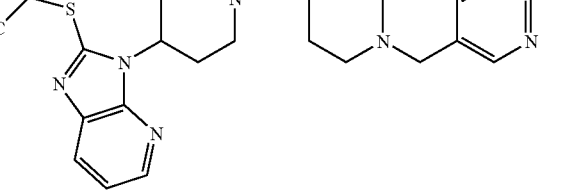 | 513 (ESMS) |
| 459 | 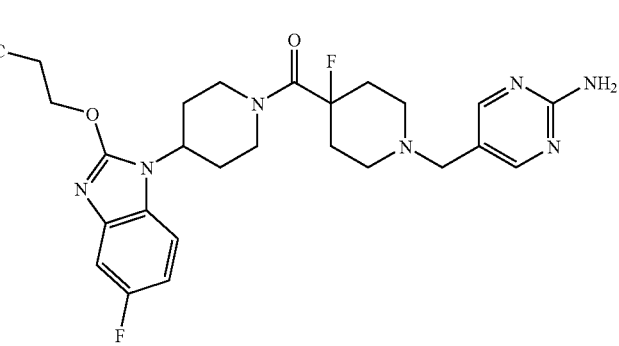 | 514 (FAB) |
| 460 | 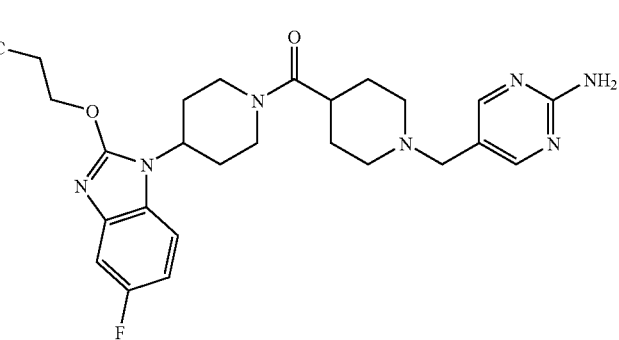 | 496 (FAB) |
| 461 | 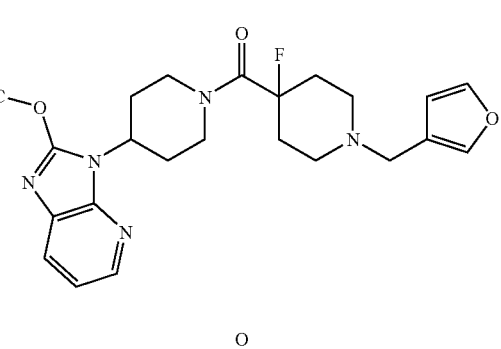 | 442 (ESMS) |
| 462 | 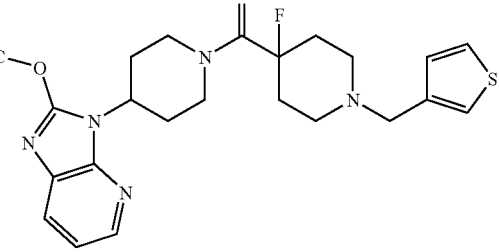 | 458 (ESMS) |

-continued
| Ex. | Structure | Mass Spec (M + H) |
|---|---|---|
| 463 | 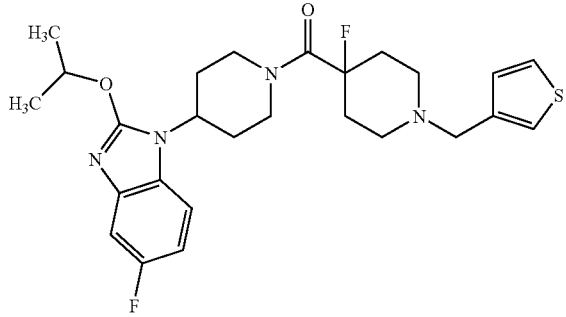 | 503 (ESMS) |
| 464 | 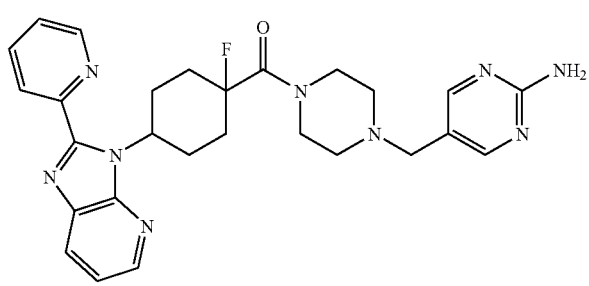 | 407 (ESMS) |
| 465 | 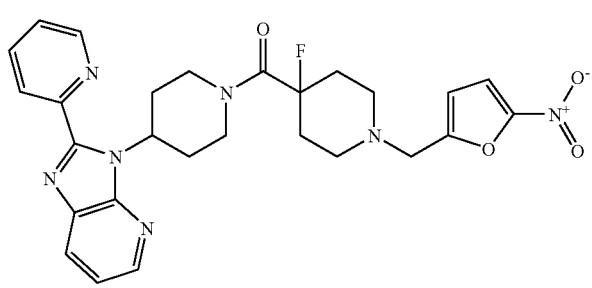 | 534 (ESMS) |
| 466 | 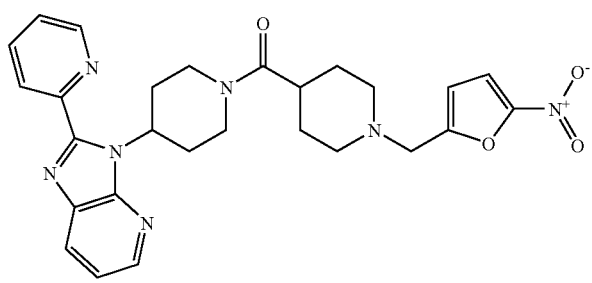 | 516 (ESMS) |
| 467 | 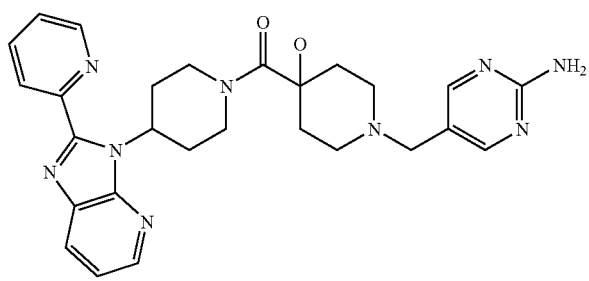 | 514 (ESMS) |

| Ex. | Structure | Mass Spec (M + H) |
|---|---|---|
| 468 | 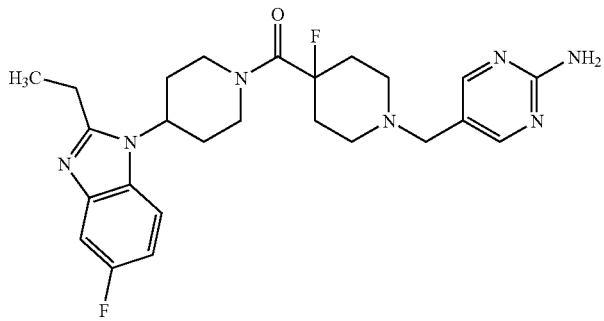 | 484 (ESMS) |
| 469 | 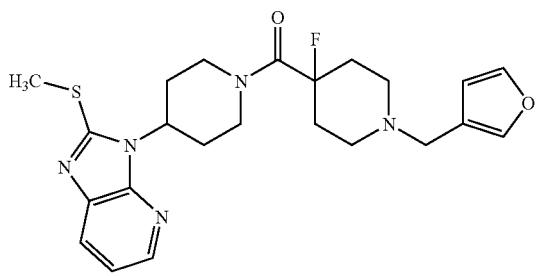 | 458 (ESMS) |
| 470 | 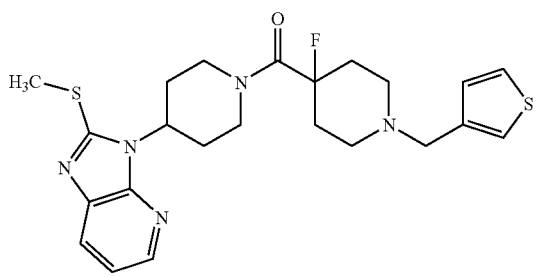 | 474 (ESMS) |
| 471 | 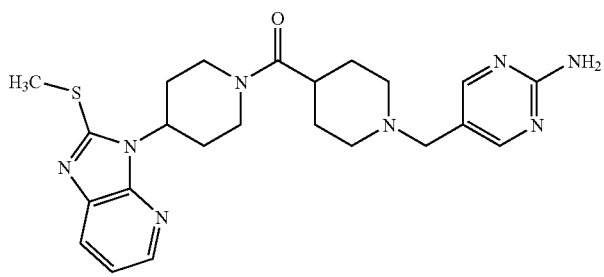 | 467 (ESMA) |
| 472 | 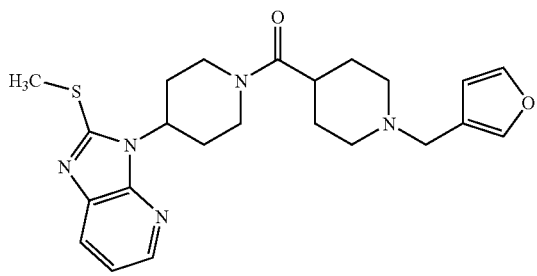 | 440 (ESMS) |

-continued
| Ex. | Structure | Mass Spec (M + H) |
|---|---|---|
| 473 | 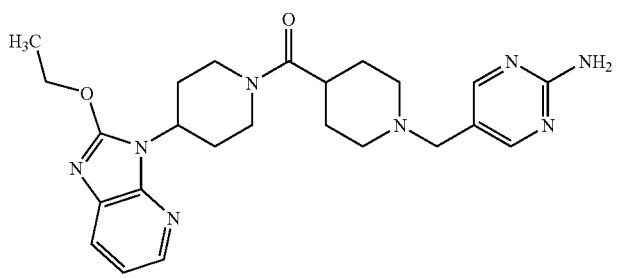 | 465 (ESMS) |
| 474 | 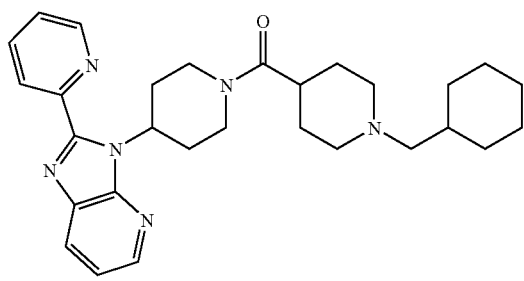 | 487 (ESMS) |
| 475 | 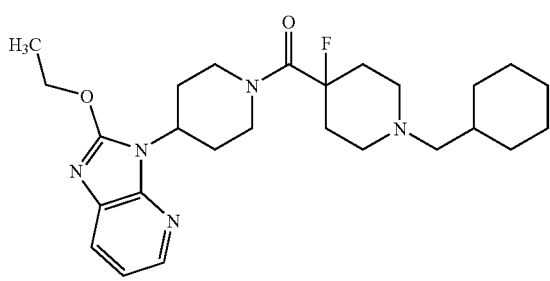 | 472 (ESMS) |
| 476 | 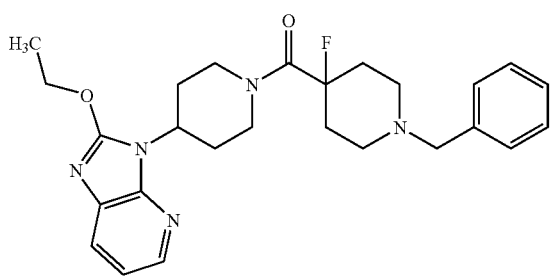 | 466 (ESMS) |
| 477 | 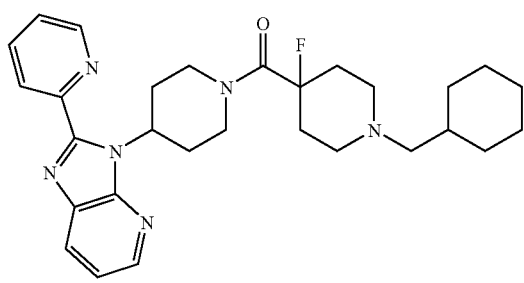 | 505 (ESMS) |

-continued
| Ex. | Structure | Mass Spec (M + H) |
|---|---|---|
| 478 | 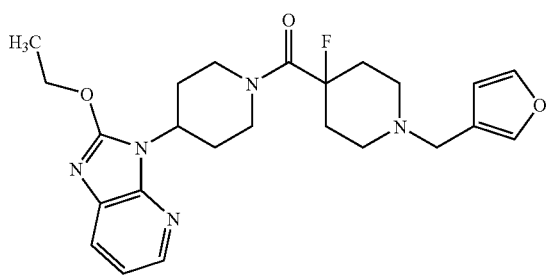 | 456 (ESMS) |
| 479 | 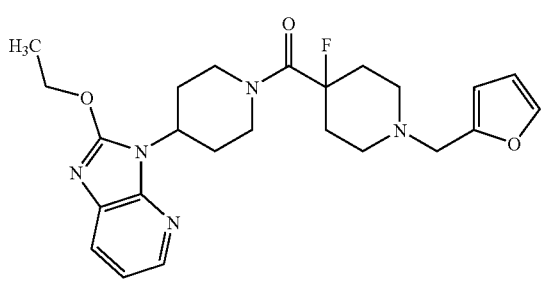 | 456 (ESMS) |
| 480 | 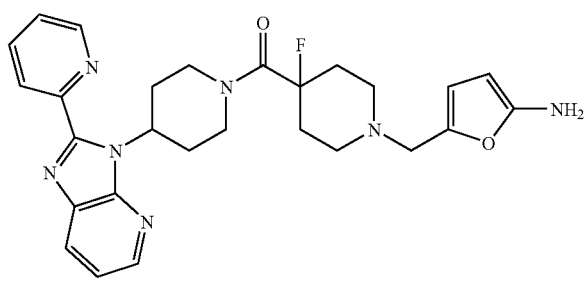 | 504 (ESMS) |
| 481 | 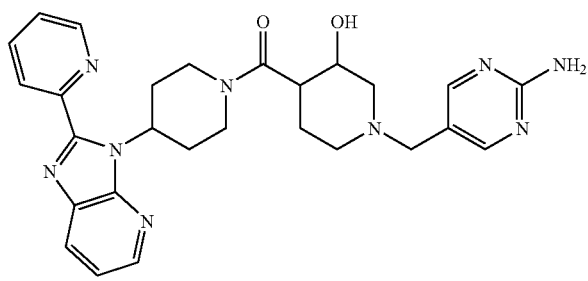 | 514 (ESMS) |
| 482 | 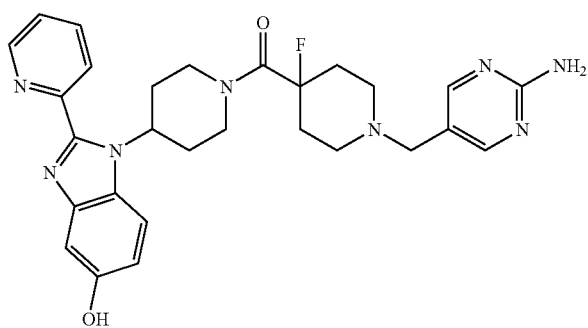 | 531 (FAB) |

| Ex. | Structure | Mass Spec (M + H) |
|---|---|---|
| 483 | 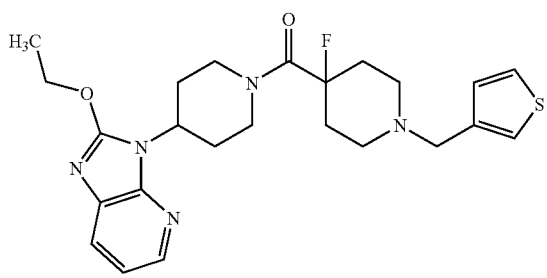 | 472 (ESMS) |
| 484 | 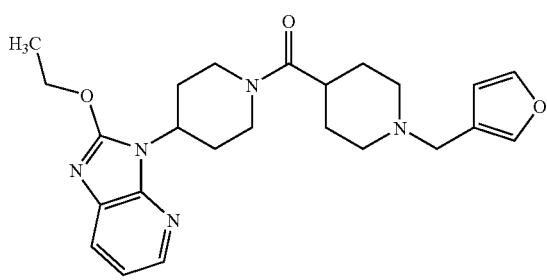 | 438 (ESMS) |
| 485 | 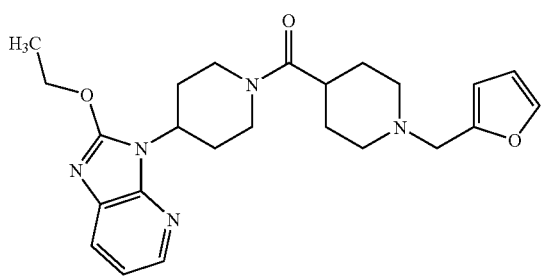 | 438 (ESMS) |
| 486 | 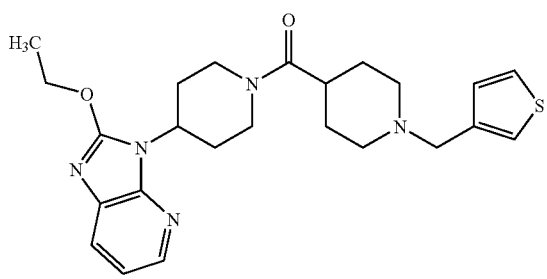 | 454 (ESMS) |
| 487 | 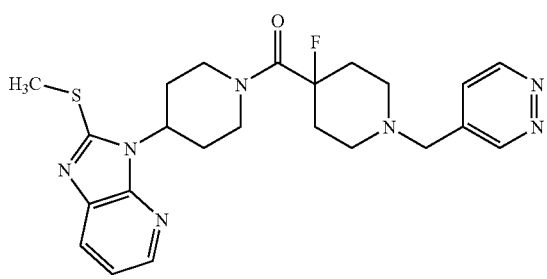 | 470 (ESMS) |

| Ex. | Structure | Mass Spec (M + H) |
|---|---|---|
| 488 | 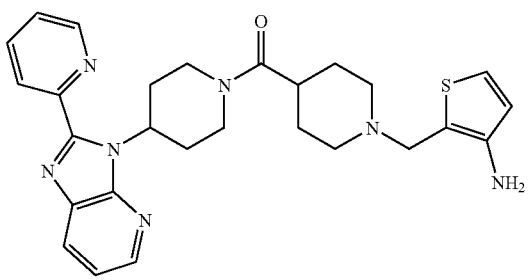 | 502 (ESMS) |
| 489 | 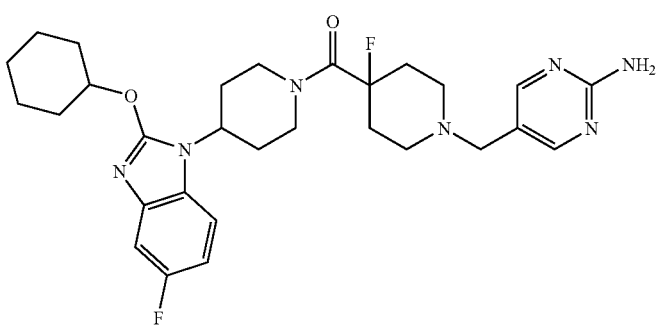 | 554 (FAB) |
| 490 | 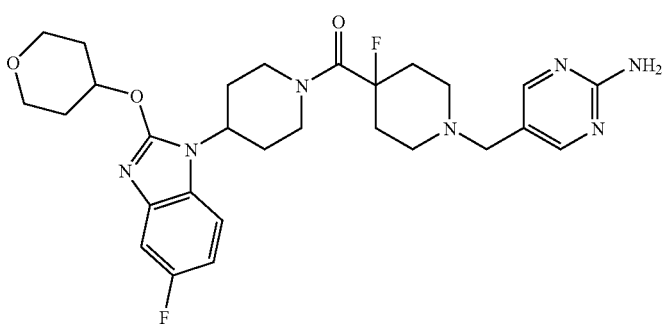 | 556 (FAB) |
| 491 | 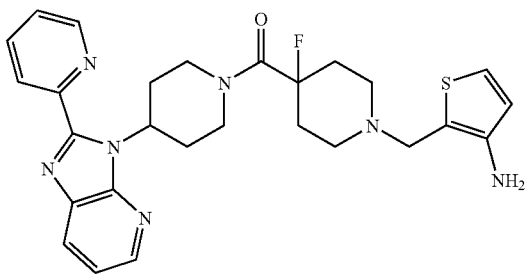 | 470 (ESMS) |
| 492 | 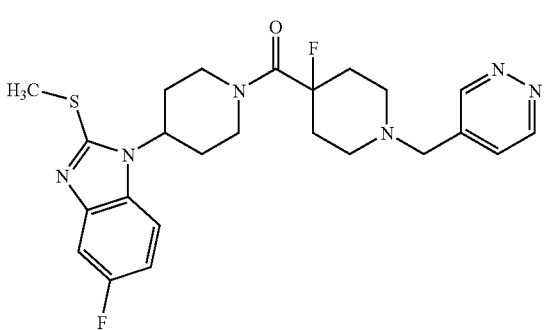 | 487 (ESMS) |

| Ex. | Structure | Mass Spec (M + H) |
|---|---|---|
| 493 | 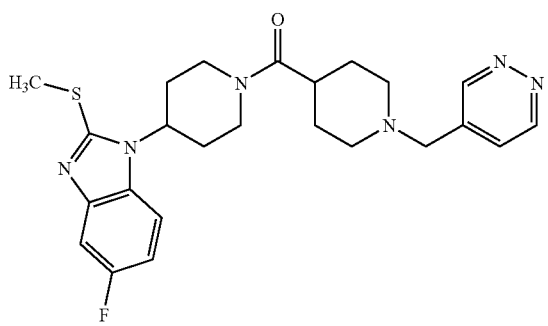 | 469 (ESMS) |
| 44 | 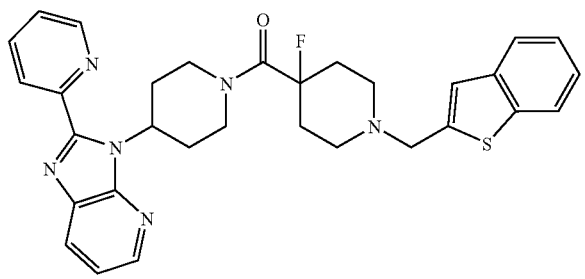 | 555 (ESMS) |
| 495 | 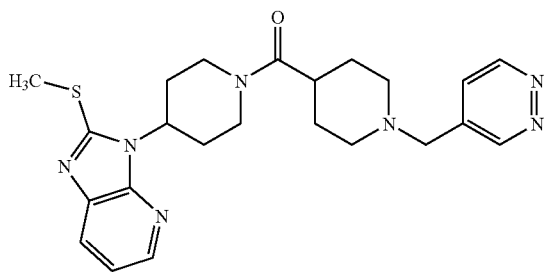 | 452 (ESMS) |
| 496 | 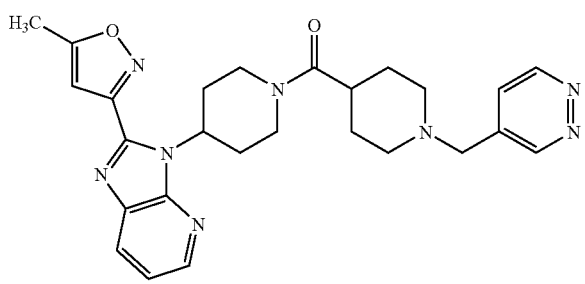 | 487 (ESMS) |
| 497 | 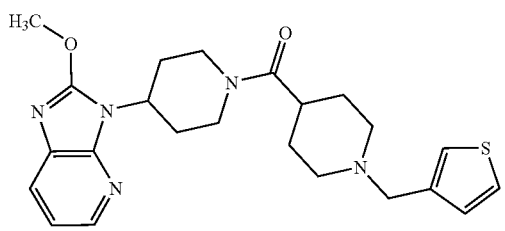 | 440 (ESMS) |

-continued
| Ex. | Structure | Mass Spec (M + H) |
|---|---|---|
| 498 | 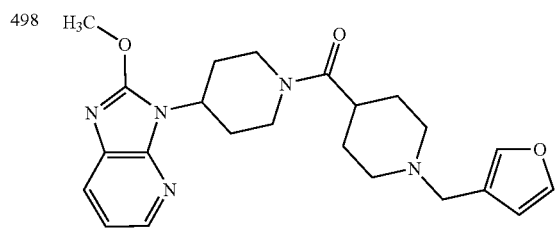 | 424 (ESMS) |
| 499 | 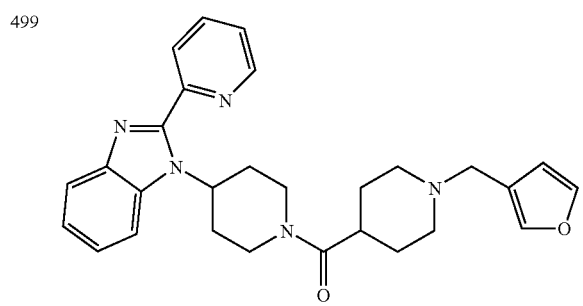 | 470 (ESMS) |
| 500 | 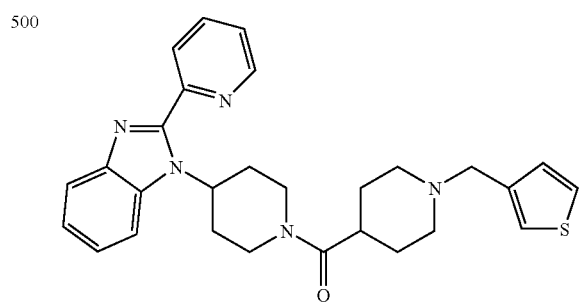 | 486 (ESMS) |
| 501 | 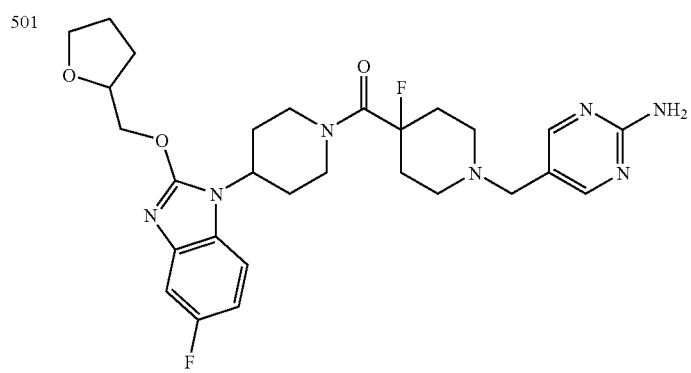 | 556 (ESMS) |
| 502 | 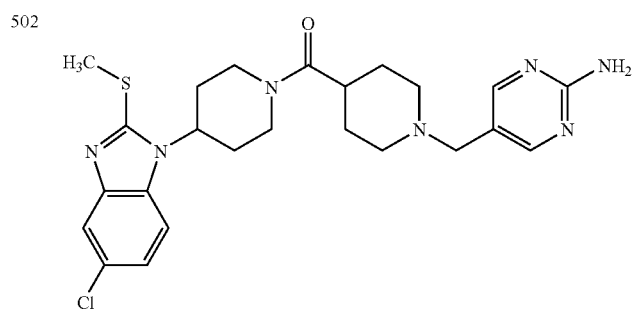 | 500 (ESMS) |

| Ex. | Structure | Mass Spec (M + H) |
|---|---|---|
| 503 | 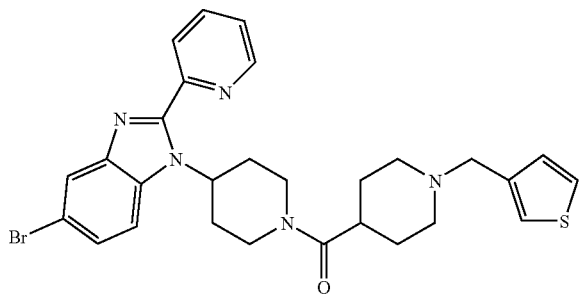 | 566 (ESMS) |
| 504 | 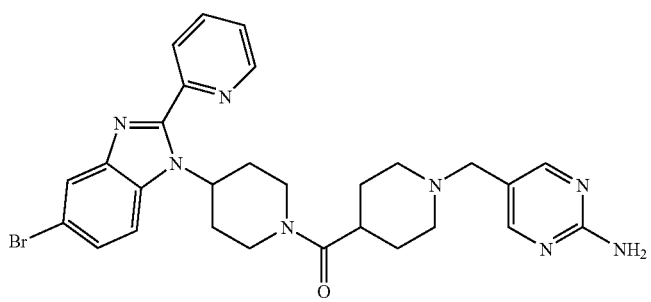 | 577 (ESMS) |
| 505 | 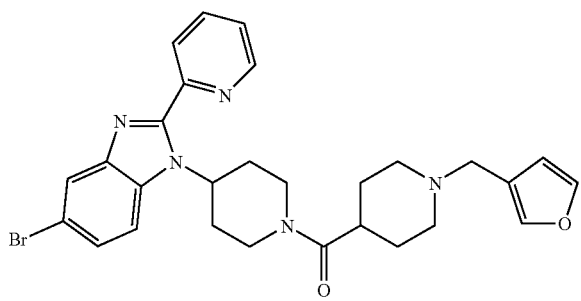 | 550 (ESMS) |
| 506 | 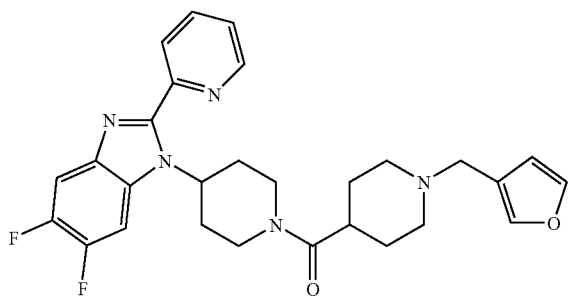 | 506 (ESMS) |
| 507 | 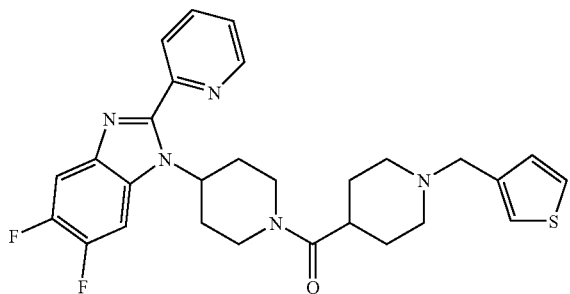 | 522 (ESMS) |

-continued

| Ex. | Structure | Mass Spec (M + H) |
|---|---|---|
| 508 | 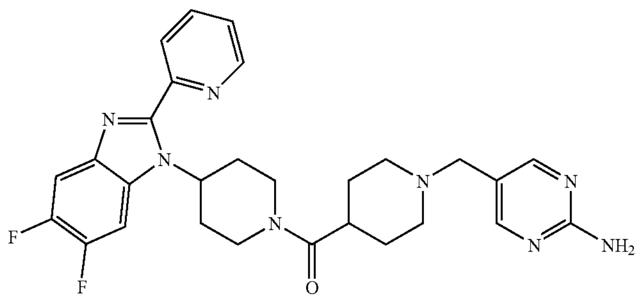 | 533 (ESMS) |
| 509 | 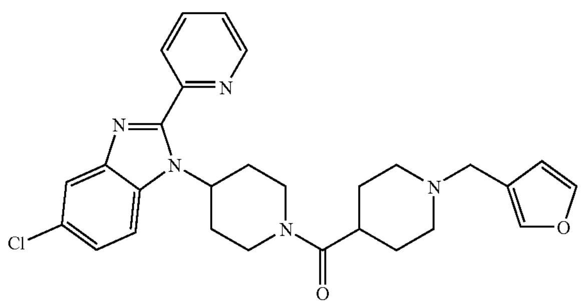 | 504 (ESMS) |
| 510 | 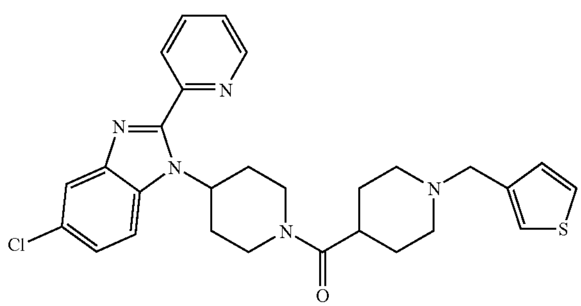 | 520 (ESMS) |
| 511 | 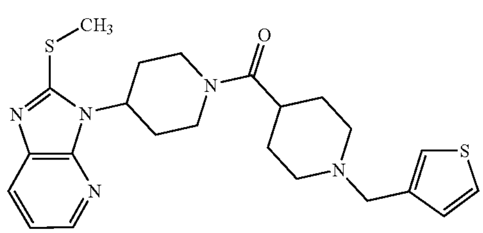 | 456 (ESMS) |
| 512 | 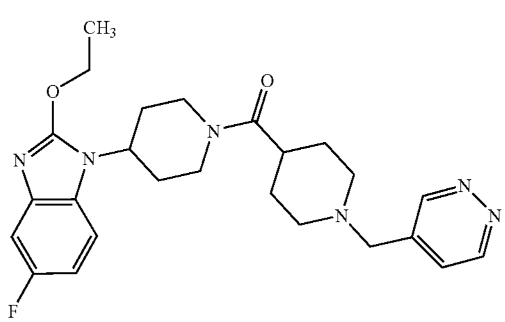 | 467 (ESMS) |

-continued
| Ex. | Structure | Mass Spec (M + H) |
|---|---|---|
| 513 | 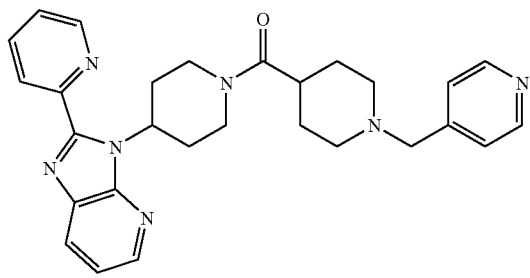 | 482 (ESMS) |
| 514 | 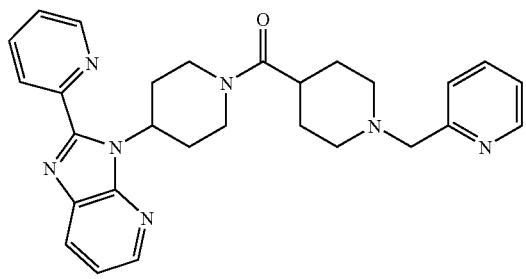 | 482 (ESMS) |
| 515 | 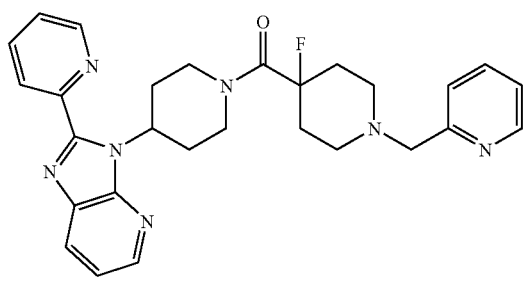 | 500 (ESMS) |
| 516 | 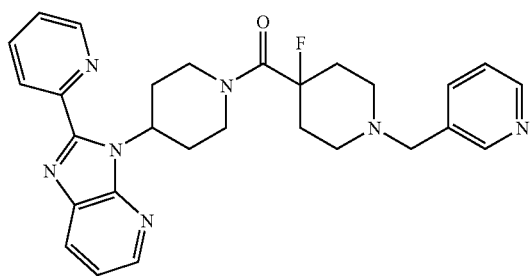 | 500 (ESMS) |
| 517 | 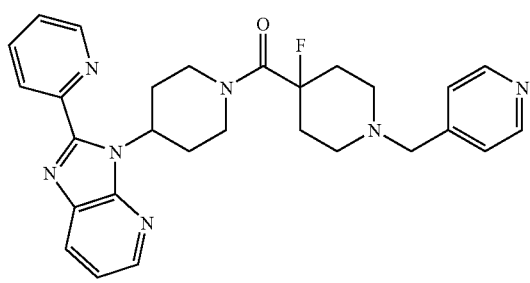 | 500 (ESMS) |

-continued
| Ex. | Structure | Mass Spec (M + H) |
|---|---|---|
| 518 | 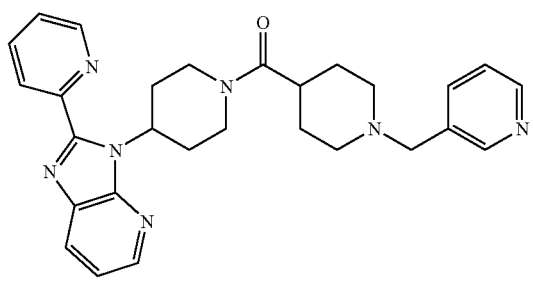 | 482 (ESMS) |
| 519 | 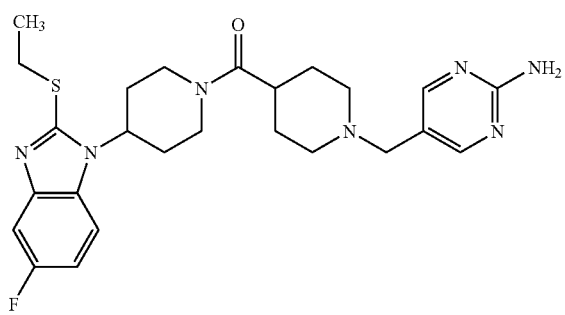 | 498 (ESMS) |
| 520 | 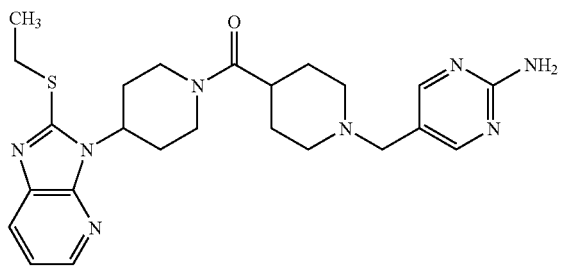 | 481 (ESMS) |
| 521 | 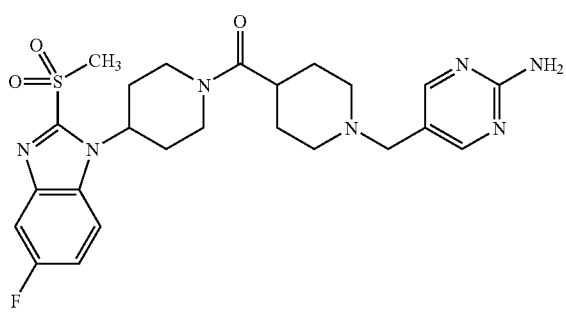 | 516 (ESMS) |
| 522 | 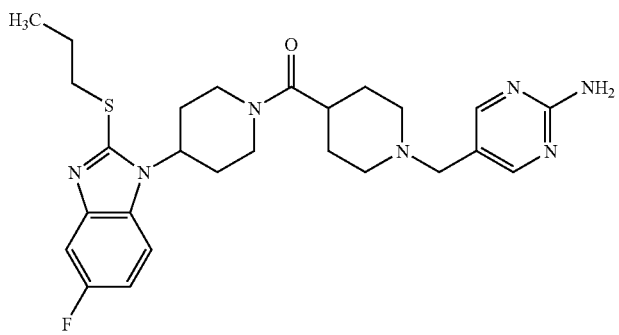 | 512 (FAB) |

-continued
| Ex. | Structure | Mass Spec (M + H) |
|---|---|---|
| 523 | 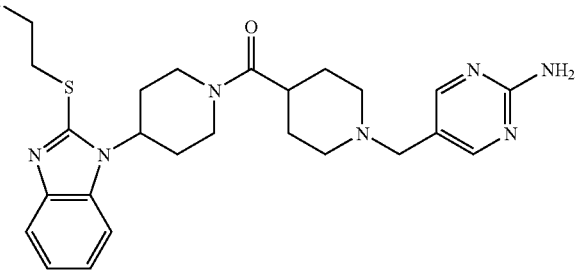 | 495 (FAB) |
| 524 | 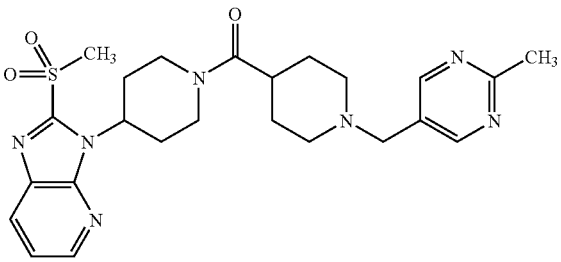 | 499 (FAB) |
| 525 | 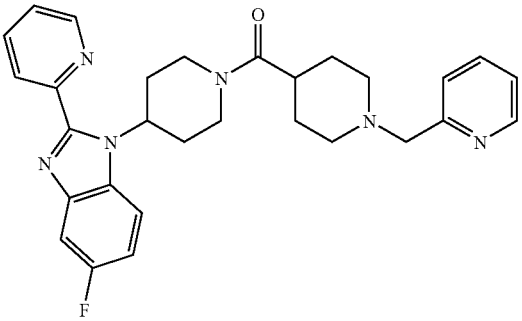 | 499 (ESMS) |
| 526 | 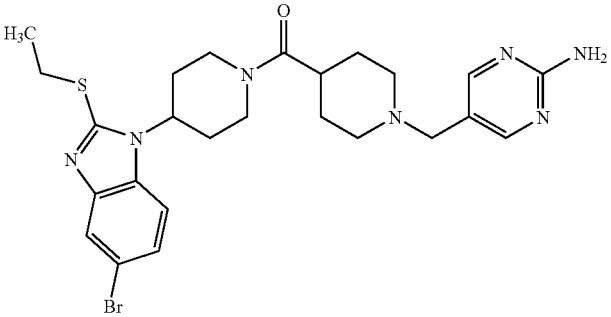 | 560 (ESMS) |
| 527 | 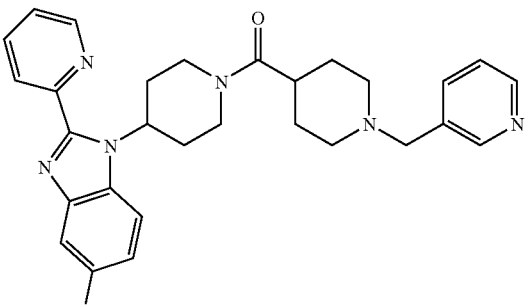 | 499 (ESMS) |

| Ex. | Structure | Mass Spec (M + H) |
|---|---|---|
| 528 | 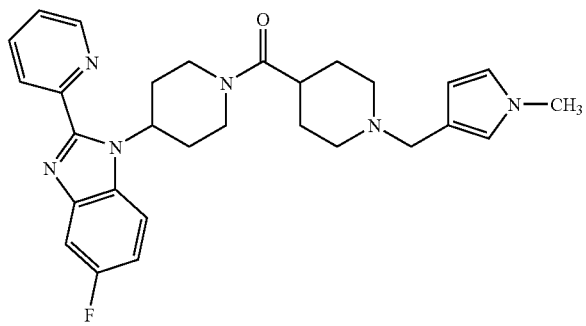 | 501 (ESMS) |
| 529 | 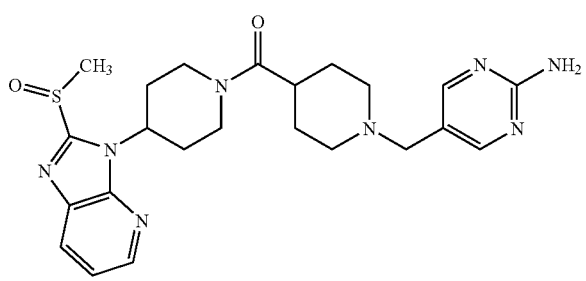 | 483 (ESMS) |
| 530 | 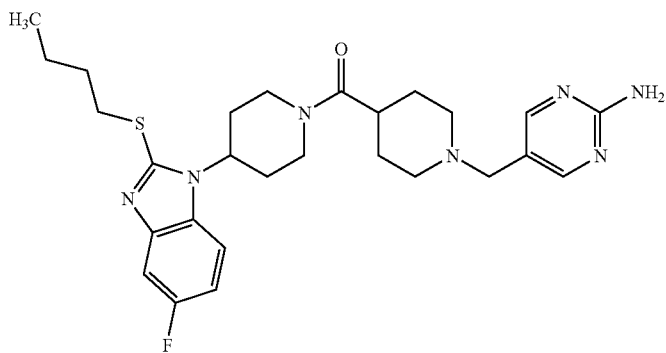 | 526 (ESMS) |
| 531 | 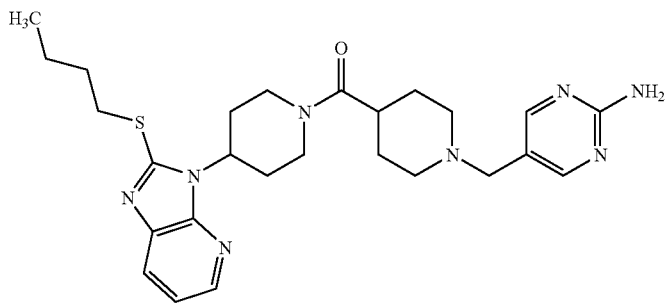 | 509 (ESMS) |
| 532 | 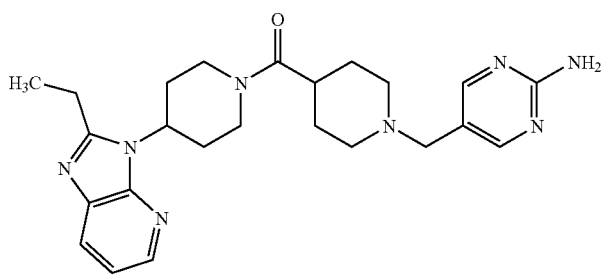 | 449 (ESMS) |

-continued

| Ex. | Structure | Mass Spec (M + H) |
|---|---|---|
| 533 | 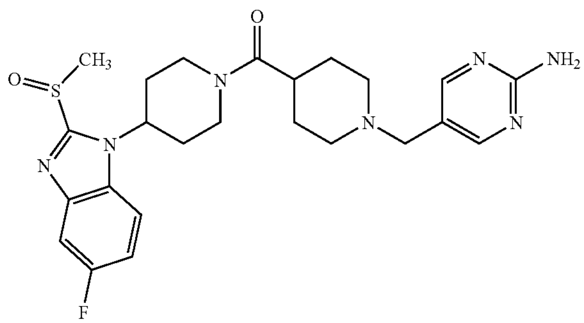 | 500 (ESMS) |
| 534 | 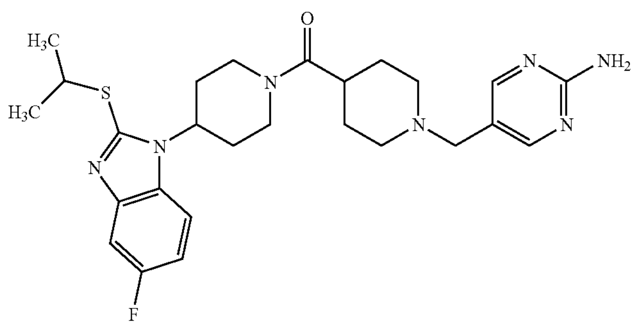 | 512 (ESMS) |
| 535 | 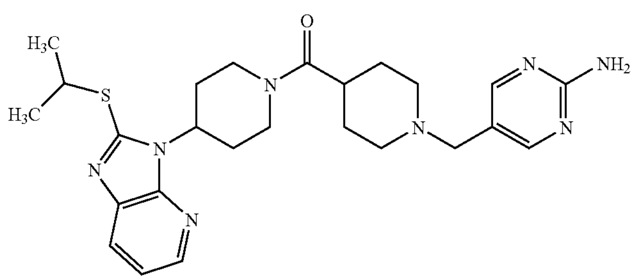 | 495 (ESMS) |
| 536 | 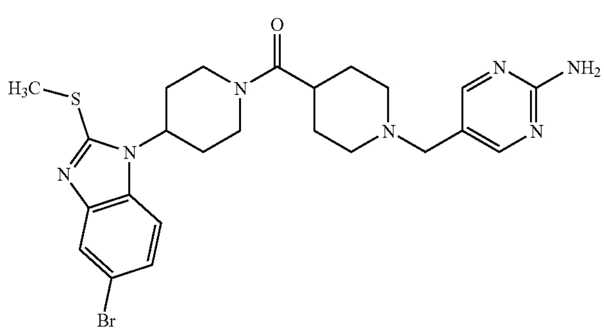 | 546 (ESMS) |
| 537 | 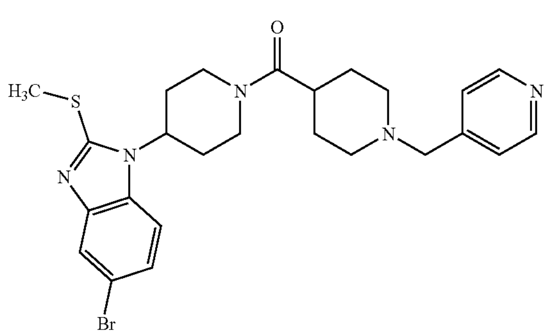 | 530 (ESMS) |

| Ex. | Structure | Mass Spec (M + H) |
|---|---|---|
| 538 | 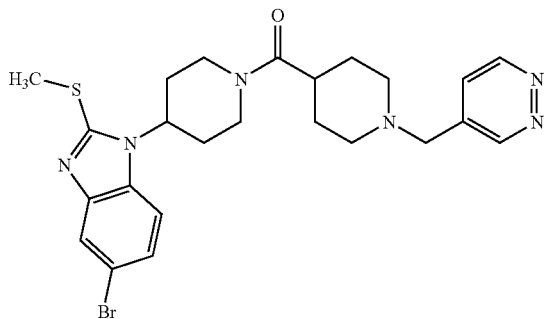 | 531 (ESMS) |
| 539 | 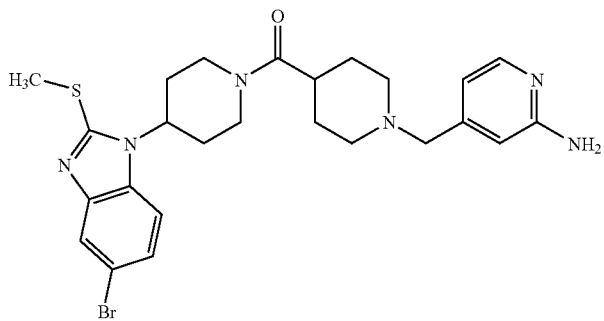 | 545 (ESMS) |
| 540 | 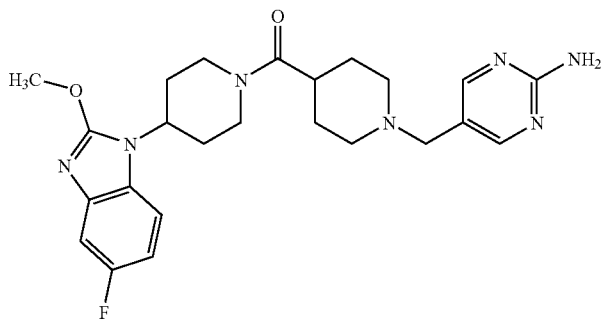 | 468 (ESMS) |
| 541 | 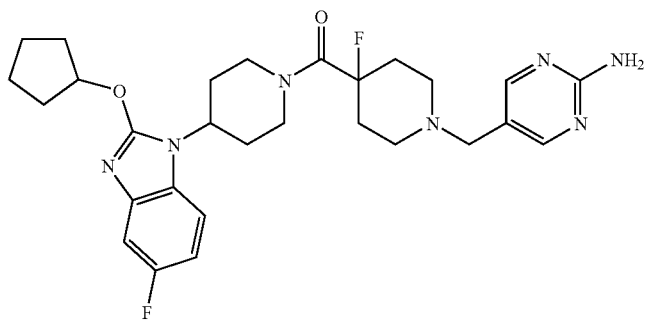 | 540 (ESMS) |

-continued
| Ex. | Structure | Mass Spec (M + H) |
|---|---|---|
| 542 | 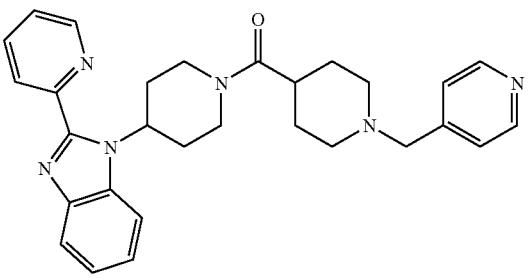 | 481 (ESMS) |
| 543 | 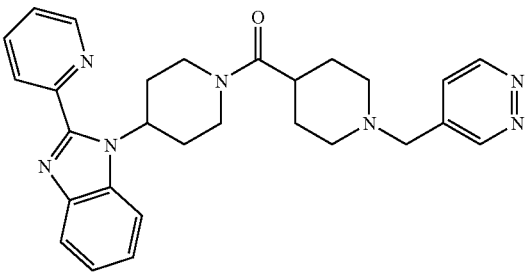 | 482 (ESMS) |
| 544 | 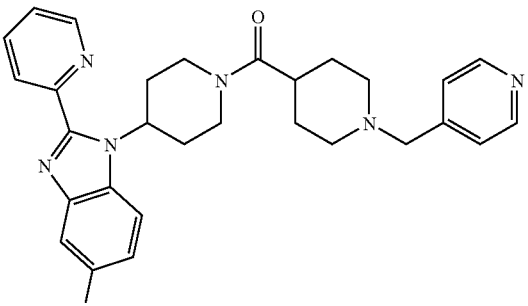 | 515 (ESMS) |
| 545 | 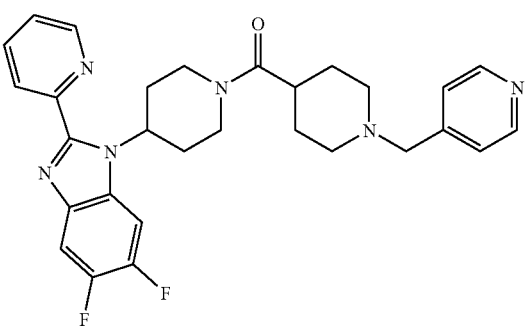 | 517 (ESMS) |
| 546 | 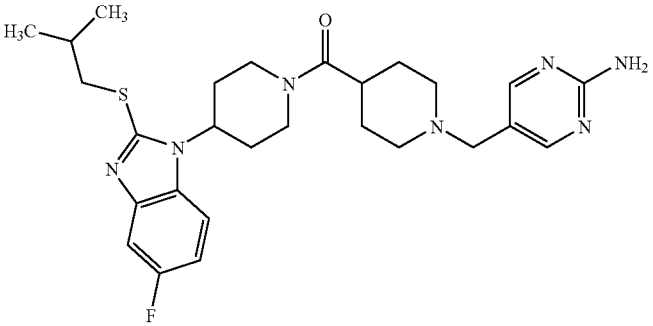 | 526 (ESMS) |

| Ex. | Structure | Mass Spec (M + H) |
|---|---|---|
| 547 | 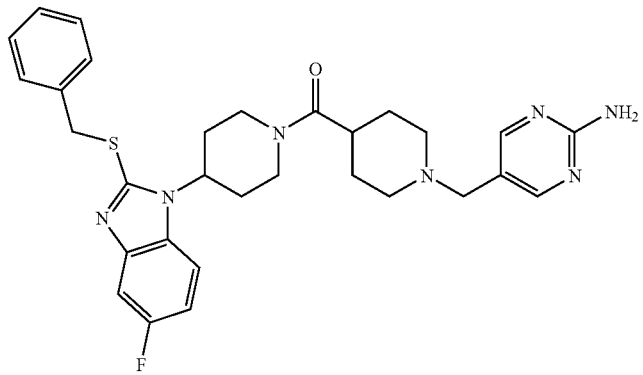 | 5560 (ESMS) |
| 548 | 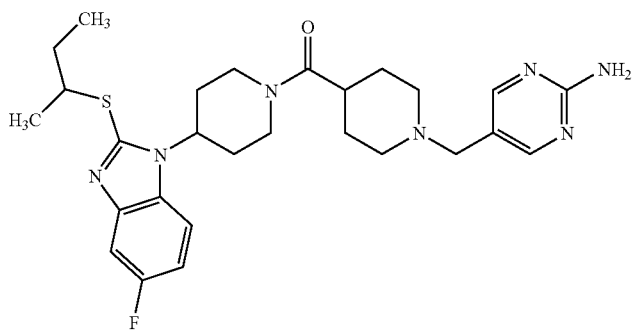 | 526 (ESMS) |
| 549 | 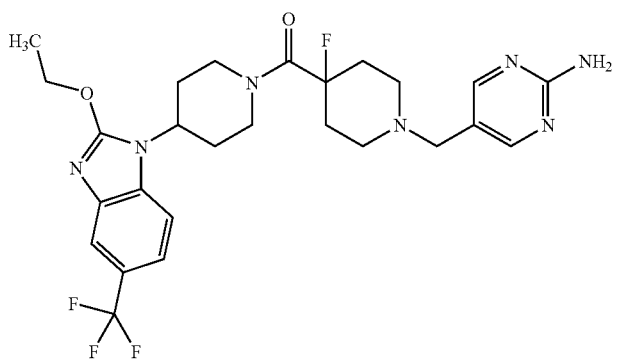 | 550 (ESMS) |
| 550 | 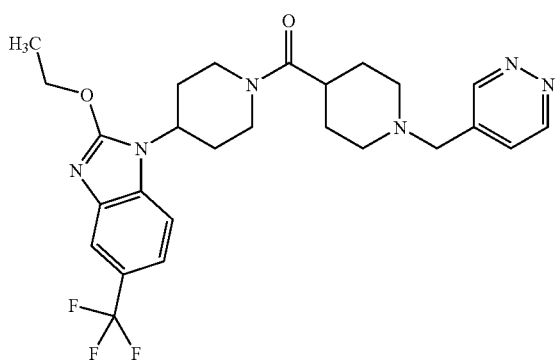 | 517 (ESMS) |

| Ex. | Structure | Mass Spec (M + H) |
|---|---|---|
| 551 | 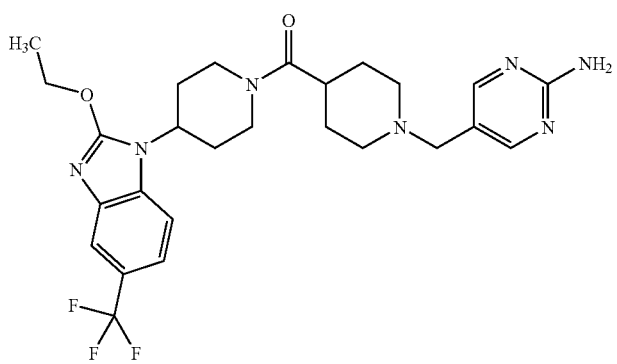 | 532 (ESMS) |
| 552 | 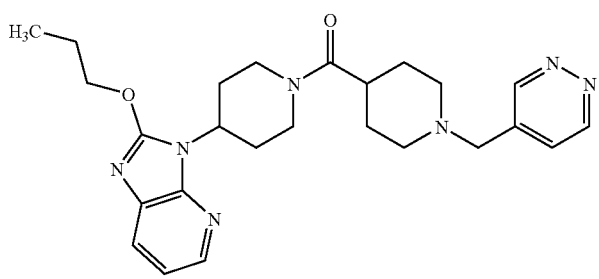 | 464 (ESMS) |
| 553 | 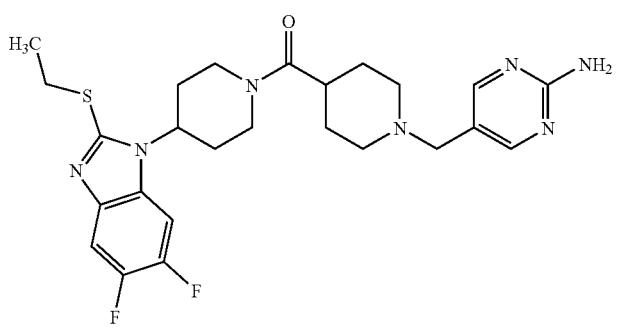 | 516 (ESMS) |
| 554 | 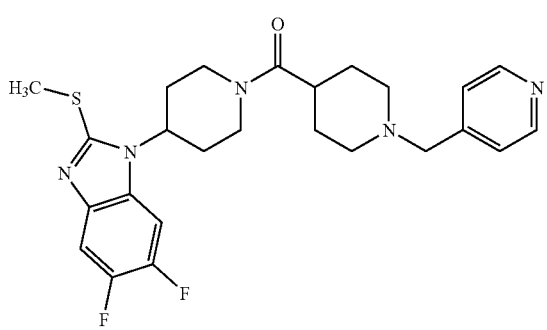 | 486 (ESMS) |

| Ex. | Structure | Mass Spec (M + H) |
|---|---|---|
| 555 | 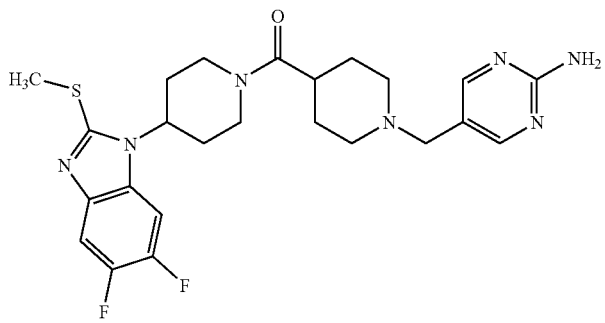 | 502 (ESMS) |
| 556 | 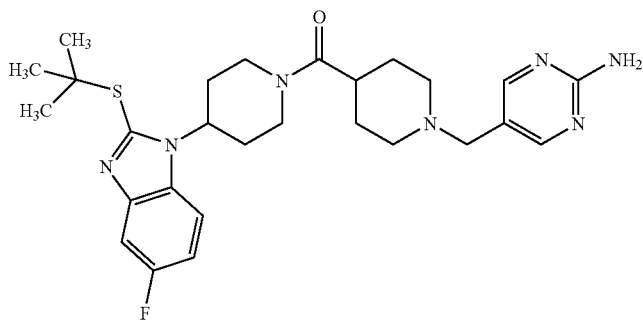 | 526 (ESMS) |
| 557 | 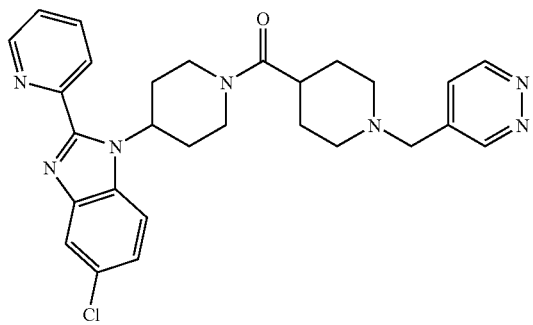 | 516 (ESMS) |
| 558 | 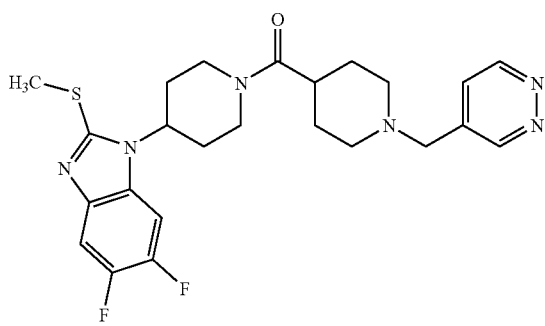 | 487 (ESMS) |

| Ex. | Structure | Mass Spec (M + H) |
|---|---|---|
| 559 | 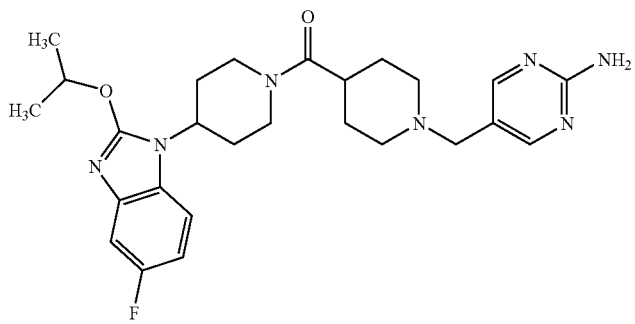 | 496 (ESMS) |
| 560 | 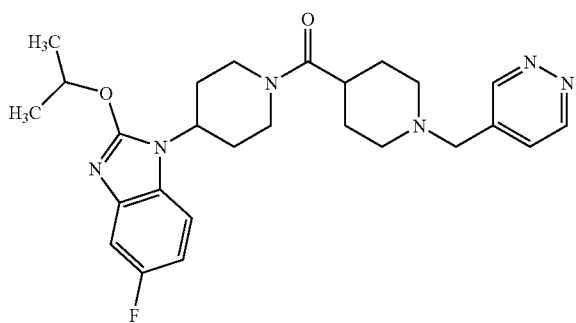 | 481 (FAB) |
| 561 | 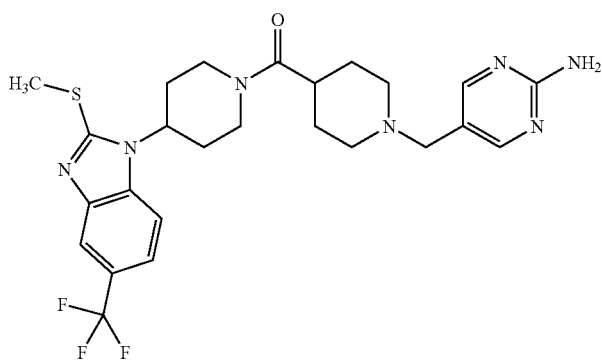 | 534 (ESMS) |
| 562 | 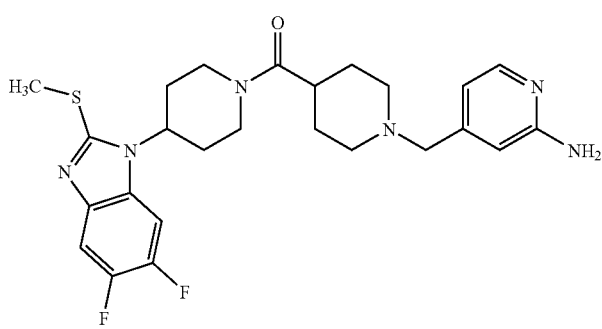 | 501 (ESMS) |

| Ex. | Structure | Mass Spec (M + H) |
|---|---|---|
| 563 | 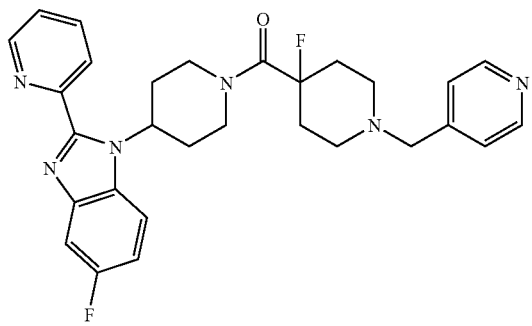 | 517 (ESMS) |
| 564 | 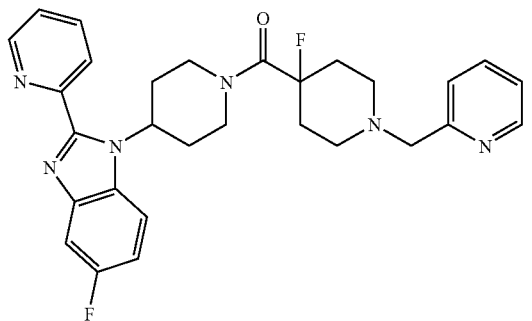 | 517 (ESMS) |
| 565 | 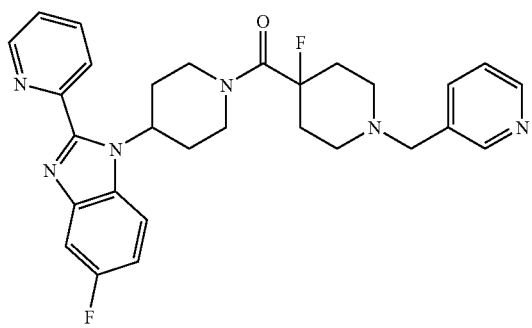 | 517 (ESMS) |
| 566 | 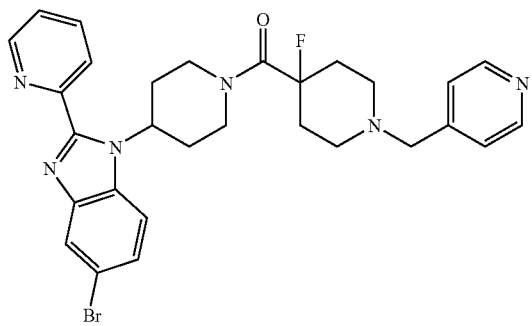 | 577 (ESMS) |

| Ex. | Structure | Mass Spec (M + H) |
|---|---|---|
| 567 | 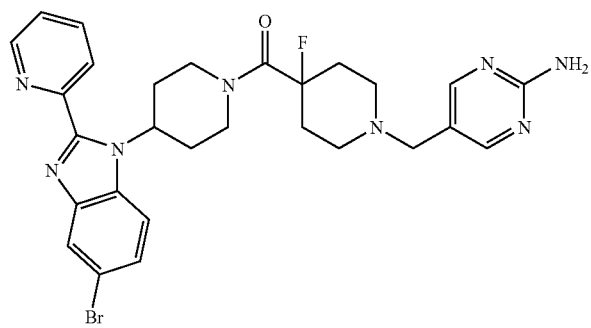 | 592 (ESMS) |
| 568 | 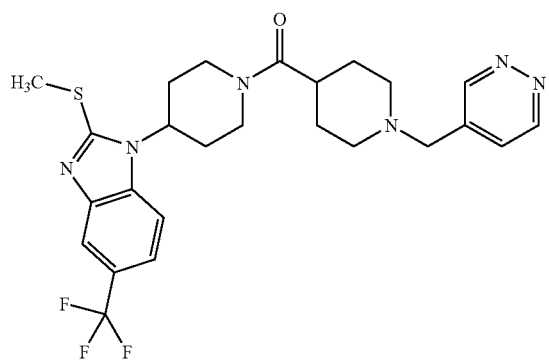 | 519 (ESMS) |
| 569 | 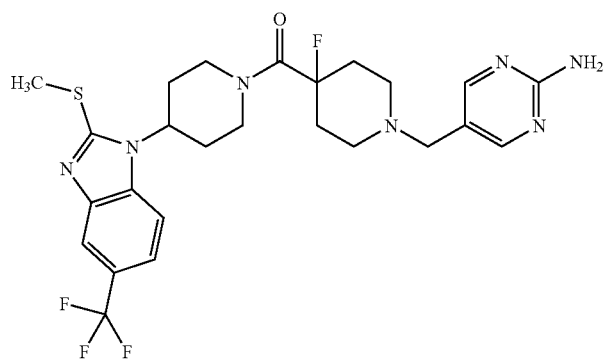 | 552 (ESMS) |
| 570 | 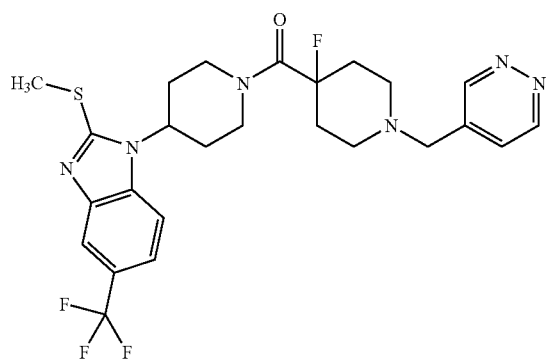 | 537 (ESMS) |

-continued
| Ex. | Structure | Mass Spec (M + H) |
|---|---|---|
| 571 | 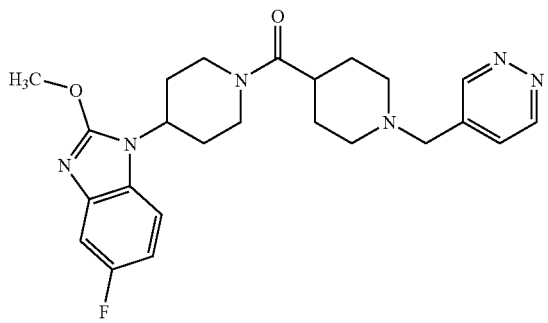 | 453 (ESMS) |
| 572 | 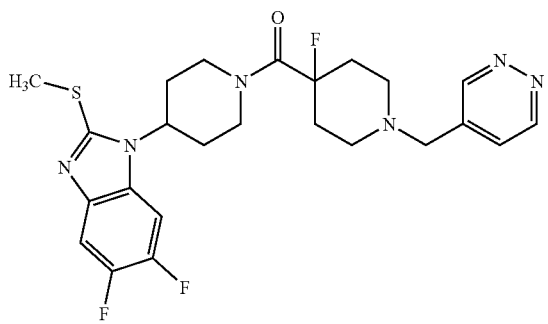 | 505 (ESMS) |
| 573 | 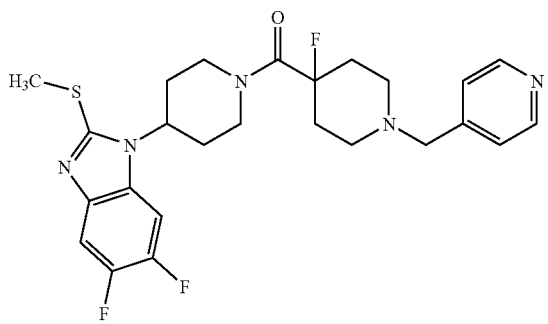 | 504 (ESMS) |
| 574 | 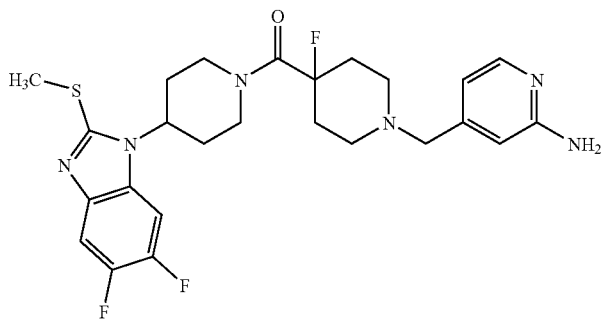 | 519 (ESMS) |

-continued
| Ex. | Structure | Mass Spec (M + H) |
|---|---|---|
| 575 | 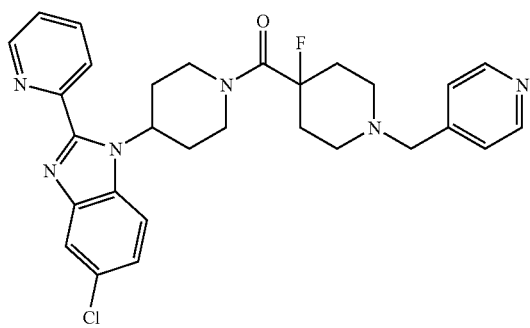 | 533 (ESMS) |
| 576 | 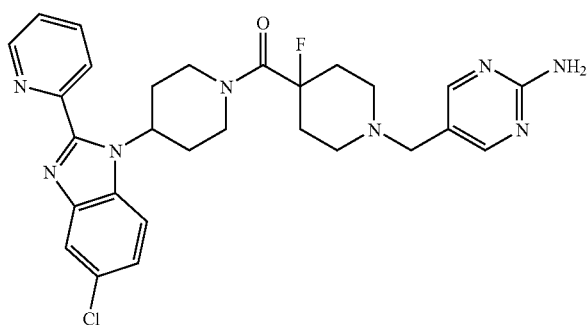 | 549 (ESMS) |
| 577 | 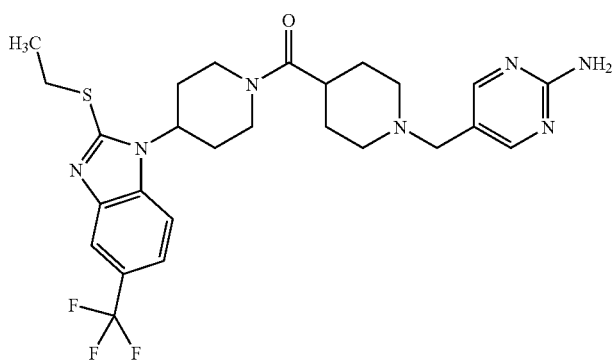 | 548 (ESMS) |
| 578 | 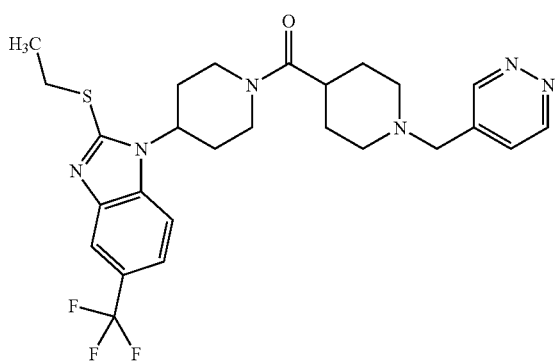 | 533 (ESMS) |

| Ex. | Structure | Mass Spec (M + H) |
|---|---|---|
| 579 | 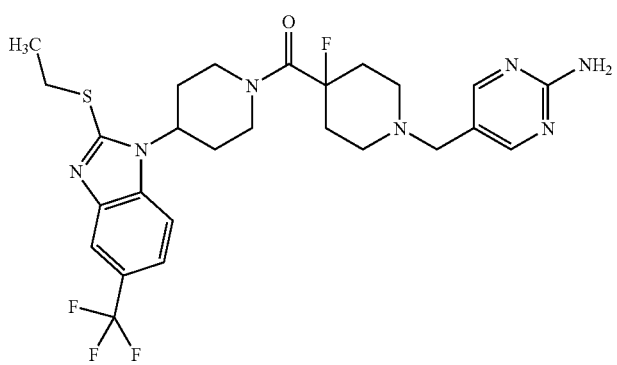 | 566 (ESMS) |
| 580 | 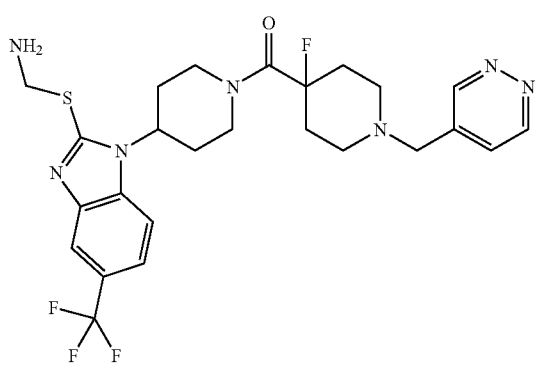 | 551 (ESMS) |
| 581 | 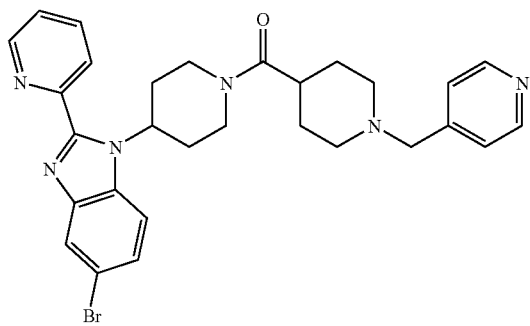 | 559 (ESMS) |
| 582 | 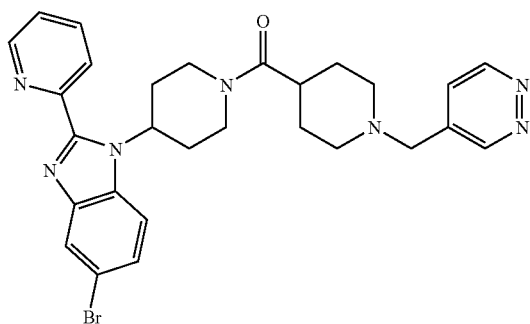 | 560 (ESMS) |

| Ex. | Structure | Mass Spec (M + H) |
|---|---|---|
| 583 | 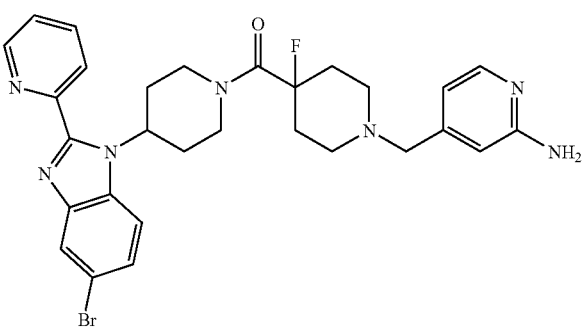 | 592 (ESMS) |
| 584 | 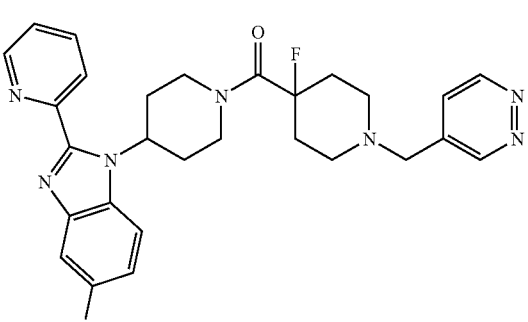 | 579 (ESMS) |
| 585 | 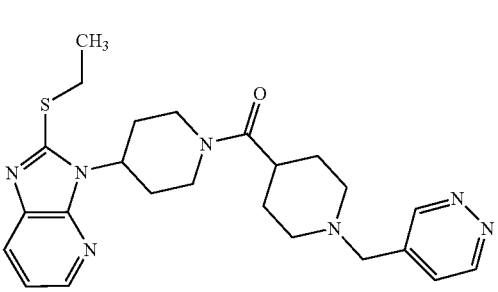 | 466 (ESMS) |
| 586 | 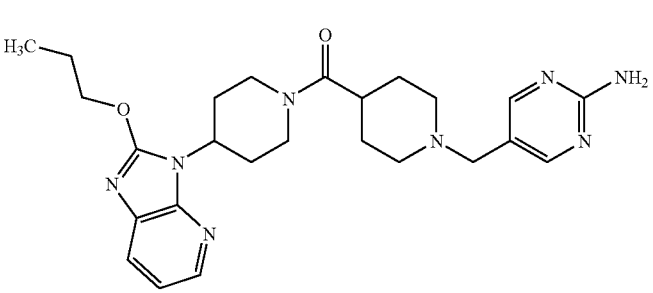 | 479 (FAB) |
| 587 | 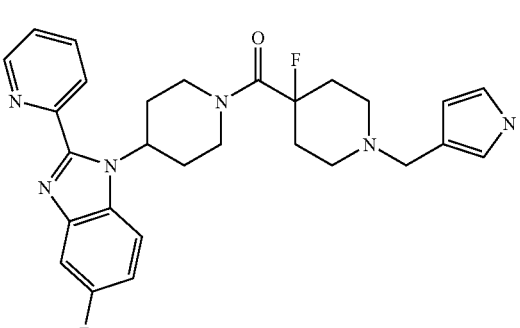 | 505 (ESMS) |

-continued
| Ex. | Structure | Mass Spec (M + H) |
|---|---|---|
| 588 | 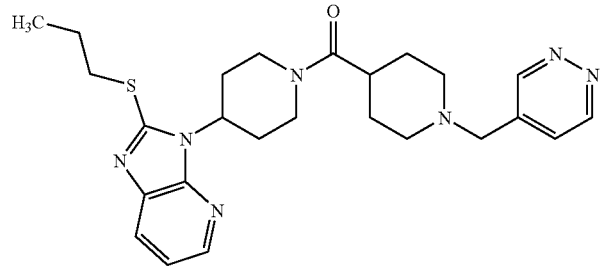 | 480 (ESMS) |
| 589 | 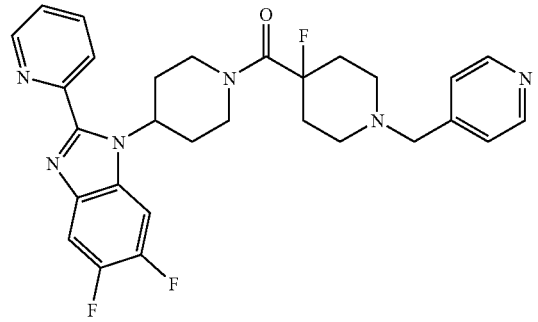 | 535 (ESMS) |
| 590 | 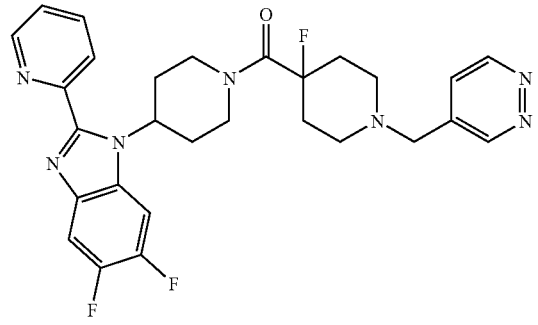 | 536 (ESMS) |
| 591 | 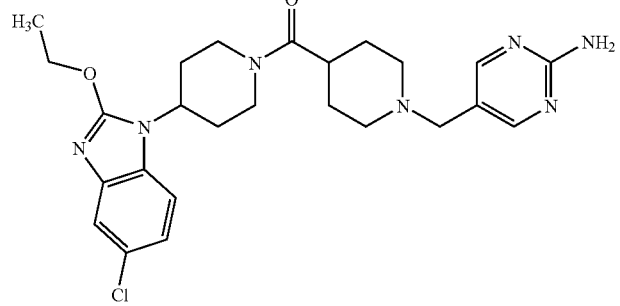 | 498 (ESMS) |
| 592 | 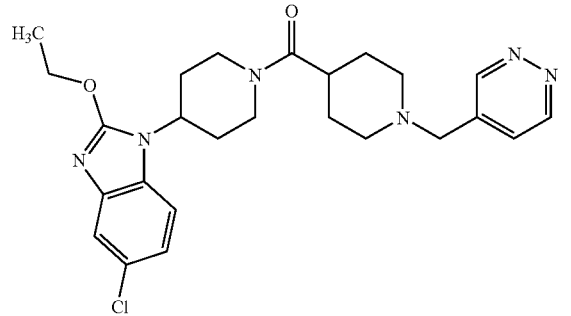 | 483 (ESMS) |

| Ex. | Structure | Mass Spec (M + H) |
|---|---|---|
| 593 | 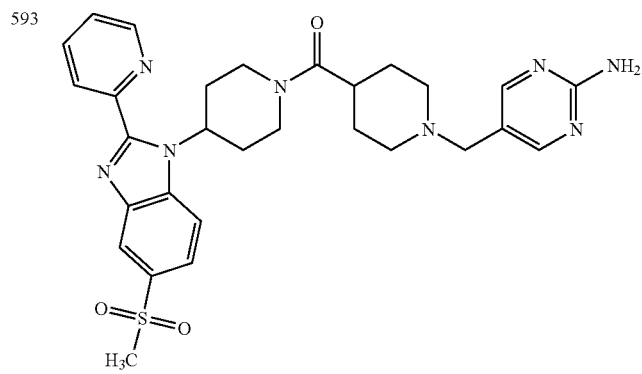 | 575 (ESMS) |
| 594 | 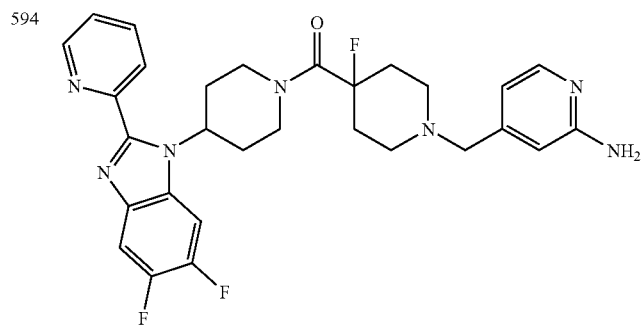 | 550 (ESMS) |
| 595 | 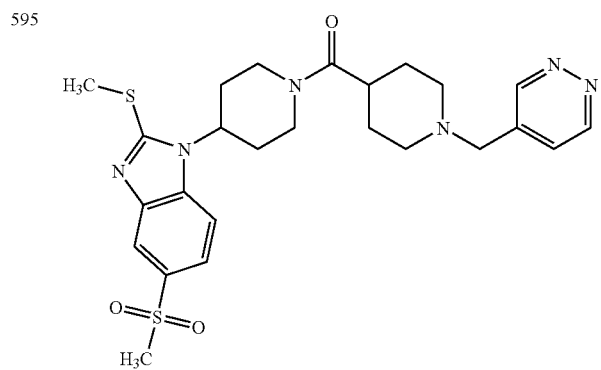 | 529 (ESMS) |
| 596 | 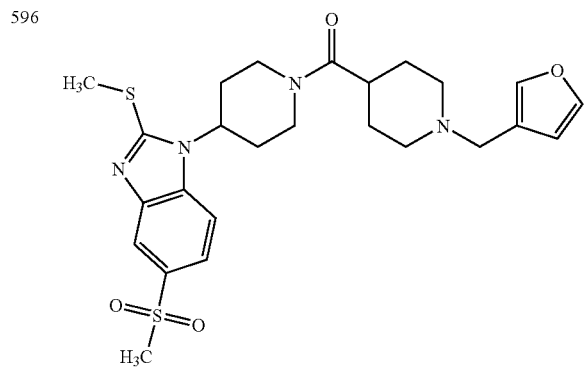 | 517 (ESMS) |

| Ex. | Structure | Mass Spec (M + H) |
|---|---|---|
| 597 | 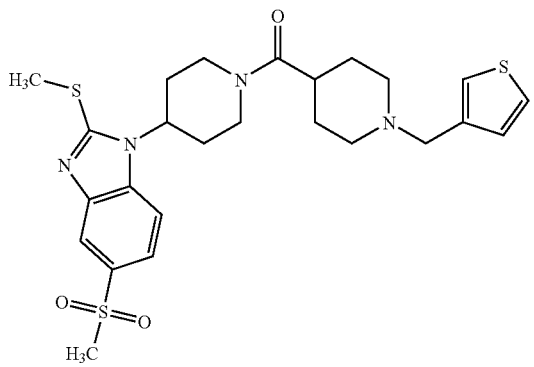 | 533 (ESMS) |
| 598 | 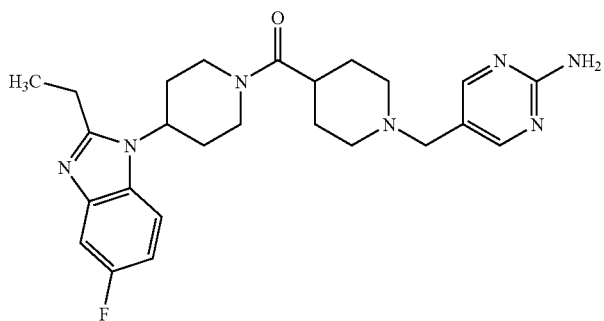 | 466 (ESMS) |
| 599 | 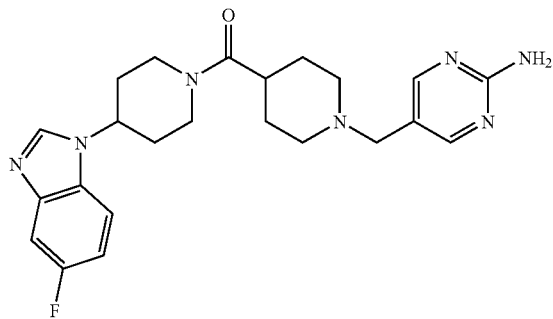 | 438 (ESMS) |
| 600 | 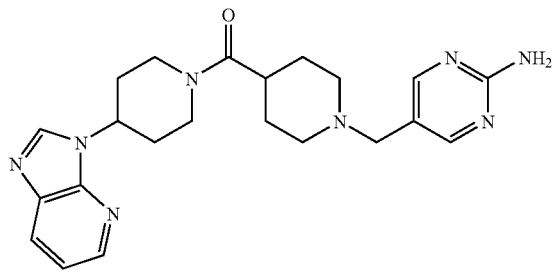 | 421 (ESMS) |

| Ex. | Structure | Mass Spec (M + H) |
|---|---|---|
| 601 | 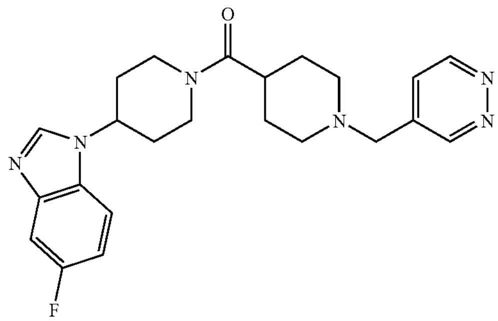 | 423 (ESMS) |
| 602 | 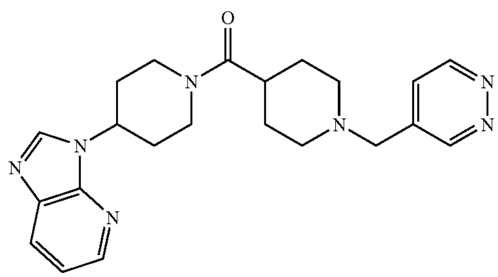 | 406 (ESMS) |
| 603 | 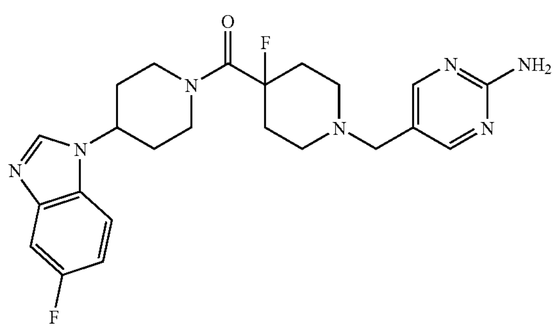 | 456 (ESMS) |
| 604 | 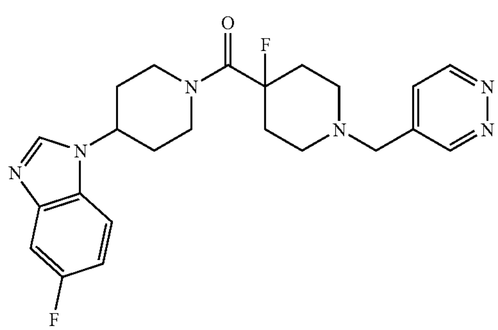 | 441 (ESMS) |
| 605 | 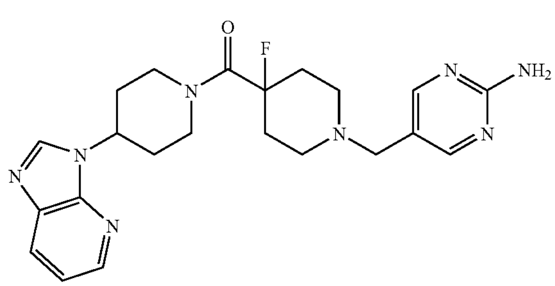 | 439 (ESMS) |

-continued
| Ex. | Structure | Mass Spec (M + H) |
|---|---|---|
| 606 | 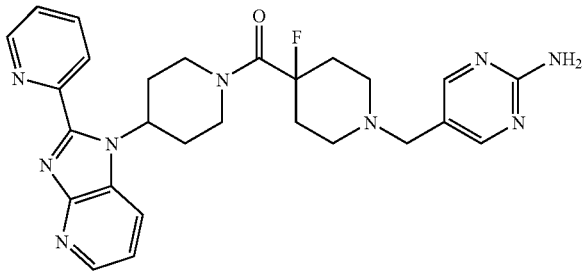 | 516 (ESMS) |
| 607 | 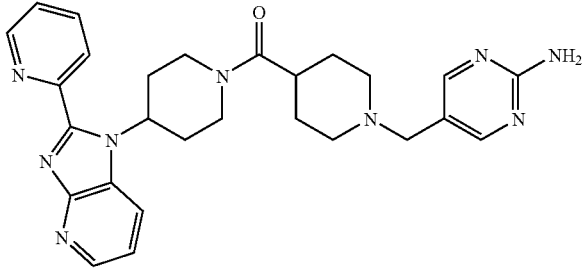 | 498 (ESMS) |
| 608 | 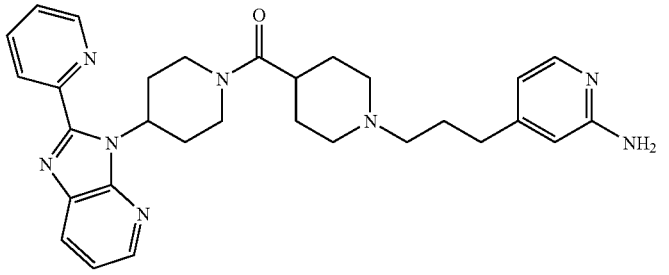 | 525 (ESMS) |
| 609 | 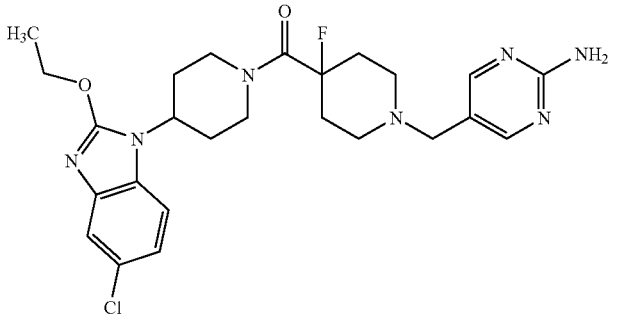 | 516 (ESMS) |
| 610 | 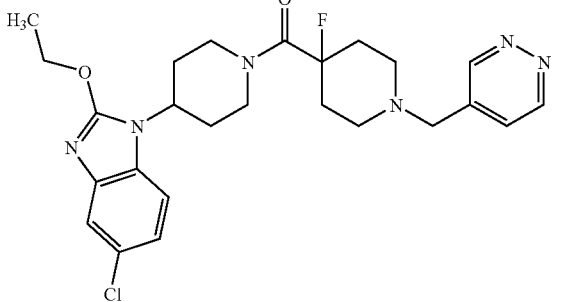 | 501 (ESMS) |

-continued
| Ex. | Structure | Mass Spec (M + H) |
|---|---|---|
| 611 | 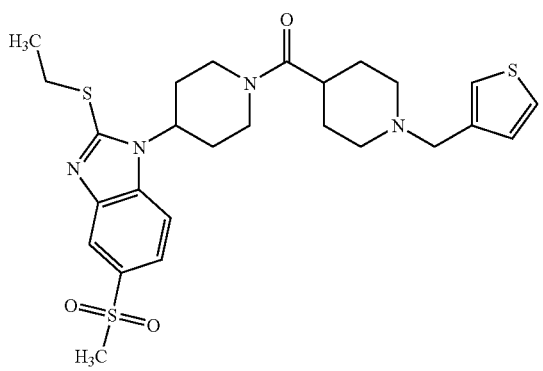 | 547 (ESMS) |
| 612 | 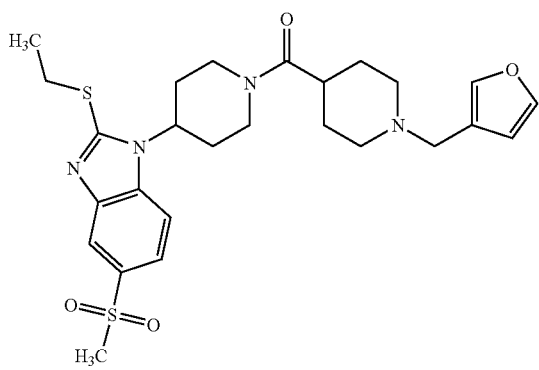 | 531 (ESMS) |
| 613 | 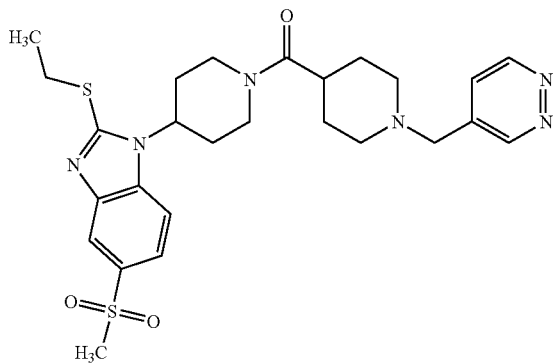 | 543 (ESMS) |
| 614 | 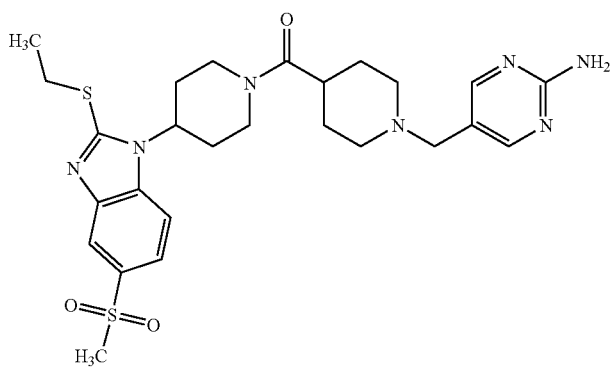 | 558 (ESMS) |

| Ex. | Structure | Mass Spec (M + H) |
|---|---|---|
| 615 | 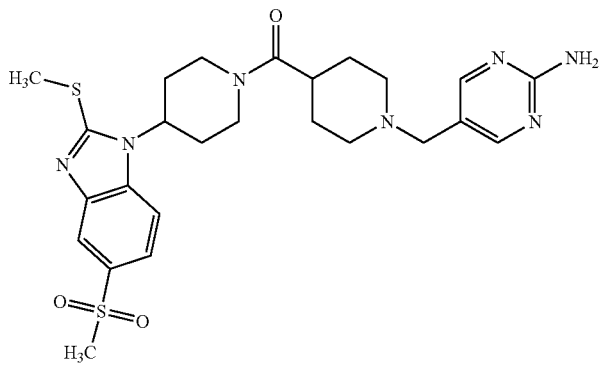 | 544 (ESMS) |
| 616 | 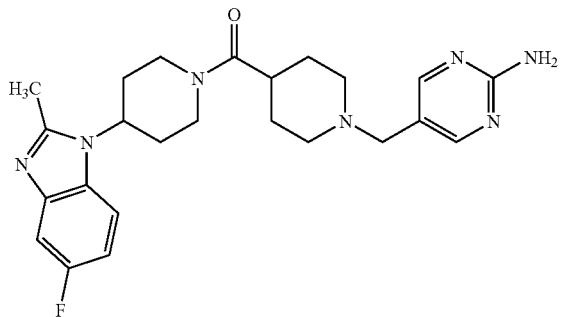 | 452 (FAB) |
| 617 | 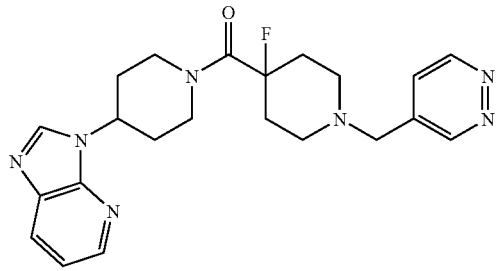 | 424 (ESMS) |
| 618 | 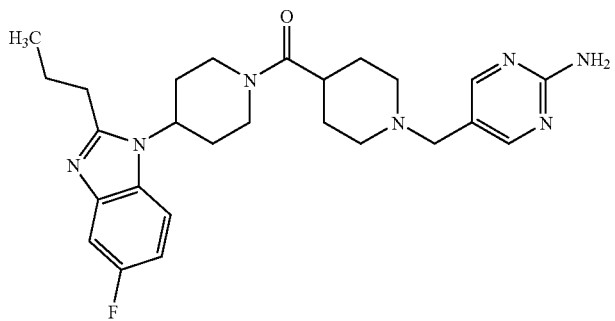 | 480 (ESMS) |

| Ex. | Structure | Mass Spec (M + H) |
|---|---|---|
| 619 | 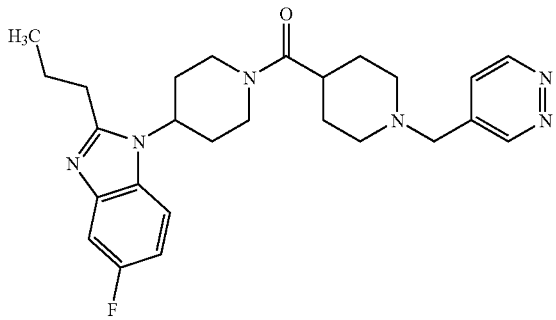 | 465 (ESMS) |
| 620 | 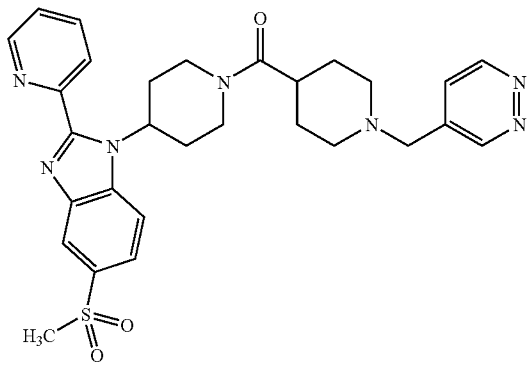 | 560 (ESMS) |
| 621 | 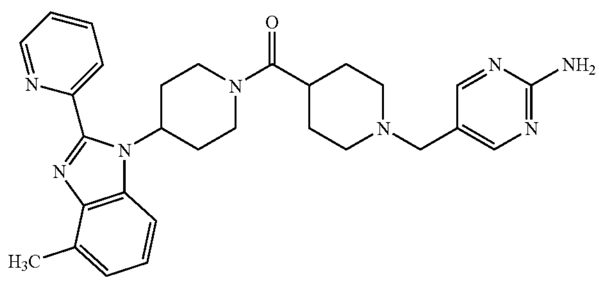 | 511 (ESMS) |
| 622 | 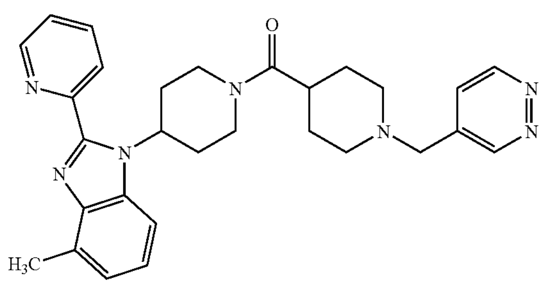 | 496 (ESMS) |
| 623 | 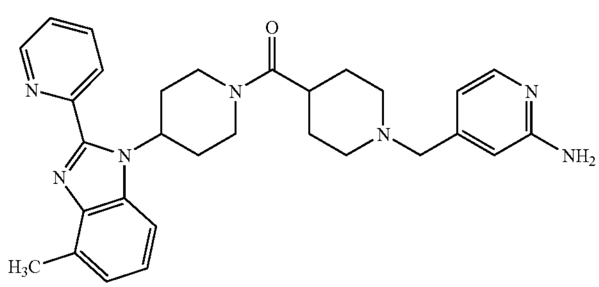 | 510 (ESMS) |

| Ex. | Structure | Mass Spec (M + H) |
|---|---|---|
| 624 | 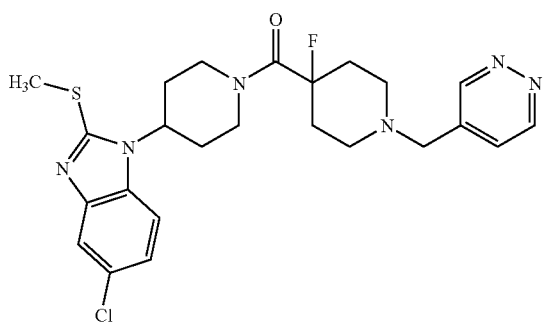 | 503 (ESMS) |
| 625 | 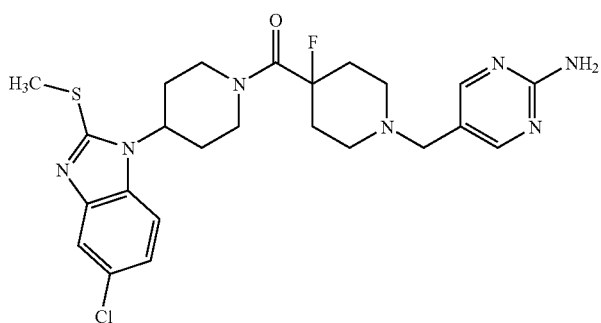 | 518 (ESMS) |
| 626 | 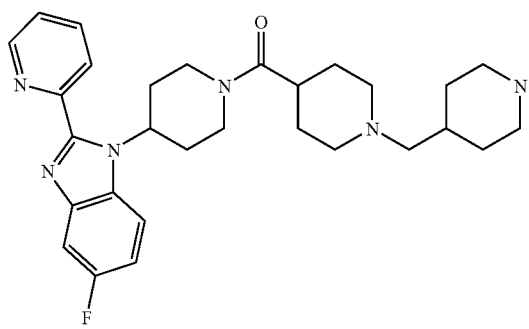 | 505 (ESMS) |
| 627 | 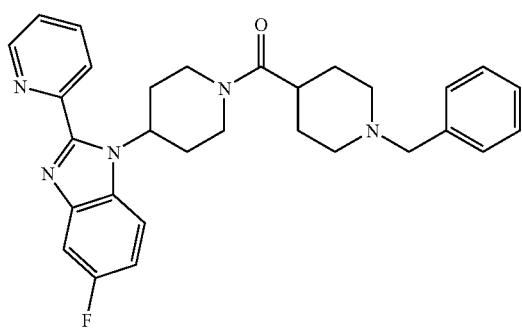 | 498 (ESMS) |

-continued

| Ex. | Structure | Mass Spec (M + H) |
|---|---|---|
| 628 | 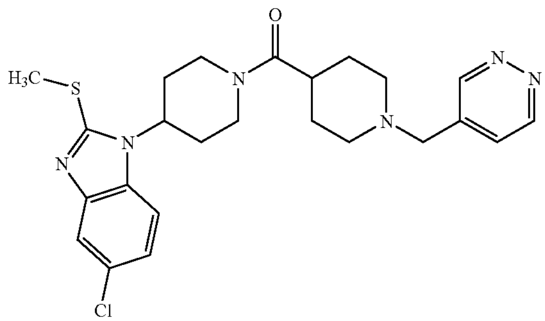 | 485 (ESMS) |
| 629 | 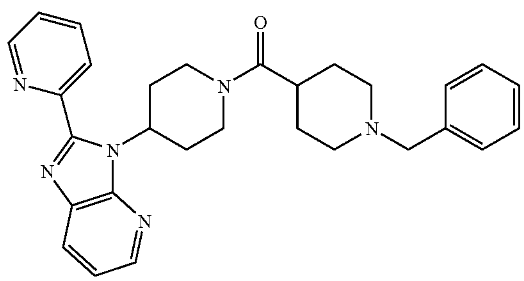 | 481 (ESMS) |
| 630 | 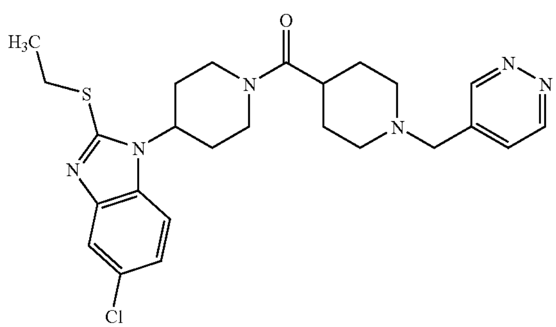 | 499 (ESMS) |
| 631 | 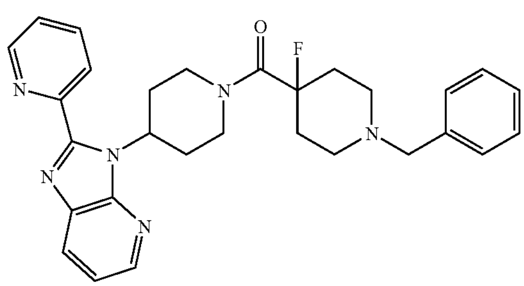 | 499 (ESMS) |
| 632 | 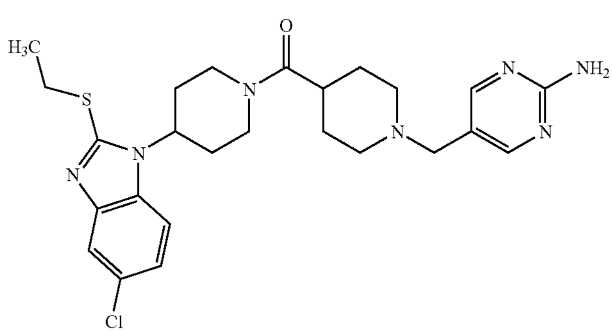 | 514 (ESMS) |

| Ex. | Structure | Mass Spec (M + H) |
|---|---|---|
| 633 | 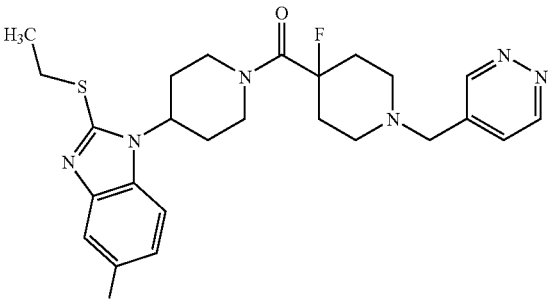 | 517 (ESMS) |
| 634 | 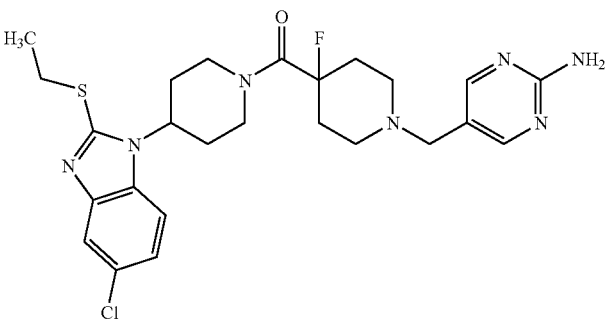 | 532 (ESMS) |
| 635 | 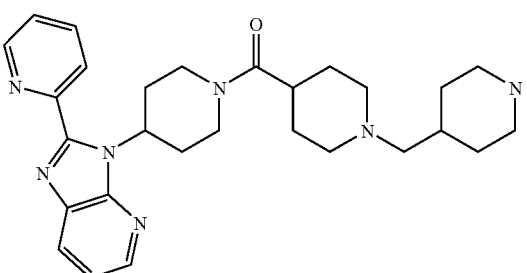 | 488 (ESMS) |
| 636 | 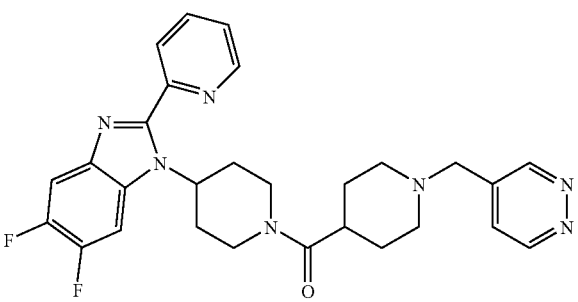 | 518 (ESMS) |
| 637 | 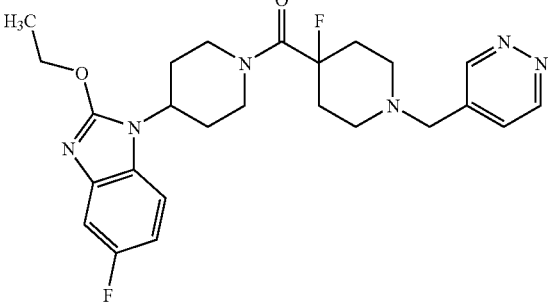 | 451 (ESMS) |

-continued

| Ex. | Structure | Mass Spec (M + H) |
|---|---|---|
| 638 | 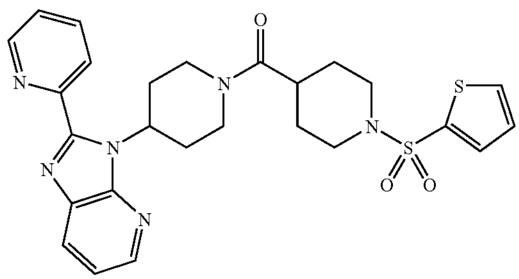 | 537 (MH+) |
| 639 | 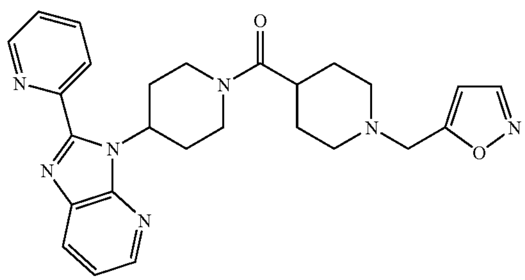 | 472 (MH+) |
| 640 | 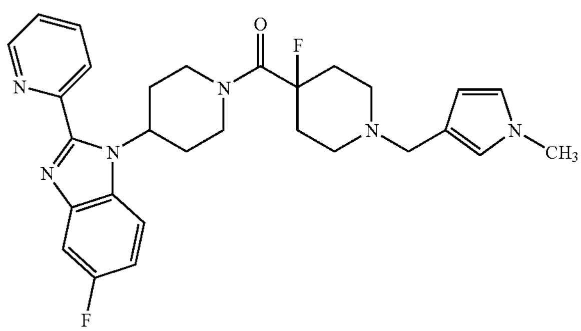 | 519 (MH+) |
| 641 | 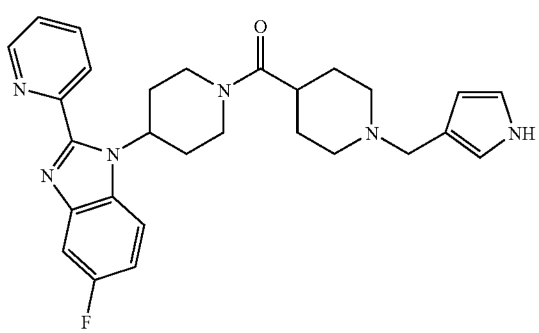 | 487 (MH+) |
| 642 | 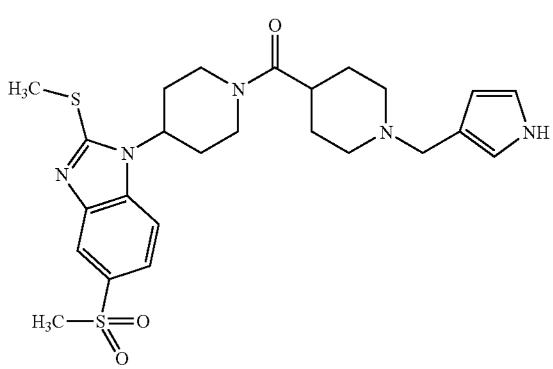 | 516 (MH+) |

| Ex. | Structure | Mass Spec (M + H) |
|---|---|---|
| 643 | 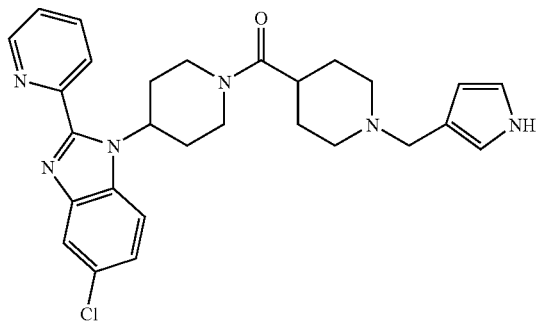 | 503 (MH+) |
| 644 | 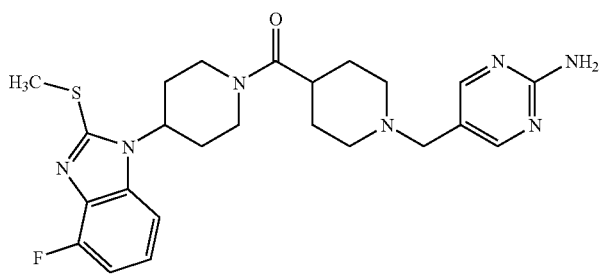 | 484 (ESMS) |
| 645 | 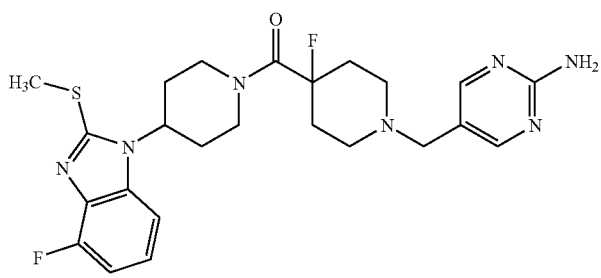 | 503 (ESMS) |
| 646 | 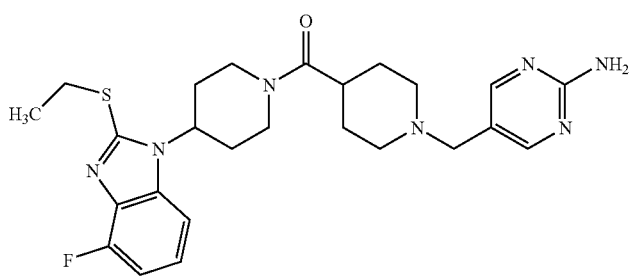 | 498 (ESMS) |
| 647 | 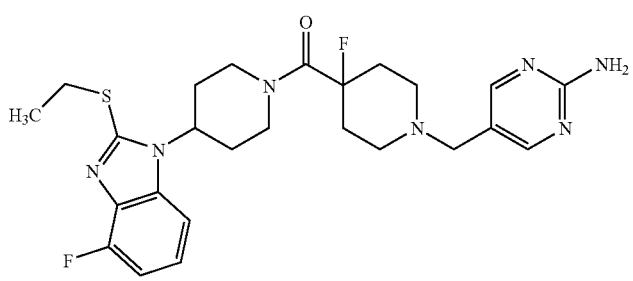 | 516 (ESMS) |

| Ex. | Structure | Mass Spec (M + H) |
|---|---|---|
| 648 | 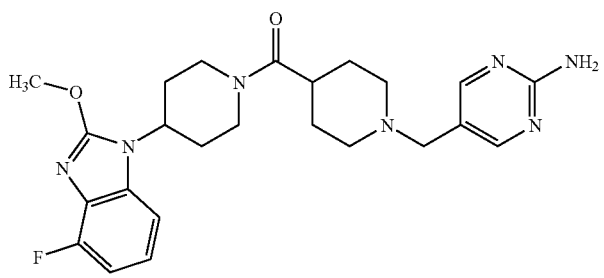 | 468 (ESMS) |
| 649 | 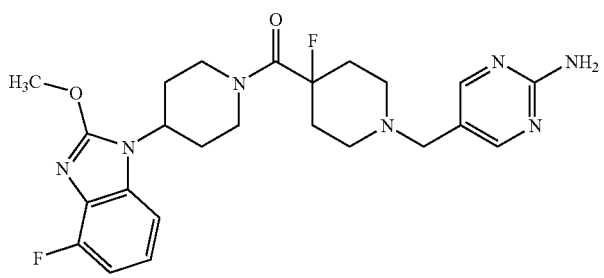 | 486 (ESMS) |
| 650 | 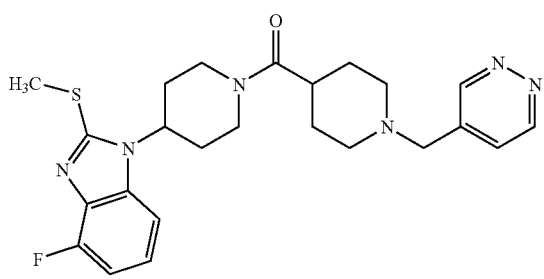 | 469 (ESMS) |
| 651 | 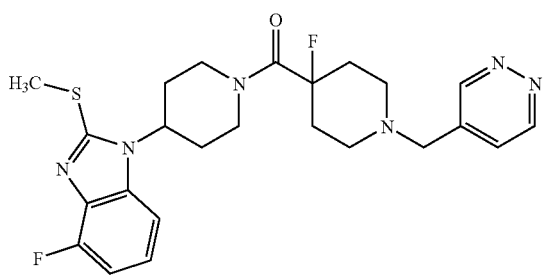 | 487 (ESMS) |
| 652 | 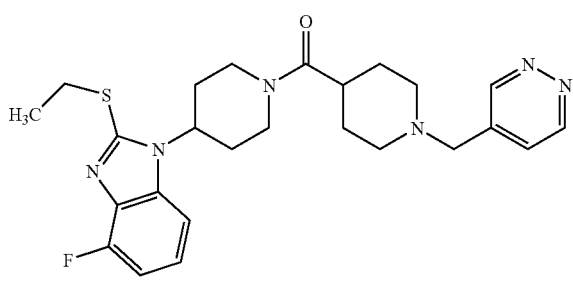 | 483 (ESMS) |

| Ex. | Structure | Mass Spec (M + H) |
|---|---|---|
| 653 | 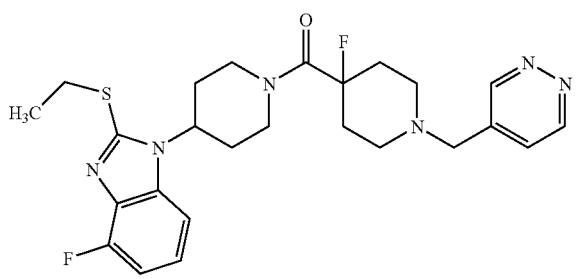 | 501 (ESMS) |
| 654 | 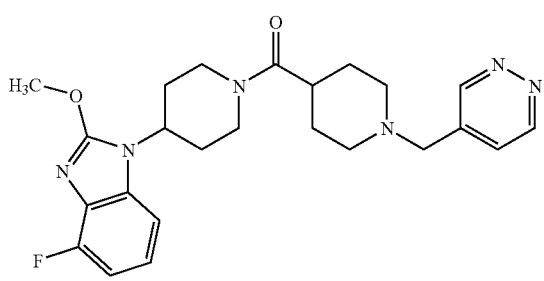 | 453 (ESMS) |
| 655 | 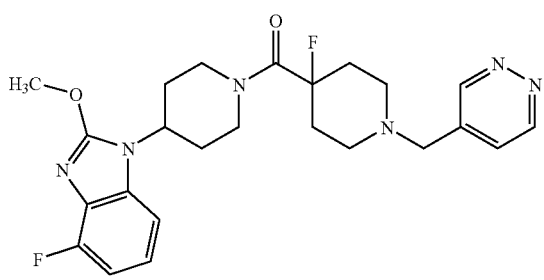 | 471 (ESMS) |
| 656 | 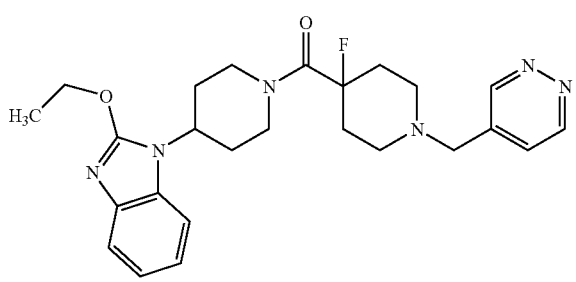 | 468 (ESMS) |
| 657 | 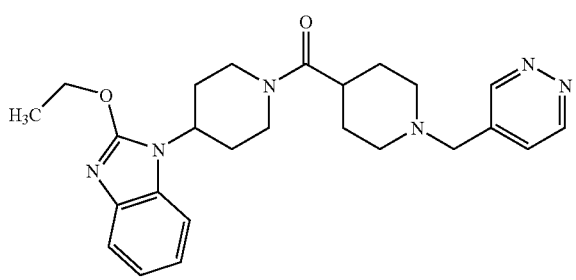 | 450 (ESMS) |

| Ex. | Structure | Mass Spec (M + H) |
|---|---|---|
| 658 | 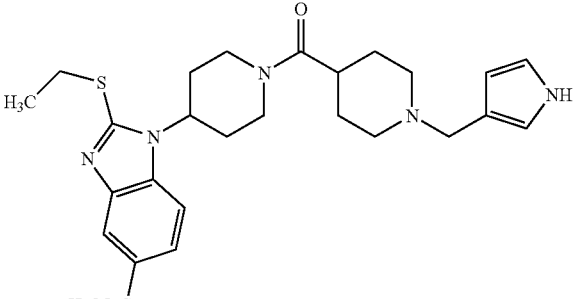 | 530 (ESMS) |
| 659 | 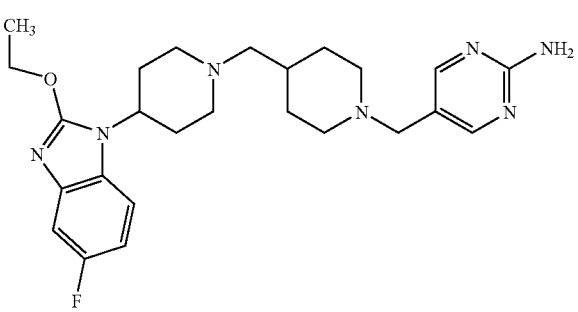 | |
| 660 | 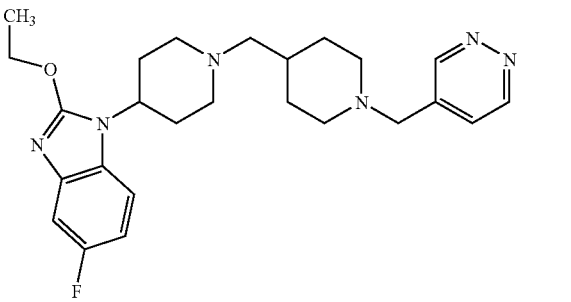 | 453 (FAB) |
| 661 | 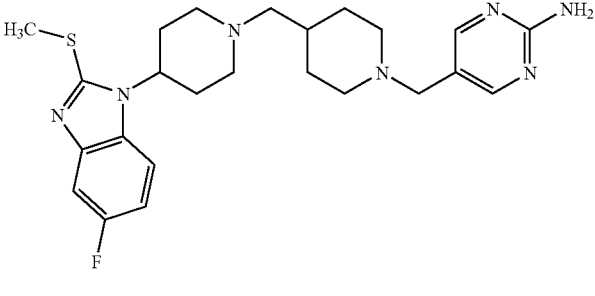 | 470 (FAB) |
| 662 | 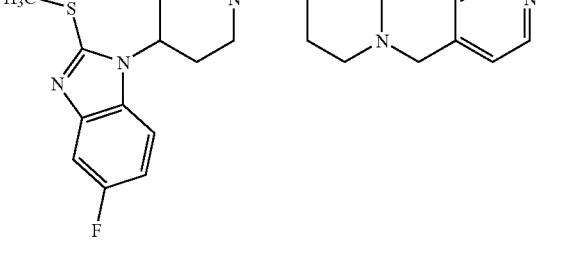 | 455 (FAB) |

-continued

| Ex. | Structure | Mass Spec (M + H) |
|---|---|---|
| 663 | 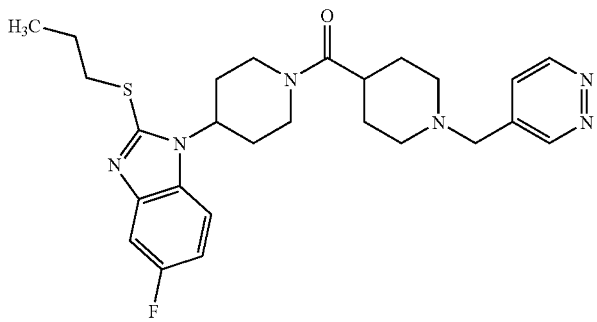 | 497 (ESMS) |
| 664 | 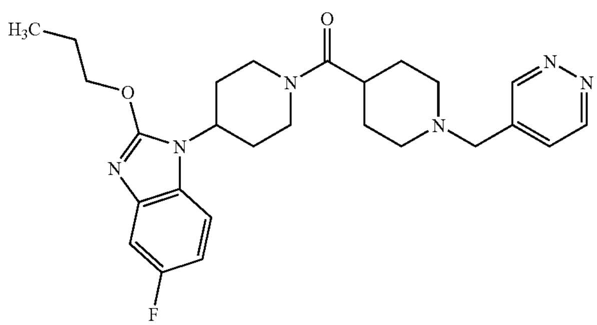 | 481 (FAB) |
| 664A | 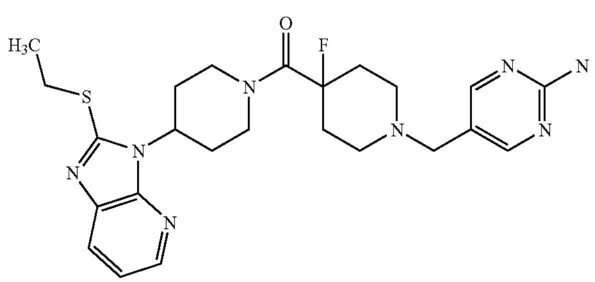 | 499 (FAB) |

EXAMPLE 665

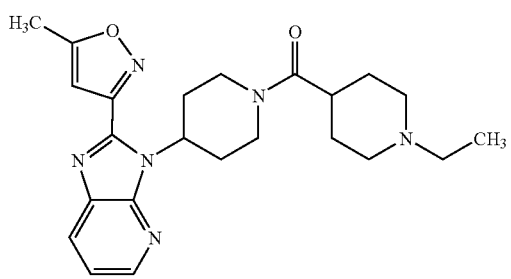

4-[[4-[2-(5-methyl-3-isoxazolyl)-3H-imidazo[4,5-b]pyridine-3-yl]-1-(4-piperidinylcarbonyl)piperidine (0.99 g, 2.51 mmoles) and pyridazine 4-Carboxaldehyde (0.35 g, 3.26 mmoles) were stirred at RT in dry CH₂Cl₂ (25 ml) containing activated 3 Å molecular sieves (6.5 g). After 5 h, triacetoxy borohydride (3.2 g, 15 mmoles) was added and the mixture was stirred for 70 h. The mixture was diluted with CH₂Cl₂ and the solid filtered through a pad of Celite. The filtrate was stirred for 20 min. with saturated aqueous NaHCO₃, then separated, washed with brine, and dried over anahydrous Na₂SO₄. The reaction mixture was purified by preparative TLC. The plates were eluted with EtOAc:Hexanes:CH₃OH(NH₃) (75:20:5). Extraction of the bands with 13% CH₃OH(NH₃)/EtOAc gave a mixture of Example 665 and Example 496. Example 658: MS (M+H): 423.

In a similar manner, using 4-[[4-[2-(methylthio)-3H-imidazo[4,5-b]pyridine-3-yl]-1-(4-piperidinylcarbonyl)piperidine (0.88 gr.; 2.44 mmoles), pyridazine 4-carboxaldehyde (0.34 g, 3.18 mmoles), and triacetoxy borohydride, a mixture of Example 666 and Example 495 was prepared:

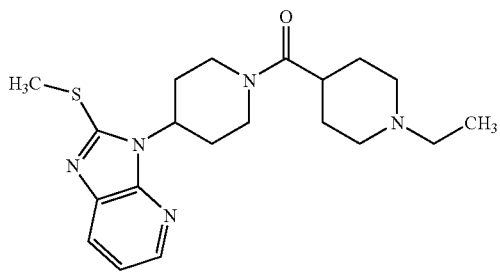

EXAMPLE 666

MS (M+H): 388

General Procedure for H$_3$Receptor Binding Assay

The source of the H$_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at –70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [$^3$H]R-α-methyl histamine (8.8 Ci/mmol) or 3 nM [$^3$H]N$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a K$_i$ (nM).

General Procedure for rHu H$_3$Binding Assay

[$^3$H]N$^\alpha$-methylhistamine (82 Ci/mmole) was obtained from Dupont NEN. Thioperamide was obtained from the Chemical Research Department, Schering-Plough Research Institute.

HEK-293 human embryonic kidney cells stably expressing the human histamine H$_3$ receptor were cultured in Dulbecco's modified Eagle's medium/10% fetal calf serum/penicillin (100 U/ml)/streptomycin (100 μg/ml)/Geneticin (0.5 mg/ml) at 37° C. in a humidified 5% CO$_2$ atmosphere. Cells were harvested between passages five and twenty at 37° C. in 5 mM EDTA/Hank's balanced salt solution and processed for membrane preparation. After low-speed centrifugation, ten min at 1000×g, they were put into ten volumes of ice-cold buffer and disrupted with a Polytron (PTA 35/2 tip, 30 sec at setting 6). After subsequent low-speed centrifugation, supernatant was centrifuged ten min at 50,000×g. The high-speed pellet was resuspended in the original volume of buffer, a sample was taken for protein assay (bicinchoninic acid, Pierce) and the suspension was centrifuged again at 50,000×g. Membranes were resuspended at 1 mg of protein/ml of buffer and frozen at –80° C. until use.

Membrane (15 μg of protein) was incubated with 1.2 nM [$^3$H]N$^\alpha$-methyl-histamine, without or with inhibitor compounds, in a total volume of 200 μl of buffer. Nonspecific binding was determined in the presence of 10$^{-5}$ M thioperamide. Assay mixtures were incubated for 30 min at 30° C. in polypropylene, 96-well, deep-well plates, then filtered through 0.3% polyethylenimine-soaked GF/B filters. These were washed three times with 1.2 ml of 4° C. buffer, dried in a microwave oven, impregnated with Meltilex wax scintillant and counted at 40% efficiency in a Betaplate scintillation counter (Wallac).

IC$_{50}$ values were interpolated from the data or were determined from curves fit to the data with Prism nonlinear least squares curve-fitting program (GraphPad Software, San Diego, Calif.). K$_i$ values were determined from IC$_{50}$ values according to the Cheng and Prusoff equation.

In these assays, compounds of formula I have a K$_i$ within the range of about 0.1 to about 600 nM. Preferred compounds of formula I have a K$_i$ within the range of about 0.1 to about 100 nM. More preferred compounds of formula I have a K$_i$ within the range of about 0.1 to about 20 nM.

Representative compounds of the present invention tested according to the above procedures have the following Ki values:

| Ex. | Receptor Source | K$_i$ |
|---|---|---|
| 1 | rHu | 1 |
| 3 | Guinea pig | 13 |
| 5 | rHu | 9 |
| 13 | Guinea Pig | 27 |
| 54 | Guinea Pig | 30 |
| 71 | Guinea Pig | 1 |
| 94 | Guinea Pig | 1 |
| 109 | rHu | 1 |
| 120 | Guinea Pig | 0.3 |
| 165 | rHu | 2 |
| 170 | Guinea Pig | 0.5 |
| 173 | Guinea Pig | 0.4 |
| 195 | Guinea Pig | 10 |
| 211 | Guinea Pig | 7 |
| 254 | Guinea Pig | 13 |
| 269 | rHu | 4 |
| 270 | rHu | 4 |
| 281 | rHu | 4 |
| 290 | rHu | 3 |
| 290 | rHu | 3 |
| 297 | rHu | 4 |
| 297 | rHu | 4 |
| 315 | rHu | 5 |
| 316 | rHu | 5 |
| 316 | rHu | 5 |
| 326 | rHu | 2 |
| 335 | rHu | 12 |
| 388 | rHu | 30 |
| 423 | rHu | 5 |
| 442 | rHu | 1 |
| 449 | rHu | 1 |
| 459 | rHu | 4 |
| 460 | rHu | 4 |
| 468 | rHu | 10 |
| 493 | rHu | 1 |
| 502 | rHu | 7 |
| 512 | rHu | 2 |
| 547 | rHu | 14 |
| 552 | rHu | 4 |
| 557 | rHu | 19 |
| 571 | rHu | 2 |
| 574 | rHu | 2 |
| 577 | rHu | 44 |
| 588 | rHu | 6 |
| 592 | rHu | 9 |
| 595 | rHu | 41 |
| 598 | rHu | 17 |
| 608 | rHu | 1 |
| 618 | rHu | 9 |
| 619 | rHu | 2 |
| 625 | rHu | 10 |
| 628 | rHu | 4 |

In this specification, the term "at least one compound of formula I" means that one to three different compounds of formula I may be used in a pharmaceutical composition or method of treatment. Preferably one compound of formula I is used. Similarly, "at least one H₁ receptor antagonist" means that one to three different H₁ antagonists may be used in a pharmaceutical composition or method of treatment. Preferably, one H₁ antagonist is used.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20th Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 350 mg, preferably from about 1 mg to about 150 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of H₃ antagonist and H₁ antagonist compounds, the two active components may be co-administered simultaneously or sequentially, or a single pharmaceutical composition comprising a H₃ antagonist and an H₁ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the H₁ antagonist can be determined from published material, and may range from 1 to 1000 mg per dose.

When separate H₃ and H₁ antagonist pharmaceutical compositions are to be administered, they can be provided in a kit comprising in a single package, one container comprising an H₃ antagonist in a pharmaceutically acceptable carrier, and a separate container comprising an H₁ antagonist in a pharmaceutically acceptable carrier, with the H₃ and H₁ antagonists being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula

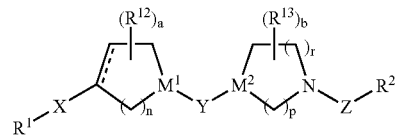

or a pharmaceutically acceptable salt or solvate thereof, wherein:

the dotted line represents an optional double bond;

a is 0 to 2;

b is 0 to 2;

n is 2;

p is 1, 2 or 3;

r is 0, 1, 2, or 3;

with the proviso that the sum of p and r is 3;

$M^1$ is N;

$M^2$ is $C(R^3)$;

X is a bond or $C_1$–$C_6$ alkylene;

Y is —C(O)—, —C(S)—, —(CH₂)$_q$—, —NR⁴C(O)—, —C(O)NR⁴—, —C(O)CH₂—, —SO₂—, —N(R⁴)—, —NH—C(=N—CN)— or —C(=N—CN)—NH—; with the provisos that when $M^1$ is N, Y is not —NR⁴C(O)— or —NH—C(=N—CN)—; when $M^2$ is N, Y is not —C(O)NR⁴— or —C(=N—CN)—NH—; and when Y is —N(R⁴)—, $M^1$ is CH and $M^2$ is $C(R^3)$;

q is 1 to 5, provided that when both $M^1$ and $M^2$ are N, q is 2 to 5;

Z is a bond, $C_1$–$C_6$ alkylene, $C_1$–$C_6$ alkenylene, —C(O)—, —CH(CN)—, —SO₂— or —CH₂C(O)NR⁴—;

$R^1$ is

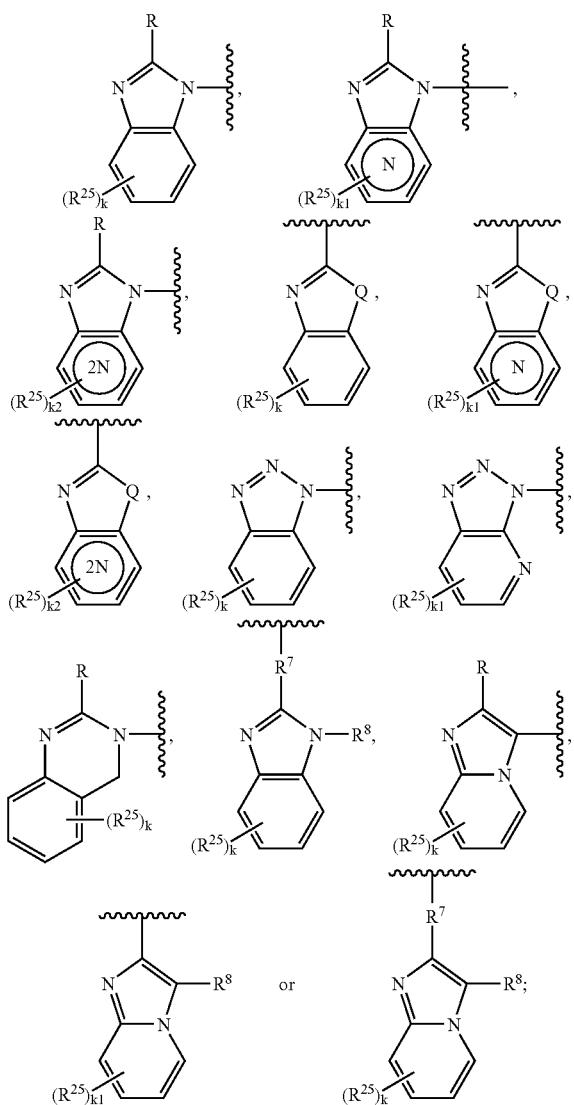

Q is —N($R^8$)—, —S— or —O—;

k is 0, 1, 2, 3 or 4;

k1 is 0, 1, 2 or 3;

k2 is 0, 1 or 2;

R is H, $C_1$–$C_6$ alkyl, halo($C_1$–$C_6$)alkyl-, $C_1$–$C_6$ alkoxy, ($C_1$–$C_6$)alkoxy-($C_1$–$C_6$)alkyl-, ($C_1$–$C_6$)-alkoxy-($C_1$–$C_6$)alkoxy, ($C_1$–$C_6$)alkoxy-($C_1$–$C_6$)alkyl-$S(O)_{0-2}$, $R^{32}$-aryl($C_1$–$C_6$)alkoxy-, $R^{32}$-aryl($C_1$–$C_6$)alkyl-, $R^{32}$-aryl, $R^{32}$-aryloxy, $R^{32}$-heteroaryl, ($C_3$–$C_6$)cycloalkyl, ($C_3$–$C_6$)cycloalkyl-($C_1$–$C_6$)alkyl, ($C_3$–$C_6$)cycloalkyl-($C_1$–$C_6$)alkoxy, ($C_3$–$C_6$)cycloalkyl-oxy-, $R^{37}$-heterocycloalkyl, $R^{37}$-heterocycloalkyl-oxy-, $R^{37}$-heterocycloalkyl-($C_1$–$C_6$)alkoxy, N($R^{30}$)($R^{31}$)—($C_1$–$C_6$)alkyl-, —N($R^{30}$)($R^{31}$), —NH—($C_1$–$C_6$)alkyl-O—($C_1$–$C_6$) alkyl, —NHC(O)NH($R^{29}$); $R^{29}$—$S(O)_{0-2}$—, halo($C_1$–$C_6$)alkyl-$S(O)_{0-2}$—, N($R^{30}$)($R^{31}$)—($C_1$–$C_6$)alkyl-$S(O)_{0-2}$— or benzoyl;

$R^8$ is H, $C_1$–$C_6$ alkyl, halo($C_1$–$C_6$)alkyl-, ($C_1$–$C_6$)alkoxy-($C_1$–$C_6$)alkyl-, $R^{32}$-aryl($C_1$–$C_6$)alkyl-, $R^{32}$-aryl, $R^{32}$-heteroaryl, ($C_3$–$C_6$)cycloalkyl, ($C_3$–$C_6$)cycloalkyl-($C_1$–$C_6$)alkyl, $R^{37}$-heterocycloalkyl, N($R^{30}$)($R^{31}$)—($C_1$–$C_6$)alkyl-, $R^{29}$—$S(O)_2$—, halo($C_1$–$C_6$)alkyl-$S(O)_2$—, $R^{29}$—$S(O)_{0-1}$—($C_2$–$C_6$)alkyl-, halo($C_1$–$C_6$)alkyl-$S(O)_{0-1}$—($C_2$–$C_6$)alkyl-;

$R^2$ is a six-membered heteroaryl ring having 1 or 2 heteroatoms independently selected from N or N—O, with the remaining ring atoms being carbon; a five-membered heteroaryl ring having 1, 2, 3 or 4 heteroatoms independently selected from N, O or S, with the remaining ring atoms being carbon; $R^{32}$-quinolyl; $R^{32}$-aryl; heterocycloalkyl; ($C_3$–$C_6$)cycloalkyl; $C_1$–$C_6$ alkyl; hydrogen; thianaphthenyl;

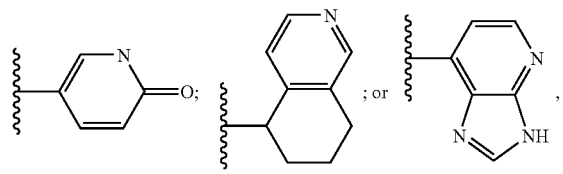

wherein said six-membered heteroaryl ring or said five-membered heteroaryl ring is optionally substituted by $R^6$;

$R^3$ is H, halogen, $C_1$–$C_6$ alkyl, —OH, ($C_1$–$C_6$)alkoxy or —NHSO₂—($C_1$–$C_6$)alkyl;

$R^4$ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, $R^{33}$-aryl, $R^{33}$-aryl($C_1$–$C_6$)alkyl, and $R^{32}$-heteroaryl;

$R^5$ is hydrogen, $C_1$–$C_6$ alkyl, —C(O)$R^{20}$, —C(O)₂$R^{20}$, —C(O)N($R^{20}$)₂, ($C_1$–$C_6$)alkyl-$SO_2$—, or ($C_1$–$C_6$) alkyl-$SO_2$—NH—;

or $R^4$ and $R^5$, together with the nitrogen to which they are attached, form an azetidinyl, pyrrolidinyl, piperidinyl, piperazinyl or morpholinyl ring;

$R^6$ is 1 to 3 substituents independently selected from the group consisting of —OH, halogen, $C_1$–$C_6$ alkyl-, $C_1$–$C_6$ alkoxy, $C_1$–$C_6$ alkylthio, —$CF_3$, —$NR^4R^5$, —$CH_2$—$NR^4R^5$, —$NHSO_2R^{22}$, —$N(SO_2R^{22})_2$, phenyl, $R^{33}$-phenyl, $NO_2$, —$CO_2R^4$, —$CON(R^4)_2$,

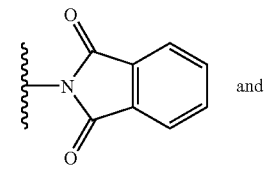 and

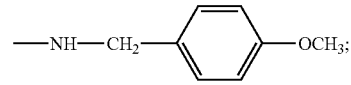

$R^7$ is —N($R^{29}$)—, —O— or —$S(O)_{0-2}$—;

$R^{12}$ is independently selected from the group consisting of $C_1$–$C_6$ alkyl, hydroxyl, $C_1$–$C_6$ alkoxy, or fluoro, provided that when $R^{12}$ is hydroxy or fluoro, then $R^{12}$ is not bound to a carbon adjacent to a nitrogen; or two $R^{12}$ substituents form a $C_1$ to $C_2$ alkyl bridge from one ring carbon to another non-adjacent ring carbon; or $R^{12}$ is =O;

$R^{13}$ is independently selected from the group consisting of $C_1$–$C_6$ alkyl, hydroxyl, $C_1$–$C_6$ alkoxy, or fluoro, provided that when $R^{13}$ is hydroxy or fluoro then $R^{13}$ is not bound to a carbon adjacent to a nitrogen; or two $R^{13}$ substituents form a $C_1$ to $C_2$ alkyl bridge from one ring carbon to another non-adjacent ring carbon; or $R^{13}$ is =O;

R²⁰ is independently selected from the group consisting of hydrogen, $C_1$–$C_6$ alkyl, or aryl, wherein said aryl group is optionally substituted with from 1 to 3 groups independently selected from halogen, —$CF_3$, —$OCF_3$, hydroxyl, or methoxy; or when two R²⁰ groups are present, said two R²⁰ groups taken together with the nitrogen to which they are bound can form a five or six membered heterocyclic ring;

R²² is $C_1$–$C_6$ alkyl, R³⁴-aryl or heterocycloalkyl;

R²⁴ is H, $C_1$–$C_6$ alkyl, —$SO_2R^{22}$ or R³⁴-aryl;

R²⁵ is independently selected from the group consisting of $C_1$-$C_6$ alkyl, halogen, —CN, —$NO_2$, —$CF_3$, —OH, $C_1$–$C_6$ alkoxy, ($C_1$–$C_6$)alkyl-C(O)—, aryl-C(O)—, —C(O)OR²⁹, —N(R⁴)(R⁵), N(R⁴)(R⁵)—C(O)—, N(R⁴)(R⁵)—S(O)$_{1-2}$—, R²²—S(O)$_{0-2}$—, halo-($C_1$–$C_6$)alkyl- or halo-($C_1$–$C_6$)alkoxy-($C_1$–$C_6$)alkyl-;

R²⁹ is H, $C_1$–$C_6$ alkyl, $C_3$–$C_6$ cycloalkyl, R³⁵-aryl or R³⁵-aryl($C_1$–$C_6$)alkyl-;

R³⁰ is H, $C_1$–$C_6$ alkyl-, R³⁵-aryl or R³⁵-aryl($C_1$–$C_6$)alkyl-;

R³¹ is H, $C_1$–$C_6$ alkyl-, R³⁵-aryl, R³⁵-aryl($C_1$–$C_6$)alkyl-, R³⁵-heteroaryl, ($C_1$–$C_6$)alkyl-C(O)—, R³⁵-aryl-C(O)—, N(R⁴)(R⁵)—C(O)—, ($C_1$–$C_6$)alkyl-S(O)$_2$— or R³⁵-aryl-S(O)$_2$—;

or R³⁰ and R³¹ together are —(CH$_2$)$_{4-5}$—, —(CH$_2$)$_2$—O—(CH$_2$)$_2$— or —(CH$_2$)$_2$—N(R³⁸)—(CH$_2$)$_2$— and form a ring with the nitrogen to which they are attached;

R³² is 1 to 3 substituents independently selected from the group consisting of H, —OH, halogen, $C_1$–$C_6$ alkyl, $C_1$–$C_6$ alkoxy, R³⁵-aryl-O—, —SR²², —$CF_3$, —$OCF_3$, —$OCHF_2$, —NR³⁹R⁴⁰, phenyl, R³³-phenyl, NO$_2$, —CO$_2$R³⁹, —CON(R³⁹)$_2$, —S(O)$_2$R²², —S(O)$_2$N(R²⁰)$_2$, —N(R²⁴)S(O)$_2$R²², —CN, hydroxy-($C_1$–$C_6$)alkyl-, —OCH$_2$CH$_2$OR²², and R³⁵-aryl($C_1$–$C_6$)alkyl-O—, or two R³² groups on adjacent carbon atoms together form a —OCH$_2$O— or —O(CH$_2$)$_2$O— group;

R³³ is 1 to 3 substituents independently selected from the group consisting of $C_1$–$C_6$ alkyl, halogen, —CN, —NO$_2$, —CF$_3$, —OCF$_3$, —OCHF$_2$ and —O—($C_1$–$C_6$) alkyl;

R³⁴ is 1 to 3 substituents independently selected from the group consisting of H, halogen, —CF$_3$, —OCF$_3$, —OH and —OCH$_3$;

R³⁵ is 1 to 3 substituents independently selected from hydrogen, halo, $C_1$–$C_6$ alkyl, hydroxy, $C_1$–$C_6$ alkoxy, phenoxy, —CF$_3$, —N(R³⁶)$_2$, —COOR²⁰ and —NO$_2$;

R³⁶ is independently selected form the group consisting of H and $C_1$–$C_6$ alkyl;

R³⁷ is 1 to 3 substituents independently selected from hydrogen, halo, $C_1$–$C_6$ alkyl, hydroxy, $C_1$–$C_6$ alkoxy, phenoxy, —CF$_3$, —N(R³⁶)$_2$, —COOR²⁰, —C(O)N(R²⁹)$_2$ and —NO$_2$, or R³⁷ is one or two =O groups;

R³⁸ is H, $C_1$–$C_6$ alkyl, R³⁵-aryl, R³⁵-aryl($C_1$–$C_6$)alkyl-, ($C_1$–$C_6$)alkyl-SO$_2$ or halo($C_1$–$C_6$)alkyl-SO$_2$—;

R³⁹ is independently selected from the group consisting of hydrogen, $C_1$–$C_6$ alkyl, $C_3$–$C_6$ cycloalkyl, ($C_3$–$C_6$)cycloalkyl($C_1$–$C_6$)alkyl, R³³-aryl, R³³-aryl($C_1$–$C_6$)alkyl, and R³²-heteroaryl; and R⁴⁰ is hydrogen, $C_1$–$C_6$alkyl, —C(O)R²⁰, —C(O)$_2$R²⁰, —C(O)N(R²⁰)$_2$, ($C_1$–$C_6$)alkyl-SO$_2$—, or ($C_1$–$C_6$) alkyl-SO$_2$—NH—;

or R³⁹ and R⁴⁰, together with the nitrogen to which they are attached, form an azetidinyl, pyrrolidinyl, piperidinyl, piperazinyl or morpholinyl ring.

2. A compound of claim 1 wherein a is 0, and the optional double bond is not present.

3. A compound of claim 2 wherein M² is C(R³) wherein R³ is hydrogen or fluorine, b is 0, r is 1, and p is 2.

4. A compound of claim 3 wherein X is a bond.

5. A compound of claim 4 wherein Y is —C(O)—.

6. A compound of claim 5 wherein Z is straight or branched $C_1$–$C_3$ alkyl.

7. A compound of claim 6 wherein R² is a six-membered heteroaryl ring, optionally substituted with one R⁶ substituent.

8. A compound of claim 7 wherein R² is pyrimidyl, R⁶⁻pyrimidyl, pyridyl R⁶⁻pyridyl or pyridazinyl and R⁶ is —NH$_2$.

9. A compound of claim 8 wherein R² is

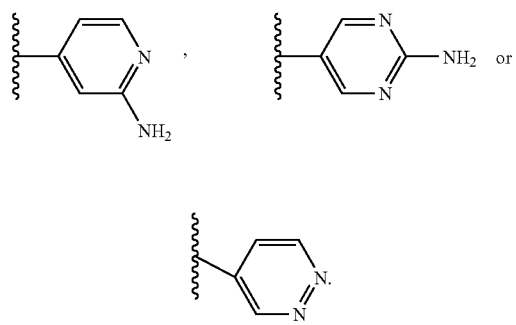

10. A compound of claim 2 wherein R¹ is

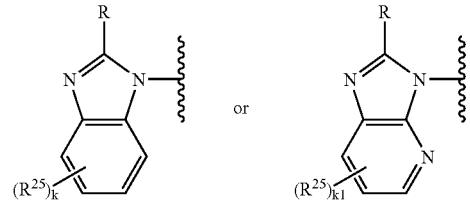

11. A compound of claim 10 wherein R is ($C_1$–$C_6$)alkyl, ($C_1$–$C_6$)alkoxy, ($C_1$–$C_6$)alkoxy($C_1$–$C_6$)alkoxy, ($C_1$–$C_6$) alkylthio, heteroaryl or R³²-aryl; R²⁵ is halogen or —CF$_3$; and k and k1 are 0 or 1.

12. A compound of claim 11 wherein R is —CH$_3$, —CH$_2$CH$_3$, —OCH$_3$, —OCH$_2$CH$_3$, —OCH$_2$CH$_2$CH$_3$, —OCH((CH$_3$)$_2$, —CH$_2$CH$_3$, —SCH$_3$, —SCH$_2$CH$_3$, pyridyl, pyrimidyl, pyrazinyl, furanyl, oxazolyl or R³²-phenyl.

13. A compound of claim 12 wherein R² is

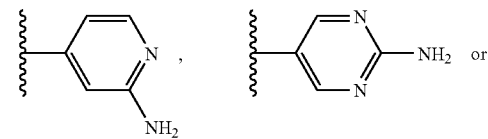

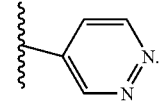

14. A compound of claim 1 selected from the group consisting of
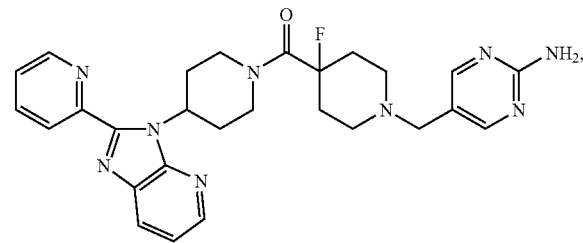
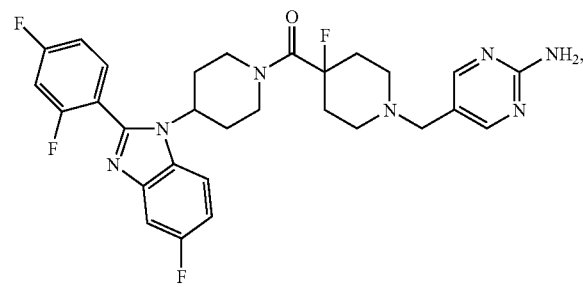
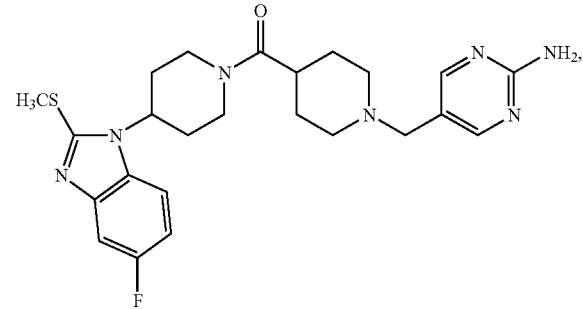
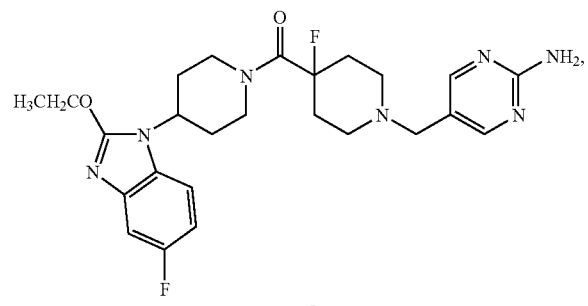
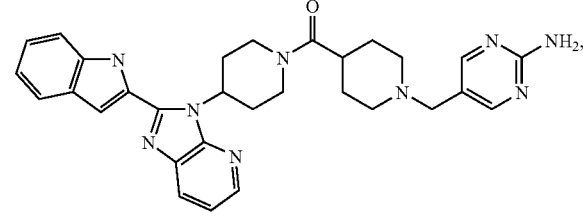
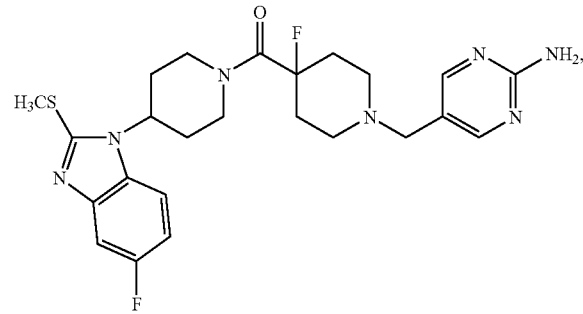
-continued
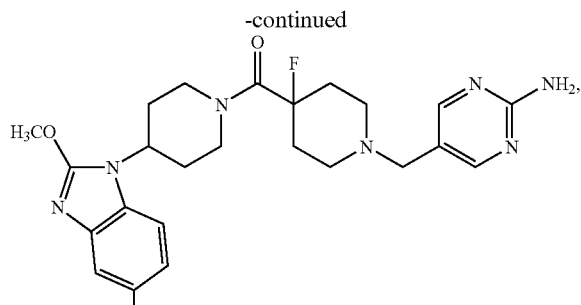
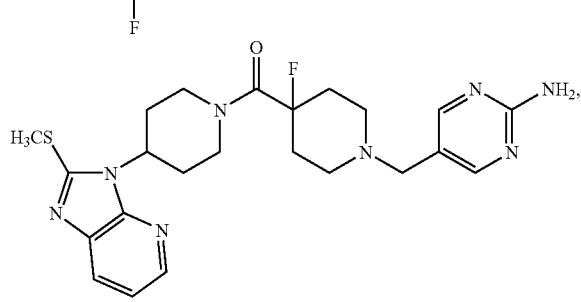
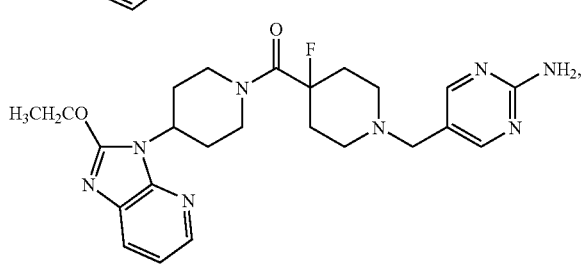
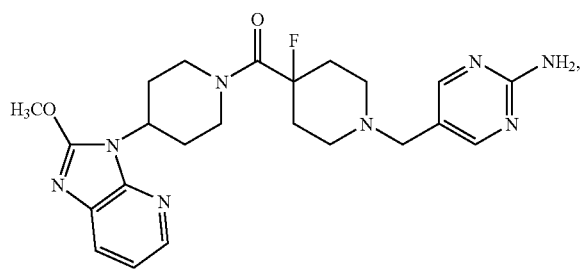
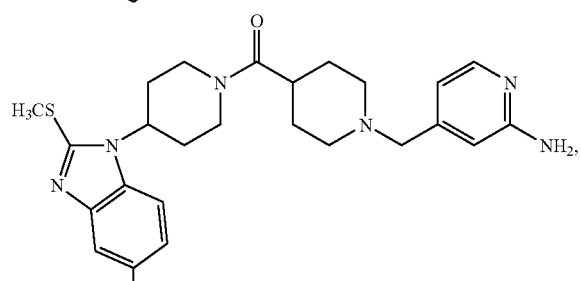
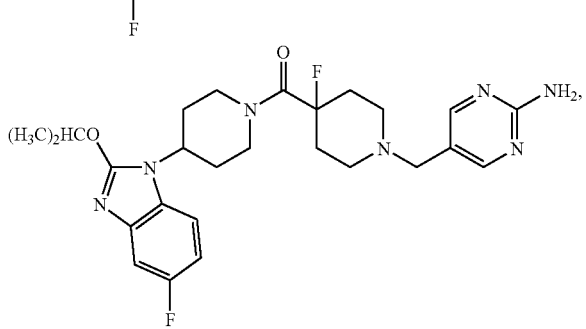

245
-continued
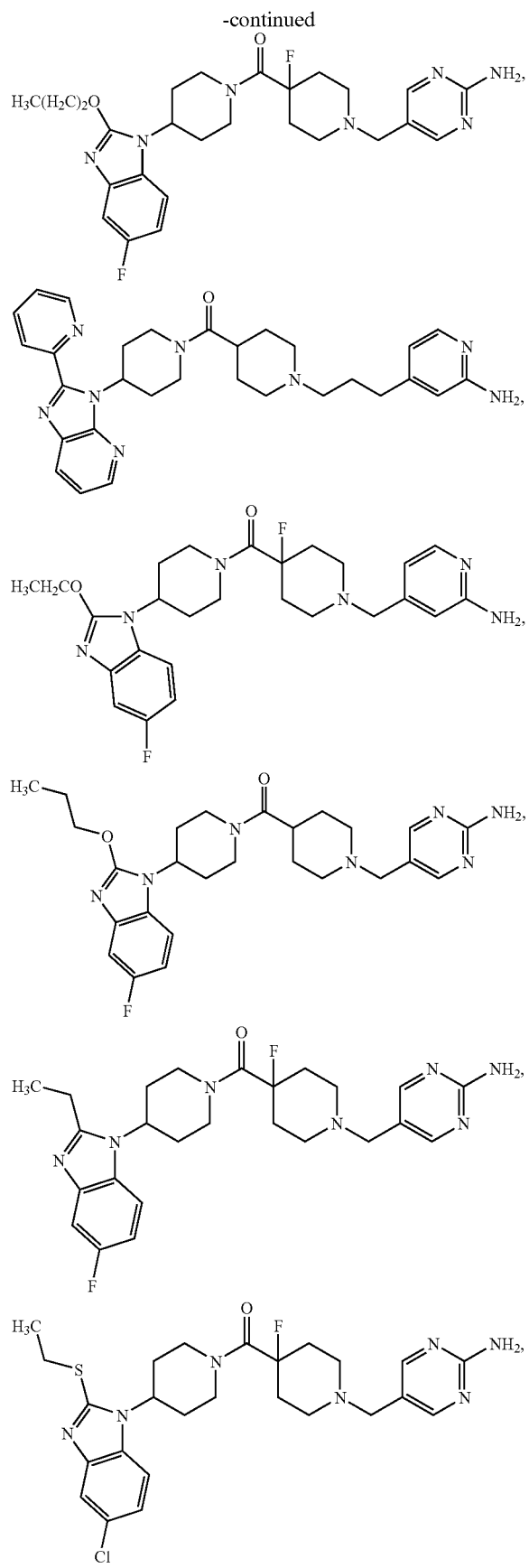
246
-continued
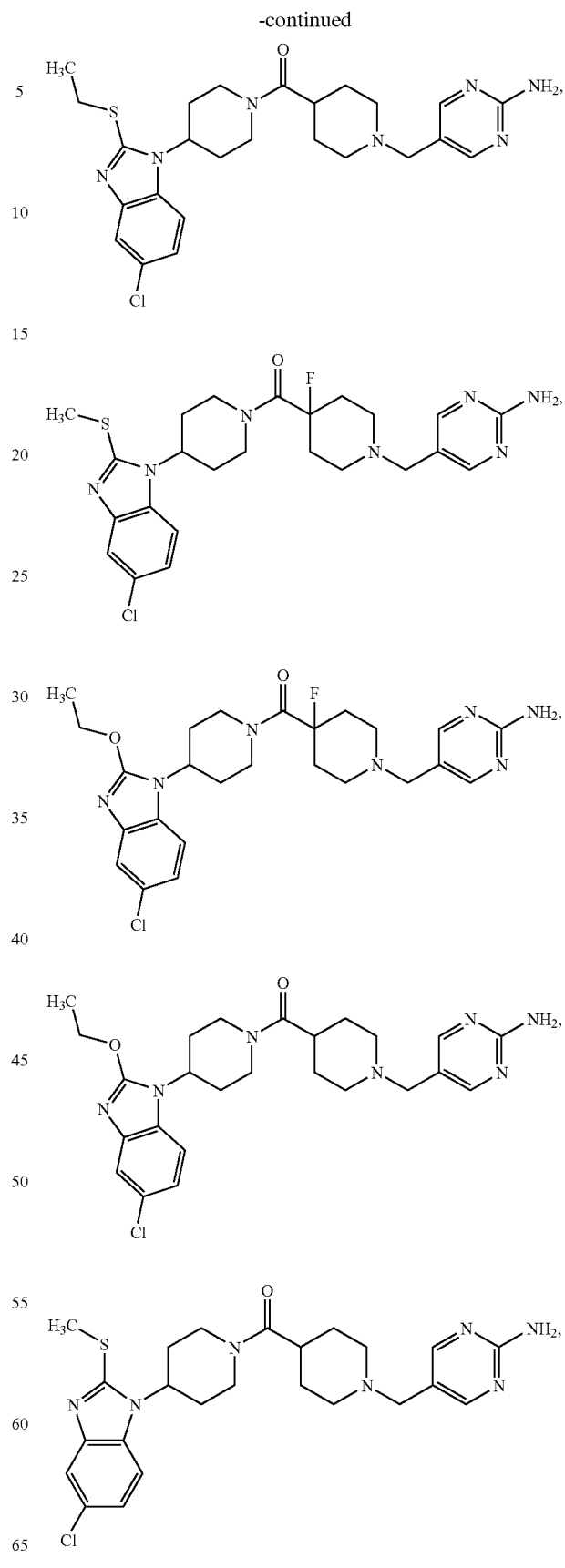

247
-continued
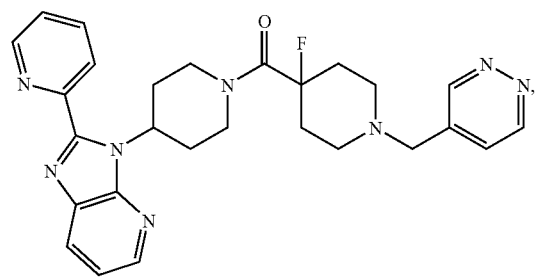
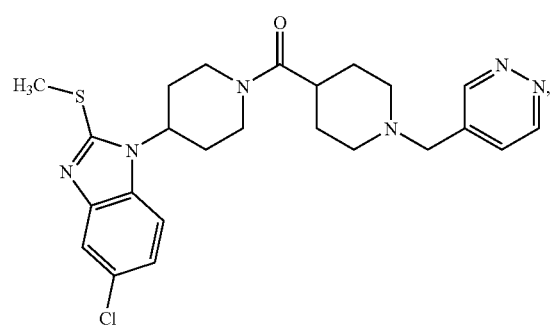
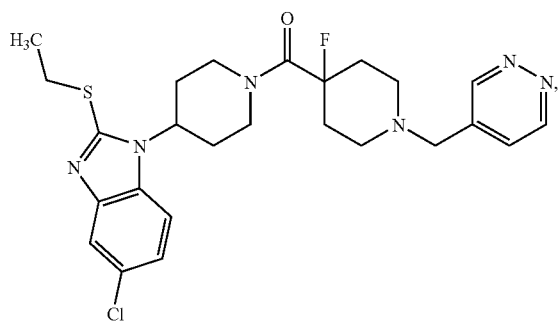
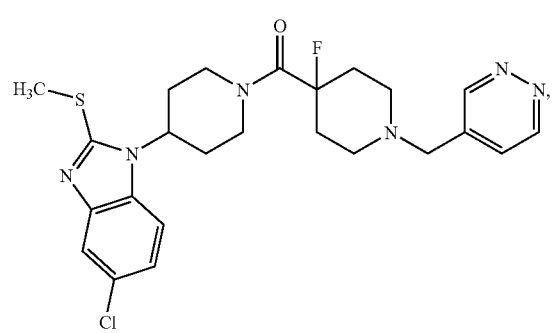
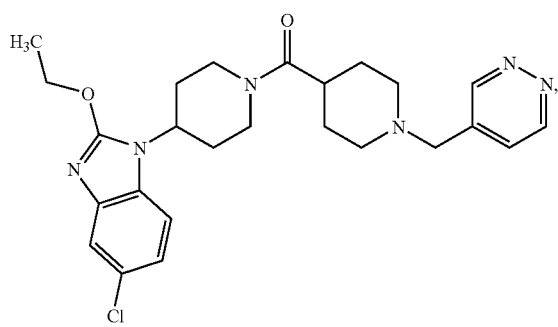
248
-continued
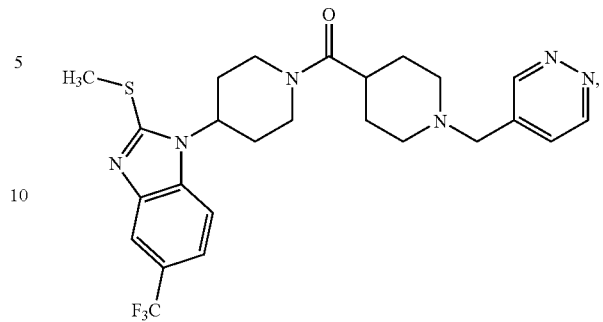
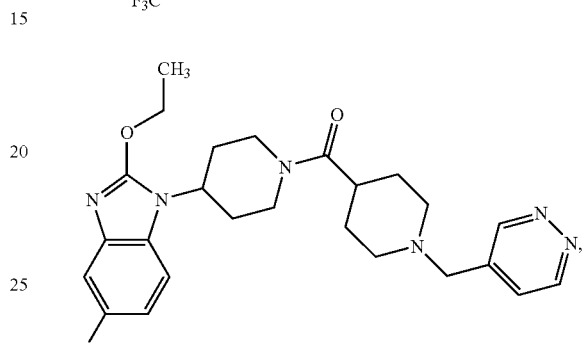
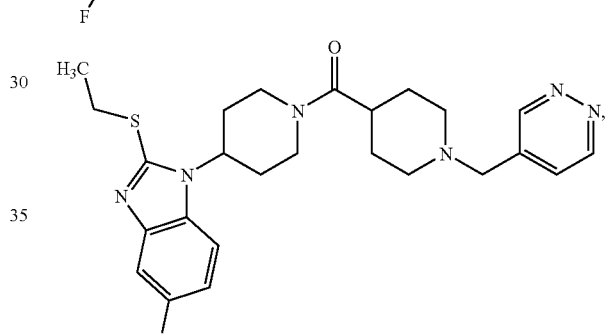
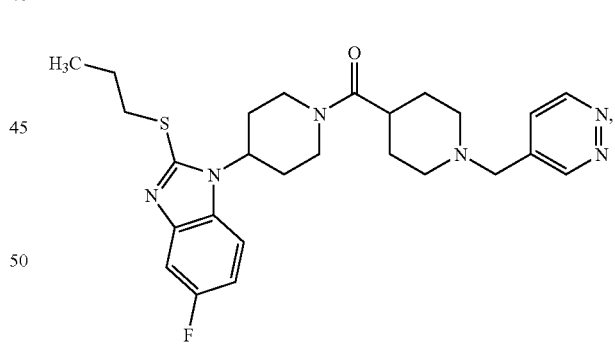
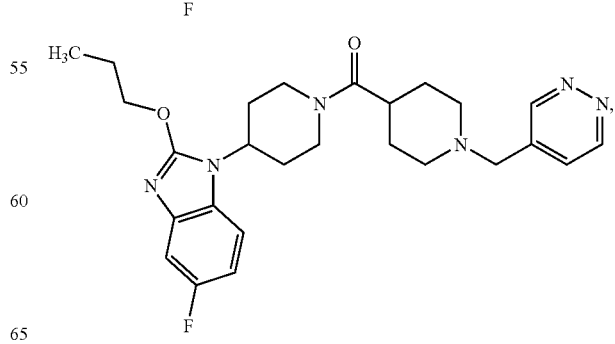

-continued

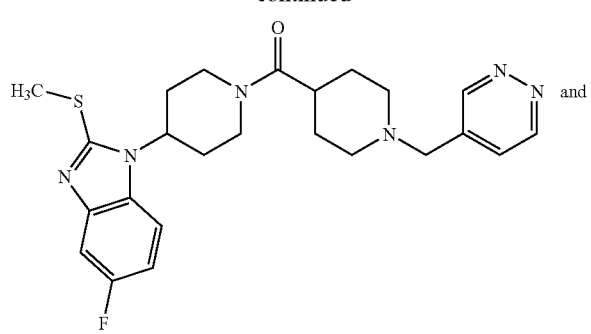

and

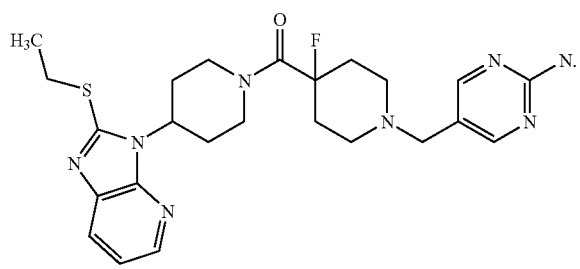

15. A pharmaceutical composition comprising an effective amount of a compound of claim 1 and a pharmaceutically effective carrier.

16. A method of treating nasal congestion obesity, somnolence, narcolepsy, attention deficit hyperactivity disorder, Alzheimer's disease, and schizophrenia comprising administering to a patient in need of such treatment an effective amount of a compound of claim 1.

17. A pharmaceutical composition comprising an effective amount of a compound of claim 1, and an effective amount of $H_1$ receptor antagonist, and a pharmaceutically effective carrier.

18. A method of treating nasal congestion comprising administering to a patient in need of such treatment an effective amount of a compound of claim 1 in combination with an $H_1$ receptor antagonist.

19. The method of claim 18 wherein said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

20. The method of claim 19 wherein said $H_1$ receptor antagonist is selected from: loratadine, descarboethoxyloratadine, fexofenadine or cetirizine.

21. The method of claim 20 wherein said $H_1$ receptor antagonist is selected from: loratadine or descarboethoxyloratadine.

22. The compound having the structure

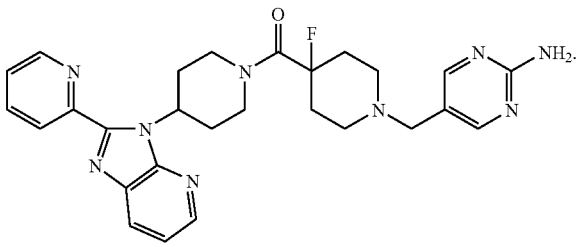

* * * * *